US009353075B2

(12) United States Patent
Piomelli et al.

(10) Patent No.: US 9,353,075 B2
(45) Date of Patent: May 31, 2016

(54) DISUBSTITUTED BETA-LACTONES AS INHIBITORS OF N-ACYLETHANOLAMINE ACID AMIDASE (NAAA)

(71) Applicants: The Regents of the University of California, Oakland, CA (US); Fondazione Istituto Italiano Di Tecnologia, Genoa (IT); Universita Degli Studi Di Parma, Parma (IT); Universita Degli Studi Di Urbino "Carlo Bo", Urbino (IT)

(72) Inventors: Daniele Piomelli, Irvine, CA (US); Tiziano Bandiera, Gambolo (IT); Marco Mor, Ghedi (IT); Giorgio Tarzia, Petriano (IT); Fabio Bertozzi, Genoa (IT); Stefano Ponzano, Florence (IT)

(73) Assignees: The Regents of the University of California, Oakland, CA (US); Fondazione Istituto Italiano Di Technologia, Genoa (IT); Universita Degli Studi Di Parma, Parma (IT); Universita Degli Studi Di Urbino "Carlo Bo", Urbino (IT)

( * ) Notice: Subject to any disclaimer, the term of this patent is extended or adjusted under 35 U.S.C. 154(b) by 0 days.

(21) Appl. No.: 13/684,017

(22) Filed: Nov. 21, 2012

(65) Prior Publication Data
US 2013/0281490 A1 Oct. 24, 2013

Related U.S. Application Data

(60) Provisional application No. 61/562,862, filed on Nov. 22, 2011.

(51) Int. Cl.
| | | |
|---|---|---|
| *C07D 305/12* | (2006.01) | |
| *A61K 31/585* | (2006.01) | |
| *A61K 31/38* | (2006.01) | |
| *C07D 405/12* | (2006.01) | |
| *C07D 407/12* | (2006.01) | |
| *C07D 409/12* | (2006.01) | |
| *A61K 31/365* | (2006.01) | |

(52) U.S. Cl.
CPC ............ *C07D 305/12* (2013.01); *A61K 31/365* (2013.01); *A61K 31/38* (2013.01); *C07D 405/12* (2013.01); *C07D 407/12* (2013.01); *C07D 409/12* (2013.01)

(58) Field of Classification Search
CPC ... A61K 31/135; A61K 31/337; A61K 31/38; C07D 305/12
See application file for complete search history.

(56) References Cited

U.S. PATENT DOCUMENTS

| | | |
|---|---|---|
| 5,260,310 A | 11/1993 | Derungs et al. |
| 6,358,978 B1 | 3/2002 | Ritzeler et al. |
| 2005/0131032 A1 | 6/2005 | Sit et al. |
| 2007/0155747 A1 | 7/2007 | Dasse et al. |
| 2008/0050336 A1 | 2/2008 | Bachand et al. |
| 2009/0054526 A1 | 2/2009 | Hansen et al. |
| 2010/0311711 A1 | 12/2010 | Piomelli et al. |
| 2014/0094508 A1 | 4/2014 | Piomelli et al. |

FOREIGN PATENT DOCUMENTS

| | | |
|---|---|---|
| WO | 2009/049238 A1 | 4/2009 |
| WO | WO-2011/082285 A1 | 7/2011 |
| WO | WO-2013/078430 A1 | 5/2013 |

OTHER PUBLICATIONS

Armirotti et al., "β-Lactones Inhibit N-acylethanolamine Acid Amidase by S-Acylation of the Catalytic N-Terminal Cysteine," ACS Medicinal Chemistry Letters (ACS), 2012, vol. 3, No. 5, pp. 422-426.

Astarita et al., "Pharmacological Characterization of Hydrolysis-Resistant Analogs of Oleoylethanolamide with Potent Anorexiant Properties," The Journal of Pharmacology and Experimental Therapeutics, vol. 318, No. 2, received Mar. 24, 2006, accepted May 12, 2006.

Dias et al., "Antimicrobial properties of highly fluorinated silver (I) tis (pyrazoili) borates," Journal of Inorganic Biochemistry, 2006, vol. 100, No. 100, pp. 158-160.

Duranti et al., "N-(2-Oxo-3-oxetanyl)carbamic Acid Esters as N-Acylethanolamine Acid Amidase Inhibitors: Synthesis and Structure—Activity and Structure—Property Relationships," Journal of Medicinal Chemistry, May 2012, pp. A-M. dx.doi.org/10.1021/jm300349j.

Higashibayashi et al "Synthetic studies on thiostrepton family of peptide antibiotics: synthesis of the pentapeptide segment containing dihydroxyisoleucine, thiazoline and dehydroamino acid," Tetrahedron Letters (Elsevier B.V.), 2004, vol. 45, No. 19, pp. 3707-3712.

(Continued)

*Primary Examiner* — Shobha Kantamneni
(74) *Attorney, Agent, or Firm* — Mintz Levin Cohn Ferris Glovsky and Popeo, P.C.

(57) ABSTRACT

The present invention provides compounds and pharmaceutical compositions for inhibiting N-acylethanolamine acid amidase (NAAA). Inhibition of NAAA is contemplated as a method to sustain the levels of palmitoylethanolamide (PEA) and oleylethanolamide (OEA), two substrates of NAAA, in conditions characterized by reduced concentrations of PEA and OEA. The invention also provides methods for treating inflammatory diseases and pain, and other disorders in which decreased levels of PEA and OEA are associated with the disorder.

2 Claims, 26 Drawing Sheets

(56) References Cited

OTHER PUBLICATIONS

Holt et al., "Inhibition of fatty acid amide hydrolase, a key endocannabinoid metabolizing enzyme, by analogues of ibuprofen and indomethacin," Eur J Pharmacol., Jun. 2007, 565(1-3)a;26-36, Epub Mar. 7, 2007 (abstract).

Lall et al., "Serine and Threonine β-Lactones: A New Class of Hepatitis A Virus 3C Cysteine Proteinase Inhibitors," Journal of Organic Chemistry (American Chemical Society), 2002, vol. 67, No. 5, pp. 1536-1547.

Li et al., "Design and Synthesis of Potent N-Acylethanolamine-hydrolyzing Acid Amidase (NAAA) Inhibitor as Anti-Inflammatory Compounds," PLoS One, Aug. 2012;7(8):e43023.

Lohse et al., "Incorporation of a phosphonic acid isostere of aspartic acid into peptides Using Fmoc-solid phase synthesis," Tetrahedron Letters, 1998, vol. 39, Issue 15, pp. 2067-2070.

Mori et at "Total Synthesis of Siomycin A: Construction of Synthetic Segments," Chemistry—An Asian Journal (Wiley—VCH Verlag), 2008, vol. 3, No. 6, pp. 984-1012.

Pu et al., "Synthesis, Stability, and Antimicrobial Activity of (+)-Obafluorin and Related β-Lactone Antibiotics," Journal of Organic Chemistry, 1994, vol. 59, No. 13, pp. 3642-3655.

Saturnino et al., "Synthesis and biological evaluation of new potential inhibitors of N-acylethanolamine hydrolyzing acid amidase," Bioorganic & Medicinal Chemistry Letters, 2010, vol. 20, Issue 3, pp. 1210-1213.

Solorzano et al., "Selective N-acylethanolamine-hydrolyzing acid amidase inhibition reveals a key role for endogenous palmitoylethanolamide in inflammation," PNAS, 2009, vol. 106, No. 49, pp. 20966-20971.

Solorzano et al., "Synthesis and structure-activity relationships of N-(2-oxo-3-oxetanyl)amides as N-acylethanolamine-hydrolyzing acid amidase inhibitors," J. Med. Chem., 2010, vol. 53, No. 15, pp. 5770-5781.

Spetzler et al., "Preparation and application of 0-amino-serine, Ams, a new building block in chemoselective ligation chemistry," Journal of Peptide Science, 1999, vol. 5, Issue 12, pp. 582-592.

Stigers et al., "Incorporation of chlorinated analogues of aliphatic amino acids during cell-free protein synthesis," Chemical Communications (Royal Soc. of Chemistry), 2011, vol. 47, No. 6, pp. 1839-1841.

Tsuboi et al., Molecular Characterization of N-Acylethanolamine-hydrolyzing Acid Amidase, a Novel Member of the Choloylglycine Hydrolase Family with Structural and Functional Similarity to Acid Ceramidase, The Journal of Biological Chemistry, vol. 280, No. 12, Issue of Mar. 25, pp. 11082-11092, 2005.

Ueda et al., "A second N-acylethanolamine hydrolase in mammalian tissues," Neuropharmacology, 2005, vol. 48, pp. 1079-1085.

Valls et al., "Synthesis of beta-chloro alpha-amino acids: (2S,3R)- and (2S,3S)-3-chloroleucine," Tetrahedron Letters, vol. 47, pp. 3701-3705, available online Apr. 12, 2006.

Wang et al., "β-Lactone probes identify a papain-like peptide ligase in *Arabidopsis thaliana*," Nature Chemical Biology (Nature Publishing Group), 2008, vol. 4, No. 9, pp. 557-563.

International Search Report and Written Opinion, Mail date Feb. 28, 2013, PCT application No. PCT/US2012/066421, pp. 11.

He, G. et al. (May 23, 2011, e-published Apr. 27, 2011). "A practical strategy for the structural diversification of aliphatic scaffolds through the palladium-catalyzed picolinamide-directed remote functionalization of unactivated C(sp3)-H bonds," *Angewandte Chemie Int. Ed.* 50(22):5192-5196.

International Search Report mailed on Dec. 17, 2008, for PCT Application No. PCT/US2008/079621, 1 page.

Pu, Y. et al. (1991). "Synthesis and Acylation of Salts of L-Threonine β-Lactone: A Route to β-Lactone Antibiotics," *J Org Chem* 56(3):1280-1283.

Pu, Y. et al. (1994). "Synthesis, Stability, and Antimicrobial Activity of (+)-Obafluorin and Related β-Lactone Antibiotics," *J Org Chem* 59(13):3642-3655.

### P < 0.001 vs Compound 6 alone ; ns = not significant vs veh ; *** P <0.001 vs veh

*** P < 0.001 vs vehicle

Notes
1. Compounds were given topically (once a day for 14 days)
2. Compound 6 and Dexamethasone were dissolved in petrolatum + 5% of lauric acid

*Therapeutic effect (repeated dosing protocol)*

Notes
1. Repeated treatment protocol
   - *First treatment with drug under testing at the time of DNFB challenge, then once a day administration for 7 days.*
   - *Efficacy tested 24 hr after last administration*
2. Compound 6 and Dexametasone were dissolved in petrolatum + 5% of lauric acid and given topically

Therapeutic effect (single dosing protocol)

Notes
1. Single treatment protocol
   - Drug under testing given at the time of DNFB challenge.
   - Efficacy tested 24 hr later.
2. Compound 6 and Dexametasone were dissolved in petrolatum + 5% of lauric acid and given topically.

*Preventive effect (repeated dosing protocol)*

Notes
1. Repeated treatment protocol
   - First treatment after second DNFB sensitization. Then once a day, for 8 days. Last treatment at the challenge,
   - Efficacy tested 24 hr later
2. Compound 6 and Dexametasone were dissolved in petrolatum + 5% of lauric acid and given topically.

Therapeutic effect on immune response (single dosing protocol)

Notes
1. Single treatment protocol
    - Drug under testing was given at the time of DNFB challenge.
    - Blood withdrawal 24 hr later.
2. Compound 6 was suspended in petrolatum + 5% of lauric acid and given topically.

Notes
1. Single treatment protocol
   - Drug under testing was given at the time of DNFB challenge.
   - Efficacy measure was made in the 2hrs period after administration.
2. Compound 6, Dexametasone, Clobetasol and Promethazine were suspended in petrolatum + 5% of lauric acid and given topically.

48-80 induced scratching
single dose protocol

Notes
1. Single treatment protocol
   - Drug under testing was given at the time of DNFB challenge.
   - Efficacy measure was done in the 60 min period after drug administration.
2. Compound 6, Dexametasone and Clobetasol were suspended in petrolatum + 5% of lauric acid and given topically.

Prom.= Prometazine
Clob. = Clobetasol

* P < 0.05 vs vehicle ; ** P< 0.01 vs vehicle

DISUBSTITUTED BETA-LACTONES AS INHIBITORS OF N-ACYLETHANOLAMINE ACID AMIDASE (NAAA)

CROSS-REFERENCES TO RELATED APPLICATIONS

This patent application claims the benefit of U.S. Provisional Patent Application No. 61/562,862, filed Nov. 22, 2011, the contents of which are hereby incorporated herein by reference in the entirety.

STATEMENT AS TO RIGHTS TO INVENTIONS MADE UNDER FEDERALLY SPONSORED RESEARCH AND DEVELOPMENT

This invention was made with Government support under Grant No. DAO 12413, Awarded by the National Institutes of Health. The Government has certain rights in this invention.

FIELD OF THE INVENTION

The present invention relates to compositions and methods of inhibiting N-acylethanolamine acid amidase (NAAA) and for the treatment and prevention of pain, inflammation, and other disorders in which modulation of fatty acid ethanolamides is clinically relevant. The present invention also provides methods for preparing these compounds, and pharmaceutical compositions comprising these compounds.

BACKGROUND OF THE INVENTION

While there are numerous compositions and methods known in the art to treat pain and inflammation, numerous difficulties remain. Most significantly, side effects over long administration periods and/or higher dosages often limit the use of such drugs. For example, certain COX-2 inhibitors have recently been implicated in adverse cardiovascular events, while aspirin-type pain medication often increases the risk of intestinal bleeding. In other examples, ibuprofen and acetaminophen tend to negatively impact hepatic function, especially at higher dosages.

Ethanolamides of long-chain fatty acids, usually referred to as N-acylethanolamines (NAEs), are present in numerous lower and higher organisms, and mammals with a wide variety of functions. For example, anandamide, a polyunsaturated fatty acid-type NAE, was demonstrated to have cannabimimetic activity and was reported to act as a ligand of TRPV1 (transient receptor potential vanilloid type 1). In contrast, saturated and monounsaturated NAEs are inactive as ligands of cannabinoid receptors. However, such compounds have been reported to possess a variety of other biological activities. For example, N-oleoylethanolamine (OEA), a monounsaturated fatty acid-type NAE, was shown to be anorexic and anti-inflammatory via the peroxisome proliferator-activated receptor-α (PPAR-α), and N-stearoylethanolamine, a saturated fatty acid-type NAE, to be pro-apoptotic and anorexic.

N-palmitoylethanolamine (PEA), the naturally occurring amide of palmitic acid and ethanolamine, is a member of the saturated fatty acid-type NAE family. PEA has been shown to inhibit peripheral inflammation and mast cell degranulation (Mazzari et al., *European Journal of Pharmacology* 1996, 300, 227-36; Berdishev et al., *Life Science* 1998, 63, 125-129; D'Agostino et al., *Journal of Pharmacology and Experimental Therapeutics* 2007, 322, 1137-1143), as well as to exert antinociceptive effects in rats and mice (Calignano et al., *Nature* 1998, 394, 277-281; Calignano et al., *European Journal of Pharmacology* 2001, 419, 191-198).

These properties have been shown to be dependent on PPAR-α expression, and PEA activates this nuclear receptor with a potency comparable to the synthetic agonist WY14, 643 (Lo Verme et al., *Molecular Pharmacology* 2005, 67, 15-19; Lo Verme et al., *Journal of Pharmacology and Experimental Therapeutics* 2006, 319, 1051-1061).

In the carrageenan-induced paw edema and phorbol ester-induced ear edema models, PEA applied as a drug attenuates inflammation in wild-type mice, but has no effect in mice lacking PPAR-α (see LoVerme et al., *Molecular Pharmacology* 2005, 67, 15-19). PEA was also found to suppress pain behaviors in mice induced by chemical tissue injury, nerve damage, or inflammation (see LoVerme et al., *Journal of Pharmacology and Experimental Therapeutics* 2006, 319, 1051-1061).

In addition to the pharmacological activities shown in animal models, PEA has been reported to attenuate skin inflammation in humans (Kemeny et al., *Skin Pharmacology and Physiology* 2007, 20, 155-161).

Activation of PPAR-α by selective receptor agonists could be envisaged as a viable approach for the treatment of inflammatory and pain states. However, the prolonged clinical use of PPAR-α agonists has been linked to serious adverse events, which include oncogenesis, renal dysfunction, and cardiovascular toxicity (Nissen et al., *JAMA* 2007, 297, 1362-1373). Sustaining PEA and OEA signaling at PPAR-α by protecting these lipid amides from degradation is envisaged as an alternative to direct PPAR-α activation by receptor agonists.

NAEs are a substrate of the N-acylethanolamine acid amidase (NAAA), an enzyme that catalytically hydrolyzes the NAE to ethanolamine and the corresponding fatty acid. NAAA is a cysteine hydrolase that belongs to the N-terminal nucleophile (Ntn) family of enzymes (Tsuboi et al., *Journal of Biological Chemistry* 2005, 280, 11082-11092; Tsuboi et al., *Chemistry and Biodiversity* 2007, 4, 1914-1925). NAAA exhibits a substantial preference for PEA and OEA over other NAEs. Therefore, inhibition of NAAA is expected to decrease the inactivation and restore the levels of PEA and OEA in pathological conditions characterized by markedly reduced concentrations of these signaling molecules.

Certain methods of treating pain and inflammation by inhibiting NAAA have been disclosed in the Patent Application WO2009/049238. Some compounds disclosed in WO2009/049238 have been shown to prevent the carrageenan- and LPS-induced reduction in PEA levels in leukocytes and RAW264.7 macrophages, respectively, and attenuate inflammation and tissue damage produced in mice by traumatic spinal cord injury (Solorzano et al., *Proceedings of the National Academy of Science USA* 2009, 106, 20966-20971; Solorzano et al., *Journal of Medicinal Chemistry* 2010, 53, 5770-5781).

The previously reported studies support the notion that inhibition of NAAA can produce therapeutically useful effects. Therefore, the identification of new and potent NAAA inhibitors is needed in order to provide new therapeutic agents for the treatment of pain and inflammation.

BRIEF SUMMARY OF THE INVENTION

The present invention provides compositions and methods of inhibiting NAAA using small organic compounds. We have now surprisingly discovered that the compounds represented by Formula I have improved potency and stability as compared to NAAA inhibitors previously described.

In a first aspect, the present invention provides compounds of Formula I

Formula I wherein:
A represents O or S;
$R_1$ and $R_2$ independently represent H, an optionally substituted lower alkyl, an optionally substituted cycloalkyl, an optionally substituted aryl, or when $R_1$ and $R_2$ are considered together with the carbon to which they are linked they represent a cycloalkyl residue;
$R_3$ represents H or an optionally substituted alkyl;
X represents O, S, or $NR_4$;
Y represents a bond, an optionally substituted alkyl, an optionally substituted alkenyl, an optionally substituted alkynyl, an optionally substituted cycloalkyl, an optionally substituted heterocyclyl, or a group —$(CR_aR_b)_n$-Q-$(CR_cR_d)_m$—; wherein Q is O, S, or $NR_6$;
W represents H, an optionally substituted aryl, an optionally substituted heteroaryl, an optionally substituted heterocyclyl, an optionally substituted cycloalkyl, a group —C(O)—$R_5$, or a group —$(CR_cR_d)_p$—$CR_eR_fR_g$;
  $R_4$ represents H, an optionally substituted alkyl, an optionally substituted aryl, an optionally substituted heterocyclyl, or when considered together with Y and the nitrogen atom to which it is linked represents a heterocyclyl;
  $R_5$ represents an optionally substituted aryl, an optionally substituted heteroaryl, or an optionally substituted heterocyclyl;
  $R_6$ represents H, an optionally substituted alkyl, an optionally substituted aryl, or an optionally substituted heterocyclyl;
  $R_a$, $R_b$, $R_c$, $R_d$, $R_e$, $R_f$ and $R_g$ are independently selected from the group consisting of H, halogen, an optionally substituted alkyl, an optionally substituted cycloalkyl, an optionally substituted heterocyclyl, or an optionally substituted aryl;
  n is an integer selected from the group consisting of 2, 3, 4, or 5;
  m is an integer from 0 to 4;
  p is an integer from 0 to 4;
or a pharmaceutically acceptable salt thereof.

In a second aspect, the present invention provides a pharmaceutical composition comprising one or more compounds of Formula I, as defined above, or a pharmaceutically acceptable salt thereof, and pharmaceutically acceptable excipients, carriers or diluents.

In a third aspect, the present invention provides a method for modulating the levels of PEA and OEA in a subject by administering a composition according to the invention. In some embodiments, the present invention provides methods for treating conditions associated with reduced levels of PEA and OEA, including inflammation and pain, by administering a therapeutically effective amount of a compound according to the invention.

In a fourth aspect, the present invention provides methods for preparing compounds of Formula I, as defined above, through a process consisting of suitable synthetic transformations.

In a fifth aspect, the present invention provides methods for treating skin disorders or atopic dermatitis.

DETAILED DESCRIPTION OF THE INVENTION

Figure 1:
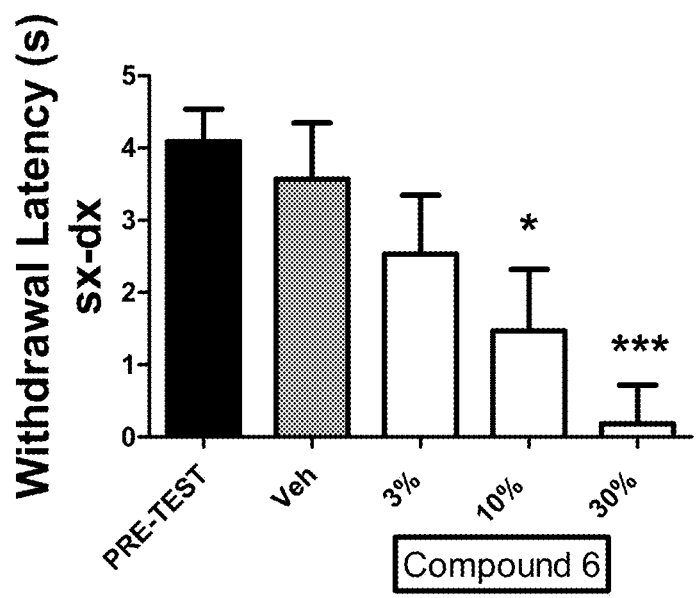
FIG. 1 shows the effect of a compound according to the invention in an animal model of UV-B irradiation in rats.

The present invention relates to the Applicants' discovery that compounds represented by Formula I have improved potency as inhibitors of NAAA coupled with higher chemical stability as compared to those described in WO2009/049238. Therefore, such compounds can more advantageously be used for the treatment of various diseases associated with reduced levels of PEA or OEA in an organ or body compartment. Such compounds can also be used for the treatment of various diseases benefiting from higher levels of PEA or OEA.

DEFINITIONS

All technical and scientific terms used herein have the same meaning as commonly understood by a person of ordinary skill in the art, unless otherwise defined.

The following terms used in the specification and claims of this application have the meaning specified hereunder, unless otherwise defined.

The term "alkyl", as used herein, indicates a saturated aliphatic hydrocarbon radical, including straight chain and branched chain radicals of 1 to 16 carbon atoms. More preferably, an alkyl group has 1 to 12 carbon atoms. The term "lower alkyl", as used herein, refers to straight chain and branched chain radicals of 1 to 6 carbon atoms. Non-limiting examples of alkyl are, for instance, methyl, ethyl, propyl, isopropyl, n-butyl, iso-butyl, tert-butyl, n-amyl, iso-amyl, n-hexyl, n-heptyl, n-octyl and the like. Any alkyl group may be unsubstituted or substituted by one or more substituents independently selected from the group consisting of halogen, trifluoromethyl, hydroxy, alkoxy, trifluoromethoxy, amino, monoalkylamino, and dialkylamino The term "alkenyl", as used herein, indicates an alkyl group, as defined herein, consisting of at least two carbon atoms and containing at least one carbon-carbon double bond. Representative examples include, but are not limited to, ethenyl, 1-propenyl, 2-propenyl, 1- or 2-butenyl, and the like. Any alkenyl group may be unsubstituted or substituted by one or more substituents independently selected from the group consisting of halogen, trifluoromethyl, hydroxy, alkoxy, trifluoromethoxy, amino, monoalkylamino, or dialkylamino The term "alkynyl", as used herein, indicates an alkyl group, as defined herein, consisting of at least two carbon atoms and containing at least one carbon-carbon triple bond. Representative examples include, but are not limited to, ethynyl, 1-propynyl, 2-propynyl, f- or 2-butynyl, and the like. Any alkynyl group may be unsubstituted or substituted by one or more substituents independently selected from the group consisting of halogen, trifluoromethyl, hydroxy, alkoxy, trifluoromethoxy, amino, monoalkylamino, or dialkylamino The term "cycloalkyl", as used herein, indicates a 3- to 7-membered all-carbon monocyclic ring, which may contain one or more double bonds but does not have a completely conjugated pi-electron system. Examples of cycloalkyl groups include, without limitation, cyclopropane, cyclobutane, cyclopentane, cyclopentene, cyclohexane, cyclohexene, cyclohexadiene, and cycloheptane. A cycloalkyl group may be unsubstituted or substituted by one to three substituents independently selected from the group consisting of lower alkyl, halogen, trifluoromethyl, hydroxy, alkoxy, trifluoromethoxy, amino, monoalkylamino, or dialkylamino.

The term "aryl", as used herein, indicates a hydrocarbon consisting of a mono-, bi- or tricyclic ring system, wherein the rings are fused together or linked to each other covalently and at least one of the carbocyclic rings is aromatic. Not limiting examples of aryl groups include, but are not limited to, phenyl, alpha- or beta-naphthyl, 9,10-dihydroanthracenyl, indanyl, fluorenyl, biphenyl and the like. An aryl group may be unsubstituted or substituted by one to three substituents independently selected from the group consisting of lower alkyl, halogen, trifluoromethyl, hydroxy, alkoxy, trifluoromethoxy, amino, monoalkylamino, or dialkylamino The term "heteroaryl", as used herein, indicates a mono-, bi- or tricyclic ring system containing from one to three heteroatoms selected from nitrogen, oxygen and sulfur, wherein the rings are fused together or linked to each other covalently and at least one of the rings is aromatic. Not limiting examples of heteroaryl groups include pyrrolyl, furoyl, thiophenyl, imidazolyl, pyrazolyl, oxazolyl, isoxazolyl, thiazolyl, isothiazolyl, indolyl, benzofuranyl, benzothiophenyl, benzimidazolyl, benzopyrazolyl, benzoxazolyl, benzoisoxazolyl, benzothiazolyl, benzoisothiazolyl, triazolyl, oxadiazolyl, tetrazolyl, pyridyl, pyrazinyl, pyrimidinyl, pyridazinyl, quinolinyl, isoquinolinyl, quinazolinyl, quinoxalinyl and the like. A heteroaryl group may be unsubstituted or substituted by one to three substituents independently selected from the group consisting of lower alkyl, halogen, trifluoromethyl, hydroxy, alkoxy, trifluoromethoxy, amino, monoalkylamino, or dialkylamino The terms "heterocyclyl" or "heterocyclic ring", as used herein, mean a 3- to 7-membered, saturated or partially unsaturated carbocyclic ring wherein one or more carbon atoms are independently replaced by nitrogen, oxygen and sulfur. The heteroatom nitrogen and sulfur are optionally oxidized, and the nitrogen atom(s) are optionally quaternized. Not limiting examples of heterocyclyl groups include, for instance, radicals derived from oxirane, aziridine, oxetane, azetidine, tetrahydrofuran, dihydrofuran, tetrahydrothiophene, dihydrothiophene, pyrrolidine, dihydropyrrole, pyran, dihydropyran, tetrahydropyran, tetrahydrothiopyran, piperidine, pyrazoline, isoxazolidine, isoxazoline, thiazolidine, thiazoline, isothiazoline, dioxane, piperazine, morpholine, thiomorpholine, examethyleneimine, homopiperazine, and the like. A heterocyclyl group or a heterocyclic ring may be unsubstituted or substituted by one to three substituents independently selected from the group consisting of lower alkyl, halogen, trifluoromethyl, hydroxy, alkoxy, trifluoromethoxy, amino, monoalkylamino, or dialkylamino.

The term "aromatic" refers to a moiety wherein the constituent atoms make up an unsaturated ring system, all atoms in the ring system are sp2 hybridized and the total number of pi electrons is equal to 4n+2, wherein n is an integer.

The term "alkoxy", as used herein, means an unsubstituted or substituted alkyl chain linked to the remainder of the molecule through an oxygen atom. Examples of alkoxy include, but are not limited to, methoxy, ethoxy, propyloxy, isopropyloxy, benzyloxy and the like.

The term "amino" means a —NH$_2$ radical.

The term "halogen", as used herein, indicates fluorine (F), chlorine (Cl), bromine (Br) or iodine (I).

The term "hydroxyl" means a —OH radical.

The term "monoalkylamino", as used herein, represents an amino group wherein one of the hydrogen atoms is substituted by an alkyl chain. Not limiting examples of monoalkylamino include methylamino, ethylamino, propylamino, butylamino and the like.

The term "dialkylamino", as used herein, represents an amino group wherein both hydrogen atoms are substituted by an alkyl chain. The two alkyl chains can be the same or different. Not limiting examples of dialkylamino include dimethylamino, diethylamino, dipropylamino, methylethylamino, methylisopropylamino and the like.

The term "trifluoromethyl" means a —CF$_3$ radical.

The term "trifluoromethoxy" means a —OCF$_3$ radical.

In certain embodiments, the chemical groups and chemical substituents which are described herein as being substituted or optionally substituted may be substituted with, but are not limited to being substituted with, methyl, ethyl, propyl, butyl, iso-butyl, tert-butyl, n-amyl, iso-amyl n-heptyl, or n-octyl. In some embodiments, the chemical groups and chemical substituents which are described herein as being substituted or optionally substituted may be substituted with, but are not limited to being substituted with methyl, benzyl, phenyl, biphenyl, benzaldehyde, adamantyl, tert-butyl, one to four halogen atoms, fluoro, chloro, iodo, bromo, phenoxy, benzyloxy, dimethyl, cyclobutyl, cyclopentyl, cyclohexyl, cyclooctyl, oxetanyl, isopropyl, cyclohexyloxy, benzo[d][1,3]dioxolyl, 4-cyclohexyl-phenyl, 1,1'-biphenyl, 4-fluoro-1,1'-biphenyl, thiophenyl, 3-phenylthiophene, or cyclohexyloxybenzene.

In some embodiments, the chemical groups and chemical substituents which are described herein as being substituted or optionally substituted may be substituted with, but are not limited to being substituted with biphenyl. In some other embodiments, the chemical groups and chemical substituents which are described herein as being substituted or optionally substituted may be substituted with, but are not limited to being substituted with unsubstituted biphenyl. In some embodiments, the chemical groups and chemical substituents which are described herein as being substituted or optionally substituted may be substituted with, but are not limited to being substituted with cyclohexyl. In some other embodiments, the chemical groups and chemical substituents which are described herein as being substituted or optionally substituted may be substituted with, but are not limited to being substituted with tert-butyl. In some embodiments, the chemical groups and chemical substituents which are described herein as being substituted or optionally substituted may be substituted with, but are not limited to being substituted with phenyl. In some embodiments, the chemical groups and chemical substituents which are described herein as being substituted or optionally substituted may be substituted with, but are not limited to being substituted with fluoro, chloro, bromo, or iodo.

In some embodiments, the chemical groups and chemical substituents which are described herein as being substituted or optionally substituted may be substituted with, but are not limited to being substituted with fluoro. In some embodiments, the chemical groups and chemical substituents which are described herein as being substituted or optionally substituted may be substituted with, but are not limited to being substituted with chloro. In some embodiments, the chemical groups and chemical substituents which are described herein as being substituted or optionally substituted may be substituted with, but are not limited to being substituted with bromo. In some embodiments, the chemical groups and chemical substituents which are described herein as being substituted or optionally substituted may be substituted with, but are not limited to being substituted with iodo.

The compounds of the present invention may also include, or optionally be substituted by, polycyclic groups. For example, the compounds of the present invention may include, or be substituted by, a bicyclic group such as, but not limited to, biphenyl, napthyl, or benzo[d][1,3]dioxolyl. For example, the compounds of the present invention may include, or be substituted by, a tricyclic group such as, but not limited to, anthrancenyl, phenanthracenyl, or adamantyl.

Compounds of the Invention

In a first aspect, the invention provides compounds for use according to the invention. These compounds are compounds of Formula I:

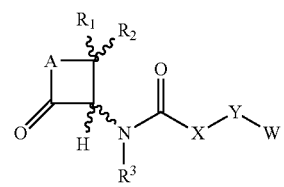

Formula I wherein:

A represents O or S;

$R_1$ and $R_2$ independently represent H, an optionally substituted lower alkyl, an optionally substituted cycloalkyl, an optionally substituted aryl, or when $R_1$ and $R_2$ are considered together with the carbon to which they are linked they represent a cycloalkyl residue;

$R_3$ represents H or an optionally substituted alkyl;

X represents O, S, or NR$_4$;

Y represents a bond, an optionally substituted alkyl, an optionally substituted alkenyl, an optionally substituted alkynyl, an optionally substituted cycloalkyl, an optionally substituted heterocyclyl, or a group —(CR$_a$R$_b$)$_n$-Q-(CR$_c$R$_d$)$_m$—;

wherein Q is O, S, or NR$_6$;

W represents H, an optionally substituted aryl, an optionally substituted heteroaryl, an optionally substituted heterocyclyl, an optionally substituted cycloalkyl, a group —C(O)—R$_5$, or a group —(CR$_c$R$_d$)$_p$—CR$_e$R$_f$R$_g$.

R$_4$ represents H, an optionally substituted alkyl, an optionally substituted aryl, an optionally substituted heterocyclyl, or when considered together with Y and the nitrogen atom to which it is linked represents a heterocyclyl;

R$_5$ represents an optionally substituted aryl, an optionally substituted heteroaryl, or an optionally substituted heterocyclyl;

$R_6$ represents H, an optionally substituted alkyl, an optionally substituted aryl, or an optionally substituted heterocyclyl;

$R_a$, $R_b$, $R_c$, $R_d$, $R_e$, $R_f$ and $R_g$ are independently selected from the group consisting of H, halogen, an optionally substituted alkyl, an optionally substituted cycloalkyl, an optionally substituted heterocyclyl, or an optionally substituted aryl;

n is an integer from 2 to 5 (i.e., n is 2, 3, 4, or 5);

m is an integer from 0 to 4 (i.e., m is selected from the group consisting of 0, 1, 2, 3 and 4);

p is an integer selected from the group consisting of 0, 1, 2, 3, and 4.

or a pharmaceutically acceptable salt thereof.

Compounds of the present invention include those encompassed by Formula I, above, with the proviso that W is

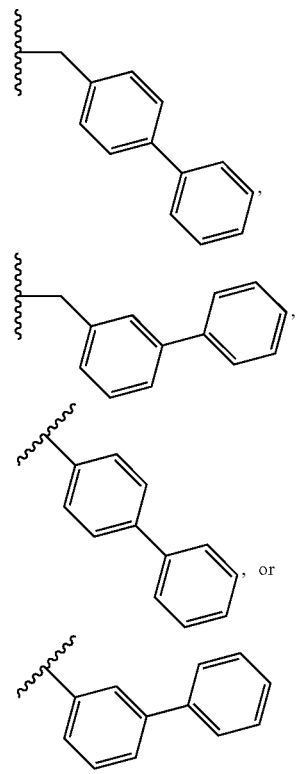

when Y is methyl or ethyl.

Certain compounds of the present invention include those encompassed by Formula I, above, wherein W is phenyl. Certain compounds of the present invention include those encompassed by Formula I, above, wherein W is biphenyl. Certain compounds of the present invention include those encompassed by Formula I, above, wherein W is 4-cyclohexylphenyl.

Certain compounds of the present invention include those encompassed by Formula I, above, wherein Y—W is

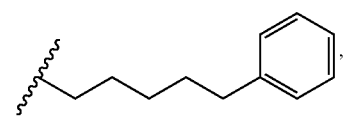

-continued

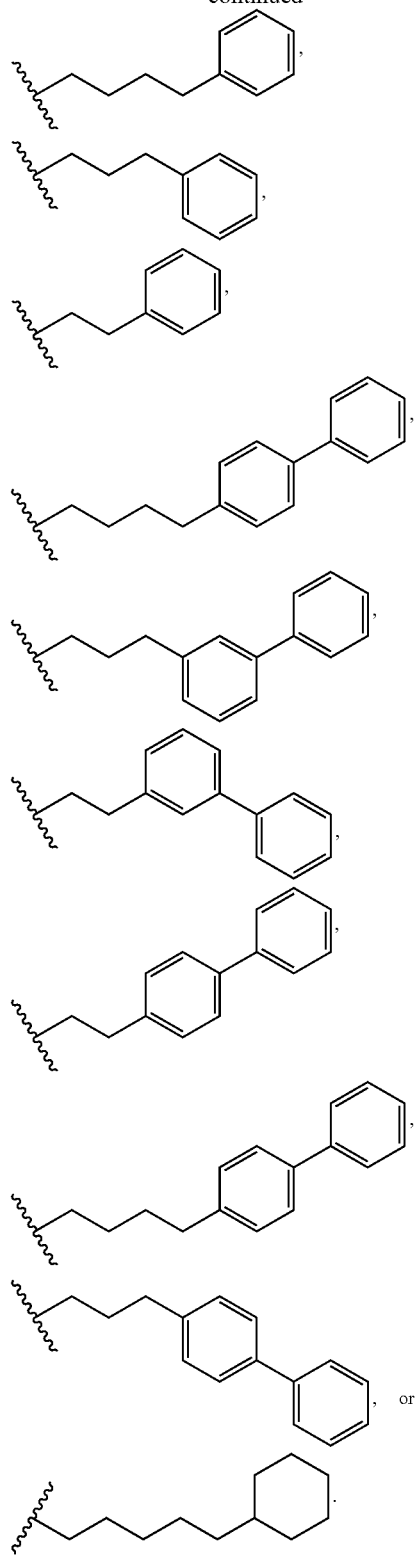

In some embodiments, the aryl group in Y—W can be substituted with 1-5 halogens selected from fluoro, chloro, bromo, or iodo.

Compounds of the present invention include those encompassed by Formula I, above, with the proviso that W is phenyl or benzyl when Y is methyl or ethyl.

Compounds of the present invention include those of Formula I, above, wherein Y is a five carbon linker.

Compounds of the present invention include those of Formula I, above, wherein W is phenyl substituted with methyl, ethyl, propyl, phenyl, biphenyl, cyclohexyl, fluoro, chloro, bromo, iodo, benzyl, benzyloxy, a fused 1,3-dioxolane ring, a thiazole, thiophene, phenyl substituted with $CF_3$, cyclohexyloxy, or phenoxy.

Compounds of Formula I containing a carbon-carbon double bond can exist as E and Z geometric isomers. Geometric isomers of compounds of Formula (I) containing one or more carbon-carbon double bonds are within the scope of the present invention.

Compounds of Formula I may contain one or more chiral centers. Compounds containing one chiral center can occur as single enantiomers or mixtures of the two enantiomers. Such mixtures occur as racemates or racemic mixtures. Compounds containing more than one chiral center can occur as single enantiomers and pairs of enantiomers, and as stereoisomers which are not enantiomers, referred to as diastereoisomers. Compounds of Formula I are meant to encompass all possible stereoisomers and mixtures thereof.

Some of the compounds described herein may exist with different points of attachment of a hydrogen atom, referred to as tautomers. Such an example may be a ketone and its enol form known as keto-enol tautomers. The individual tautomers as well as mixture thereof are encompassed by the Formula I.

The compounds of Formula I may have unnatural ratios of atomic isotopes at one or more of their atoms. For example, the compounds may be radiolabeled with isotopes such as tritium or carbon-14. All isotopic variations of the compounds of the present invention, whether radioactive or not, are within the scope of the present invention Compounds of Formula I may be isolated in the form of their pharmaceutically acceptable acid addition salts, such as the salts derived from inorganic and organic acids. The term "pharmaceutically acceptable salts" refers to salts prepared from pharmaceutically acceptable, non-toxic acids including inorganic or organic acids. Such acids include hydrochloric, sulfuric, phosphoric, glycolic, malic, maleic, tartaric, succinic, citric, malonic acid and the like.

The invention also encompasses active metabolites of compounds of Formula I. Certain compounds of Formula I are preferred for use according to the invention, as outlined herein after.

Preferred compounds of Formula I are the compounds wherein:
A represents O or S;
$R_1$ and $R_2$ independently represent H, an optionally substituted lower alkyl, an optionally substituted cycloalkyl, or an optionally substituted aryl;
$R_3$ represents H;
X represents O or $NR_4$;
Y represents a bond, an optionally substituted alkyl, an optionally substituted alkenyl, an optionally substituted alkynyl, an optionally substituted cycloalkyl, an optionally substituted heterocyclyl, or a group $—(CR_aR_b)_n-Q-(CR_cR_d)_m—$, wherein Q is as defined above;
W represents H, an optionally substituted aryl, an optionally substituted heteroaryl, an optionally substituted heterocyclyl, an optionally substituted cycloalkyl, a group $—C(O)—R_5$, or a group $—(CR_cR_d)_p—CR_eR_fR_g$;
  $R_4$ represents H, an optionally substituted alkyl, an optionally substituted aryl, an optionally substituted heterocyclyl, or when considered together with Y and the nitrogen atom to which it is linked represents a heterocyclyl;
  $R_5$ represents an optionally substituted aryl, an optionally substituted heteroaryl, or an optionally substituted heterocyclyl;
  $R_6$ represents H, an optionally substituted alkyl, an optionally substituted aryl, or an optionally substituted heterocyclyl;
  $R_a$, $R_b$, $R_c$, $R_d$, $R_e$, $R_f$ and $R_g$ are independently selected from the group consisting of H, halogen, an optionally substituted alkyl, an optionally substituted cycloalkyl, an optionally substituted heterocyclyl, or an optionally substituted aryl;
  n is an integer selected from the group consisting of 2, 3, 4 and 5;
  m is an integer selected from the group consisting of 0, 1, 2, 3 and 4;
  p is an integer selected from the group consisting of 0, 1, 2, 3, or 4;
or a pharmaceutically acceptable salt thereof.

Other preferred compounds of Formula I are the compounds wherein:
A represents O;
$R_1$ and $R_2$ independently represent H, an optionally substituted lower alkyl or an optionally substituted cycloalkyl;
$R_3$ represents H;
X represents O, or $NR_4$;
Y represents a bond, an optionally substituted alkyl, an optionally substituted alkenyl, an optionally substituted cycloalkyl, an optionally substituted heterocyclyl, or a group $—(CR_aR_b)_n-Q-(CR_cR_d)_m—$;
W represents H, an optionally substituted aryl, an optionally substituted heteroaryl, an optionally substituted heterocyclyl, an optionally substituted cycloalkyl, a group $—C(O)—R_5$, or a group $—(CR_cR_d)_p—CR_eR_fR_g$;
  $R_4$ represents H, an optionally substituted alkyl, or an optionally substituted aryl;
  $R_5$ represents an optionally substituted aryl, or an optionally substituted heteroaryl;
  $R_a$, $R_b$, $R_c$, $R_d$, $R_e$, $R_f$ and $R_g$ are independently selected from the group consisting of H, halogen, an optionally substituted alkyl, an optionally substituted cycloalkyl, an optionally substituted heterocyclyl, or an optionally substituted aryl;
  n is an integer from 2 to 4;
  m is an integer from 0 to 3;
  p is an integer from 0 to 3;
or a pharmaceutically acceptable salt thereof.

Further preferred compounds of Formula I are the compounds wherein:
A represents O;
One of $R_1$ and $R_2$ represents H and the other represents a lower alkyl;
$R_3$ represents H;
X represents O;
Y represents a bond, an optionally substituted alkyl, an optionally substituted alkenyl, an optionally substituted cycloalkyl, or a group $—(CR_aR_b)_n-Q-(CR_cR_d)_m—$;
W represents H, an optionally substituted aryl, an optionally substituted heteroaryl, an optionally substituted heterocyclyl, an optionally substituted cycloalkyl, a group $—C(O)—R_5$, or a group $—(CR_cR_d)p-CR_eR_fR_g$;
  $R_5$ represents an optionally substituted aryl, or an optionally substituted heteroaryl;
  $R_a$, $R_b$, $R_c$, $R_d$, $R_e$, $R_f$ and $R_g$ are independently selected from the group consisting of H, halogen, an optionally substituted alkyl, an optionally substituted cycloalkyl, an optionally substituted heterocyclyl, or an optionally substituted aryl;

n is an integer from 2 to 4 (i.e., 2, 3, or 4);
m is an integer from 0 to 3 (i.e., 0, 1, 2, 3);
p is an integer selected from the group consisting of 0, 1, 2, 3, or 4;
or a pharmaceutically acceptable salt thereof.

Most preferred compounds of Formula I are the compounds wherein:
A represents O;
One of $R_1$ and $R_2$ represents H and the other represents methyl;
$R_3$ represents H;
X represents O;
Y represents a bond, an optionally substituted alkyl, an optionally substituted alkenyl, an optionally substituted cycloalkyl, an optionally substituted heterocyclyl, or a group —$(CR_aR_b)_n$-Q-$(CR_cR_d)_m$—;
W represents H, an optionally substituted aryl, an optionally substituted heteroaryl, an optionally substituted cycloalkyl, a group —C(O)—$R_5$, or a group —$(CR_cR_d)_p$—$CR_eR_fR_g$;
  $R_5$ represents an optionally substituted aryl, or an optionally substituted heteroaryl;
  $R_a$, $R_b$, $R_c$, $R_d$, $R_e$, $R_f$ and $R_g$ are independently selected from the group consisting of H, an optionally substituted alkyl, an optionally substituted cycloalkyl, or an optionally substituted aryl;
  n is an integer from 2 to 4;
  m is an integer selected from 0, 1, 2, or 3;
  p is a integer selected from 0, 1, 2, or 3;
or a pharmaceutically acceptable salt thereof.

In preferred embodiments of any of the above m is 0, and n is, 2, 3 or 4; or m is 1 and n is 2, 3, or 4; or m is 2 and n is 2, 3, or 4. In further of each of these preferred embodiments, p is 0, 1, 2, or 3. In still further embodiments of each of these embodiments, Q is O. In yet still further of any of the above embodiments, A is O. In still further additional embodiments, X is O.

In some embodiments of the compounds of formula I, m is 0, and n is, 2, 3 or 4; or m is 1 and n is 2, 3, or 4; or m is 2 and n is 2, 3, or 4. In further of each of these preferred embodiments, p is 0, 1, 2, or 3. In still further embodiments of each of these embodiments, Q is O or $NR_6$. In yet still further of any of the above embodiments, A is O. In still further additional embodiments, X is O or $NR_4$.

In still further embodiments of any of the above, W is an optionally substituted cycloalkyl (e.g., optionally substituted cyclohexyl, cyclopentyl, cycloheptyl). In other embodiments W is an optionally substituted phenyl or biphenyl. In still further embodiments, W is a cycloalkyl (e.g., cyclohexyl, cyclopentyl, cycloheptyl), phenyl, or biphenyl that is unsubstituted.

In some embodiments of the compounds of Formula I:
A represents O or S;
$R_1$ and $R_2$ independently represent H, an unsubstituted lower alkyl, unsubstituted cycloalkyl, or an unsubstituted aryl, or when $R_1$ and $R_2$ are considered together with the carbon to which they are linked they represent a cycloalkyl residue;
$R_3$ represents a substituted alkyl;
X represents O, S, or $NR_4$;
Y represents a bond, an unsubstituted alkyl, an unsubstituted alkenyl, an unsubstituted alkynyl, an unsubstituted cycloalkyl, an unsubstituted heterocyclyl, or a group —$(CR_aR_b)_n$-Q-$(CR_cR_d)_m$—; wherein Q is O, S, or $NR_6$,
W represents H, an unsubstituted aryl, an unsubstituted heteroaryl, an unsubstituted heterocyclyl, an unsubstituted cycloalkyl, a group —C(O)—$R_5$, or a group —$(CR_cR_d)_p$—$CR_eR_fR_g$.
$R_4$ represents H, an unsubstituted alkyl, an unsubstituted aryl, an unsubstituted heterocyclyl, or when considered together with Y and the nitrogen atom to which it is linked represents a heterocyclyl;
$R_5$ represents an unsubstituted aryl, an unsubstituted heteroaryl, or an unsubstituted heterocyclyl;
$R_6$ represents H, an unsubstituted alkyl, an unsubstituted aryl, or an unsubstituted heterocyclyl;
$R_a$, $R_b$, $R_c$, $R_d$, $R_e$, $R_f$ and $R_g$ are independently selected from the group consisting of H, halogen, an unsubstituted alkyl, an unsubstituted cycloalkyl, an unsubstituted heterocyclyl, or an optionally unsubstituted aryl;
n is an integer from 2 to 5 (i.e., n is 2, 3, 4, or 5);
m is an integer from 0 to 4 (i.e., m is selected from the group consisting of 0, 1, 2, 3 and 4);
p is an integer selected from the group consisting of 0, 1, 2, 3, and 4.
or a pharmaceutically acceptable salt thereof.

In some embodiments of the compounds of Formula I:
A represents O or S;
$R_1$ and $R_2$ independently represent H, a substituted lower alkyl, a substituted cycloalkyl, or a substituted aryl, or when $R_1$ and $R_2$ are considered together with the carbon to which they are linked they represent a cycloalkyl residue;
$R_3$ represents H or an unsubstituted alkyl;
X represents O, S, or $NR_4$;
Y represents a bond, a substituted alkyl, a substituted alkenyl, a substituted alkynyl, a substituted cycloalkyl, a substituted heterocyclyl, or a group —$(CR_aR_b)_n$-Q-$(CR_cR_d)_m$—;
wherein Q is O, S, or $NR_6$,
W represents H, an unsubstituted aryl, an unsubstituted heteroaryl, an unsubstituted heterocyclyl, an unsubstituted cycloalkyl, a group —C(O)—$R_5$, or a group —$(CR_cR_d)_p$—$CR_eR_fR_g$.
$R_4$ represents H, an unsubstituted alkyl, an unsubstituted aryl, an unsubstituted heterocyclyl, or when considered together with Y and the nitrogen atom to which it is linked represents a heterocyclyl;
$R_5$ represents an unsubstituted aryl, an unsubstituted heteroaryl, or an unsubstituted heterocyclyl;
$R_6$ represents H, an unsubstituted alkyl, an unsubstituted aryl, or an unsubstituted heterocyclyl;
$R_a$, $R_b$, $R_c$, $R_d$, $R_e$, $R_f$ and $R_g$ are independently selected from the group consisting of H, halogen, an unsubstituted alkyl, an unsubstituted cycloalkyl, an unsubstituted heterocyclyl, or an optionally unsubstituted aryl;
n is an integer from 2 to 5 (i.e., n is 2, 3, 4, or 5);
m is an integer from 0 to 4 (i.e., m is selected from the group consisting of 0, 1, 2, 3 and 4);
p is an integer selected from the group consisting of 0, 1, 2, 3, and 4.
or a pharmaceutically acceptable salt thereof.

In some embodiments of the compounds of Formula I:
A represents O or S;
$R_1$ and $R_2$ independently represent H, an unsubstituted lower alkyl, unsubstituted cycloalkyl, or an unsubstituted aryl, or when $R_1$ and $R_2$ are considered together with the carbon to which they are linked they represent a cycloalkyl residue;
$R_3$ represents H or an unsubstituted alkyl;
X represents O, S, or $NR_4$;
Y represents a bond, an unsubstituted alkyl, an unsubstituted alkenyl, an unsubstituted alkynyl, an unsubstituted cycloalkyl, an unsubstituted heterocyclyl, or a group —$(CR_aR_b)_n$-Q-$(CR_cR_d)_m$—; wherein Q is O, S, or $NR_6$,
W represents H, a substituted aryl, a substituted heteroaryl, a substituted heterocyclyl, a substituted cycloalkyl, a group —C(O)—$R_5$, or a group —$(CR_cR_d)_p$—$CR_eR_fR_g$.

R₄ represents H, an unsubstituted alkyl, an unsubstituted aryl, an unsubstituted heterocyclyl, or when considered together with Y and the nitrogen atom to which it is linked represents a heterocyclyl;

R₅ represents an unsubstituted aryl, an unsubstituted heteroaryl, or an unsubstituted heterocyclyl;

R₆ represents H, an unsubstituted alkyl, an unsubstituted aryl, or an unsubstituted heterocyclyl;

R_a, R_b, R_c, R_d, R_e, R_f and R_g are independently selected from the group consisting of H, halogen, an unsubstituted alkyl, an unsubstituted cycloalkyl, an unsubstituted heterocyclyl, or an optionally unsubstituted aryl;

n is an integer from 2 to 5 (i.e., n is 2, 3, 4, or 5);

m is an integer from 0 to 4 (i.e., m is selected from the group consisting of 0, 1, 2, 3 and 4);

p is an integer selected from the group consisting of 0, 1, 2, 3, and 4.

or a pharmaceutically acceptable salt thereof.

In some embodiments of the compounds of Formula I:

A represents O or S;

R₁ and R₂ independently represent H, an unsubstituted lower alkyl, unsubstituted cycloalkyl, or an unsubstituted aryl, or when R₁ and R₂ are considered together with the carbon to which they are linked they represent a cycloalkyl residue;

R₃ represents H or an unsubstituted alkyl;

X represents O, S, or NR₄;

Y represents a bond, an unsubstituted alkyl, an unsubstituted alkenyl, an unsubstituted alkynyl, an unsubstituted cycloalkyl, an unsubstituted heterocyclyl, or a group —(CR_aR_b)_n-Q-(CR_cR_d)_m—; wherein Q is O, S, or NR₆, W represents H, an unsubstituted aryl, an unsubstituted heteroaryl, an unsubstituted heterocyclyl, an unsubstituted cycloalkyl, a group —C(O)—R₅, or a group —(CR_cR_d)_p—CR_eR_fR_g.

R₄ represents H, a substituted alkyl, a substituted aryl, a substituted heterocyclyl, or when considered together with Y and the nitrogen atom to which it is linked represents a heterocyclyl;

R₅ represents an unsubstituted aryl, an unsubstituted heteroaryl, or an unsubstituted heterocyclyl;

R₆ represents H, an unsubstituted alkyl, an unsubstituted aryl, or an unsubstituted heterocyclyl;

R_a, R_b, R_c, R_d, R_e, R_f and R_g are independently selected from the group consisting of H, halogen, an unsubstituted alkyl, an unsubstituted cycloalkyl, an unsubstituted heterocyclyl, or an optionally unsubstituted aryl;

n is an integer from 2 to 5 (i.e., n is 2, 3, 4, or 5);

m is an integer from 0 to 4 (i.e., m is selected from the group consisting of 0, 1, 2, 3 and 4);

p is an integer selected from the group consisting of 0, 1, 2, 3, and 4.

or a pharmaceutically acceptable salt thereof.

In some embodiments of the compounds of Formula I:

A represents O or S;

R₁ and R₂ independently represent H, an unsubstituted lower alkyl, unsubstituted cycloalkyl, or an unsubstituted aryl, or when R₁ and R₂ are considered together with the carbon to which they are linked they represent a cycloalkyl residue;

R₃ represents H or an unsubstituted alkyl;

X represents O, S, or NR₄;

Y represents a bond, an unsubstituted alkyl, an unsubstituted alkenyl, an unsubstituted alkynyl, an unsubstituted cycloalkyl, an unsubstituted heterocyclyl, or a group —(CR_aR_b)_n-Q-(CR_cR_d)_m—; wherein Q is O, S, or NR₆, W represents H, an unsubstituted aryl, an unsubstituted heteroaryl, an unsubstituted heterocyclyl, an unsubstituted cycloalkyl, a group —C(O)—R₅, or a group —(CR_cR_d)_p—CR_eR_fR_g.

R₄ represents H, an unsubstituted alkyl, an unsubstituted aryl, an unsubstituted heterocyclyl, or when considered together with Y and the nitrogen atom to which it is linked represents a heterocyclyl;

R₅ represents an unsubstituted aryl, an unsubstituted heteroaryl, or an unsubstituted heterocyclyl;

R₆ represents H, a substituted alkyl, a substituted aryl, or a substituted heterocyclyl;

R_a, R_b, R_c, R_d, R_e, R_f and R_g are independently selected from the group consisting of H, halogen, an unsubstituted alkyl, an unsubstituted cycloalkyl, an unsubstituted heterocyclyl, or an optionally unsubstituted aryl;

n is an integer from 2 to 5 (i.e., n is 2, 3, 4, or 5);

m is an integer from 0 to 4 (i.e., m is selected from the group consisting of 0, 1, 2, 3 and 4);

p is an integer selected from the group consisting of 0, 1, 2, 3, and 4.

or a pharmaceutically acceptable salt thereof.

Particularly preferred compounds of Formula I are the following:

1. Pentyl-[(2S,3R)-2-methyl-4-oxooxetan-3-yl]-carbamate;
2. Octyl-[(2S,3R)-2-methyl-4-oxooxetan-3-yl]-carbamate;
3. 3-Phenylpropyl-[(2S,3R)-2-methyl-4-oxooxetan-3-yl]-carbamate;
4. 4-Phenylbutyl-[(2S,3R)-2-methyl-4-oxooxetan-3-yl]-carbamate;
5. 5-Phenylpentyl-[(2S,3R)-2-methyl-4-oxooxetan-3-yl]-carbamate;
6. 7-Phenylheptyl-N-[(2S,3R)-2-methyl-4-oxo-oxetan-3-yl]-carbamate;
7. 3-Benzyloxypropyl-N-[(2S,3R)-2-methyl-4-oxo-oxetan-3-yl]-carbamate;
8. 4-Cyclohexylbutyl-N-[(2S,3R)-2-methyl-4-oxo-oxetan-3-yl]-carbamate;
9. (4-Phenylphenyl)methyl-N-[(2S,3R)-2-methyl-4-oxo-oxetan-3-yl]-carbamate;
10. [(1S)-1-Methyloctyl]-N-[(2S,3R)-2-methyl-4-oxo-oxetan-3-yl]-carbamate;
11. (1S) and (1R)-1-(4-Phenylphenyl)-ethyl-N-[(2S,3R)-2-methyl-4-oxo-oxetan-3-yl]-carbamate;
12. (1R) and [(1S)-1-Methyl-5-phenyl-pentyl]-N-[(2S,3R)-2-methyl-4-oxo-oxetan-3-yl]-carbamate;
13. (1,1-Dimethyl-5-phenyl-pentyl)-N-[(2S,3R)-2-methyl-4-oxo-oxetan-3-yl]-carbamate;
14. (4-Benzyloxyphenyl)-N-[(2S,3R)-2-methyl-4-oxo-oxetan-3-yl]-carbamate;
15. [3-(4-Phenylbutyl)oxetan-3-yl]-N-[(2S,3R)-2-methyl-4-oxo-oxetan-3-yl]-carbamate;
16. (1-Methylcyclohexyl)-[(2S,3R)-2-methyl-4-oxo-oxetan-3-yl]-carbamate;
17. 2-(4-Methylphenyl)ethyl-[(2S,3R)-2-methyl-4-oxooxetan-3-yl]-carbamate;
18. (1-Benzoyl-4-piperidyl)-N-[(2S,3R)-2-methyl-4-oxo-oxetan-3-yl]-carbamate;
19. 4-Methyltetrahydropyran-4-yl)-N-[(2S,3R)-2-methyl-4-oxo-oxetan-3-yl]-carbamate;
20. Tricyclo[3.3.1.1$^{3,7}$]dec-1-yl [(2S,3R)-2-methyl-4-oxooxetan-3-yl]-carbamate;
21. (3-Phenylphenyl)-methyl-N-[(2S,3R)-2-methyl-4-oxooxetan-3-yl]-carbamate;
22. 5-(4-Fluorophenyl)-pentyl-N-[(2S,3R)-2-methyl-4-oxooxetan-3-yl]-carbamate;

23. (2,2-Dimethyl-4-phenyl-butyl)-N-[(2S,3R)-2-methyl-4-oxo-oxetan-3-yl]-carbamate;
24. (1-Benzyl-4-piperidyl)-N-[(2S,3R)-2-methyl-4-oxo-oxetan-3-yl]-carbamate;
25. (1-Methylcyclopentyl) N-[(2S,3R)-2-methyl-4-oxo-oxetan-3-yl]-carbamate;
26. tert-Butyl-N-[(2S*,3R*)-2-ethyl-4-oxo-oxetan-3-yl]-carbamate;
27. tert-Butyl-N-[(2S*,3S*)-2-ethyl-4-oxo-oxetan-3-yl]-carbamate;
28. (3-Butyloxetan-3-yl)-N-[(2S,3R)-2-methyl-4-oxo-oxetan-3-yl]-carbamate;
29. 5-Cyclohexylpentyl-N-[(2S,3R)-2-methyl-4-oxo-oxetan-3-yl]-carbamate;
30. 6-phenylhexyl-N-[(2S,3R)-2-methyl-4-oxo-oxetan-3-yl]-carbamate;
31. Phenethyl-N-[(2S,3R)-2-methyl-4-oxo-oxetan-3-yl]-carbamate;
32. 5-Phenylpentyl-N-[(2S,3 S)-2-methyl-4-oxooxetan-3-yl]-carbamate;
33. (R,Z) and (S,E)-(4-Benzylidenecyclohexyl)-N-[(2S,3R)-2-methyl-4-oxooxetan-3-yl]-carbamate;
34. (1s,4S) and (1r,4R)-(4-Benzylcyclohexyl)-N-[(2S,3R)-2-methyl-4-oxooxetan-3-yl]-carbamate;
35. Cyclohexyl-N-[(2S,3R)-2-methyl-4-oxooxetan-3-yl]-carbamate;
36. (1-Isopropyl-5-phenyl-pentyl)-N-[(2S,3R)-2-methyl-4-oxo-oxetan-3-yl]-carbamate;
37. 2-Phenethyloxyethyl N-[(2S,3R)-2-methyl-4-oxo-oxetan-3-yl]carbamate;
38. 5-Phenylpentyl-N-[(2R,3 S)-2-methyl-4-oxo-oxetan-3-yl]-carbamate;
39. 5-Phenylpentyl-N-[(2R,3R)-2-methyl-4-oxo-oxetan-3-yl]-carbamate;
40. Hexyl-N-[(2S,3R)-2-methyl-4-oxo-oxetan-3-yl]-carbamate;
41. Heptyl-N-[(2S,3R)-2-methyl-4-oxo-oxetan-3-yl]-carbamate;
42. 5-Phenylpentyl-N-methyl-N-[(2S,3R)-2-methyl-4-oxo-oxetan-3-yl]-carbamate;
43. (4-Cyclohexylphenyl)-methyl-N-[(2S,3R)-2-methyl-4-oxo-oxetan-3-yl]-carbamate;
44. 1,3-Benzodioxol-5-yl-methyl-N-[(2S,3R)-2-methyl-4-oxo-oxetan-3-yl]-carbamate;
45. [4-[4-(Trifluoromethyl)-phenyl]-phenyl]-methyl-N-[(2S,3R)-2-methyl-4-oxo-oxetan-3-yl]-carbamate;
46. [4-(3-Thienyl)-phenyl]-methyl-N-[(2S,3R)-2-methyl-4-oxo-oxetan-3-yl]-carbamate;
47. [4-(Cyclohexoxy)-phenyl]-methyl-N-[(2S,3R)-2-methyl-4-oxo-oxetan-3-yl]-carbamate;
48. 5-Phenylpentyl-N-[(2R*,3R*)-2-ethyl-4-oxo-oxetan-3-yl]-carbamate;
49. (4-Phenylphenyl)-methyl-N-[(2R*,3R*)-2-ethyl-4-oxo-oxetan-3-yl]-carbamate;
50. 5-Phenylpentyl-N-[(2S*,3R*)-2-ethyl-4-oxo-oxetan-3-yl]-carbamate;
51. (4-Phenylphenyl)-methyl-N-[(2S*,3R*)-2-ethyl-4-oxo-oxetan-3-yl]-carbamate;
52. 5-Phenylpentyl-N-[(2R*,3R*)-2-isopropyl-4-oxo-oxetan-3-yl]-carbamate;
53. (4-Phenylphenyl)-methyl-N-[(2R*,3R*)-2-isopropyl-4-oxo-oxetan-3-yl]-carbamate;
54. 5-Phenylpentyl-N-[(2S*,3R*)-2-isopropyl-4-oxo-oxetan-3-yl]-carbamate;
55. (4-Phenylphenyl)-methyl-N-[(2S*,3R*)-2-isopropyl-4-oxo-oxetan-3-yl]-carbamate;
56. (1,1-Dimethyl-5-phenyl-pentyl)-N-[(2R*,3R*)-2-isopropyl-4-oxo-oxetan-3-yl]-carbamate;
57. 5-Phenylpentyl-N-[(2R*,3R*)-2-tert-butyl-4-oxo-oxetan-3-yl]-carbamate;
58. (4-Phenylphenyl)-methyl-N-[(2R*,3R*)-2-tert-butyl-4-oxo-oxetan-3-yl]-carbamate;
59. 5-Phenylpentyl-N-[(2S*,3R*)-2-tert-butyl-4-oxo-oxetan-3-yl]-carbamate; and
60. (4-Phenylphenyl)-methyl-N-[(2S*,3R*)-2-tert-butyl-4-oxo-oxetan-3-yl]-carbamate.

Preferred compounds of Formula I also include compounds encompassed by the following Formula IX-LX, wherein the substituents in these Formula are as defined in this application.

Formula IX

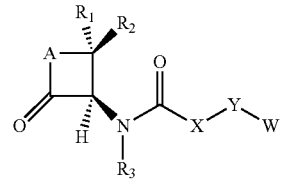

Formula X

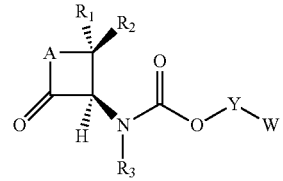

Formula XI

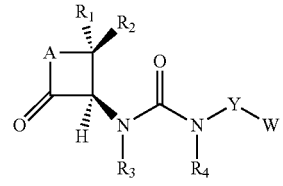

Formula XII

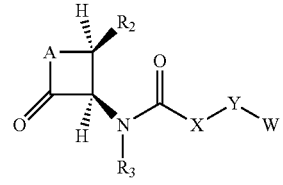

Formula XIII

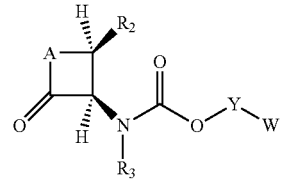

Formula XIV

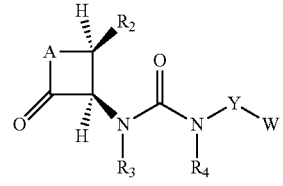

Formula XV
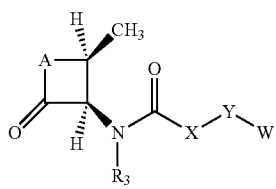

Formula XVI
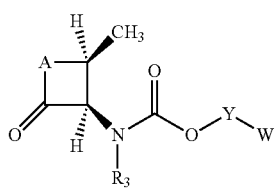

Formula XVII
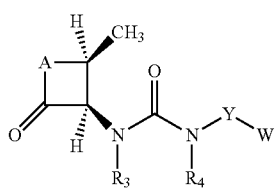

Preferred compounds also include the following in which q is an integer from 0-5 and $R_8$ is a substituent selected from the group consisting of alkyl, alkenyl, alkynyl, aryl, heteroaryl, acyl, halogen, amino, hydroxyl, cyano, nitro, alkoxy, aryloxy, arylalkoxy, cycloalkyl, heterocycloalkyl, haloalkyl, alkylheterocycl, alkylcycloalkyl, alkylaryl, and alkylheteroaryl. $R_8$ may also be selected from the group consisting of H, methyl, ethyl, propyl, n-propyl, i-propyl, butyl, n-butyl, t-butyl, benzyl, phenyl, fluorine, chlorine, bromine, iodine, cyclohexyl, $CF_3$, $CCl_3$, $CBr_3$, $Cl_3$, OH, $NH_2$, $NO_2$, C(O)—F, C(O)—Cl, C(O)—Br, and C(O)—I. Preferred compounds also include the following in which q is an integer from 1-3 and $R_8$ is as defined above.

Formula IXX
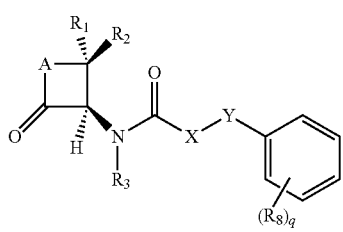

Formula XX
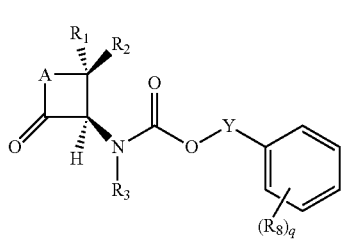

Formula XXI
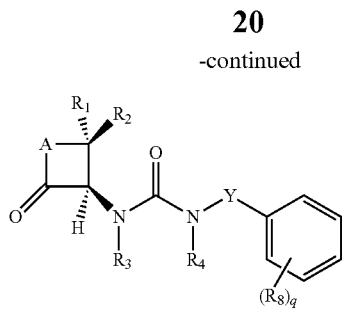

Formula XXII
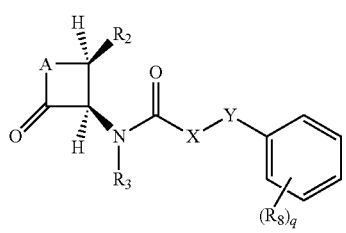

Formula XXIII
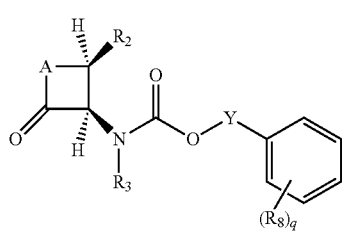

Formula XXIV
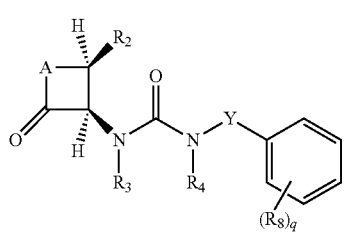

Formula XXV
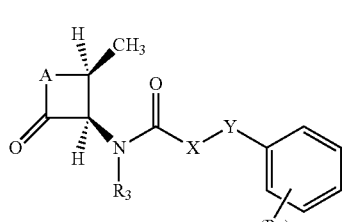

Formula XXVI
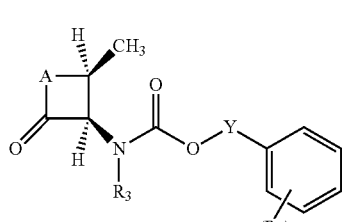

Formula XXVII
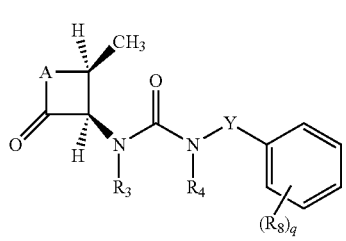

When q is other than 0 or 1, each $R_8$ substituent may be either the same as or different from the other $R_8$ groups present. In some further embodiment of the above, $R_3$ is preferrably H. In still further embodiments, when q is 1 the $R_8$, is in the para position. In still further embodiments, when q is 1, the $R_8$ is in the meta position. In still further embodiments, when q is 1, the $R_8$ is in the ortho position.

In any of the Formula described herein, Y may include methyl. In any of the Formula described herein, Y may include ethyl. In any of the Formula described herein, Y may include propyl. In any of the Formula described herein, Y may include n-propyl. In any of the Formula described herein, Y may include i-propyl. In any of the Formula described herein, Y may include butyl. In any of the Formula described herein, Y may include t-butyl. In any of the Formula described herein, Y may include n-butyl. In any of the Formula described herein, Y may include pentyl. In any of the Formula described herein, Y may include i-pentyl. In any of the Formula described herein, Y may include n-pentyl. In any of the Formula described herein, Y may include hexyl. In any of the Formula described herein, Y may include heptyl.

Preferred compounds also include those encompassed by the following Formula:

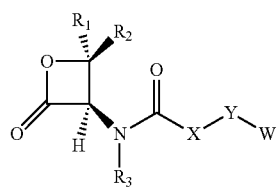
Formula XXVIII

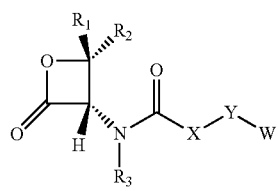
Formula XXIX

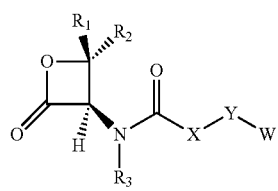
Formula XXX

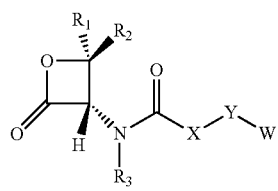
Formula XXXI

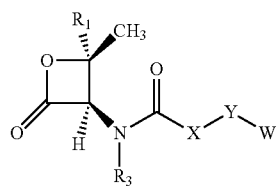
Formula XXXII

-continued

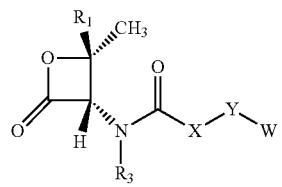
Formula XXXIII

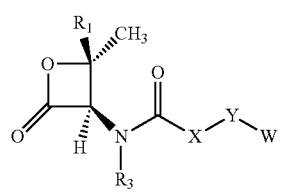
Formula XXXIV

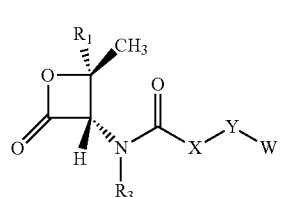
Formula XXXV

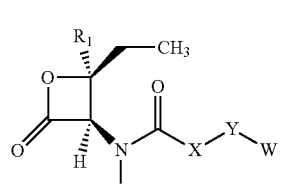
Formula XXXVI

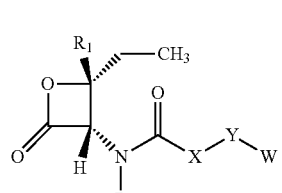
Formula XXXVII

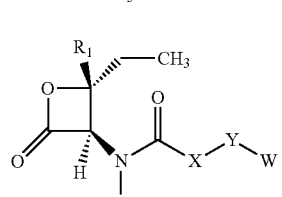
Formula XXXVIII

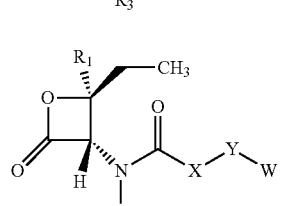
Formua XXXIX

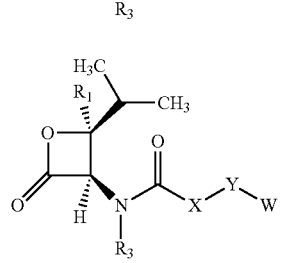
Formula XXXX

-continued

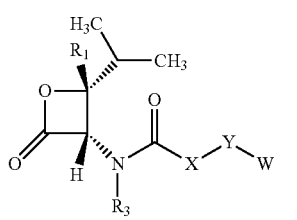
Formula XXXXI

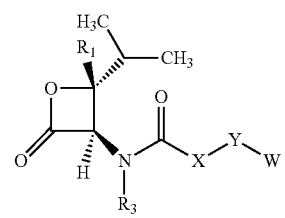
Formula XXXXII

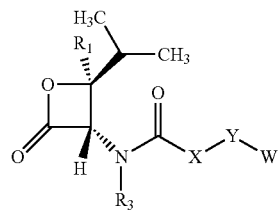
Formula XXXXIII

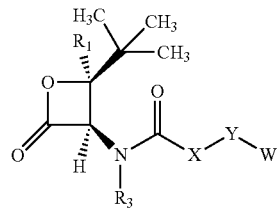
Formula XXXXIV

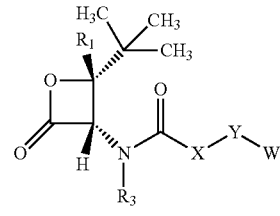
Formula XXXXV

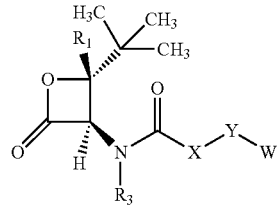
Formula XXXXVI

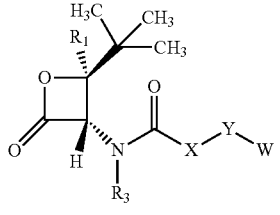
Formula XXXXVII

In one set of alternative embodiments, the compounds of the invention are compounds embraced by the below formula in which wherein $R_2$, rather than being H, is selected from alkyl, lower alkyl, alkenyl, lower alkenyl, methyl, ethyl, propyl, i-propyl, or n-propyl. The remaining members of the below formula are as described above.

The present invention also includes compounds of Formula I having the below structures according to the substituents defined above.

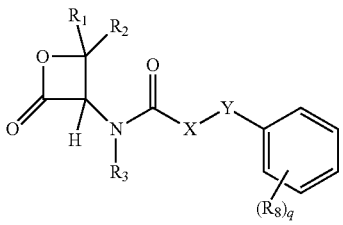
Formula XXXXVIII

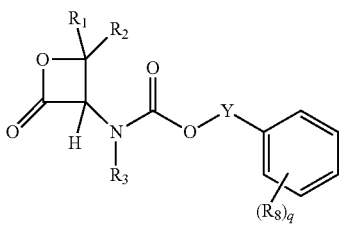
Formula IL

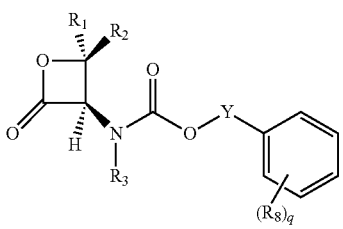
Formula L

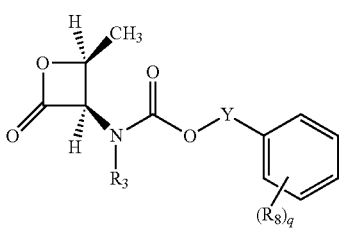
Formula LI

In some of the embodiments of Formulae XXXXVIII, IL, L, and LI, Y is propyl.

In some of the embodiments of Formulae XXXXVIII, IL, L, and LI, Y is butyl.

In some of the embodiments of Formulae XXXXVIII, IL, L, and LI, Y is pentyl. In certain embodiments, Y is n-pentyl.

In some of the embodiments of Formulae XXXXVIII, IL, L, and LI, Y is a linker including an alkyl, heteroalkyl, cycloalkyl, or heterocycloalkyl group of 4-6 carbons.

In some of the embodiments of Formulae XXXXVIII, IL, L, and LI, Y is ethyl, propyl, butyl, pentyl, or hexyl. In further embodiments of any of the above, q is 0, 1, 2, or 3. In further embodiments of any of the above, q is 0.

In some of the embodiments of Formulae XXXXVIII, IL, L, and LI, Y is propyl, butyl, pentyl, or hexyl. In further embodiments of any of the above, q is 0, 1, 2, or 3. In further embodiments of any of the above, q is 0.

In some of the embodiments of Formulae XXXXVIII, IL, L, and LI, Y is butyl, pentyl, or hexyl. In further embodiments of any of the above, q is 0, 1, 2, or 3. In further embodiments of any of the above, q is 0.

In some of the embodiments of Formulae XXXXVIII, IL, L, and LI, Y is pentyl or hexyl. In further embodiments of any of the above, q is 0, 1, 2, or 3. In further embodiments of any of the above, q is 0.

In some of the embodiments of Formulae XXXXVIII, IL, L, and LI, Y is hexyl. In certain embodiments, q is 0, 1, 2, or 3. In certain other embodiments, q is 0.

In some of the embodiments of Formulae XXXXVIII, IL, L, and LI, Y is heptyl. In certain embodiments, q is 0, 1, 2, or 3. In certain other embodiments, q is 0.

In further embodiments of any of the above, q is 0, 1, 2, or 3. In further of these embodiments, $R_8$ is selected from the group consisting of H, methyl, ethyl, propyl, OH, $NH_2$, F, Cl, Br, or I.

In further embodiments of any of the above, Y is a linker member of 4-6 carbon atoms. In certain embodiments, q is 0, 1, 2, or 3. In certain other embodiments, q is 0. In some further embodiments, compounds of the present invention may include those encompassed by Formula I wherein Y—W is not tert-butyl when X is O, $R_1$ is H, and $R_2$ is methyl.

In some embodiments, compounds of the present invention may include those encompassed by Formula I, or any Formula described herein, wherein Y—W is not tert-butyl when X is O, $R_1$ is H, and $R_2$ is isopropyl.

In some embodiments, compounds of the present invention may include those compounds encompassed by Formula I, or any Formula described herein, wherein W is not phenyl when Y is $CH_2$, X is O, $R_1$ is H, and $R_2$ is methyl.

In some embodiments, compounds of the present invention may include those encompassed by Formula I, or any Formula described herein, wherein W is not an unsubstituted phenyl when Y is $CH_2$, X is O or NH, $R_1$ is H and $R_2$ is H.

In some embodiments, compounds of the present invention may include those encompassed by Formula I, or any Formula described herein, wherein Y—W is not tert-butyl when $R_1$ is H, and $R_2$ is hydrogen or methyl; and wherein W is not an unsubstituted phenyl when Y is $CH_2$, $R_1$ is H, and $R_2$ is hydrogen, methyl, or isopropyl.

In some embodiments, compounds of the present invention may include those encompassed by Formula I, or any Formula described herein, wherein Y—W is not tert-butyl when X is O, $R_1$ is H, and $R_2$ is methyl and also wherein W is not phenyl when Y is $CH_2$, X is O, $R_1$ is H, and $R_2$ is methyl.

Compounds of the present invention may include those compounds encompassed by Formula I, or any Formula described herein, wherein $R_1$ or $R_2$ is not a side chain of the twenty most common amino acids in human protein.

In some embodiments, compounds of the present invention may include those encompassed by Formula I, or any Formula described herein, wherein W is not an unsubstituted phenyl when Y is $CH_2$, X is O or NH, $R_1$ is H and $R_2$ is H.

In some embodiments, compounds of the present invention may include those encompassed by Formula I, or any Formula described herein, wherein Y—W is not tert-butyl when $R_1$ is H, and $R_2$ is hydrogen or methyl; and wherein W is not an unsubstituted phenyl when Y is $CH_2$, $R_1$ is H, and $R_2$ is hydrogen, methyl, or isopropyl;

The compounds of the present invention may include those compounds encompassed by

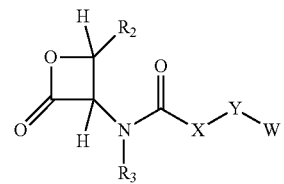

Formula LII

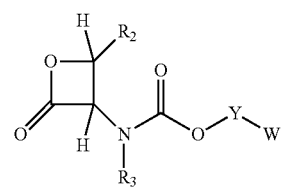

Formula LIII

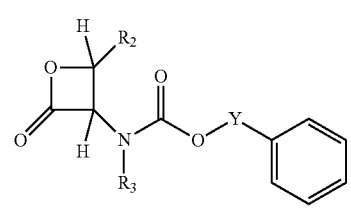

Formula LIV

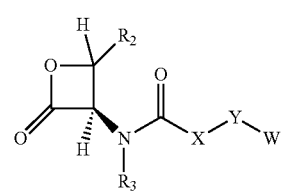

Formula LV

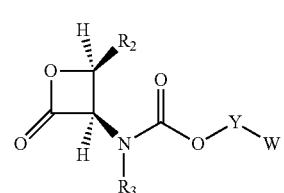

Formula LVI

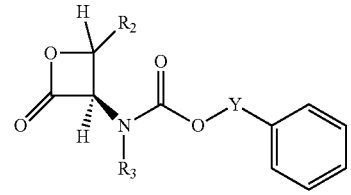

Formula LVII

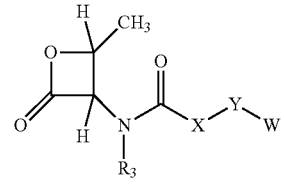

Formula LVIII

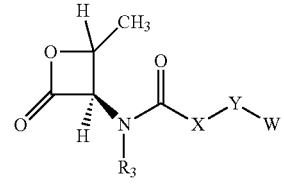

Formula LIX

-continued

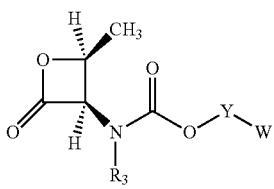

Formula LX

The compounds of the present invention, and the generic formulae describing and encompassing these compounds, may be suitable for use with any of the methods set forth herein.

Methods for Preparing Compounds

The present invention also provides methods for preparing compounds of Formula I.

The compounds of Formula I can be prepared through a process consisting of synthetic transformations reported, for instance, in Michael Smith, Jerry March—*March's Advanced Organic Chemistry: reactions mechanisms and structure—6th Edition*, John Wiley & Sons Inc., 2007, which is herein incorporated as reference. It is well known to one of ordinary skill in the art that transformation of a chemical function into another may require that one or more reactive centers in the compound containing this function be protected in order to avoid undesired side reactions. Protection of such reactive centers, and subsequent de-protection at the end of the synthetic transformations, can be accomplished following standard procedures described, for instance, in Theodora W. Green and Peter G. M. Wuts—*Protective Groups in Organic Synthesis, Fourth Edition*, John Wiley & Sons Inc., 2006, which is herein incorporated as reference.

In one embodiment, a compound of Formula I can be obtained by cyclization of a compound of Formula II,

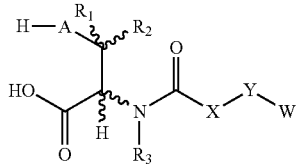

II wherein A, $R_1$, $R_2$, $R_3$, X, Y, and W are as defined above.

A compound of Formula II, wherein X represents O or S, and A, $R_1$, $R_2$, $R_3$, Y, and W are as defined above, can be obtained by reaction of a compound of Formula III, wherein A, $R_1$, $R_2$, and $R_3$ are as defined above, with a compound of Formula IV,

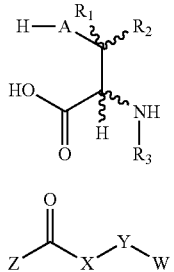

III

IV wherein Z represents chlorine, azido, or a residue selected from, but not limited to, 1-imidazolyl, p-nitrophenoxy, or 2-pyridyloxy, X represents O or S, and Y and W are as defined above.

Amino acids of Formula III are either commercially available or can be obtained according to standard synthetic methods for the preparation of amino acids as described, for instance, in Blaskovich M. A., *Handbook on Syntheses of Amino Acids—General Routes to Amino Acids* Oxford University Press, USA, 2010, and references cited therein, which is herein incorporated as reference.

A compound of Formula IV can be obtained by reaction of a compound of Formula V, wherein Z is as defined above, and U represents a residue selected from chlorine, $OCH_2CH_3$, 1-imidazolyl, p-nitrophenoxy, 2-pyridyloxy, or the compound of Formula V represents triphosgene, with a compound of Formula VI

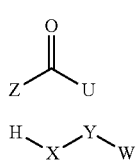

V

VI wherein X represents O or S, and Y and W are as defined above.

A compound of Formula V is generally a commercially available compound used in the activation of alcohols and thiols.

A compound of Formula VI, wherein X represents O or S, is either a commercially available alcohol or thiol or can be prepared from suitable precursors, as known to a person skilled in the art, such as the corresponding halides, according to standard synthetic methods as reported, for instance, in Michael Smith, Jerry March—*March's Advanced Organic Chemistry: reactions mechanisms and structure—6th Edition*, John Wiley & Sons Inc., 2007, and references cited therein, which is incorporated herein as reference.

In another embodiment, a compound of Formula I, wherein X is O or S, can be obtained by the reaction of a compound of Formula VII, or a salt thereof,

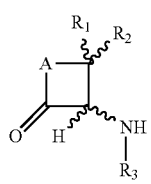

VII wherein A, $R_1$, $R_2$, and $R_3$ are as defined above, with a compound of Formula IV, as defined above.

In another embodiment, a compound of Formula I, wherein A, $R_1$, $R_2$, $R_3$, Y, and W are as defined above, and X is $NR_4$, wherein $R_4$ is H, can be obtained by reaction of a compound of Formula VII, or a salt thereof, with an isocyanate of Formula VIII

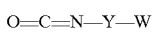

O=C=N—Y—W    VIII wherein Y and W are as defined above.

A compound of Formula VII can be obtained from a compound of Formula I, wherein A, $R_1$, $R_2$ and $R_3$ are as defined above, X is O, Y is a bond, and W is a group —(CR$_c$R$_d$)$_p$—CR$_e$R$_f$R$_g$ wherein p=0 and each of R$_e$, R$_f$, and R$_g$ is methyl, by treatment with a suitable acid. A compound of Formula I, wherein A, R$_1$, R$_2$ and R$_3$ are as defined above, X is O, Y is a bond, and W is a group —(CR$_c$R$_d$)p-CR$_e$R$_f$R$_g$ wherein p=0 and each of R$_e$, R$_f$, and R$_g$ is methyl, can be obtained by cyclization of a compound of Formula II wherein A, R$_1$, R$_2$ and R$_3$ are as defined above, X is O, Y is a bond, and W is a group —(CR$_c$R$_d$)$_p$—CR$_e$R$_f$R$_g$ wherein p=0 and each of R$_e$, R$_f$, and R$_g$ is methyl.

A compound of Formula II, wherein A, R$_1$, R$_2$ and R$_3$ are as defined above, X is O, Y is a bond, and W is a group —(CR$_c$R$_d$)$_p$—CR$_e$R$_f$R$_g$ wherein p=0 and each of R$_e$, R$_f$, and R$_g$ is methyl, can be obtained by reaction of a compound of Formula III, as defined above, with di-tert-butyl dicarbonate.

An isocyanate of Formula VIII is either commercially available or can be prepared by synthetic methods reported, for instance, in Molina P., Tarraga A., Argues A. in Katritzky A. R., Taylor R. J. k., *Comprehensive Organic Functional Group Transformations II*, Elsevier, 2004, Vol. 5, pag. 949-973; or in Michael Smith, Jerry March—*March's Advanced Organic Chemistry: reactions mechanisms and structure—6th Edition*, John Wiley & Sons Inc., 2007, and references cited therein, which are herein incorporated as reference.

The synthesis of a compound of Formula I, according to the synthetic processes described above, can be conducted in a stepwise manner, whereby each intermediate is isolated and purified by standard purification techniques, like, for example, column chromatography, before carrying out the subsequent reaction. Alternatively, two or more steps of the synthetic sequence can be carried out in a so-called "one-pot" procedure, as known in the art, whereby only the compound resulting from the two or more steps is isolated and purified.

The compounds described above can be prepared as exemplified in the following procedures.

A compound of Formula I, as defined above, can be obtained by separating diastereoisomers or enantiomers of Formula I. In a typical procedure, diastereoisomers can be separated by fractional crystallization from a suitable solvent or by standard chromatographic techniques. The pair of enantiomers thus obtained may be separated into individual stereoisomers by standard techniques described, for example, in J. Jacques, A. Collet, S. H. Wilen—*Enantiomers, Racemates, and Resolutions*, John Wiley & Sons Inc., New York (NY), 1981 and in G. Subramanian (Ed.), *Chiral Separation Techniques: a practical approach*—Wiley, Weinheim 2007, which are herein incorporated as reference. Alternatively, an enantiomer of a compound of Formula I may be obtained by stereospecific synthesis using optically pure starting materials of known configuration.

A pharmaceutically acceptable salt of a compound of Formula I, containing a basic group, can be obtained by dissolving said compound in a solvent like, for instance, acetonitrile, dioxane, tetrahydrofuran, or dichloromethane, or mixtures thereof, and adding the proper amount of an inorganic or organic acid, dissolved in a suitable solvent such as, for instance, acetonitrile, dioxane, tetrahydrofuran, or dichloromethane, or mixtures thereof, at a temperature ranging from −20° C. to room temperature. The salt is usually isolated by filtration of the precipitate obtained by a) cooling; or b) addition of a precipitating solvent, usually diethyl ether or diisopropyl ether; or c) partial evaporation of the solvent.

A compound of Formula I can be obtained by cyclization of a compound of Formula II, as defined above. Such reaction can be performed by reacting a compound of Formula II with a condensing agent selected from, but not limited to, O-(7-azabenzotriazol-1-yl)-N,N,N',N'-tetramethyluronium hexafluorophosphate, O-benzotriazole-N,N,N',N'-tetramethyl-uronium-hexafluorophosphate, benzotriazol-1-yl-oxytripyrrolidinophosphonium hexafluorophosphate, 1-hydroxybenzotrizole, 1,1'-carbonyldiimidazole, and the like, in a suitable solvent, such as dichloromethane, tetrahydrofuran, or mixtures thereof, in the presence of an organic base, such as di-isopropylethylamine or triethylamine, at a temperature ranging from −10° C. to 40° C., and for a period of time from 1 hour to 24 hours.

A compound of Formula II, wherein X is O or S, can be obtained by reaction of a compound of Formula III, as defined above, with a compound of Formula IV, as defined above. The reaction can be performed in a suitable solvent, such as dioxane, tetrahydrofuran, dimethoxyethane, acetonitrile, water, or mixtures thereof, in the presence of a suitable organic or inorganic base, such as triethylamine, di-isopropylethylamine or sodium hydrogen carbonate, and at a temperature ranging from −10° C. to 60° C., and for a period of time from 1 hour to 24 hours.

A compound of Formula IV, as defined above, can be prepared by reaction of a compound of Formula VI, as defined above, with a compound represented by Formula V, as defined above, such as phosgene, ethyl choloroformate, p-nitrophenylchloroformate, 1,1'-carbonyldiimidazole, di-2-pyridyl carbonate, triphosgene, and the like. Such reaction is conducted in a suitable solvent such as dichloromethane, chloroform, acetonitrile, tetrahydrofuran, or mixtures thereof, in the presence of a suitable base such as triethylamine, di-isopropylethylamine, or pyridine, at a temperature ranging from −10° C. to 40° C., and for a period of time from 1 to 72 hours.

A compound of Formula VII, as defined above, or a salt thereof, can be obtained by reaction of a compound of Formula I, wherein A, R$_1$, R$_2$ and R$_3$ are as defined above, X is O, Y is a bond, and W is a group —(CR$_c$R$_d$)$_p$—CR$_e$R$_f$R$_g$ wherein p=0 and each of R$_e$, R$_f$, and R$_g$ is methyl, by treatment with trifluoroacetic acid, benzensulphonic acid, p-toluensulphonic acid and the like in a suitable solvent, such as dichloromethane or tetrahydrofuran, at a temperature ranging from −10° C. to room temperature, and for a period of time from 10 minutes to 2 hours. A compound of Formula VII is usually isolated as the organic acid salt, such as the trifluoroacetic, benzensulphonic, or p-toluensulphonic acid salt or the like.

A compound of Formula I, wherein A, R$_1$, R$_2$ and R$_3$ are as defined above, X is O, Y is a bond, and W is a group —(CR$_c$R$_d$)$_p$—CR$_e$R$_f$R$_g$ wherein p=0 and each of R$_e$, R$_f$, and R$_g$ is methyl, can be obtained by cyclization of a compound of Formula II wherein A, R$_1$, R$_2$ and R$_3$ are as defined above, X is oxygen, Y is a bond, and W is a group —(CR$_c$R$_d$)$_p$—CR$_e$R$_f$R$_g$ wherein p=0 and each of R$_e$, R$_f$, and R$_g$ is methyl, according to the general procedure reported above for the preparation of compounds of Formula I.

A compound of Formula II, wherein A, R$_1$, R$_2$ and R$_3$ are as defined above, X is O, Y is a bond, and W is a group —(CR$_c$R$_d$)$_p$—CR$_e$R$_f$R$_g$ wherein p=0 and each of R$_e$, R$_f$, and R$_g$ is methyl, can be obtained by reaction of a compound of Formula III, as defined above, with di-tert-butyl dicarbonate according to the general procedure described above for the preparation of compounds of Formula II.

A compound of Formula I, wherein A, R$_1$, R$_2$ and R$_3$, Y, and W are as defined above, and X is O or S, can be obtained by reaction of a compound of Formula VII, or a salt thereof, with a compound of Formula IV, as defined above, in a suitable solvent such as dichloromethane, tetrahydrofuran, dimethoxyethane or the like, in the presence of a tertiary amine such as di-isopropyl ethyl amine, triethyl amine or the like, at a temperature ranging from 0° C. to 40° C., and for a period of time from 1 to 24 hours.

A compound of Formula I, wherein A, $R_1$, $R_2$ and $R_3$, Y, and W are as defined above, and X is $NR_4$, wherein $R_4$ is H, can be obtained by reaction of a compound of Formula VII, or a salt thereof, with an isocyanate of Formula VIII in a suitable solvent, such as dichloromethane, tetrahydrofuran, dimethylsulfoxide, pyridine, or mixtures thereof, at a temperature ranging from room temperature to 60° C., and for a period of time from 1 to 48 hours. Occasionally, the reaction can be conducted in the presence of tertiary amines such as 4-dimethylaminopyridine, di-isopropyl ethyl amine and the like.

Pharmaceutical Compositions

The invention provides pharmaceutical compositions of compounds of Formula I for modulation of the levels of PEA and OEA in a subject. The pharmaceutical compositions of the present invention encompass any composition made by admixing a compound of the present invention and a pharmaceutically acceptable carrier and/or excipient or diluent. Such compositions are suitable for pharmaceutical use in an animal (e.g., a mammal, rat, mouse, primate) or human.

The pharmaceutical compositions of the present invention comprise a compound of Formula I, or a pharmaceutically acceptable salt thereof, as an active ingredient and a pharmaceutically acceptable carrier and/or excipient or diluent. A pharmaceutical composition may optionally contain other therapeutic ingredients.

The compounds of the present invention can be combined as the active ingredient in intimate admixture with a suitable pharmaceutical carrier and/or excipient according to conventional pharmaceutical compounding techniques. Any carrier and/or excipient suitable for the form of preparation desired for administration is contemplated for use with the compounds disclosed herein.

The compositions include compositions suitable for topical, parenteral, pulmonary, nasal, rectal or oral administration. The most suitable route of administration in any given case will depend in part on the nature and severity of the conditions being treated and on the nature of the active ingredient.

The compositions of the present invention are suitable for local application strategies. For example, the compositions described herein are useful, for example, but not limited to, a topical for skin; an aerosol/powder for the nose, bronchi and/or lungs; an ointment or suppository for the rectum and/or the colon; or a formation for infiltration into the joints.

The preferred compositions include compositions suitable for topical, subcutaneous, or pulmonary, in the form of nasal or buccal inhalation, administration.

The compositions may be prepared by any of the methods well-known in the art of pharmacy.

Compositions for topical administration include, but are not limited to, ointments, creams, lotions, solutions, pastes, gels, sticks, liposomes, nanoparticles, patches, bandages and wound dressings. In certain embodiments, the topical formulation comprises a penetration enhancer.

Compositions for pulmonary administration include, but are not limited to, dry powder compositions consisting of the powder of a compound of Formula I, or a salt thereof, and the powder of a suitable carrier and/or lubricant. The compositions for pulmonary administration can be inhaled from any suitable dry powder inhaler device known to a person skilled in the art.

Administration of the compositions is performed under a protocol and at a dosage sufficient to reduce the inflammation and pain in the subject.

The compounds described herein are useful for treating diseases or conditions such as, but not limited to, skin inflammatory dermatoses (e.g., atopic dermatitis, seborrhoic dermatitis, psoriasis, allergic contact dermatitis), allergic rhinitis, buccal mucositis, acute and chronic cough, asthma, chronic obstructive pulmonary disorder, proctitis and hemorrhoids.

In some embodiments, in the pharmaceutical compositions of the present invention the active principle or active principles are generally formulated in dosage units. The dosage unit may contain from 0.1 to 1000 mg of a NAAA inhibitor per dosage unit for daily administration.

In some embodiments, the amounts effective for topical formulation will depend on the severity of the disease, disorder or condition, previous therapy, the individual's health status and response to the drug. In some embodiments, the dose is in the range from 0.001% by weight to about 60% by weight of the formulation.

When used in combination with one or more other active ingredients, the compound of the present invention and the other active ingredients may be used in lower doses than when each is used singly. With respect to formulations with respect to any variety of routes of administration, methods and formulations for the administration of drugs are disclosed in *Remington: The Science and Practice of Pharmacy, 21st Edition*, Lippincott Williams & Wilkins Eds., 2005; and in *Ansel's Pharmaceutical Dosage Forms and Drug Delivery Systems, 8th Edition*. Lippincott Williams & Wilkins Eds., 2005, which are herein incorporated as reference.

Another aspect of the present invention provides pharmaceutical compositions which comprise compounds of the invention and a pharmaceutically acceptable carrier.

The pharmaceutical compositions of the present invention comprise one or more compounds of the instant invention as an active ingredient or a pharmaceutically acceptable salt thereof, and may also contain a pharmaceutically acceptable carrier and optionally other therapeutic ingredients. The compositions include compositions suitable for topical, rectal parenteral (including subcutaneous, intramuscular, and intravenous), ocular (ophthalmic), pulmonary (nasal or buccal inhalation), or nasal intraarticular (i.e. in the joints) or oral administration, although the most suitable route in any given case will depend in part on the nature and severity of the conditions being treated and on the nature of the active ingredient. An exemplary route of administration is the topical route. Another exemplary route of administration is the topical route. The compositions may be conveniently presented in unit dosage form and prepared by any of the methods well-known in the art of pharmacy.

In practical use, the compounds of the invention can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, hard and soft capsules and tablets, with the solid oral preparations being preferred over the liquid preparations.

Because of their ease of administration, tablets and capsules represent the most advantageous oral dosage unit form in which case solid pharmaceutical carriers are obviously employed. If desired, tablets may be coated by standard aqueous or nonaqueous techniques. Such compositions and preparations can contain at least 0.1 percent of active compound. The percentage of active compound in these compositions may, of course, be varied and may conveniently be between about 1 percent to about 60 percent of the weight of the unit. The amount of active compound in such therapeutically useful compositions is such that a therapeutically effective dosage will be obtained. The active compounds can also be administered intranasally as, for example, liquid drops or spray.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor. To prevent breakdown during transit through the upper portion of the GI tract, the composition may be an enteric coated formulation.

With respect to formulations with respect to any variety of routes of administration, methods and formulations for the administration of drugs are disclosed in Remington's Pharmaceutical Sciences, 17th Edition, (Gennaro et al. Eds., Mack Publishing Co., 1985). Remington's Pharmaceutical Sciences, Gennaro A R ed. 20th edition, 2000: Williams & Wilkins Pa., USA.

Administration

The compounds of the invention may also be administered parenterally. Solutions or suspensions of these active compounds can be prepared in water suitably mixed with a surfactant such as hydroxypropylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), suitable mixtures thereof, and vegetable oils.

The compounds of the invention can be effective over a wide dosage range. For example, in the treatment of adult humans, dosages from about 10 to about 1000 mg, about 100 to about 500 mg or about 1 to about 100 mg may be needed. Doses of the 0.05 to about 100 mg, and more preferably from about 0.1 to about 100 mg, per day may be used. A most preferable dosage is about 0.1 mg to about 70 mg per day. In choosing a regimen for patients, it may frequently be necessary to begin with a dosage of from about 2 to about 70 mg per day and when the condition is under control to reduce the dosage as low as from about 0.1 to about 10 mg per day. For example, in the treatment of adult humans, dosages from about 0.05 to about 100 mg, preferably from about 0.1 to about 100 mg, per day may be used. The exact dosage will depend upon the mode of administration, the compound of the invention involved, on the therapy desired, form in which administered, the subject to be treated and the body weight of the subject to be treated, and the preference and experience of the physician or veterinarian in charge.

Generally, the compounds of the present invention can be dispensed in unit dosage form comprising preferably from about 0.1 to about 100 mg of active ingredient together with a pharmaceutically acceptable carrier per unit dosage. Usually, dosage forms suitable for oral, nasal, pulmonary or transdermal administration comprise from about 0.001 mg to about 100 mg, preferably from about 0.01 mg to about 50 mg of the compounds admixed with a pharmaceutically acceptable carrier or diluent. For storage and use, these preparations preferably contain a preservative to prevent the growth of microorganisms.

Generally, the compounds of the present invention can be dispensed in unit dosage form comprising preferably from about 0.1 to about 100 mg of active ingredient together with a pharmaceutically acceptable carrier per unit dosage. Usually, dosage forms suitable for oral, nasal, pulmonary or dermal delivery administration comprise from about 0.001 mg to about 100 mg, preferably from about 0.01 mg to about 50 mg of the compounds admixed with a pharmaceutically acceptable carrier or diluent. For storage and use, these preparations preferably contain a preservative to prevent the growth of microorganisms.

Kits providing a unit dosage of the compounds and compositions set forth herein are contemplated as within the present invention. Kits providing many unit dosages of the compounds and compositions set forth herein are contemplated as within the present invention. Still further, kits providing several unit dosages of the compounds and compositions set forth herein are contemplated as within the present invention. In some embodiments, the kits of the present invention include a unit dosage of a pharmaceutical composition of a compound set forth herein. In certain embodiments, the kits of the present invention include many unit dosages of a pharmaceutical composition of a compound set forth herein. In certain other embodiments, the kits of the present invention include a unit dosage of a pharmaceutical composition set forth herein.

Administration of an appropriate amount the candidate compound may be by any means known in the art such as, for example, oral or rectal, parenteral, intraperitoneal, intravenous, subcutaneous, subdermal, intranasal, or intramuscular. In some embodiments, administration is transdermal. In some other embodiments, the administration is for dermal delivery. An appropriate amount or dose of the candidate compound may be determined empirically as is known in the art. An appropriate or therapeutic amount is an amount sufficient to effect a loss of body fat or a loss in body weight in the animal over time. The candidate compound can be administered as often as required to effect a loss of body fat or loss in body weight, for example, hourly, every six, eight, twelve, or eighteen hours, daily, or weekly Formulations suitable for oral administration can consist of (a) liquid solutions, such as an effective amount of the packaged nucleic acid suspended in diluents, such as water, saline or PEG 400; (b) capsules, sachets or tablets, each containing a predetermined amount of the active ingredient, as liquids, solids, granules or gelatin; (c) suspensions in an appropriate liquid; and (d) suitable emulsions. Tablet forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, e.g., sucrose, as well as pastilles comprising the active ingredient in an inert base, such as gelatin and glycerin or sucrose and acacia emulsions, gels, and the like containing, in addition to the active ingredient, carriers known in the art.

Injection solutions and suspensions can be prepared from sterile powders, granules, and tablets of the kind previously described. Formulations suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives.

With respect to transdermal or dermal delivery routes of administration, methods for transdermal administration of drugs are disclosed in Remington's Pharmaceutical Sciences, Gennaro A R ed. 20th edition, 2000: Williams & Wilkins Pa., USA. Dermal or skin patches are a preferred means for transdermal delivery of the compounds of the invention. Patches preferably provide an absorption enhancer such as DMSO to increase the absorption of the compounds. Other methods for transdermal drug delivery are disclosed in U.S. Pat. Nos. 5,962,012, 6,261,595, and 6,261,595. Each of which is incorporated by reference in its entirety.

Preferred patches include those that control the rate of drug delivery to the skin. Patches may provide a variety of dosing systems including a reservoir system or a monolithic system, respectively. The reservoir design may, for example, have four layers: the adhesive layer that directly contacts the skin, the control membrane, which controls the diffusion of drug molecules, the reservoir of drug molecules, and a water-resistant backing. Such a design delivers uniform amounts of the drug over a specified time period, the rate of delivery has to be less than the saturation limit of different types of skin.

The monolithic design, for example, typically has only three layers: the adhesive layer, a polymer matrix containing the compound, and a water-proof backing. This design brings a saturating amount of drug to the skin. Thereby, delivery is controlled by the skin. As the drug amount decreases in the patch to below the saturating level, the delivery rate falls.

Compounds of the invention may be used in combination with other compounds of the invention or with other drugs that may also be useful in the treatment, prevention, suppression of a neurological or psychological disorder. Such other drugs may be administered, by a route and in an amount commonly used therefor, contemporaneously or sequentially with a compound of the invention. When a compound of the invention is used contemporaneously with one or more other drugs, a pharmaceutical composition in unit dosage form containing such other drugs and the compound is preferred. When used in combination with one or more other active ingredients, the compound of the present invention and the other active ingredients may be used in lower doses than when each is used singly.

In the pharmaceutical compositions of the present invention for oral, sublingual, subcutaneous, intramuscular, intravenous, transdermal, dermal delivery, local or rectal administration, the active principle, by itself or in association with another active principle, can be administered to animals and humans in unit forms of administration mixed with conventional pharmaceutical carriers. The appropriate unit forms of administration include oral forms such as tablets, gelatin capsules, powders, granules and solutions or suspensions to be taken orally, sublingual and buccal forms of administration, aerosols, implants, subcutaneous, intramuscular, intravenous, intranasal or intraocular forms of administration and rectal forms of administration.

In other embodiments, the pharmaceutical compositions of the present invention, the active principle or active principles are generally formulated in dosage units. The dosage unit may contain from 0.1 to 1000 mg, advantageously from 1 to 500 mg and preferably from 2 to 200 mg per dosage unit for daily administration.

In certain embodiments, the pharmaceutical compositions of the present invention are suitable for dermal delivery.

Methods of Use

In some embodiments, the compounds of Formula I, and their pharmaceutical compositions and methods of administering them are useful in treating acute inflammation, chronic inflammation, pain (including acute pain, acute inflammatory pain, chronic inflammatory pain, and neuropathic pain), and other disorders in which decreased levels of palmitoylethanolamine are associated with the disorder. The treatment may be prophylactic or therapeutic. The subject to be treated may be an animal (e.g., mouse, rat, primate, mammal) or human.

Pain

In some embodiments, the compounds of Formula I and their pharmaceutical compositions may be administered in therapeutically effective amounts to alleviate or treat pain in a subject in need thereof. The treatment may be prophylactic or therapeutic. The treatment may be administered in a combination therapy with another pain reliever or anti-inflammatory agent.

The pain is associated with disease states including, but not limited to, pulmonary edema, migraine, sinus headaches, trigeminal disease, dental pain, type I diabetes, type II diabetes, multiple sclerosis, sarcoidosis, polymyositis, gingivitis, swelling occurring after injury, pre-term labor, sprains, contusions, pre surgical medication, post surgical trauma, bone damage, and cancer.

The pain may also be associated with carpal tunnel, abdominal pain, hip pain, chronic knee pain, back pain, neck pain, or shoulder pain.

In other embodiments, the pain can be a neuropathic pain selected from the group of, but not limited to, post herpetic neuralgia, post trigeminal neuralgia, diabetic neuropathy, neuropathic low back pain, peripheral or polyneuropathic pain, toxic neuropathy, chronic neuropathy caused by chemotherapeutic agents, retinopathy of prematurity, diabetic retinopathy, macular degeneration with the wet type preferred, corneal neovascularization, polymyositis, vasculitis, and periodontitis.

The pain may be somatic, visceral, or neuropathic. The pain may include muscle pain or nerve pain. The pain may be incidental pain or phantom pain.

Dermal Diseases, Disorders or Conditions

In some embodiments, the compositions of the invention may be administered in therapeutically effective amounts to alleviate or treat dermal diseases, disorders or conditions in a subject. The treatment may be prophylactic or therapeutic. The treatment may serve to reduce pain or inflammation. The treatment may be administered in a combination therapy with another agent use in the treatment of such dermatological diseases, disorders or conditions. In some embodiments, dermal diseases, disorders or conditions include, but are not limited to, allergic contact dermatitis, atopic dermatitis, seborrhoic dermatitis, eczema, urticaria, rosacea, acne, psoriasis, pruritis, lichen, psoriatic arthritis acne, scarring, skin wound healing, skin burns deriving from various origins, such as sunburns or radiation therapy burns, and of various severities (first degree burn, second degree burn, third degree burn, fourth degree burns), scleroderma, solar keratosis, squamous cell carcinoma, and melanoma.

In some embodiments, the compounds, compositions, pharmaceutical compositions, and methods of administering them are useful for treating inflammation.

The compounds and compositions described herein are useful for treating arthritis, wherein arthritis may include osteoarthritis, rheumatoid arthritis, gout, fibromyalgia, general arthritis, psoriatic arthritis, systemic lupus erythematosus, or septic arthritis.

The compounds and compositions described herein are useful for treating asthma, wherein asthma may include exercise-induced asthma, asthma due to an allergy, cough-variant asthma, occupational asthma, or nocturnal asthma.

The compounds and compositions described herein are useful for treating neurogenerative inflammation, wherein neurodegenerative inflammation may include Parkinson's disease or multiple sclerosis.

The compounds and compositions described herein are useful for treating neurodermatitis.

The irritable bowel syndrome (IBS) described herein may include, but is not limited to, IBS with constipation, IBS with diarrhea, or IBS with alternating constipation and diarrhea.

The Crohn's disease described herein may include ulcerative colitis, ileocolits, ileitis, gastroduodenal Crohn's disease, or jejunoileitis.

In some embodiments, the compositions of the invention may be administered in therapeutically effective amounts to alleviate or treat disease such as, but not limited to, pain, inflammation, and neurodegenerative diseases, neuropathic pain, trigeminal neuralgia, postherpetic neuralgia, diabetic neuropathy, cancer pain, phantom limb pain, complex regional pain syndrome, and fibromyalgia; rheumatoid arthritis, ankolysing spondylitis, ulcerative colitis, tendonitis, psoriasis, Faber's Disease, Crohn's Disease, rhinitis, skin allergies, asthma, autoimmune diseases with inflammatory components such as multiple sclerosis and other demyelenating disorders; Alzheimer's Disease, traumatic brain injury, conditions and diseases characterizable by abnormal PEA and/or OEA, metabolic disorders, appetite regulation, and obesity Inflammation and Inflammatory Pain In some embodiments, the compounds of Formula I and their pharmaceutical compositions may be administered in therapeutically effective amounts to alleviate or treat inflammation in a subject. The treatment may be prophylactic or therapeutic. The treatment may be administered in a combination therapy with another pain reliever or anti-inflammatory agent. In some embodiments, the pain is a pain caused by inflammation or injury of a tissue. Inflammatory pain develops in response to tissue damage occurring from the noxious stimuli. The inflammation is associated with disease states including, but not limited to, acute inflammation, chronic inflammation, arthritis, rheumatoid arthritis, asthma, chronic obstructive pulmonary disease (COPD), adult respiratory disease, chronic bronchitis, emphysema, cough, arthritis, inflammatory bowel disease, ulcerative colitis, lupus, graft vs. host reaction (i.e., graft vs. host disease), acute and chronic allograft rejection, acute respiratory distress syndrome, osteoarthritis, multiple sclerosis, restinosis, cystic fibrosis, crystal induced arthritis, ocular inflammation, hyperoxia-induced inflammations, dyslipidemia, myofasciitis, carpal tunnel, Alzheimer disease, Parkinson disease.

Enhanced Penetration of Compounds and Compositions of the Present Invention

Compounds and compositions of the present invention can have surprisingly enhanced penetrating properties, particularly with respect to certain known compounds, e.g., (S)-OOPP. In some embodiments, the compounds and compositions of the present invention penetrate dermal, mucosal, or topical layers at an enhanced rate as compared to certain known compounds, e.g., (S)-OOPP. For example, compound 6, described herein, has enhanced potency, stability, and selectivity properties with respect to certain known compounds, e.g., (S)-OOPP. See, for example, FIG. 26, which shows the surprisingly greatly enhanced dermal efficacy of compound 6 with respect to (S)-OOPP.

In some embodiments, the compounds and compositions of the present invention are selective and do not interfere with AC to produce an effect that would be functionally opposite to that of inhibiting NAAA. In still further embodiments of the invention, this selectivety provides that the compounds and compositions of the present invention have an enhanced ability to penetrate skin or other topical, dermal, or mucosal surfaces in, for example, a mammal.

Patient Populations

The compounds and compositions described herein are useful for treating diseases, conditions, and disorders. The present inventions includes methods for treating these disease, conditions, and disorders.

In some embodiments, the methods include administering the compounds and compositions of the present invention to men. In other embodiments, the methods include administering the compounds and compositions of the present invention to women. In certain embodiments, the methods include administering the compounds and compositions of the present invention to women of child-bearing age. In some other embodiments, the methods include administering the compounds and compositions to women who pregnant. In certain other embodiments, the methods include administering the compounds and compositions of the present invention to children.

In certain embodiments, the methods include administering the compounds and compositions to children under the age of 18 years old. In further embodiments, the methods include administering the compounds and compositions to children under the age of 16 years old. In certain embodiments, the methods include administering the compounds and compositions to children under the age of 14 years old. In further embodiments, the methods include administering the compounds and compositions to children under the age of 12 years old. In further other embodiments, the methods include administering the compounds and compositions to children under the age of 10 years old.

In some embodiments, the methods include administering the compounds and compositions to pre-pubescent children.

In other embodiments, the methods described herein are useful for treating a patient in need of treatment with a compound or composition set forth herein. In other embodiments, the methods include treating a patient in need thereof. In some embodiments, the patient in need thereof suffers from multiple conditions or disease. In other embodiment, the patient in need thereof includes a patient having pain. In some embodiments, the patient in need thereof includes a patient having dermatitis.

In some embodiments, the compounds and compositions set forth herein are administered daily. In other embodiments, the compounds and compositions set forth herein are administered twice a day. In other embodiments, the compounds and compositions set forth herein are administered three times a day. In other embodiments, the compounds and compositions set forth herein are administered four times a day. In other embodiments, the compounds and compositions set forth herein are administered five times a day.

In some embodiments, the compounds and compositions set forth herein are administered weekly. In other embodiments, the compounds and compositions set forth herein are administered monthly. In other embodiments, the compounds and compositions set forth herein are administered twice a week. In other embodiments, the compounds and compositions set forth herein are administered three times a week. In other embodiments, the compounds and compositions set forth herein are administered four times a week. In other embodiments, the compounds and compositions set forth herein are administered five times a week. In other embodiments, the compounds and compositions set forth herein are administered six times a week. In other embodiments, the compounds and compositions set forth herein are administered seven times a week. In other embodiments, the compounds and compositions set forth herein are administered eight times a week. In other embodiments, the compounds and compositions set forth herein are administered nine times a week. In other embodiments, the compounds and compositions set forth herein are administered ten times a week. In other embodiments, the compounds and compositions set forth herein are administered eleven times a week. In other embodiments, the compounds and compositions set forth herein are administered twelve times a week. In other embodiments, the compounds and compositions set forth herein are administered thirteen times a week. In other embodiments, the compounds and compositions set forth herein are administered fourteen times a week.

EXAMPLES

Method for Testing Compounds for Stability in Buffer

Chemical stability of select compounds was evaluated under physiological pH conditions (0.01M Phosphate-Buffered Saline, pH 7.4) for up to 24 h. Stock solutions of each compound (10 mM) were prepared freshly in DMSO. Each compound was incubated at a final concentration of 10 µM (1% DMSO) in pre-heated buffer (0.01M Phosphate-Buffered Saline (PBS), pH 7.4 at 37° C.). The sample solutions were divided into aliquots in glass vials (pre-heated at 37° C.) for each time point. The samples were maintained at 37° C. in the UPLC/MS Autosampler during the study (no shaking). A reference solution of each compound (final concentration: 10 µM at 1% DMSO) in pre-heated $CH_3CN$ (37° C.) was prepared from the stock solutions (10 mM in DMSO). The reference solutions were maintained at 37° C. in the UPLC/MS Autosampler during the study (no shaking). An internal standard (100 nM) was added to the sample and reference solutions. For each time point, the samples were analyzed directly by LC/MS without any further sample preparation. The samples were analyzed (triplicate injection) by monitoring the MS trace by Multiple Reaction Monitoring (MRM). The compound concentration (expressed as %) was calculated by dividing the peak area at each time point by the peak area at t=0 min. The reference solution was analyzed at the beginning (t=0 min.), and at the end of the study (t=24 h). The apparent half-lives ($t_{1/2}$) of the disappearance of compound were calculated by a one-phase decay equation using a non-linear regression of compound concentration versus time.

The analyses were performed on a Waters ACQUITY UPLC/MS TQD system consisting of a TQD (Triple Quadropole Detector) Mass Spectrometer equipped with an Electrospray Ionization interface and a Photodiode Array Detector. The analyses were run on an ACQUITY UPLC BEH $C_{18}$ 1.7 µm 2.1×50 mm column with a VanGuard BEH $C_{18}$ 1.7 µm pre-column at 40° C. The mobile phase was 0.1% HCOOH in $H_2O$ (A) and 0.1% HCOOH in $CH_3CN$ (B) using a linear gradient: 0-0.2 min.: 5% B, 0.2-2.2 min.: 5-95% B, 2.2-2.3 min.: 95-5% B, 2.3-3 min.: 5% B with flow rate at 0.5 mL/min. Electrospray ionization (ESI) was applied in positive mode using the following generic MS tune settings for all compounds: Capillary voltage: 3.00 kV, cone voltage: 25 kV, ion source temperature: 125° C. and desolvation temperature: 500° C. $N_2$ was used as drying cone gas at a flow rate of 100 L/h and desolvation gas at 1000 L/h. Argon was used as collision gas. Compound-dependent parameters as MRM transitions and collision energy were optimized for each compound. The chemical stability of example 6 of the present invention and of the corresponding amide analog and the compound lacking the methyl substituent at position 2 is reported in Table 1.

TABLE 1

Chemical stability in PBS pH 7.4 of example 6 of the present invention and of the corresponding amide analog and the compound lacking the methyl substituent at position 2 of the oxo-oxetan ring.

| Compound | Stability in PBS buffer, pH 7.4 $t_{1/2}$ (min) |
|---|---|
| Example 6 | 102 |
| | 63 |
| | 23 |

The example 6 of the present invention shows higher chemical stability ($t_{1/2}$ = 102 min) than the corresponding amide analog ($t_{1/2}$ = 63 min) and of the compound lacking the methyl group at position 2 of the oxo-oxetan ring ($t_{1/2}$ = 23 min).

Methods for Testing Compounds on NAAA

Lysosomal NAAA protein preparation were obtained by homogenizing male Sprague-Dawley rat lungs (Charles River) in 20 mM Tris-HCl buffer pH 7.4 containing 0.32M sucrose. Samples were centrifuged at 800×g for 15 minutes at 4° C. Supernatants were then centrifuged at 12,000 g for 30 minutes at 4° C. Pellets were then resuspended in PBS pH 7.4 and subjected to a freeze/thaw cycle at −80° C. The suspension was finally centrifuged at 105,000×g for 1 hour at 4° C. The supernatant was then used in the enzymatic assay.

NAAA protein preparation was pre-incubated with various concentrations of test compounds or vehicle control in 100 mM $NaH_2PO_4$/Citrate buffer, 1% Triton-X, 3 mM DTT (pH 4.5) for 30 minutes at 37° C. Samples were then incubated with heptadecenoylethanolamide (50 μM, Avanti Polar Lipids) at 37° C. for 30 min. The reaction was terminated by addition of cold methanol containing heptadecanoic acid (NuCheck Prep) as internal standard. Samples were then analyzed by UPLC/MS (Acquity, Waters). Heptadecenoic and heptadecanoic acids were eluted on an Acquity UPLC BEH C18 column (50 mm length, 2.1 mm i.d., 1.7 μm pore size, Waters) isocratically at 0.5 mL/min for 1.5 min with a solvent mixture of 95% methanol and 5% water, both containing 0.25% Acetic Acid and 5 mM Ammonium Acetate. The column temperature was 40° C. Electrospray ionization was in the negative mode, capillary voltage was 0.5 kV, cone voltage was 25 kV, desolvation temperature was 500° C. $N_2$ was used as drying gas at a flow rate of 1000 L/hour and a temperature of 500° C. The [M–H]⁻ ion was monitored in the selected-ion monitoring mode (m/z values: heptadecenoic acid 267.37, heptadecanoic acid 269.37). Calibration curves were generated using commercial heptadecenoic acid (NuCheck Prep). Inhibition of NAAA activity was calculated as reduction of heptadecenoic acid in the samples compared to vehicle controls. $IC_{50}$ values were calculated by non-linear regression analysis of log [concentration]/inhibition curves using GraphPad Prism 5 (GraphPad Software Inc., CA—USA) applying a standard slope curve fitting.

Compounds of the present invention inhibited NAAA activity with $IC_{50}$ lower than 50 μM. The $IC_{50}$ values of representative compounds of the invention are reported in Table 2.

TABLE 2

NAAA and AC (Acid Ceramidase) $IC_{50}$ values of representative compounds of the invention

| Example | Structure | r-NAAA $IC_{50}$ (μM) or % inhib. | UPLC/MS h-NAAA $IC_{50}$ (μM) | Fluorogenic h-NAAA $IC_{50}$ (μM) | r-AC $IC_{50}$ (μM) or % inhib. |
|---|---|---|---|---|---|
| 1 | 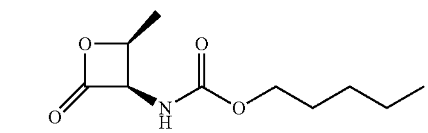 | 0.67 | | | |
| 2 | 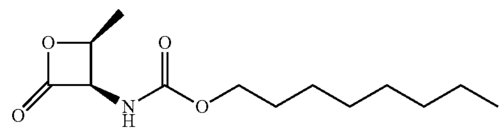 [SMILES: CCCCCCCCOC(=O)N[C@H]1C(=O)O[C@H]1C] | 0.03 | | | <10% inhib. @ 0.3 μM |
| 3 | 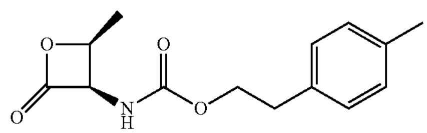 [SMILES: Cc1ccc(CCOC(=O)N[C@H]2C(=O)O[C@H]2C)cc1] | 1.21 | | | |
| 4 | 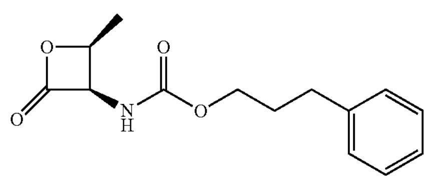 [SMILES: C[C@@H]1OC(=O)[C@@H]1NC(=O)OCCCc1ccccc1] | 0.084 | | | |
| 5 | 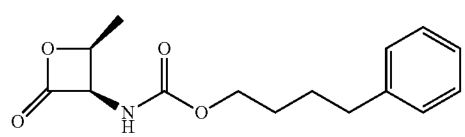 [SMILES: C[C@@H]1OC(=O)[C@@H]1NC(=O)OCCCCc1ccccc1] | 0.39 | | | <10% inhib. @ 0.3 μM |
| 6 | 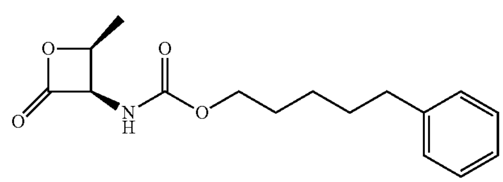 | 0.05 | 0.007 | 0.014 | <10% inhib. @ 10 μM |
| 7 | 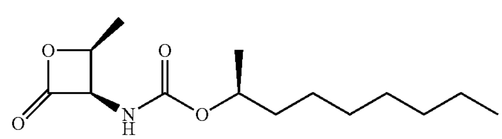 [SMILES: CCCCCCC[C@H](C)OC(=O)N[C@H]1C(=O)O[C@H]1C] | 0.016 | 0.005 | | 45% inhib. @ 10 μM |

TABLE 2-continued

NAAA and AC (Acid Ceramidase) IC$_{50}$ values of representative compounds of the invention

| Example | Structure | r-NAAA IC$_{50}$ (μM) or % inhib. | UPLC/MS h-NAAA IC$_{50}$ (μM) | Fluorogenic h-NAAA IC$_{50}$ (μM) | r-AC IC$_{50}$ (μM) or % inhib. |
|---|---|---|---|---|---|
| 8 | 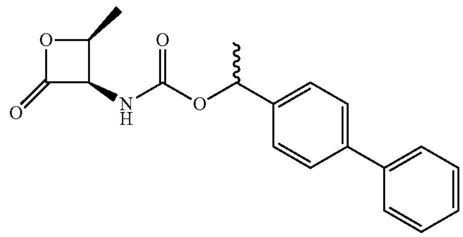 [SMILES: CC(OC(=O)N[C@H]1C(=O)O[C@H]1C)c1ccc(-c2ccccc2)cc1] | 0.05 | 0.010 | | |
| 9 | 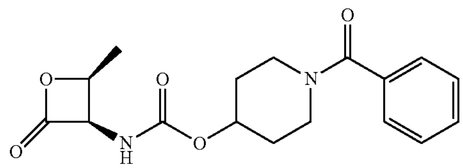 [SMILES: C[C@@H]1OC(=O)[C@@H]1NC(=O)OC1CCN(C(=O)c2ccccc2)CC1] | 1.31 | | | |
| 10 | 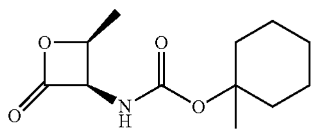 [SMILES: C[C@@H]1OC(=O)[C@@H]1NC(=O)OC1(C)CCCCC1] | 0.84 | | | |
| 11 | 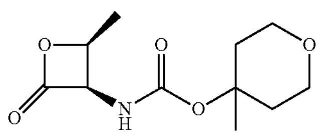 [SMILES: C[C@@H]1OC(=O)[C@@H]1NC(=O)OC1(C)CCOCC1] | 40 | | | |
| 12 | 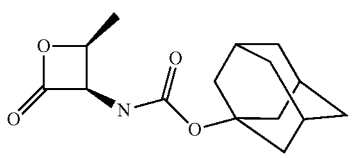 [SMILES: C[C@@H]1OC(=O)[C@@H]1NC(=O)OC12CC3CC(CC(C3)C1)C2] | 0.87 | 0.54 | | |
| 13 | 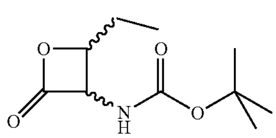 | 48% inhib. @ 3 μM | | | |
| 14 | 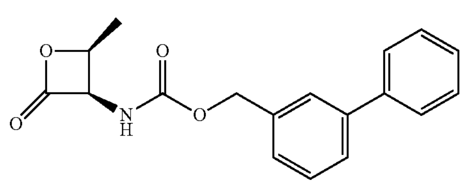 [SMILES: C[C@@H]1OC(=O)[C@@H]1NC(=O)OCc1cccc(-c2ccccc2)c1] | 28% inhib. @ 10 μM | | | |
| 15 | 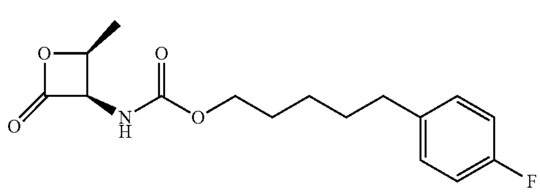 [SMILES: C[C@@H]1OC(=O)[C@@H]1NC(=O)OCCCCCc1ccc(F)cc1] | 0.24 | | | |

TABLE 2-continued

NAAA and AC (Acid Ceramidase) IC$_{50}$ values of representative compounds of the invention

| Example | Structure | r-NAAA IC$_{50}$ (μM) or % inhib. | UPLC/MS h-NAAA IC$_{50}$ (μM) | Fluorogenic h-NAAA IC$_{50}$ (μM) | r-AC IC$_{50}$ (μM) or % inhib. |
|---|---|---|---|---|---|
| 16 | 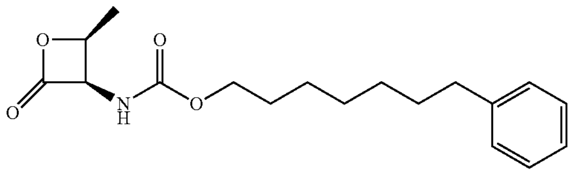 [SMILES: C[C@@H]1OC(=O)[C@@H]1NC(=O)OCCCCCCCc1ccccc1] | 0.11 | | | |
| 17 | 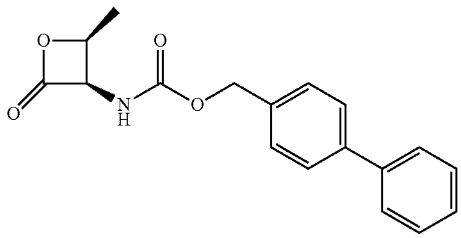 [SMILES: C[C@@H]1OC(=O)[C@@H]1NC(=O)OCc1ccc(-c2ccccc2)cc1] | 0.007 | 0.007 | | 30% inhib. @ 10 μM |
| 18 | 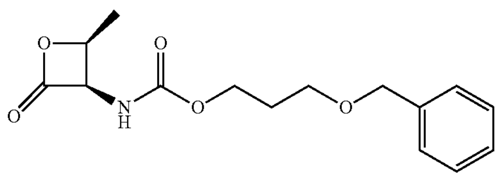 [SMILES: C[C@@H]1OC(=O)[C@@H]1NC(=O)OCCCOCc1ccccc1] | 0.05 | 0.018 | | <10% inhib. @ 10 μM |
| 19 | 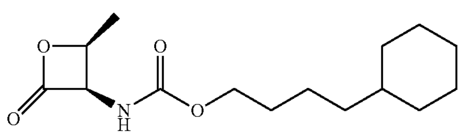 [SMILES: C[C@@H]1OC(=O)[C@@H]1NC(=O)OCCCCC1CCCCC1] | 0.02 | 0.009 | 0.008 | |
| 20 | 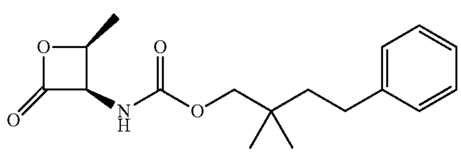 [SMILES: C[C@@H]1OC(=O)[C@@H]1NC(=O)OCC(C)(C)CCc1ccccc1] | 3.43 | | | |
| 21 | 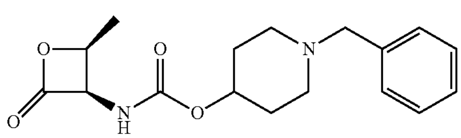 [SMILES: C[C@@H]1OC(=O)[C@@H]1NC(=O)OC1CCN(Cc2ccccc2)CC1] | 21% inhib. @ 3 μM | | | |
| 22 | 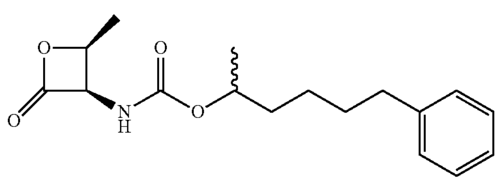 [SMILES: CC(CCCCc1ccccc1)OC(=O)N[C@H]1C(=O)O[C@H]1C] | 0.03 | 0.014 | | <10% inhib. @ 0.3 μM |
| 23 | 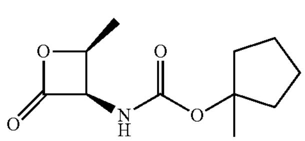 [SMILES: C[C@@H]1OC(=O)[C@@H]1NC(=O)OC1(C)CCCC1] | 1.23 | | | |
| 24 | 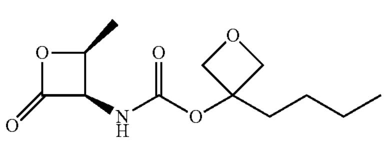 [SMILES: CCCCC1(OC(=O)N[C@H]2C(=O)O[C@H]2C)COC1] | 3.76 | | | |

TABLE 2-continued

NAAA and AC (Acid Ceramidase) IC$_{50}$ values of representative compounds of the invention

| Example | Structure | r-NAAA IC$_{50}$ (μM) or % inhib. | UPLC/MS h-NAAA IC$_{50}$ (μM) | Fluorogenic h-NAAA IC$_{50}$ (μM) | r-AC IC$_{50}$ (μM) or % inhib. |
|---|---|---|---|---|---|
| 25 | 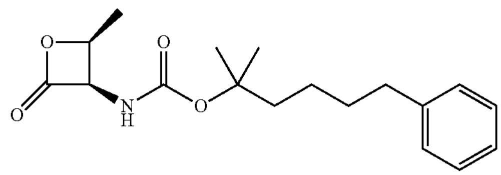 [SMILES: C[C@@H]1OC(=O)[C@@H]1NC(=O)OC(C)(C)CCCCc1ccccc1] | 0.31 | | | <10% inhib. @ 0.3 μM |
| 26 | 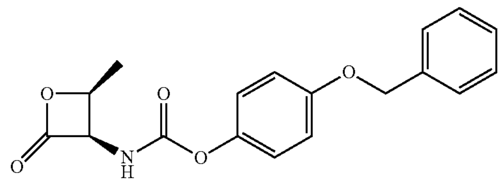 [SMILES: C[C@@H]1OC(=O)[C@@H]1NC(=O)Oc1ccc(OCc2ccccc2)cc1] | 0.29 | | | |
| 27 | 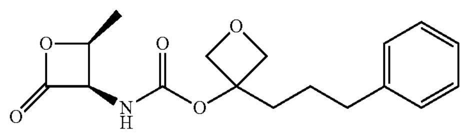 [SMILES: C[C@@H]1OC(=O)[C@@H]1NC(=O)OC1(CCCc2ccccc2)COC1] | 0.51 | | | <10% inhib. @ 0.3 μM |
| 28 | 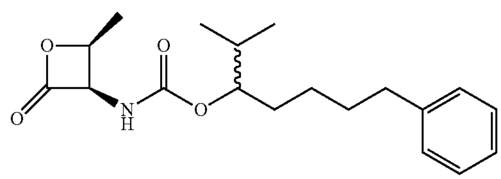 [SMILES: CC(C)C(CCCCc1ccccc1)OC(=O)N[C@H]1C(=O)O[C@H]1C] | 0.10 | | | |
| 29 | 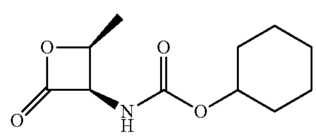 [SMILES: C[C@@H]1OC(=O)[C@@H]1NC(=O)OC1CCCCC1] | 5.42 | | | |
| 30 | 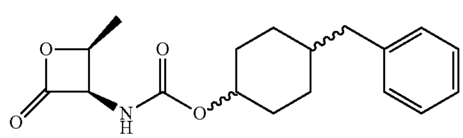 [SMILES: C[C@@H]1OC(=O)[C@@H]1NC(=O)OC1CCC(Cc2ccccc2)CC1] | 0.31 | | | |
| 31 | 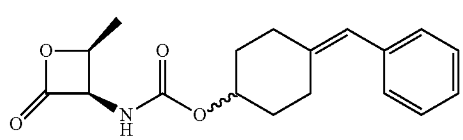 [SMILES: C[C@@H]1OC(=O)[C@@H]1NC(=O)OC1CCC(=Cc2ccccc2)CC1] | 0.75 | | | |
| 32 | 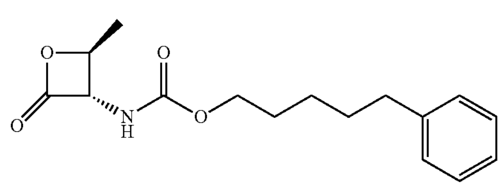 [SMILES: C[C@@H]1OC(=O)[C@H]1NC(=O)OCCCCCc1ccccc1] | 0.48 | | | 3.8 |
| 33 | 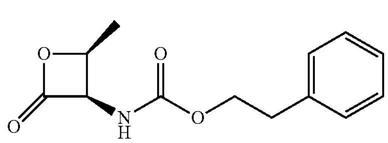 [SMILES: C[C@@H]1OC(=O)[C@@H]1NC(=O)OCCc1ccccc1] | 2.52 | | | |

TABLE 2-continued

NAAA and AC (Acid Ceramidase) IC$_{50}$ values of representative compounds of the invention

| Example | Structure | r-NAAA IC$_{50}$ (μM) or % inhib. | UPLC/MS h-NAAA IC$_{50}$ (μM) | Fluorogenic h-NAAA IC$_{50}$ (μM) | r-AC IC$_{50}$ (μM) or % inhib. |
|---|---|---|---|---|---|
| 34 | 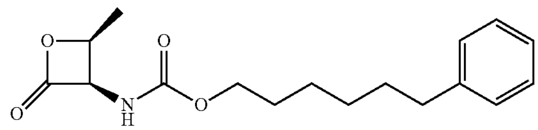 [SMILES: C[C@@H]1OC(=O)[C@@H]1NC(=O)OCCCCCCc1ccccc1] | 1.17 | | | |
| 35 | 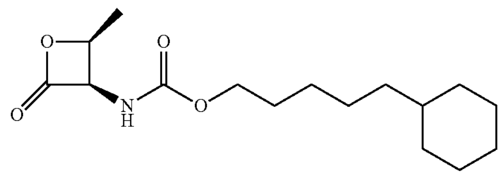 [SMILES: C[C@@H]1OC(=O)[C@@H]1NC(=O)OCCCCCC1CCCCC1] | 0.016 | 0.005 | | <10% inhib. @ 10 μM |
| 36 | 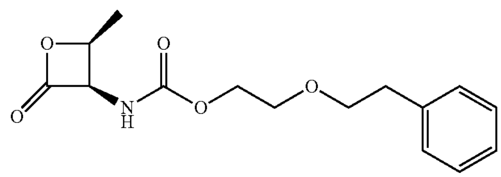 [SMILES: C[C@@H]1OC(=O)[C@@H]1NC(=O)OCCOCCc1ccccc1] | 0.14 | | | |
| 37 | 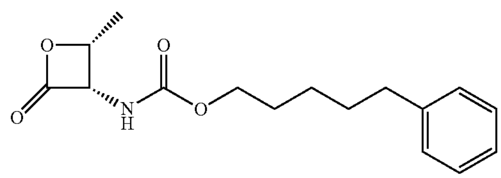 [SMILES: C[C@H]1OC(=O)[C@H]1NC(=O)OCCCCCc1ccccc1] | 3.53 | | | |
| 38 | 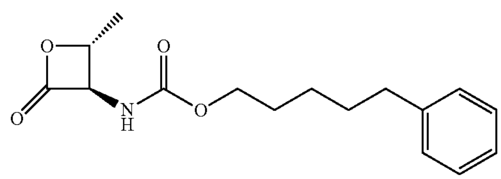 [SMILES: C[C@H]1OC(=O)[C@@H]1NC(=O)OCCCCCc1ccccc1] | 0.018 | | | |
| 39 | 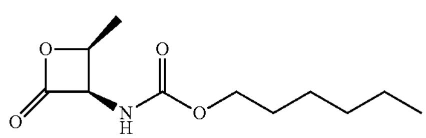 [SMILES: CCCCCCOC(=O)N[C@H]1C(=O)O[C@H]1C] | 0.27 | | | |
| 40 | 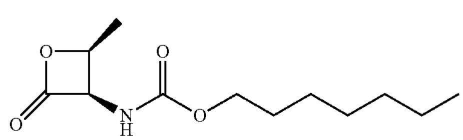 [SMILES: CCCCCCCOC(=O)N[C@H]1C(=O)O[C@H]1C] | 0.04 | | | |
| 41 | 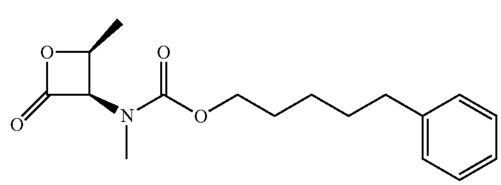 [SMILES: C[C@@H]1OC(=O)[C@@H]1N(C)C(=O)OCCCCCc1ccccc1] | No inhib. | | | |

TABLE 2-continued

NAAA and AC (Acid Ceramidase) IC$_{50}$ values of representative compounds of the invention

| Example | Structure | r-NAAA IC$_{50}$ (μM) or % inhib. | UPLC/MS h-NAAA IC$_{50}$ (μM) | Fluorogenic h-NAAA IC$_{50}$ (μM) | r-AC IC$_{50}$ (μM) or % inhib. |
|---|---|---|---|---|---|
| 42 | 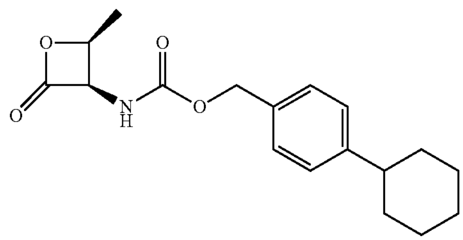 [SMILES: C[C@@H]1OC(=O)[C@@H]1NC(=O)OCc1ccc(C2CCCCC2)cc1] | 0.007 | | | |
| 43 | 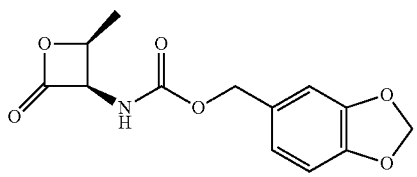 [SMILES: C[C@@H]1OC(=O)[C@@H]1NC(=O)OCc1ccc2c(c1)OCO2] | 0.176 | | | |
| 44 | 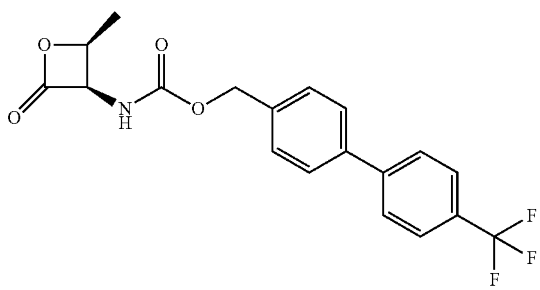 [SMILES: C[C@@H]1OC(=O)[C@@H]1NC(=O)OCc1ccc(-c2ccc(C(F)(F)F)cc2)cc1] | 0.024 | | | |
| 45 | 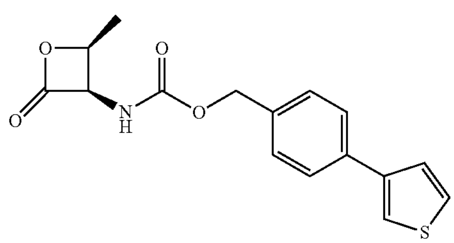 [SMILES: C[C@@H]1OC(=O)[C@@H]1NC(=O)OCc1ccc(-c2ccsc2)cc1] | 0.021 | | | |
| 46 | 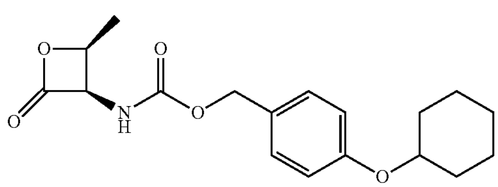 [SMILES: C[C@@H]1OC(=O)[C@@H]1NC(=O)OCc1ccc(OC2CCCCC2)cc1] | 0.023 | | | |
| 47 | 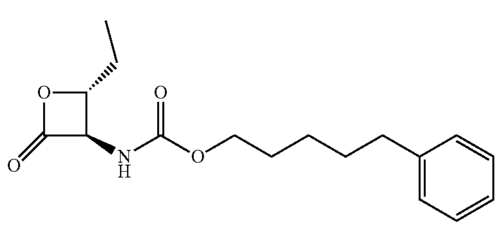 [SMILES: CC[C@H]1OC(=O)[C@@H]1NC(=O)OCCCCCc1ccccc1] | 92% inhib. @ 3 μM | | | 0.004 |

TABLE 2-continued
NAAA and AC (Acid Ceramidase) IC$_{50}$ values of representative compounds of the invention
| Example | Structure | r-NAAA IC$_{50}$ (μM) or % inhib. | UPLC/MS h-NAAA IC$_{50}$ (μM) | Fluorogenic h-NAAA IC$_{50}$ (μM) | r-AC IC$_{50}$ (μM) or % inhib. |
|---|---|---|---|---|---|
| 48 | 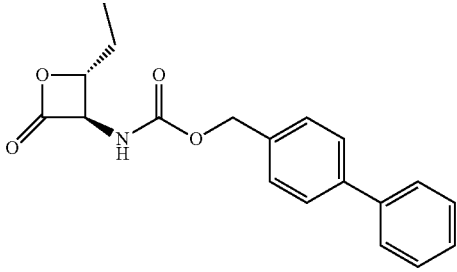 [SMILES: CC[C@H]1OC(=O)[C@@H]1NC(=O)OCc1ccc(-c2ccccc2)cc1] | 100% inhib. @ 3 μM | | 0.006 | |
| 49 | 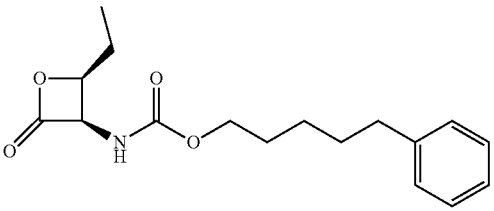 [SMILES: CC[C@@H]1OC(=O)[C@@H]1NC(=O)OCCCCCc1ccccc1] | 89% inhib. @ 3 μM | | 0.009 | |
| 50 | 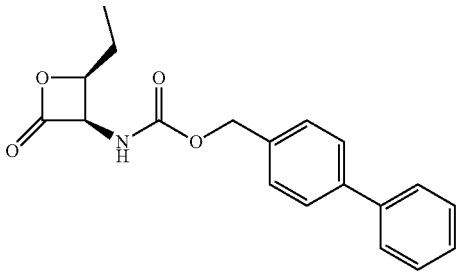 [SMILES: CC[C@@H]1OC(=O)[C@@H]1NC(=O)OCc1ccc(-c2ccccc2)cc1] | 100% inhib. @ 3 μM | | 0.015 | |
| 51 | 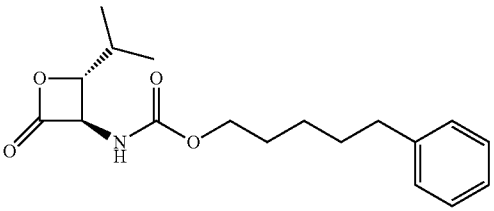 | 92% inhib. @ 3 μM | | 0.019 | |
| 52 | 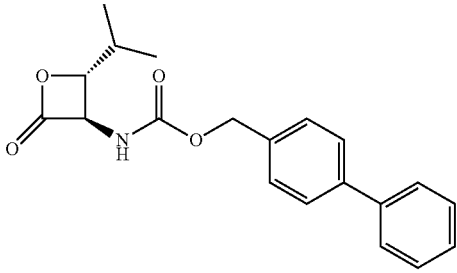 [SMILES: CC(C)[C@H]1OC(=O)[C@@H]1NC(=O)OCc1ccc(-c2ccccc2)cc1] | 93% inhib. @ 3 μM | | 0.023 | |
| 53 | 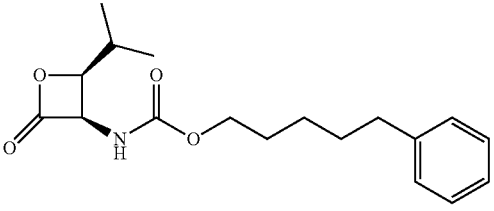 [SMILES: CC(C)[C@@H]1OC(=O)[C@@H]1NC(=O)OCCCCCc1ccccc1] | 55% inhib. @ 3 μM | | 0.068 | |

TABLE 2-continued

NAAA and AC (Acid Ceramidase) IC$_{50}$ values of representative compounds of the invention

| Example | Structure | r-NAAA IC$_{50}$ (μM) or % inhib. | UPLC/MS h-NAAA IC$_{50}$ (μM) | Fluorogenic h-NAAA IC$_{50}$ (μM) | r-AC IC$_{50}$ (μM) or % inhib. |
|---|---|---|---|---|---|
| 54 | 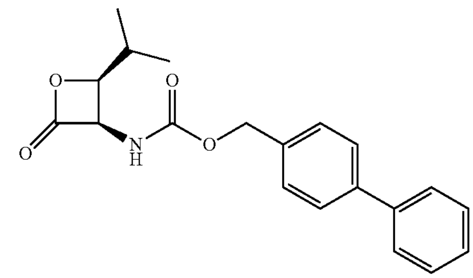 [SMILES: CC(C)[C@@H]1OC(=O)[C@@H]1NC(=O)OCc1ccc(-c2ccccc2)cc1] | 53% inhib. @ 3 μM | | 0.037 | |
| 55 | 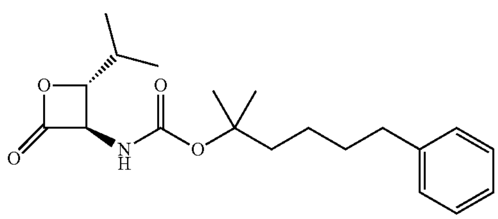 [SMILES: CC(C)[C@H]1OC(=O)[C@@H]1NC(=O)OC(C)(C)CCCCc1ccccc1] | 98% inhib. @ 3 μM | | 0.012 | |
| 56 | 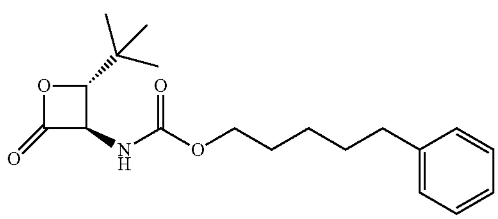 [SMILES: CC(C)(C)[C@H]1OC(=O)[C@@H]1NC(=O)OCCCCCc1ccccc1] | 75% inhib. @ 3 μM | | 0.267 | |
| 57 | 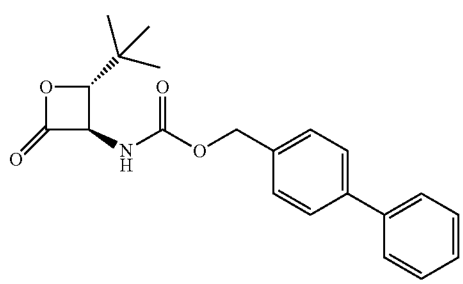 [SMILES: CC(C)(C)[C@H]1OC(=O)[C@@H]1NC(=O)OCc1ccc(-c2ccccc2)cc1] | 73% inhib. @ 3 μM | | 0.465 | |
| 58 | 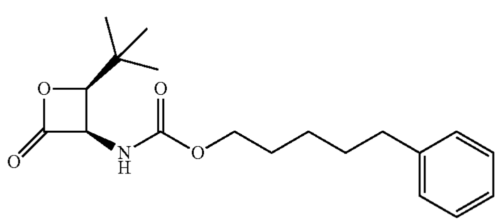 [SMILES: CC(C)(C)[C@@H]1OC(=O)[C@@H]1NC(=O)OCCCCCc1ccccc1] | 67% inhib. @ 3 μM | | 0.278 | |
| 59 | 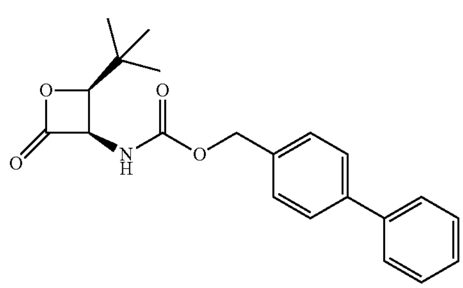 [SMILES: CC(C)(C)[C@@H]1OC(=O)[C@@H]1NC(=O)OCc1ccc(-c2ccccc2)cc1] | 57% inhib. @ 3 μM | | 0.897 | |

Method for Testing Compounds on Acid Ceramidase

The selectivity of select compounds versus Acid Ceramidase (AC) was determined Rat AC (r-AC) was cloned from a brain cDNA library using primers based on the sequence obtained from the National Center for Biotechnology Information (NCBI) database: 5' rAC (5'-GACCATGCTGGGC-CGTAGT-3') and 3' rAC (5'-CCAGCCTATACAAGGGTCT-3'). The PCR (High Fidelity PCR Master, Roche) product was subcloned into a pEF6-V5/His vector (Invitrogen) to construct a mammalian expression vector encoding V5/His-tagged rat AC. HEK293 cells were transfected with pEF6-rAC-V5/His using Super-Fect reagent (Qiagen) and screened with G418 (0.3 mg/mL). Cells were suspended in 20 mM Tris HCl (pH 7.5) containing 0.32M sucrose, sonicated and centrifuged at 800×g for 15 minutes at 4° C. The supernatants were centrifuged again at 12,000×g for 30 minutes at 4° C. The pellets were suspended in phosphate-buffered saline (PBS) and subjected to 2 freeze—thaw cycles at −80° C. The suspensions were centrifuged at 105,000×g for 1 hour at 4° C. The supernatants containing recombinant AC were kept at −80° C. until use. Protein concentration was measured using the bicinchoninic acid (BCA) assay (Pierce). Recombinant rat AC (50 μg) was preincubated with inhibitors (final DMSO concentration 1%) in assay buffer (100 mM sodium phosphate, 0.1% Nonidet P-40, 150 mM NaCl, 3 mM DTT, 100 mM sodium citrate, pH 4.5) for 30 minutes at 37° C. Reactions were started by the addition of 100 μM N-lauroyl ceramide (Nu-Chek Prep, Elysian, Minn.) and carried on for 30 minutes at 37° C. Reactions were stopped by addition of a mixture of chloroform/methanol (2:1, vol/vol) containing 1 nmol of heptadecanoic acid (HDA; NuChek Prep). The organic phases were collected, dried under N2, and analyzed by LC-MS in the negative-ion mode using heptadecenoic acid (HDA) as internal standard (m/z=199 for lauric acid, m/z=269 for HDA). HDA was eluted on an XDB Eclipse C18 column isocratically at 2.2 mL/min for 1 minute with a solvent mixture of 95% methanol and 5% water, both containing 0.25% acetic acid and 5 mM ammonium acetate. The column temperature was 50° C. Electrospray ionization (ESI) was in the negative mode, capillary voltage as 4 kV, and fragmentor voltage was 100 V. N2 was used as drying gas at a flow rate of 13 L/min and a temperature of 350° C. Nebulizer pressure was set at 60 psi. We monitored [M−H]− in the selected-ion monitoring (SIM) mode using HDA as internal standard. Calibration curves were generated using commercial lauric acid (Nu-Chek Prep; m/z=199).

The $IC_{50}$ values of representative compounds of the invention on NAAA and AC are reported in Table 2.

Compounds of the present invention showed increased potency on NAAA and increased selectivity versus AC with respect to analogs of the amide series or analogs lacking a methyl substituent at position 2 of the oxo-oxetan ring. A comparison of potency on NAAA and AC of example 6 of the present invention and the corresponding amide analog and the compounds lacking the methyl substituent at position 2 of the oxo-oxetan ring is reported in Table 3.

TABLE 3

Comparison of potency on NAAA and AC of example 6 of the present invention and the corresponding amide analog and the compounds lacking the methyl substituent at position 2 of the oxo-oxetan ring.

| Compound | r-NAAA $IC_{50}$ (μM) | r-AC $IC_{50}$ (μM) or % inhib. |
|---|---|---|
| Example 6 | 0.05 | <10% inhib. @ 10 μM |
| (amide analog) | 0.54 | <10% inhib. @ 10 μM |
| (no methyl, carbamate) | 0.51 | 30 ± 2.5 |
| (no methyl, stereoisomer) | 6.85 | 1.53 |

The present invention provide methods for inhibiting AC, comprising contacting a compound set forth herein with AC. These methods are useful for treating or alleviating the symptoms of cellular senescence and inflammation, which are effects of ceramide in cells.

In one aspect the invention provides NAAA inhibitors which are selective for NAAA over AC. The present invention also provides compounds having an $IC_{50}$ for inhibiting NAAA that is at least 10 fold-less than that for inhibiting AC. The compounds and compositions described herein are useful for inducing or modulating apoptosis, senescence and inflammation. The compounds and compositions set forth herein are useful in avoiding side effects due to modulation of ceramide levels.

Methods for Screening Compounds for a Therapeutic Activity

A variety of animal models can be used to test the compounds of the present invention for their therapeutic effectiveness in treating inflammatory and pain states. With the aim to better illustrate the present invention, without limiting it, certain methods for testing the compounds of the present invention for therapeutic effectiveness are reported hereunder.

UV-B Irradiation

Male Sprague Dawley rats (150-175 g, Charles River, Calco, Italy) were anaesthetized with a mixture of Tiletamine (15 mg/Kg) and Zolazepam (15 mg/Kg) administered in a single intra-peritoneal injection.

Rats were then placed on their backs and shrouded in a UV opaque material with only the relevant surface of the plantar right hind paw exposed, perpendicular to the narrowband UVB light source situated above the level of the limb.

The UVB source used for all experiments consisted of a bank of four TL01 fluorescent tubes (Philips, UK, $\lambda_{max}$=312 nm) spaced 2.5 cm apart producing an even field of irradiation. The irradiance produced by the bulbs during each irradiation was determinate at the distance of the limb from the light source using a calibrate meter (IL1400A with SEL240/UVB-1/TD filter, ABLE Instruments & Controls Ltd, UK). From this, the doses of UVB to which the rats were exposed were calculated.

Behavioral Testing

After plantar irradiation, nociceptive withdrawal responses to both thermal and mechanical stimuli were tested.

Heat hypersensitivity was assessed using the rat plantar test equipment (Ugo Basile, Italy) following the method described by Hargreaves et al. (1988). Briefly, each animal was placed in a clear acrylic cubicle (22×16.5×14 cm) on top of glass floor in a temperature controlled room (22° C.) and allowed to acclimatize for 15 min before testing. A mobile infrared heat source was applied to the plantar surface of the hind paws. The paw withdrawal latency (PWL) was defined as the time (in seconds) taken by the rat to remove its hind paw from the heat source. The heat source was calibrated to give a response on 14-16 sec on uninjured paw. An automatic cut off point of 20 sec was applied to prevent tissue damage. Uninjured paw was always assessed first.

Mechanical withdrawal thresholds were tested using a Dynamic Plantar Anesthesiometer (Ugo Basile, Italy). Briefly, each animal was placed in a clear acrylic cubicle (22×16.5×14) on top of a metal grid in a temperature controlled room (22° C.) and allowed to acclimatize for 15 min before testing. The stimulus was applied via an actuator filament (0.5 mm diameter) which under computer control, applied a linear force ramp of 2.5 g/s to the plantar surface of the paw. Paw withdrawal stops the stimulation and records the threshold. The withdrawal threshold is calculated as the average of three consecutive tests with at list 5 minutes between each test. A cut-off of 50 g was imposed to prevent any significant tissue damage.

Fresh drug suspensions of compound 6 were prepared immediately before use in a vehicle of vaseline oil plus 5% lauric acid and given in a volume of 50 µL/rat. Compound 6 dose-dependently reduced the UVB-induced inflammation as shown in FIG. 1. Thermal hyperalgesia induced by irradiation with 250 mJ/cm$^2$ of UVB was significantly reduced by the two higher doses of compound 6 (10 and 30% w/w) compared to vehicle treated animals (*p<0.05 and ***p<0.001 vs pre-test; Bonferroni's test).

Contact Dermatitis 2,4-dinitrofluorobenzene (DNFB) (Sigma-Aldrich, Italy) was dissolved in acetone. On day 1 and 2, mice (CD1, 25-30 g, Charles River, Calco, Italy) were sensitized on the skin of the abdomen with hapten (20 µL of 0.5% DNFB). After 5 days, on day 7, mice were challenged with hapten (20 µL of 0.2% DNFB) in the earlobe and treated with drugs to be tested. Control group received the vehicle used to dissolve drugs. Mice (five per group) were placed in a plastic cage. On day 8, ear thickness was determined after challenge using a caliper. Results are expressed as absolute ear thickness.

Figure 2:
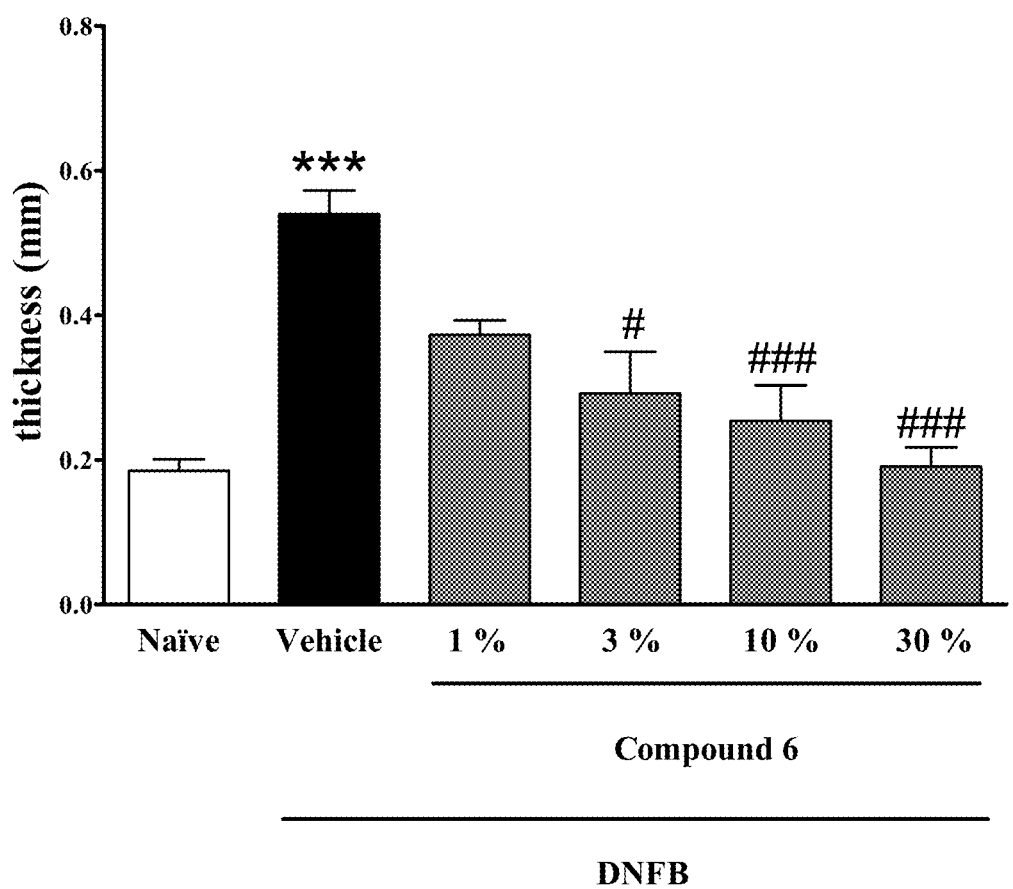
FIG. 2 shows the effect of a compound according to the invention on a mouse model of contact dermatitis (DNFB model).
Figure 3:
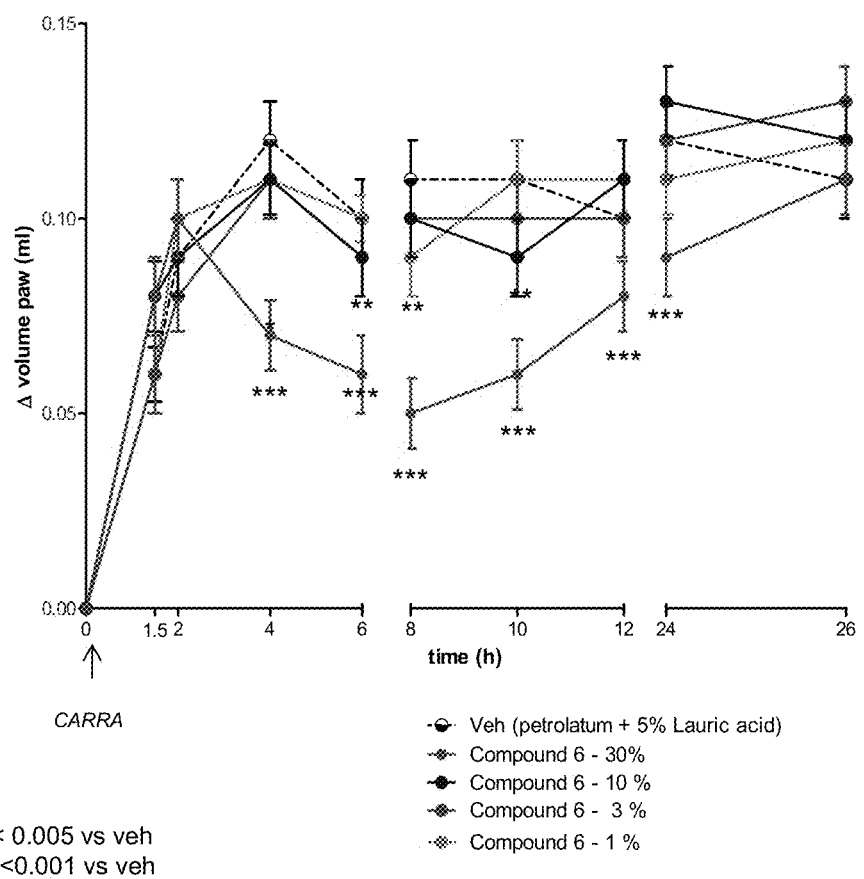
FIG. 3 shows the effect of compound 6 on carrageenan-induced paw edema. A time course of the effect is also included. Compound 6 was administered ninety minutes after carrageenan.
Figure 4:
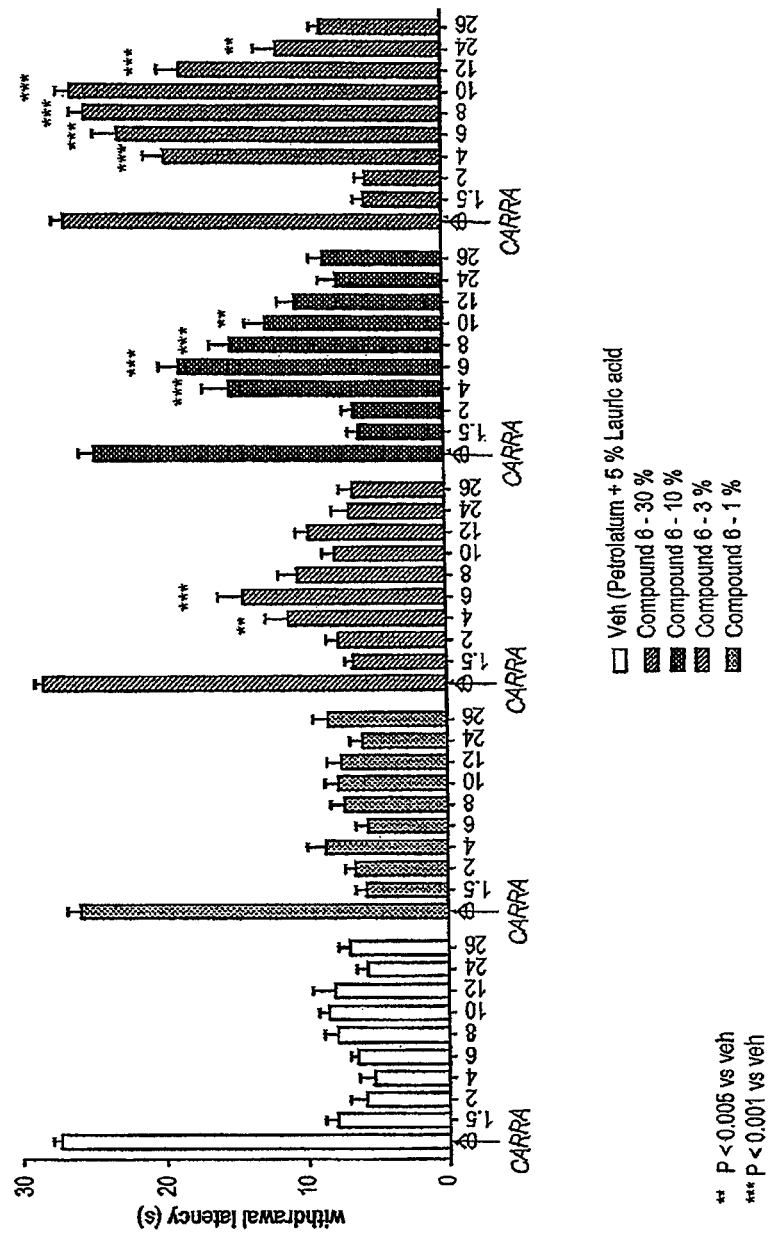
FIG. 4 shows that a topical administration of compound 6 dose-dependently reduces carrageenan-induced hyperalgesia. A time course of the effect is also included. Compound 6 was administered ninety minutes after carrageenan.
Figure 5:
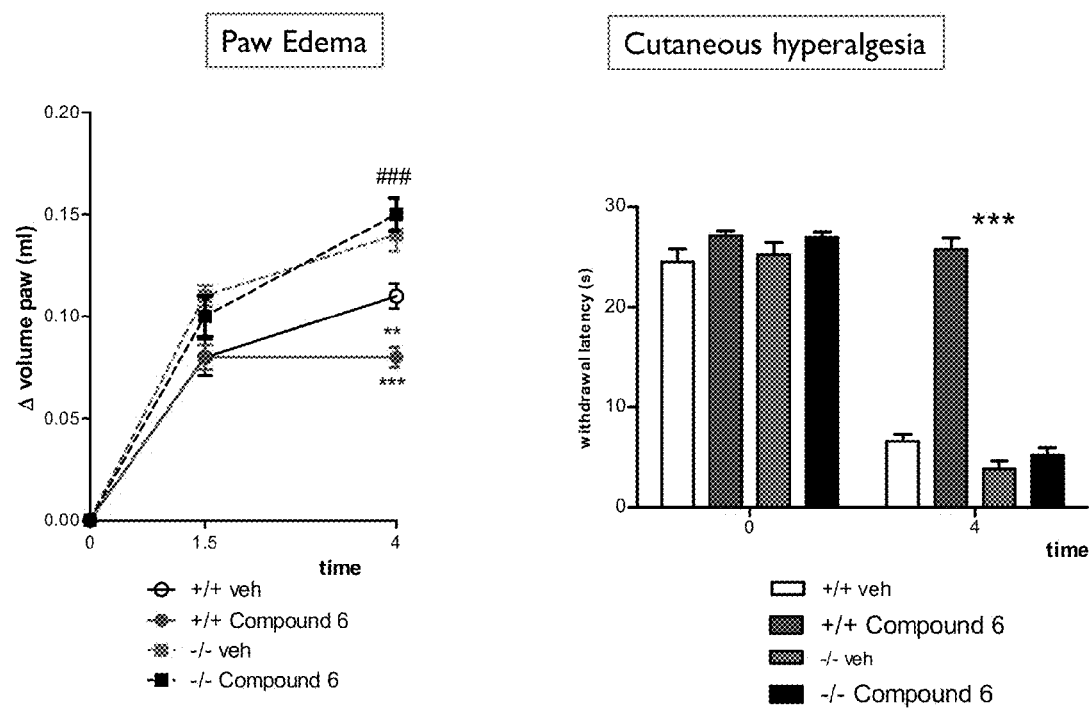
FIG. 5 shows that the anti-inflammatory effects on paw edema and cutaneous hyperalgesia of a topical administration of compound 6 are absent in mice lacking PPAR-α. Compound 6 was administered ninety minutes after carrageenan.
Figure 6:
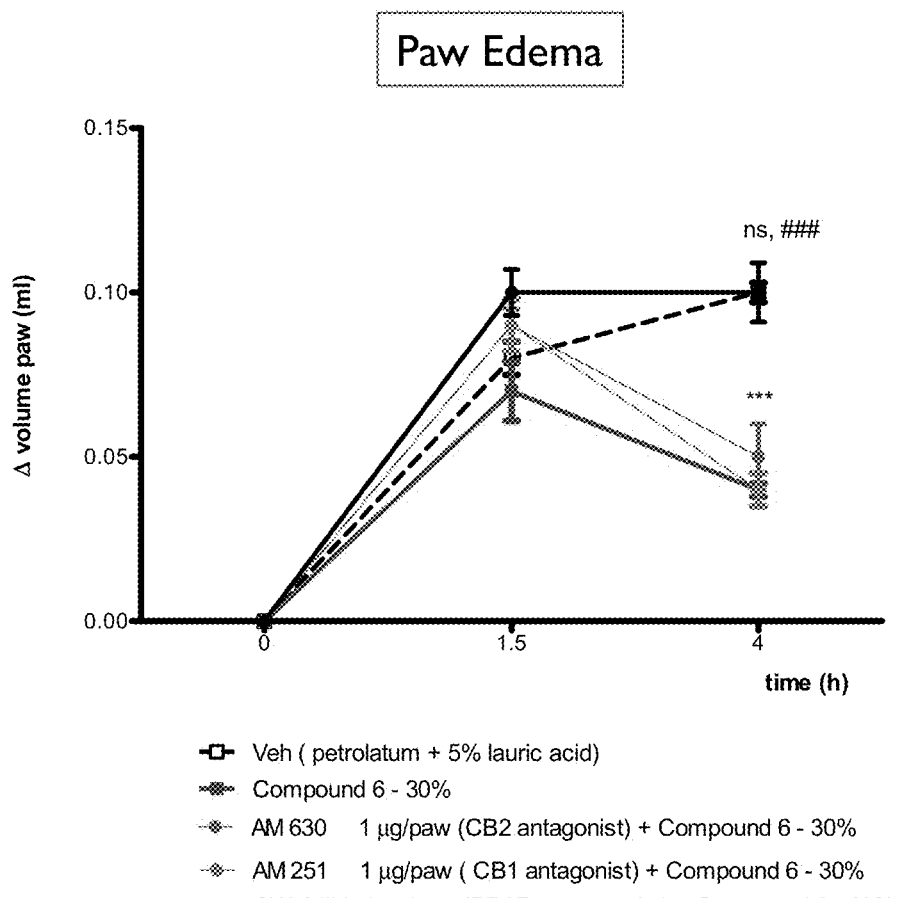
FIG. 6 shows that the anti-inflammatory effect of a topical administration of compound 6 on paw edema is blocked by PPAR-α antagonists, but not by $CB_1$ or $CB_2$ cannabinoid receptor antagonists. Antagonists (1 μg/paw) were administered intraplantarly 60 minutes after carrageenan; compound 6 (30%) was given topically 90 minutes after carrageenan.
Figure 7:
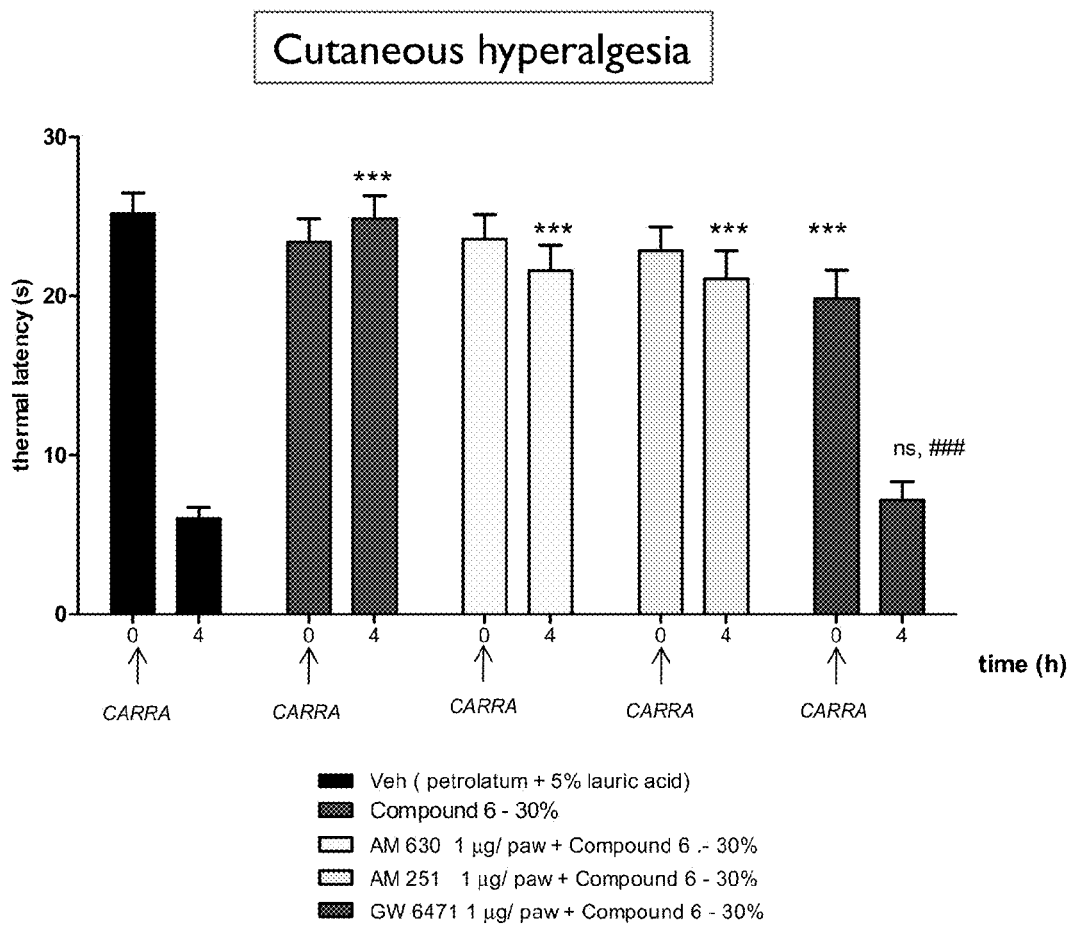
FIG. 7 shows that the anti-inflammatory effect of a topical administration of compound 6 on cutaneous hyperalgesia is blocked by PPAR-α antagonists, but not by $CB_1$ or $CB_2$ receptor antagonists. Antagonists (1 μg/paw) were administered intraplantarly 60 minutes after carrageenan; compound 6 (30%) was given topically 90 minutes after carrageenan.
Figure 8:
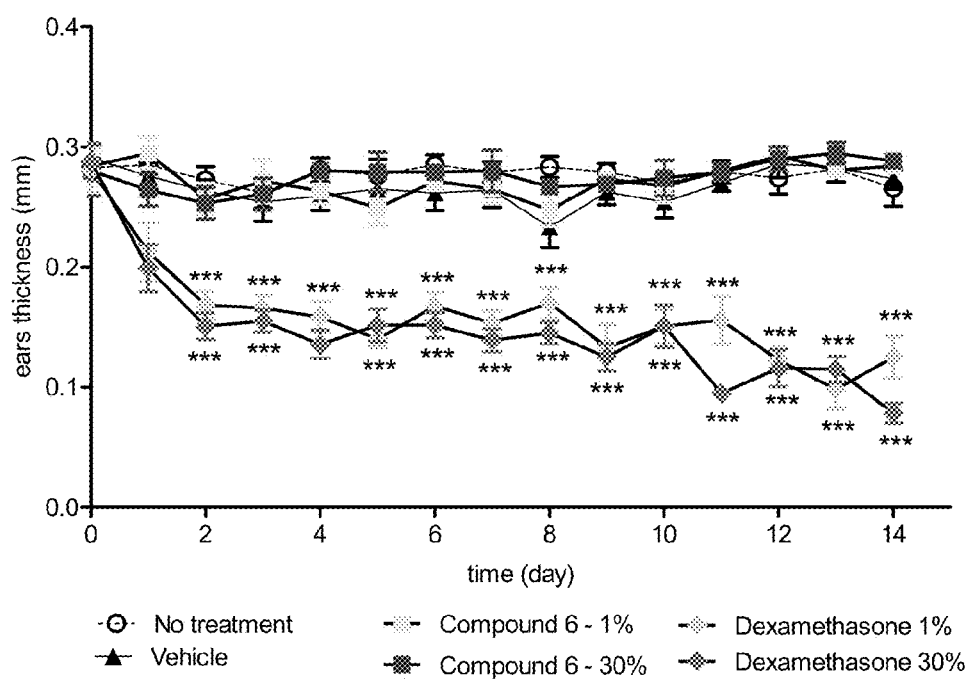
FIG. 8 shows that repeated administration of dexamethasone, but not compound 6, causes skin atrophy (decrease of ear thickness). Compounds were administered once a day for fourteen days.
Figure 9:
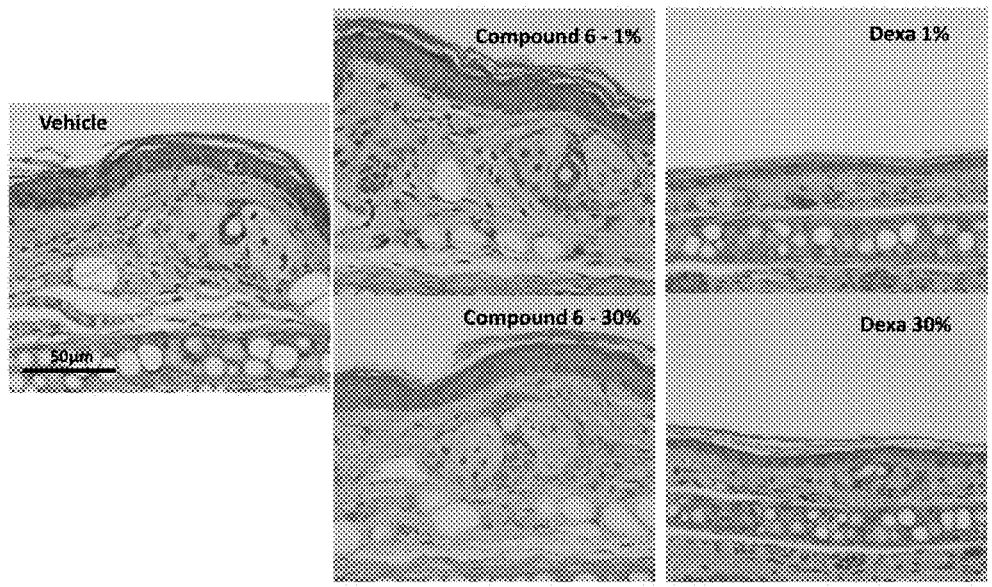
FIG. 9 shows that repeated administration of dexamethasone, but not compound 6, altered cellular architecture. The histopathological analysis was conducted at day 14.
Figure 10:
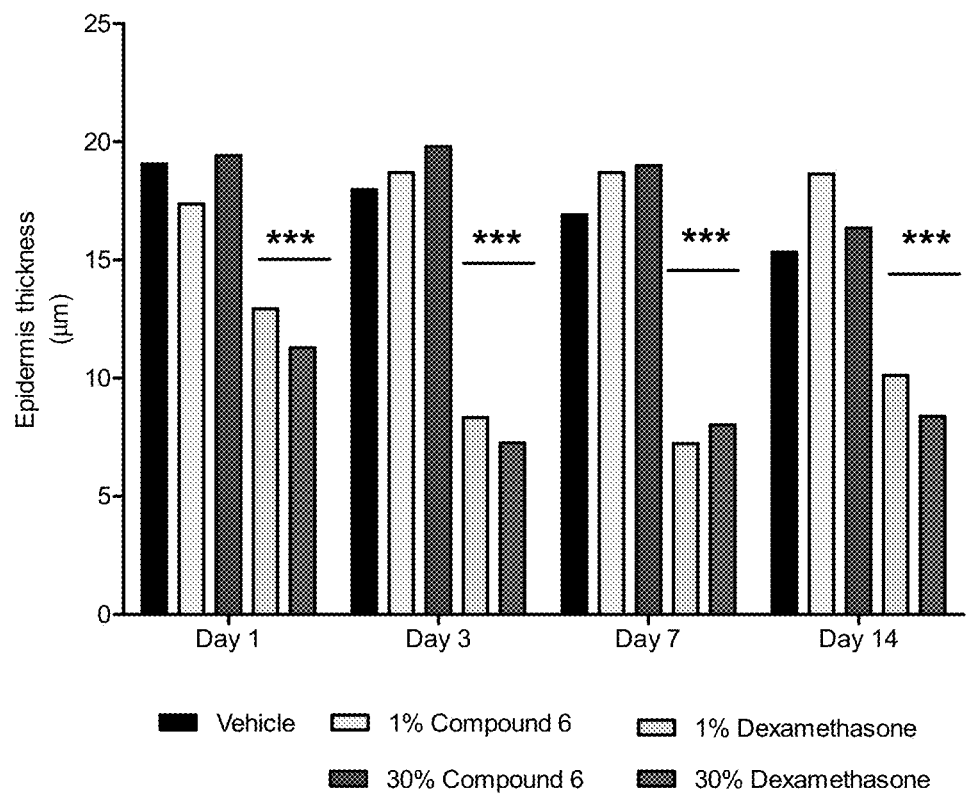
FIG. 10 shows that morphometric analysis of epidermal thickness after repeated administration of compound 6 or dexamethasone.
Figure 11:
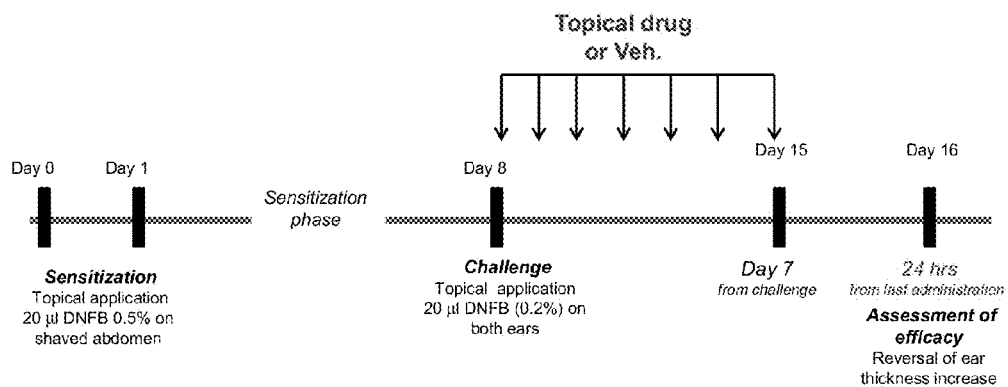
FIG. 11 shows the experimental protocol used to test the therapeutic effect of compound 6 on established DNFB-induced symptoms in mice (repeated dosing).
Figure 12:
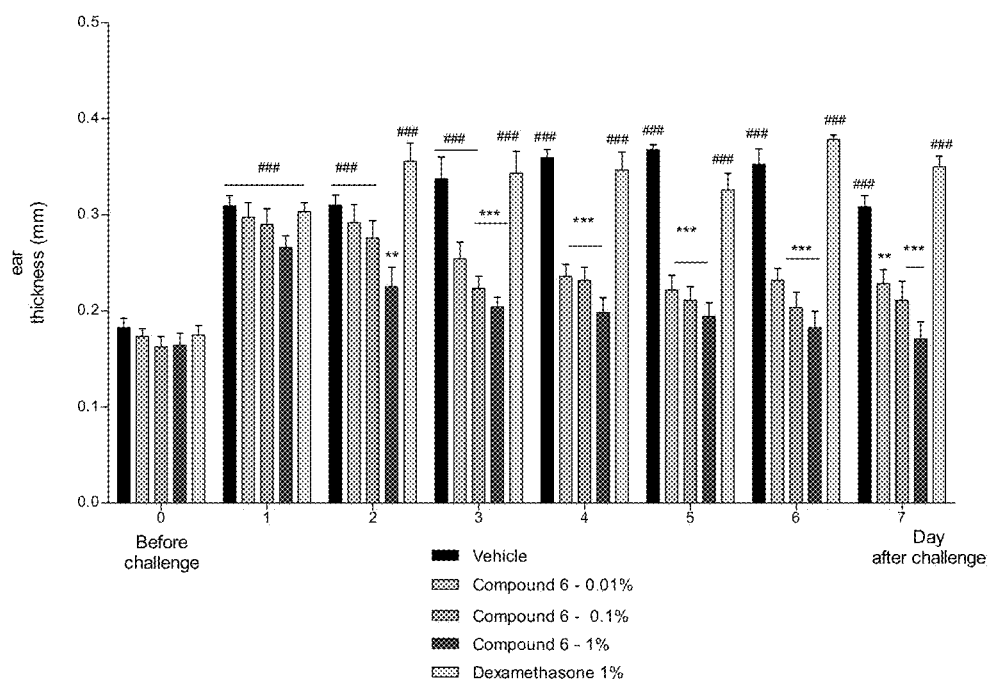
FIG. 12 shows that repeated administration of compound 6 reverses ear thickness increase in the DNFB model of dermatitis in mice. The time of the onset of the effect depends upon the dose.
Figure 13:
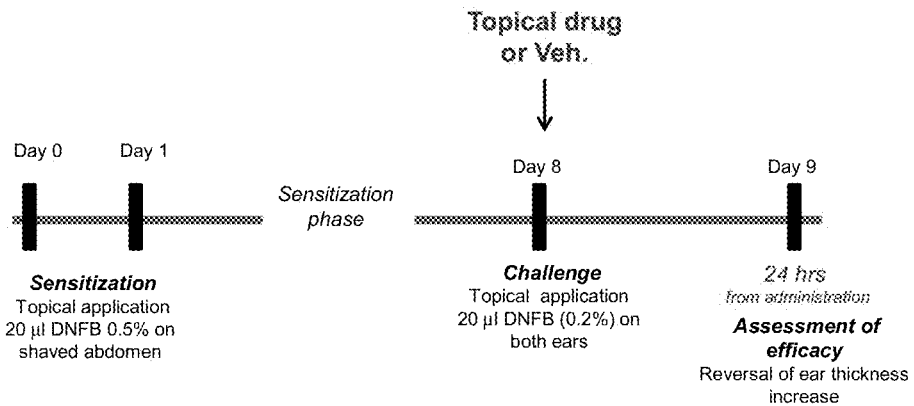
FIG. 13 shows the experimental protocol used to test the therapeutic effect of compound 6 on established DNFB-induced symptoms in mice (single dosing).
Figure 14:
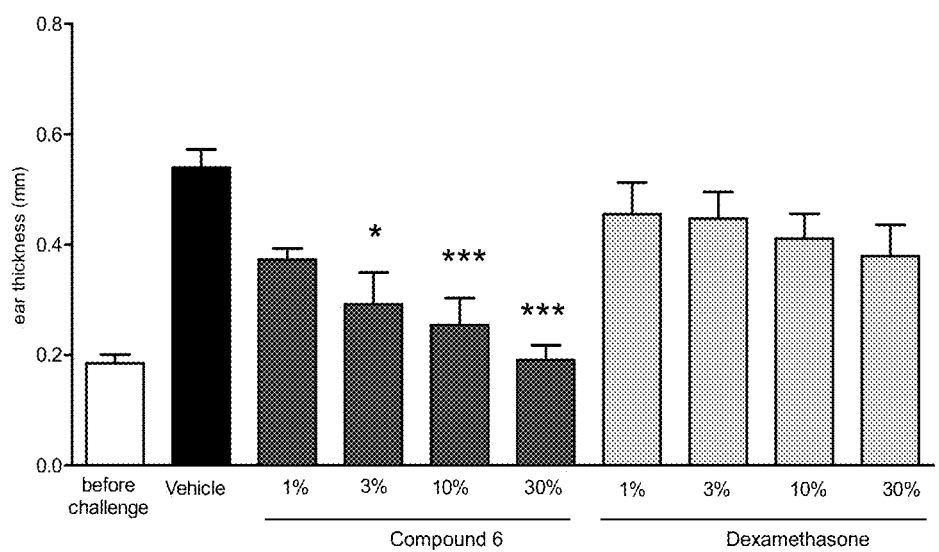
FIG. 14 shows that a single administration of compound 6 reverses ear thickness increase in the DNFB model of dermatitis in mice.
Figure 15:
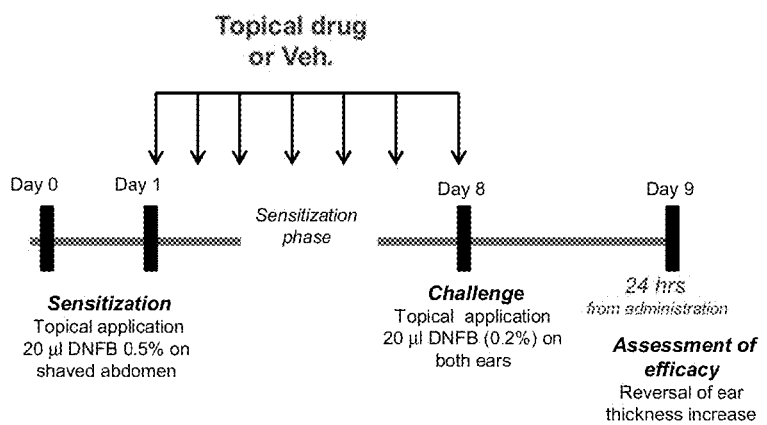
FIG. 15 shows the experimental protocol used to test the prophylactic effect of compound 6 on DNFB-induced symptoms in mice (repeated dosing).
Figure 16:
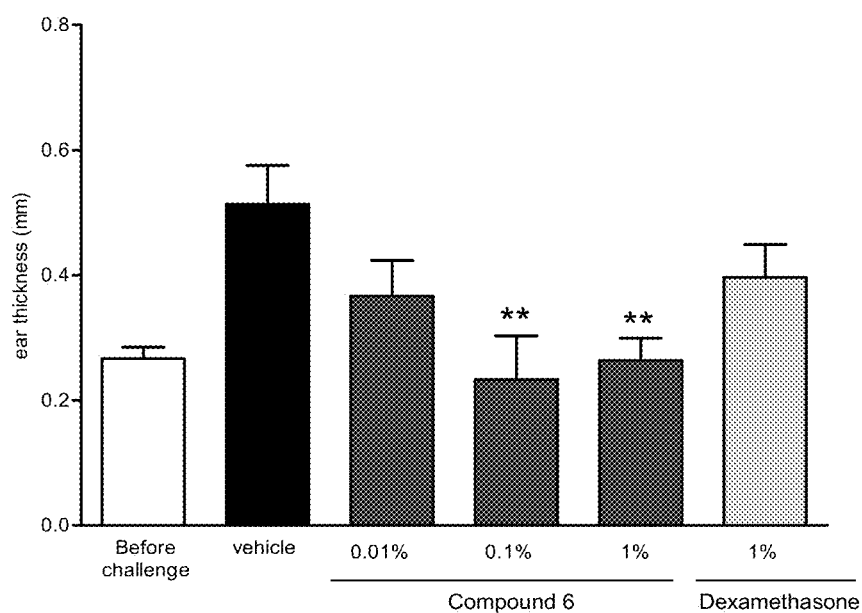
FIG. 16 shows that repeated administration of compound 6 prevents the development of DNFB-induced symptoms in mice.
Figure 17:
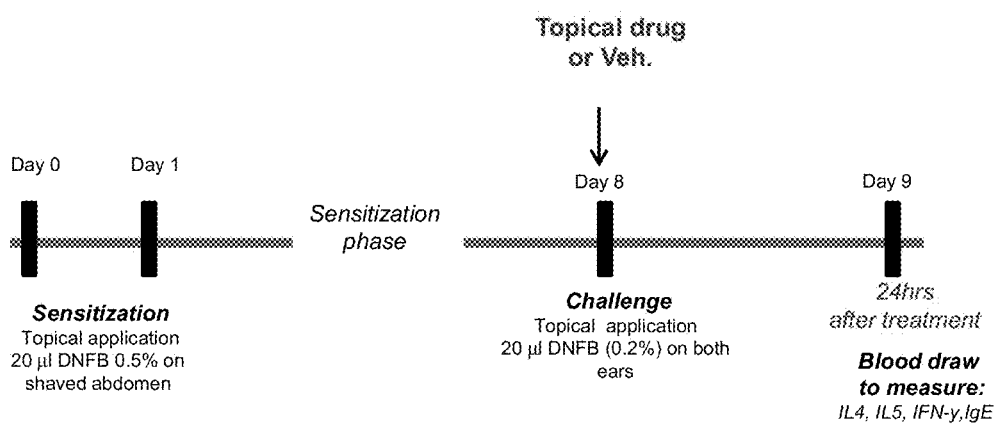
FIG. 17 shows the experimental protocol used to test the therapeutic effect of compound 6 on DNFB-induced dysregulation of the immune response in mice (single dosing).
Figure 18:
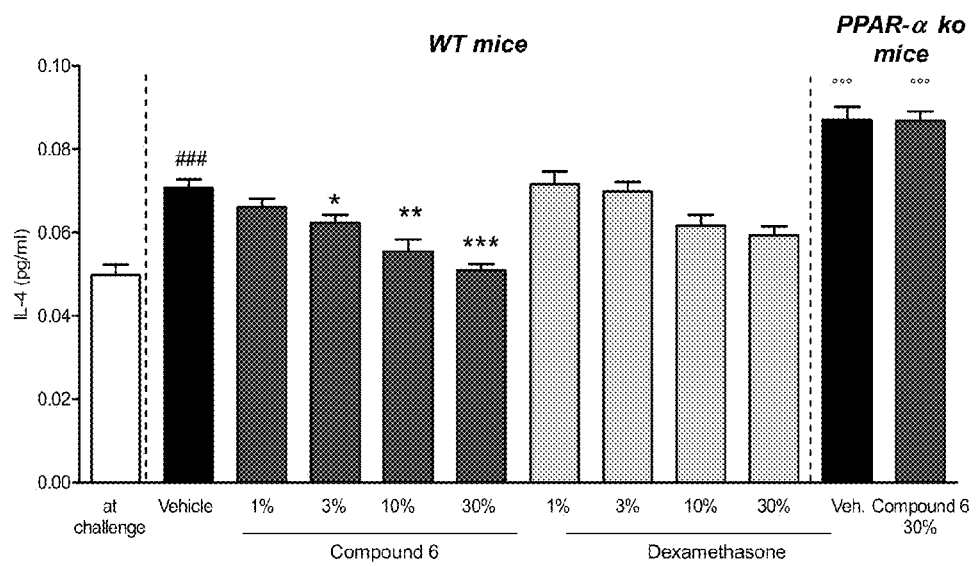
FIG. 18 shows that topical administration of compound 6 reverses DNFB-induced IL-4 increase through a PPAR-α mediated effect.
Figure 19:
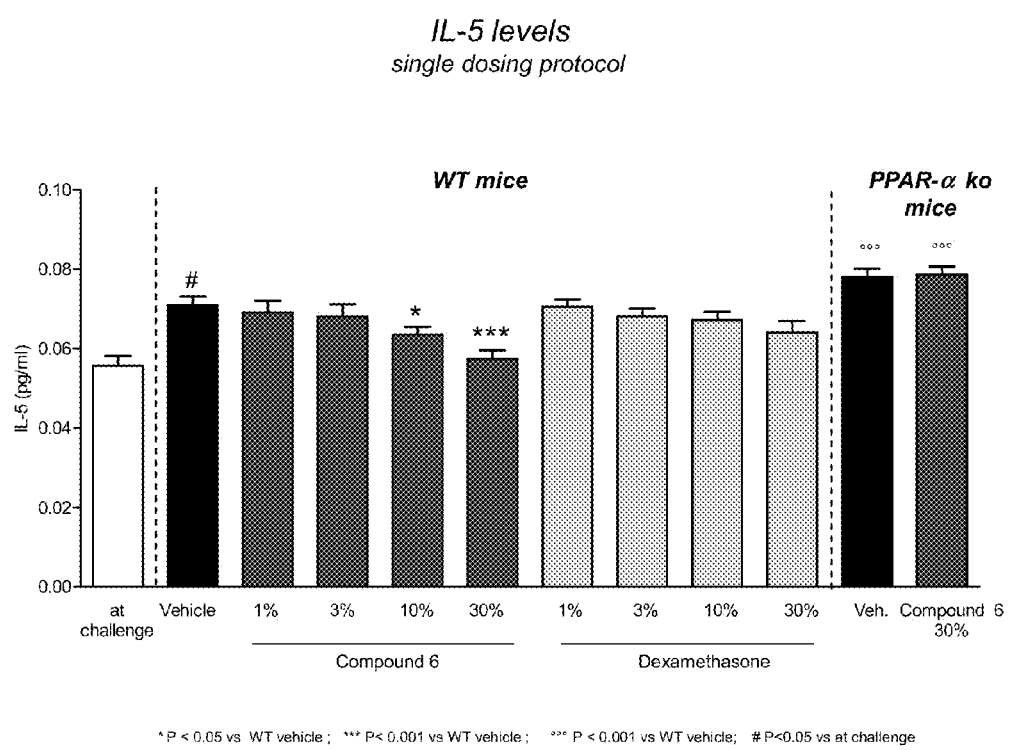
FIG. 19 shows that topical administration of compound 6 reverses DNFB-induced IL-5 increase through a PPAR-α mediated effect.
Figure 20:
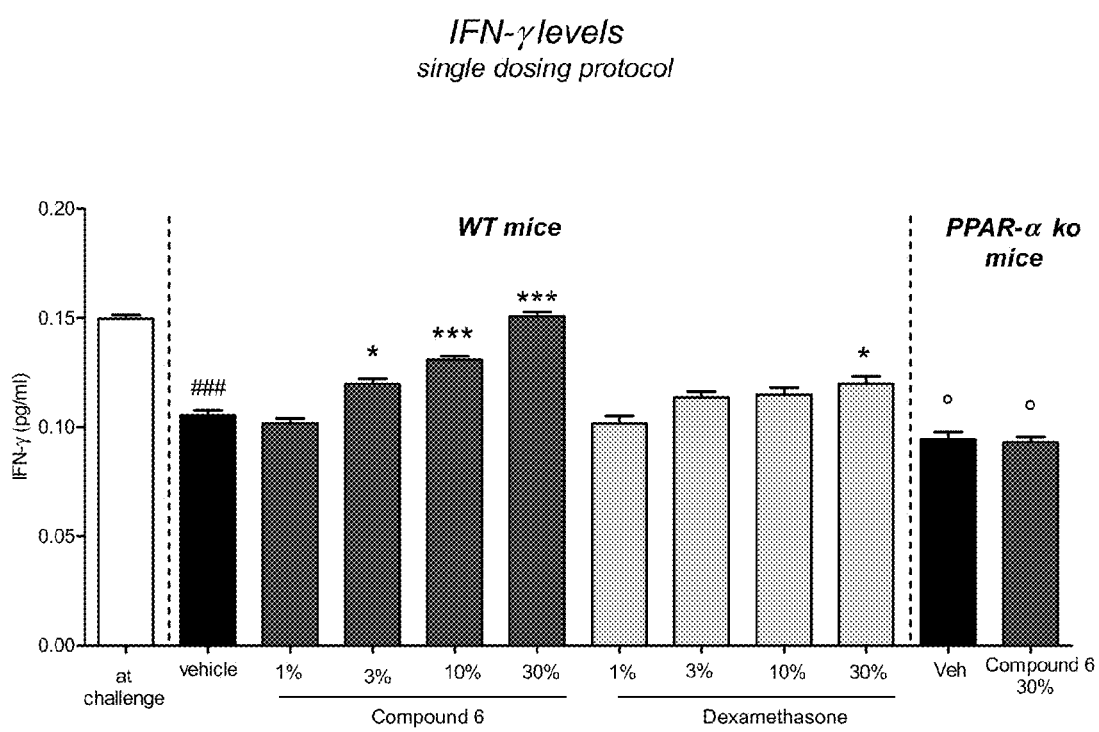
FIG. 20 shows that topical administration of compound 6 reverses DNFB-induced IFN-γ decrease through a PPAR-α mediated effect.
Figure 21:
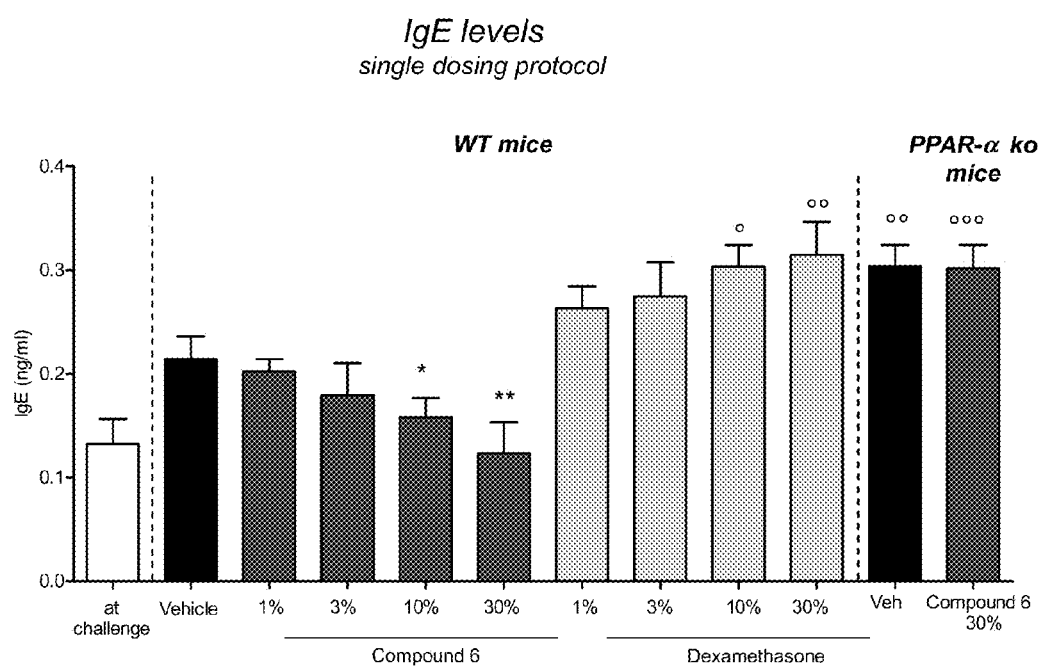
FIG. 21 shows that topical administration of compound 6 reverses DNFB-induced IgE increase through a PPAR-α mediated effect.
Figure 22:
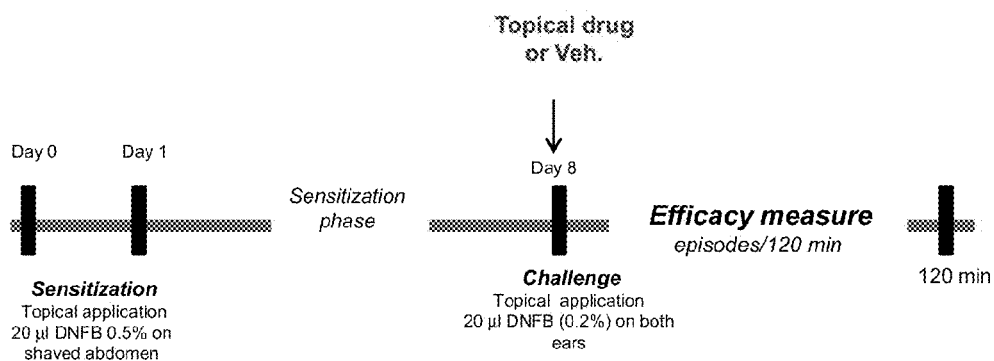
FIG. 22 shows the experimental protocol used to test the therapeutic effect of compound 6 (i.e., TSN1077) on DNFB-induced scratching (single dosing).
Figure 23:
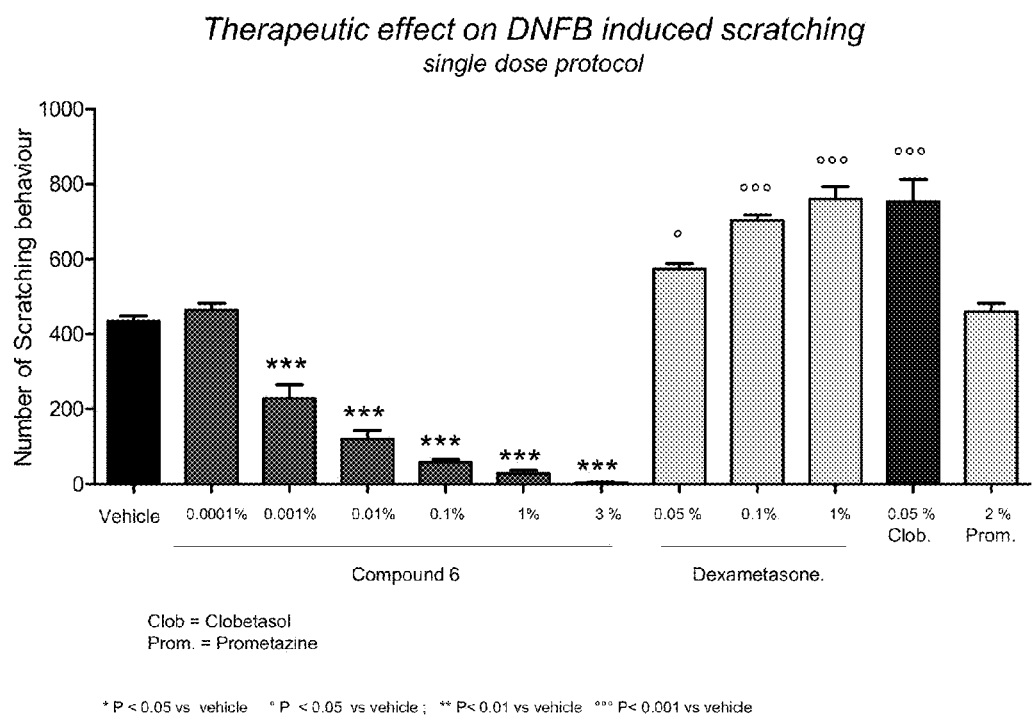
FIG. 23 shows that topical administration of compound 6 prevents DNFB-induced scratching. Dexametasone and clobetasol increased scratching while promethazine was without effect.
Figure 24:
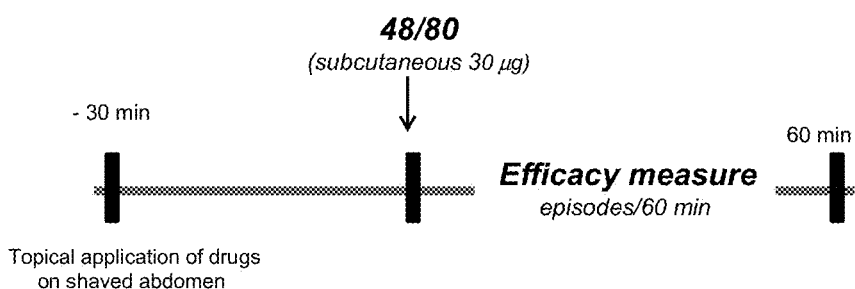
FIG. 24 shows the experimental protocol used to test the therapeutic effect of compound 6 (i.e., TSN1077) on compound 48/80-induced scratching in mice (single dosing).
Figure 25:
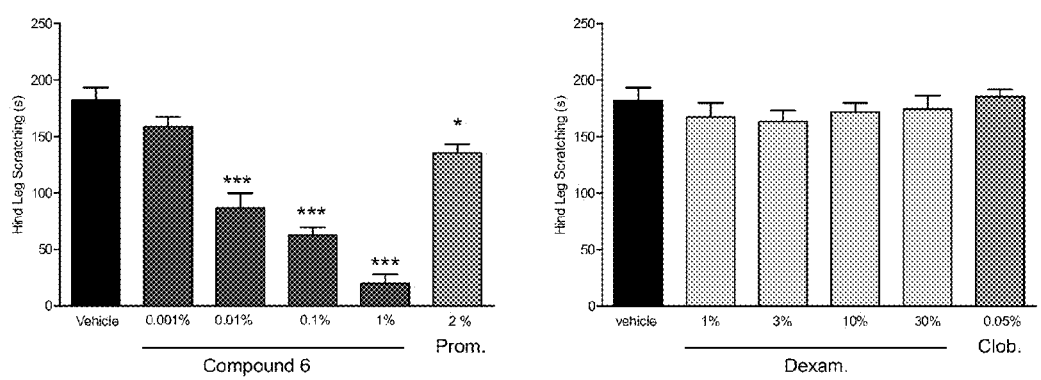
FIG. 25 shows that topical administration of compound 6 prevents 48/80-induced scratching. Promethazine was effective while dexamethasone and clobetasol were without effect.

Fresh drug suspensions of compound 6 were prepared immediately before use in a vehicle consisting of petrolatum plus 5% lauric acid and given in a volume of 20 µL/mouse. Mice were treated with different concentrations of compound 6 or vehicle together with DNFB challenge on day 8. Application of compound 6 (1-30% w/w suspension) dose-dependently inhibited ear swelling 24 h after the challenge, as shown in FIG. 2. Treatment with vehicle did not inhibit contact sensitivity response (***p<0.001 vs naïve group, and #p<0.05 ###p<0.001 vs vehicle group; Bonferroni's test).

Figure 26:
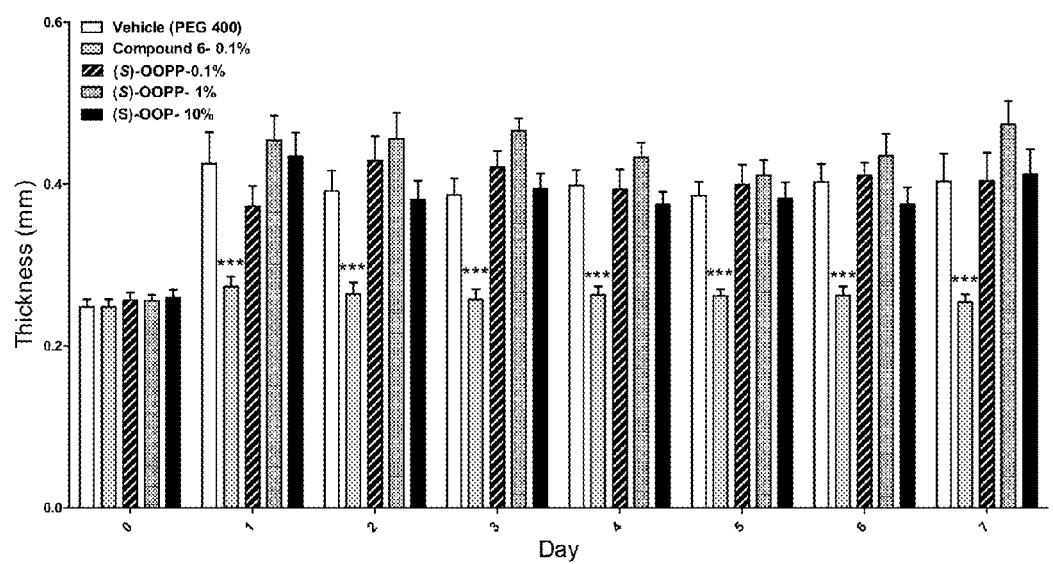
FIG. 26 shows that application of (S)-OOPP (0.1-10% w/v) did not inhibit contact sensitivity response, whereas 0.1% compound 6 produced a significant decrease in ear swelling.

Compound 6 and the reported β-lactone NAAA inhibitor (S)-OOPP (Solorzano et al., *Proceedings of the National Academy of Science USA* 2009, 106, 20966-20971; Solorzano et al., *Journal of Medicinal Chemistry* 2010, 53, 5770-5781) were tested in this model for their contact sensitivity response. Fresh drug solutions of (S)-OOPP and compound 6 were prepared immediately before use in polyethylene glycol 400 (PEG 400) and given in a volume of 20 µL/ear. Mice were treated with different concentrations of (S)-OOPP, 0.1% compound 6 or vehicle each day for 7 days. Ear thickness was determined on day 0 and every day before challenge using a caliper. Results are expressed as absolute ear thickness. Application of (S)-OOPP (0.1-10% w/v) did not inhibit contact sensitivity response, whereas 0.1% compound 6 produced a significant decrease in ear swelling, as shown in FIG. 26 (*** p<0.001 vs naïve group, 2Way ANOVA followed by Bonferroni's post-test).

(S)-OOPP is N-[(3S)-2-oxo-3-oxetanyl]-3-phenylpropanamide, e.g.,

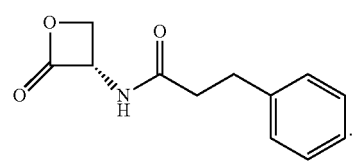 [SMILES: O=C(CCc1ccccc1)N[C@H]1COC1=O]

General Purification and Analytical Methods

UPLC/MS analyses were run on a Waters ACQUITY UPLC/MS instrument consisting of a SQD Single Quadropole Mass Spectrometer equipped with an electrospray ionization interface and a photodiode array detector. The analyses were performed on an ACQUITY UPLC BEH C18 column (50×2.1 mmID, particle size 1.7 μm) with a VanGuard BEH C18 pre-column (5×2.1 mmID, particle size 1.7 μm). The mobile phases were 10 mM NH4OAc at pH 5 adjusted with AcOH (A) and 10 mM NH$_4$OAc in MeCN—H2O (95:5) at pH 5 (B). Electrospray ionization in positive and negative mode was used in the mass scan range 100-500 Da.

Automated column chromatography purification was done using a Teledyne ISCO apparatus (CombiFlash® Rf) with normal phase pre-packed silica gel columns of different sizes (from 4 g until 120 g). Typical silica gel column chromatography is intended as a purification performed using normal glass columns filled with Merck silica gel 60 (230-400 mesh) as stationary phase. In both cases, mixtures of increasing polarity of cyclohexane and TBME or ethyl acetate were used as eluents.

Purifications by preparative HPLC/MS were run on a Waters Autopurification system consisting of a 3100 Single Quadropole Mass Spectrometer equipped with an electrospray ionization interface and a 2998 Photodiode Array Detector. The HPLC system included a 2747 Sample Manager, 2545 Binary Gradient Module, System Fluidic Organizer and 515 HPLC Pump. The purifications were performed on a XBridge™ Prep C$_{18}$ OBD column (100×19 mmID, particle size 5 nm) with a XBridge™ Prep C$_{18}$ (10×19 mmID, particle size 5 nm) Guard Cartridge. The mobile phases were either 1) H$_2$O and MeCN (B) or 2) 10 mM NH$_4$OAc at pH 5 adjusted with AcOH (A) and 10 mM NH$_4$OAc in MeCN—H$_2$O (95:5) at pH 5 (B). Electrospray ionization in positive and negative mode was used in the mass scan range 100-500 Da.

Hydrogenation reactions were performed using H-Cube® continuos hydrogenation equipment (SS-reaction line version), employing disposable catalyst cartridges (CatCart®) preloaded with the required heterogeneous catalyst.

Microwave heating was performed using Explorer®-48 positions instrument (CEM).

FTIR were recorded on Jasco FT/1R-420 Fourier transform infrared spectrometer.

NMR experiments were run on a Bruker Avance III 400 system (400.13 MHz for 1H, and 100.62 MHz for 13C), equipped with a BBI inverse probe and Z-gradients. Unless indicated, spectra were acquired at 300 K, using deuterated dimethylsulfoxyde (DMSO-d$_6$) and deuterated chloroform (CDCl$_3$) as solvents.

With the aim to better illustrate the present invention, without limiting it, the examples reported in Table 4 are provided.

TABLE 4

Examples of compounds of the invention

| Example | Structure | Formula | Name |
|---|---|---|---|
| 1 | 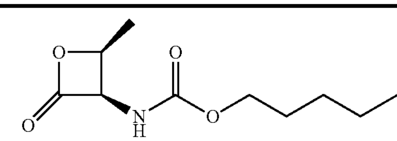 | $C_{10}H_{17}NO_4$ | Pentyl-[(2S,3R)-2-methyl-4-oxooxetan-3-yl]-carbamate |
| 2 | 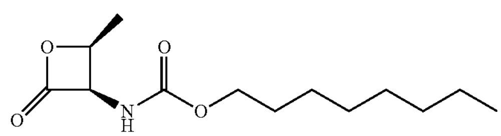 [SMILES: CCCCCCCCOC(=O)N[C@H]1C(=O)O[C@H]1C] | $C_{13}H_{23}NO_4$ | Octyl-[(2S,3R)-2-methyl-4-oxooxetan-3-yl]-carbamate |
| 3 | 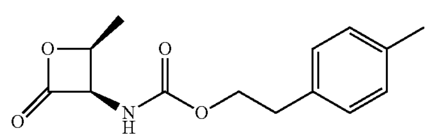 [SMILES: Cc1ccc(CCOC(=O)N[C@H]2C(=O)O[C@H]2C)cc1] | $C_{14}H_{17}NO_4$ | 2-(4-methylphenyl)-ethyl-[(2S,3R)-2-methyl-4-oxooxetan-3-yl]-carbamate |
| 4 | 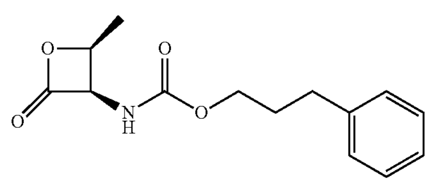 [SMILES: C[C@@H]1OC(=O)[C@@H]1NC(=O)OCCCc1ccccc1] | $C_{14}H_{17}NO_4$ | 3-phenylpropyl-[(2S,3R)-2-methyl-4-oxooxetan-3-yl]-carbamate |
| 5 | 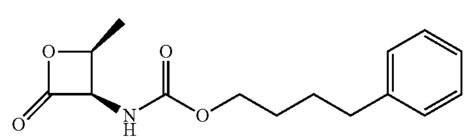 [SMILES: C[C@@H]1OC(=O)[C@@H]1NC(=O)OCCCCc1ccccc1] | $C_{15}H_{19}NO_4$ | 4-phenylbutyl-[(2S,3R)-2-methyl-4-oxooxetan-3-yl]-carbamate |
| 6 | 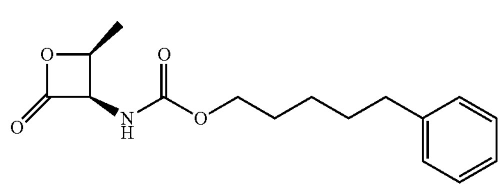 [SMILES: C[C@@H]1OC(=O)[C@@H]1NC(=O)OCCCCCc1ccccc1] | $C_{16}H_{21}NO_4$ | 5-phenylpentyl-[(2S,3R)-2-methyl-4-oxooxetan-3-yl]-carbamate |

TABLE 4-continued

Examples of compounds of the invention

| Example | Structure | Formula | Name |
|---|---|---|---|
| 7 | 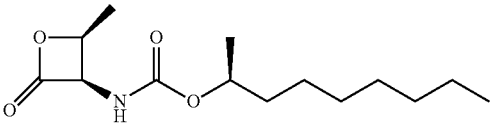 [SMILES: CCCCCCC[C@H](C)OC(=O)N[C@H]1C(=O)O[C@H]1C] | $C_{14}H_{25}NO_4$ | [(1S)-1-methyloctyl]-N-[(2S,3R)-2-methyl-4-oxo-oxetan-3-yl]-carbamate |
| 8 | 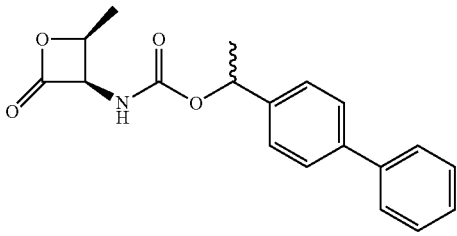 [SMILES: CC(OC(=O)N[C@H]1C(=O)O[C@H]1C)c1ccc(-c2ccccc2)cc1] | $C_{19}H_{19}NO_4$ | (1S) and (1R)-1-(4-phenylphenyl)-ethyl-N-[(2S,3R)-2-methyl-4-oxo-oxetan-3-yl]-carbamate |
| 9 | 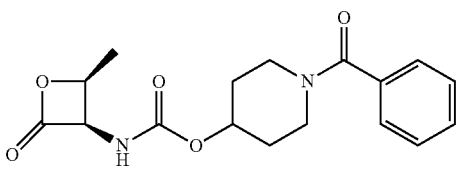 [SMILES: C[C@@H]1OC(=O)[C@@H]1NC(=O)OC1CCN(C(=O)c2ccccc2)CC1] | $C_{17}H_{20}N_2O_5$ | (1-benzoyl-4-piperidyl)-N-[(2S,3R)-2-methyl-4-oxo-oxetan-3-yl]-carbamate |
| 10 | 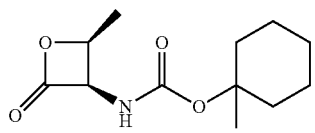 [SMILES: C[C@@H]1OC(=O)[C@@H]1NC(=O)OC1(C)CCCCC1] | $C_{12}H_{19}NO_4$ | (1-methylcyclohexyl)-[(2S,3R)-2-methyl-4-oxo-oxetan-3-yl]-carbamate |
| 11 | 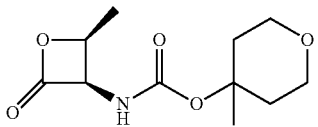 | $C_{11}H_{17}NO_5$ | 4-methyltetrahydropyran-4-yl)-N-[(2S,3R)-2-methyl-4-oxo-oxetan-3-yl]-carbamate |
| 12 | 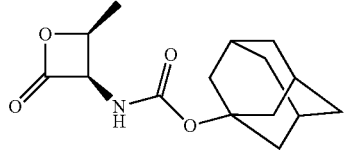 [SMILES: C[C@@H]1OC(=O)[C@@H]1NC(=O)OC12CC3CC(CC(C3)C1)C2] | $C_{15}H_{21}NO_4$ | Tricyclo[3.3.1.1$^{3,7}$]dec-1-yl [(2S,3R)-2-methyl-4-oxooxetan-3-yl]carbamate |
| 13 | 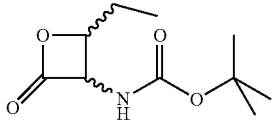 | $C_{10}H_{17}NO_4$ | tert-Butyl-N-[(2S*,3R*)-2-ethyl-4-oxo-oxetan-3-yl]-carbamate and tert-Butyl-N-(2S*,3S*)-2-ethyl-4-oxo-oxetan-3-yl]-carbamate |
| 14 | 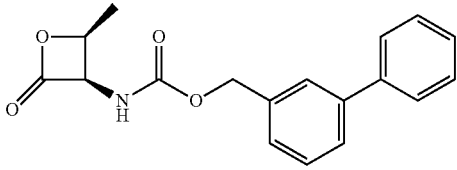 [SMILES: C[C@@H]1OC(=O)[C@@H]1NC(=O)OCc1cccc(-c2ccccc2)c1] | $C_{15}H_{17}NO_4$ | (3-phenylphenyl)-methyl-N-[(2S,3R)-2-methyl-4-oxo-oxetan-3-yl]-carbamate |
| 15 | 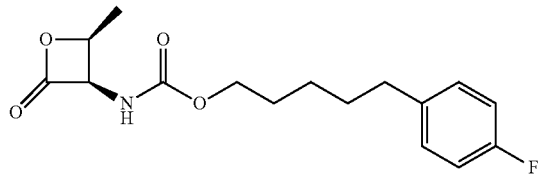 [SMILES: C[C@@H]1OC(=O)[C@@H]1NC(=O)OCCCCCc1ccc(F)cc1] | $C_{16}H_{20}FNO_4$ | 5-(4-fluorophenyl)-pentyl-N-[(2S,3R)-2-methyl-4-oxo-oxetan-3-yl]-carbamate |

TABLE 4-continued

Examples of compounds of the invention

| Example | Structure | Formula | Name |
|---|---|---|---|
| 16 | 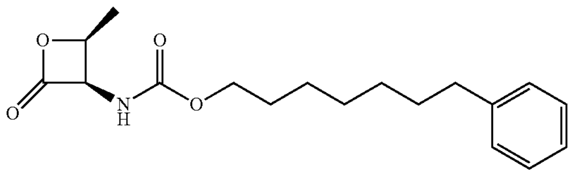 [SMILES: C[C@@H]1OC(=O)[C@@H]1NC(=O)OCCCCCCCc1ccccc1] | $C_{18}H_{25}NO_4$ | 7-phenylheptyl-N-[(2S,3R)-2-methyl-4-oxo-oxetan-3-yl]carbamate |
| 17 | 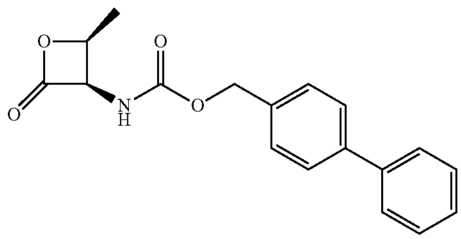 [SMILES: C[C@@H]1OC(=O)[C@@H]1NC(=O)OCc1ccc(-c2ccccc2)cc1] | $C_{18}H_{17}NO_4$ | (4-phenylphenyl)methyl-N-[(2S,3R)-2-methyl-4-oxo-oxetan-3-yl]-carbamate |
| 18 | 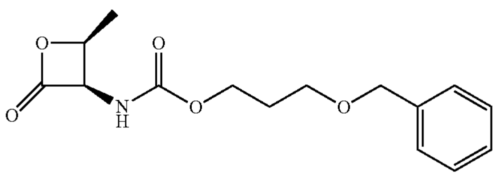 | $C_{15}H_{19}NO_5$ | 3-benzyloxypropyl-N-[(2S,3R)-2-methyl-4-oxo-oxetan-3-yl]-carbamate |
| 19 | 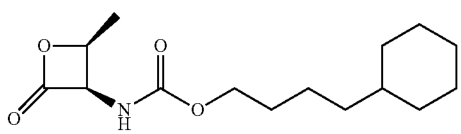 [SMILES: C[C@@H]1OC(=O)[C@@H]1NC(=O)OCCCCC1CCCCC1] | $C_{15}H_{25}NO_4$ | 4-cyclohexylbutyl-N-[(2S,3R)-2-methyl-4-oxo-oxetan-3-yl]-carbamate |
| 20 | 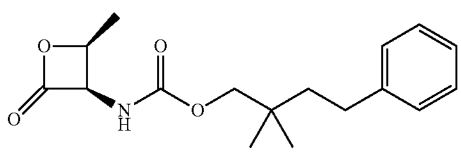 [SMILES: C[C@@H]1OC(=O)[C@@H]1NC(=O)OCC(C)(C)CCc1ccccc1] | $C_{17}H_{23}NO_4$ | (2,2-dimethyl-4-phenyl-butyl)-N-[(2S,3R)-2-methyl-4-oxo-oxetan-3-yl]-carbamate |
| 21 | 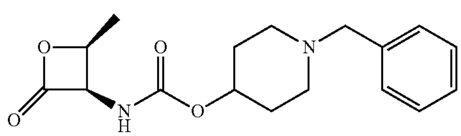 [SMILES: C[C@@H]1OC(=O)[C@@H]1NC(=O)OC1CCN(Cc2ccccc2)CC1] | $C_{17}H_{22}N_2O_4$ | (1-benzyl-4-piperidyl)-N-[(2S,3R)-2-methyl-4-oxo-oxetan-3-yl]-carbamate |
| 22 | 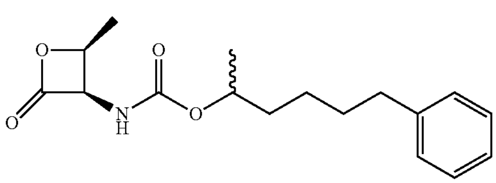 [SMILES: CC(CCCCc1ccccc1)OC(=O)N[C@H]1C(=O)O[C@H]1C] | $C_{17}H_{23}NO_4$ | [(1R) and (1S)-1-methyl-5-phenyl-pentyl]-N-[(2S,3R)-2-methyl-4-oxo-oxetan-3-yl]-carbamate |
| 23 | 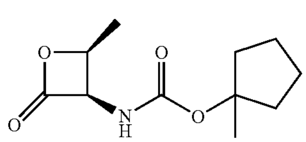 [SMILES: C[C@@H]1OC(=O)[C@@H]1NC(=O)OC1(C)CCCC1] | $C_{11}H_{17}NO_4$ | (1-methylcyclopentyl) N-[(2S,3R)-2-methyl-4-oxo-oxetan-3-yl]-carbamate |
| 24 | 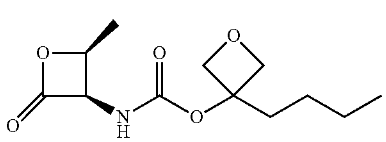 [SMILES: CCCCC1(OC(=O)N[C@H]2C(=O)O[C@H]2C)COC1] | $C_{12}H_{19}NO_5$ | (3-butyloxetan-3-yl)-N-[(2S,3R)-2-methyl-4-oxo-oxetan-3-yl]-carbamate |

TABLE 4-continued

Examples of compounds of the invention

| Example | Structure | Formula | Name |
|---|---|---|---|
| 25 | 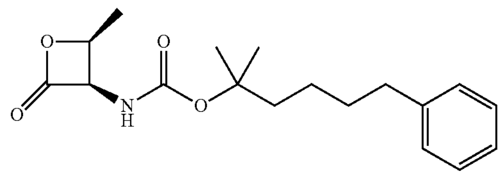 [SMILES: C[C@@H]1OC(=O)[C@@H]1NC(=O)OC(C)(C)CCCCc1ccccc1] | $C_{18}H_{25}NO_4$ | (1,1-dimethyl-5-phenyl-pentyl)-N-[(2S,3R)-2-methyl-4-oxo-oxetan-3-yl]-carbamate |
| 26 | 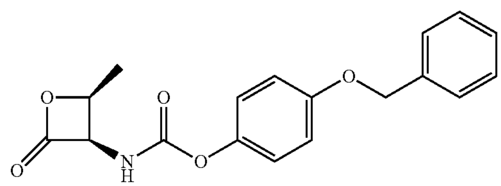 [SMILES: C[C@@H]1OC(=O)[C@@H]1NC(=O)Oc1ccc(OCc2ccccc2)cc1] | $C_{18}H_{17}NO_5$ | (4-benzyloxyphenyl)-N-[(2S,3R)-2-methyl-4-oxo-oxetan-3-yl]-carbamate |
| 27 | 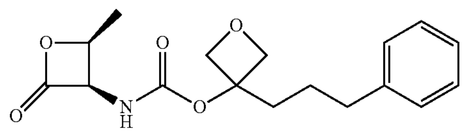 [SMILES: C[C@@H]1OC(=O)[C@@H]1NC(=O)OC1(CCCc2ccccc2)COC1] | $C_{17}H_{21}NO_5$ | [3-(4-phenylbutyl)oxetan-3-yl]-N-[(2S,3R)-2-methyl-4-oxo-oxetan-3-yl]-carbamate |
| 28 | 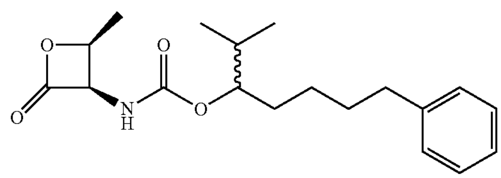 [SMILES: CC(C)C(CCCCc1ccccc1)OC(=O)N[C@H]1C(=O)O[C@H]1C] | $C_{19}H_{27}NO_4$ | (1-isopropyl-5-phenyl-pentyl)-N-[(2S,3R)-2-methyl-4-oxo-oxetan-3-yl]-carbamate |
| 29 | 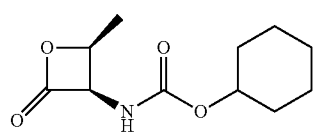 [SMILES: C[C@@H]1OC(=O)[C@@H]1NC(=O)OC1CCCCC1] | $C_{11}H_{17}NO_4$ | Cyclohexyl-N-(2S,3R)-2-methyl-4-oxooxetan-3-yl]-carbamate |
| 30 | 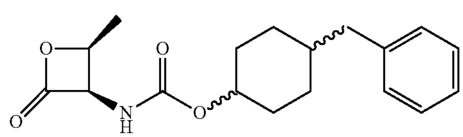 [SMILES: C[C@@H]1OC(=O)[C@@H]1NC(=O)OC1CCC(Cc2ccccc2)CC1] | $C_{18}H_{23}NO_4$ | (1s,4S) and (1r,4R)-(4-Benzylcyclohexyl)-N-[(2S,3R)-2-methyl-4-oxooxetan-3-yl]-carbamate |
| 31 | 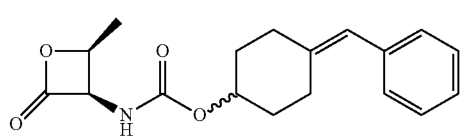 [SMILES: C[C@@H]1OC(=O)[C@@H]1NC(=O)OC1CCC(=Cc2ccccc2)CC1] | $C_{18}H_{21}NO_4$ | (R,Z) and (S,E)-(4-Benzylidenecyclohexyl)-N-[(2S,3R)-2-methyl-4-oxooxetan-3-yl]-carbamate |
| 32 | 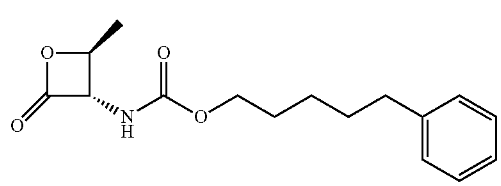 [SMILES: C[C@@H]1OC(=O)[C@H]1NC(=O)OCCCCCc1ccccc1] | $C_{16}H_{21}NO_4$ | 5-Phenylpentyl-N-[(2S,3S)-2-methyl-4-oxooxetan-3-yl]-carbamate |
| 33 | 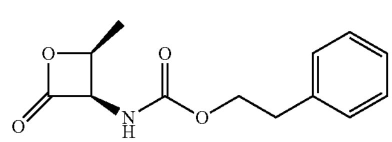 [SMILES: C[C@@H]1OC(=O)[C@@H]1NC(=O)OCCc1ccccc1] | $C_{13}H_{15}NO_4$ | Phenethyl-N-[(2S,3R)-2-methyl-4-oxo-oxetan-3-yl]-carbamate |

TABLE 4-continued

Examples of compounds of the invention

| Example | Structure | Formula | Name |
|---|---|---|---|
| 34 | 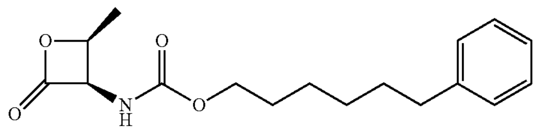 [SMILES: C[C@@H]1OC(=O)[C@@H]1NC(=O)OCCCCCCc1ccccc1] | $C_{17}H_{23}NO_4$ | 6-phenylhexyl-N-[(2S,3R)-2-methyl-4-oxo-oxetan-3-yl]-carbamate |
| 35 | 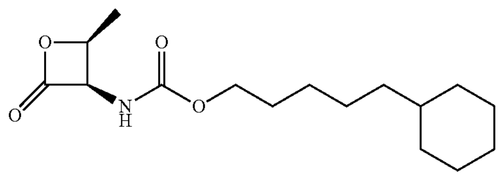 [SMILES: C[C@@H]1OC(=O)[C@@H]1NC(=O)OCCCCCC1CCCCC1] | $C_{16}H_{27}NO_4$ | 5-Cyclohexylpentyl-N-[(2S,3R)-2-methyl-4-oxo-oxetan-3-yl]-carbamate |
| 36 | 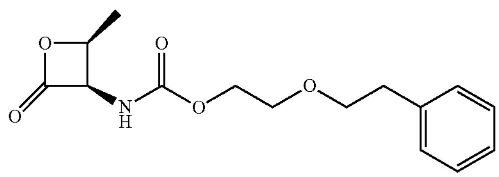 | $C_{15}H_{19}NO_5$ | 2-phenethyloxyethyl-N-[(2S,3R)-2-methyl-4-oxo-oxetan-3-yl]carbamate |
| 37 | 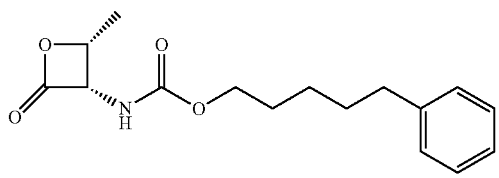 [SMILES: C[C@H]1OC(=O)[C@H]1NC(=O)OCCCCCc1ccccc1] | $C_{16}H_{21}NO_4$ | 5-Phenylpentyl-N-[(2R,3S)-2-methyl-4-oxo-oxetan-3-yl]-carbamate |
| 38 | 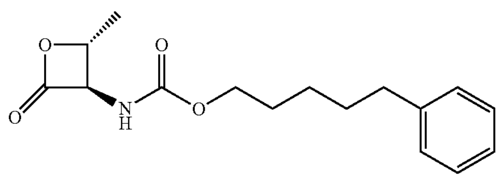 [SMILES: C[C@H]1OC(=O)[C@@H]1NC(=O)OCCCCCc1ccccc1] | $C_{16}H_{21}NO_4$ | 5-Phenylpentyl-N-[(2R,3R)-2-methyl-4-oxo-oxetan-3-yl]-carbamate |
| 39 | 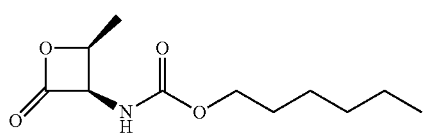 [SMILES: CCCCCCOC(=O)N[C@H]1C(=O)O[C@H]1C] | $C_{11}H_{19}NO_4$ | Hexyl-N-[(2S,3R)-2-methyl-4-oxo-oxetan-3-yl]-carbamate |
| 40 | 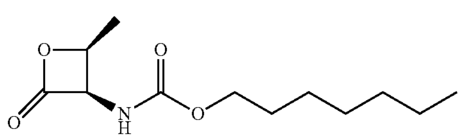 [SMILES: CCCCCCCOC(=O)N[C@H]1C(=O)O[C@H]1C] | $C_{12}H_{21}NO_4$ | Heptyl-N-[(2S,3R)-2-methyl-4-oxo-oxetan-3-yl]-carbamate |
| 41 | 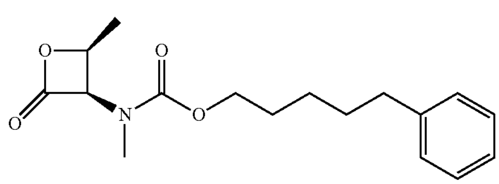 [SMILES: C[C@@H]1OC(=O)[C@@H]1N(C)C(=O)OCCCCCc1ccccc1] | $C_{17}H_{23}NO_4$ | 5-Phenylpentyl-N-methyl-N-[(2S,3R)-2-methyl-4-oxo-oxetan-3-yl]-carbamate |

TABLE 4-continued

Examples of compounds of the invention

| Example | Structure | Formula | Name |
|---------|-----------|---------|------|
| 42 | 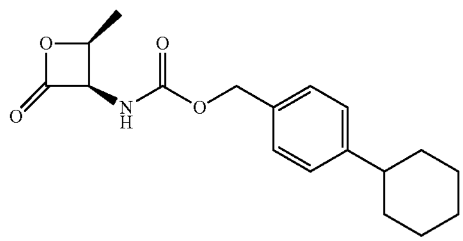 [SMILES: C[C@@H]1OC(=O)[C@@H]1NC(=O)OCc1ccc(C2CCCCC2)cc1] | $C_{18}H_{23}NO_4$ | (4-Cyclohexylphenyl)-methyl-N-[(2S,3R)-2-methyl-4-oxo-oxetan-3-yl]-carbamate |
| 43 | 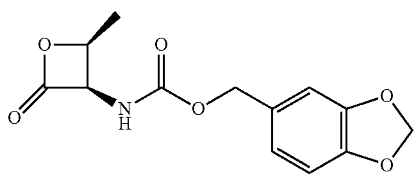 [SMILES: C[C@@H]1OC(=O)[C@@H]1NC(=O)OCc1ccc2c(c1)OCO2] | $C_{13}H_{13}NO_6$ | 1,3-Benzodioxol-5-yl-methyl-N-[(2S,3R)-2-methyl-4-oxo-oxetan-3-yl]-carbamate |
| 44 | 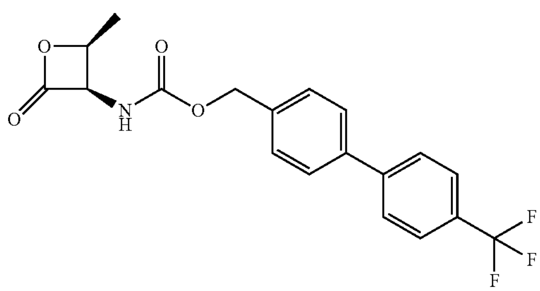 [SMILES: C[C@@H]1OC(=O)[C@@H]1NC(=O)OCc1ccc(-c2ccc(C(F)(F)F)cc2)cc1] | $C_{19}H_{16}F_3NO_4$ | [4-[4-(Trifluoromethyl)-phenyl]-phenyl]-methyl-N-[(2S,3R)-2-methyl-4-oxo-oxetan-3-yl]-carbamate |
| 45 | 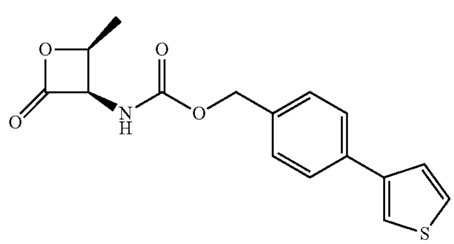 [SMILES: C[C@@H]1OC(=O)[C@@H]1NC(=O)OCc1ccc(-c2ccsc2)cc1] | $C_{16}H_{15}NO_4S$ | [4-(3-Thienyl)-phenyl]-methyl-N-[(2S,3R)-2-methyl-4-oxo-oxetan-3-yl]-carbamate |
| 46 | 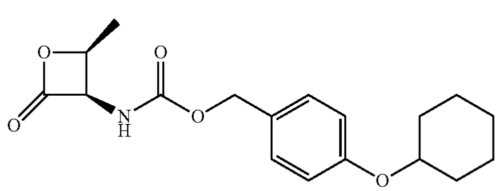 [SMILES: C[C@@H]1OC(=O)[C@@H]1NC(=O)OCc1ccc(OC2CCCCC2)cc1] | $C_{18}H_{23}NO_5$ | [4-(Cyclohexoxy)-phenyl]-methyl-N-[(2S,3R)-2-methyl-4-oxo-oxetan-3-yl]-carbamate. |
| 47 | 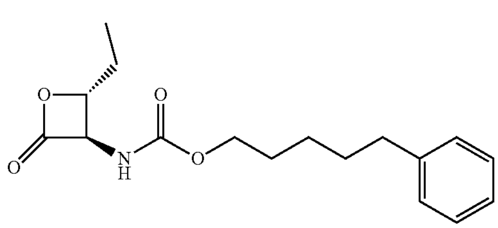 [SMILES: CC[C@H]1OC(=O)[C@@H]1NC(=O)OCCCCCc1ccccc1] | $C_{17}H_{23}NO_4$ | 5-Phenylpentyl-N-[(2R*,3R*)-2-ethyl-4-oxo-oxetan-3-yl]-carbamate |

TABLE 4-continued

Examples of compounds of the invention

| Example | Structure | Formula | Name |
|---|---|---|---|
| 48 | 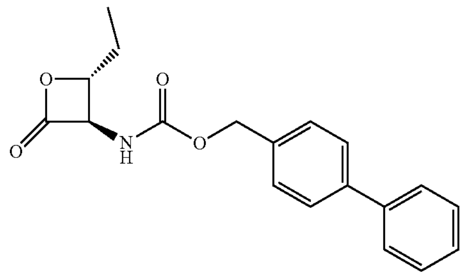 [SMILES: CC[C@H]1OC(=O)[C@@H]1NC(=O)OCc1ccc(-c2ccccc2)cc1] | $C_{19}H_{19}NO_4$ | (4-Phenylphenyl)-methyl-N-[(2R*,3R*)-2-ethyl-4-oxo-oxetan-3-yl]-carbamate |
| 49 | 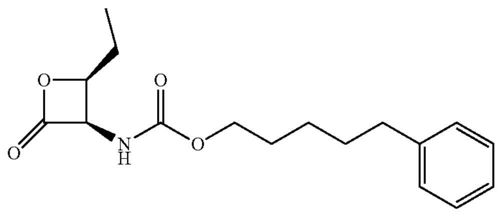 [SMILES: CC[C@@H]1OC(=O)[C@@H]1NC(=O)OCCCCCc1ccccc1] | $C_{17}H_{23}NO_4$ | 5-Phenylpentyl-N-[(2S*,3R*)-2-ethyl-4-oxo-oxetan-3-yl]-carbamate |
| 50 | 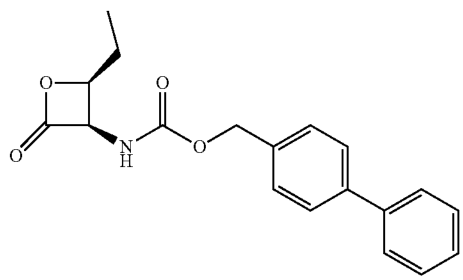 [SMILES: CC[C@@H]1OC(=O)[C@@H]1NC(=O)OCc1ccc(-c2ccccc2)cc1] | $C_{19}H_{19}NO_4$ | (4-Phenylphenyl)-methyl-N-[(2S*,3R*)-2-ethyl-4-oxo-oxetan-3-yl]-carbamate |
| 51 | 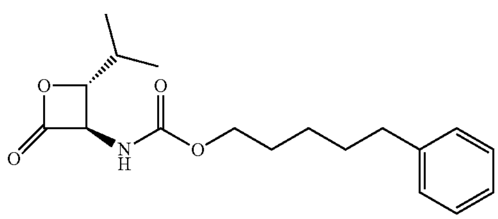 [SMILES: CC(C)[C@H]1OC(=O)[C@@H]1NC(=O)OCCCCCc1ccccc1] | $C_{18}H_{25}NO_4$ | 5-Phenylpentyl-N-[(2R*,3R*)-2-isopropyl-4-oxo-oxetan-3-yl]-carbamate |
| 52 | 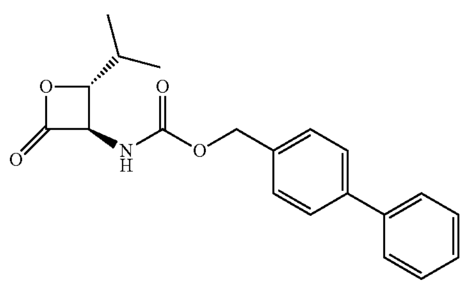 [SMILES: CC(C)[C@H]1OC(=O)[C@@H]1NC(=O)OCc1ccc(-c2ccccc2)cc1] | $C_{20}H_{21}NO_4$ | (4-Phenylphenyl)-methyl-N-[(2R*,3R*)-2-isopropyl-4-oxo-oxetan-3-yl]-carbamate |
| 53 | 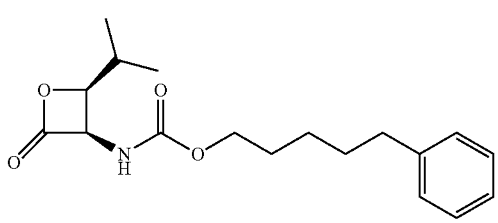 [SMILES: CC(C)[C@@H]1OC(=O)[C@@H]1NC(=O)OCCCCCc1ccccc1] | $C_{18}H_{25}NO_4$ | 5-Phenylpentyl-N-[(2S*,3R*)-2-isopropyl-4-oxo-oxetan-3-yl]-carbamate |

TABLE 4-continued

Examples of compounds of the invention

| Example | Structure | Formula | Name |
|---------|-----------|---------|------|
| 54 | 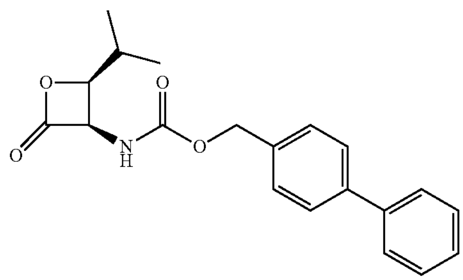 [SMILES: CC(C)[C@@H]1OC(=O)[C@@H]1NC(=O)OCc1ccc(-c2ccccc2)cc1] | $C_{20}H_{21}NO_4$ | (4-Phenylphenyl)-methyl-N-[(2S*,3R*)-2-isopropyl-4-oxo-oxetan-3-yl]-carbamate |
| 55 | 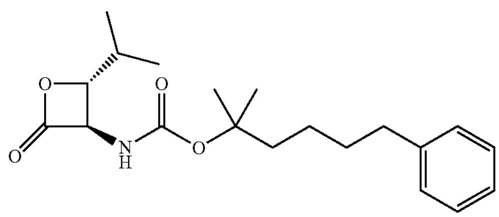 [SMILES: CC(C)[C@H]1OC(=O)[C@@H]1NC(=O)OC(C)(C)CCCCc1ccccc1] | $C_{20}H_{29}NO_4$ | (1,1-Dimethyl-5-phenyl-pentyl)-N-[(2R*,3R*)-2-isopropyl-4-oxo-oxetan-3-yl]-carbamate |
| 56 | 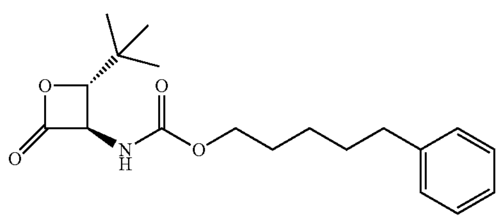 [SMILES: CC(C)(C)[C@H]1OC(=O)[C@@H]1NC(=O)OCCCCCc1ccccc1] | $C_{19}H_{27}NO_4$ | 5-Phenylpentyl-N-[(2R*,3R*)-2-tert-butyl-4-oxo-oxetan-3-yl]-carbamate |
| 57 | 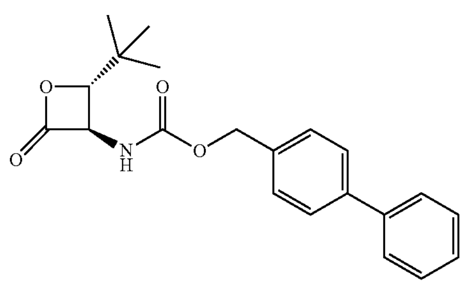 [SMILES: CC(C)(C)[C@H]1OC(=O)[C@@H]1NC(=O)OCc1ccc(-c2ccccc2)cc1] | $C_{21}H_{23}NO_4$ | (4-Phenylphenyl)-methyl-N-[(2R*,3R*)-2-tert-butyl-4-oxo-oxetan-3-yl]-carbamate |
| 58 | 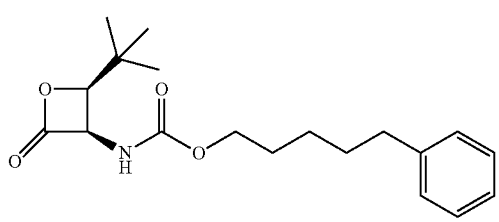 [SMILES: CC(C)(C)[C@@H]1OC(=O)[C@@H]1NC(=O)OCCCCCc1ccccc1] | $C_{19}H_{27}NO_4$ | 5-Phenylpentyl-N-[(2S*,3R*)-2-tert-butyl-4-oxo-oxetan-3-yl]-carbamate |
| 59 | 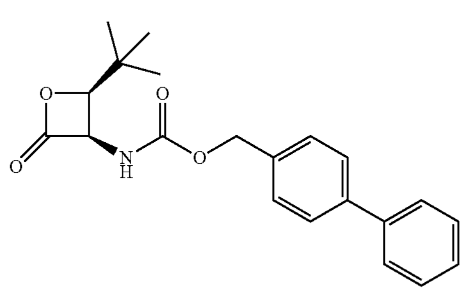 [SMILES: CC(C)(C)[C@@H]1OC(=O)[C@@H]1NC(=O)OCc1ccc(-c2ccccc2)cc1] | $C_{21}H_{23}NO_4$ | (4-Phenylphenyl)-methyl-N-[(2S*,3R*)-2-tert-butyl-4-oxo-oxetan-3-yl]-carbamate |

The compounds reported in Table 4 were synthesized as described below.

Solvents and reagents were obtained from commercial suppliers and were used without further purification. For simplicity, solvents and reagents were indicated as follows.

Tetrahydrofuran (THF), diethyl ether (Et$_2$O), ethyl acetate (AcOEt), dichlorometane (CH$_2$Cl$_2$), dimethylsulfoxyde (DMSO) hydrochloric acid (HCl), cyclohexane (Cy), acetic acid (CH$_3$COOH), trifluoroacetic acid (TFA), N,N-dimethylformamide (DMF), triethylamine (Et$_3$N), methanol (MeOH), acetonitrile (CH$_3$CN), methyl tert-butyl ether (MTBE), ethanol (EtOH), N,N-Diisopropylethylamine (DIPEA), sodium bicarbonate (NaHCO$_3$), sodium solfate (Na$_2$SO$_4$), sodium hydroxide (NaOH), ammonium chloride (NH$_4$Cl), silica gel (SiO$_2$), sodium nitrite (NaNO$_2$), sodium carbonate (Na$_2$CO$_3$), potassium carbonate (K$_2$CO$_3$), potassium hydrogen sulfate (KHSO$_4$), 4-(dimethylamino)-pyridine (DMAP), di-2-pyridyl carbonate (2-DPC), carbonyl-diimidazole (CDI), lithium bis-(trimethylsilyl)-amide (LHMDS), n-butyllithium (BuLi), lithium aluminum hydride (LiAlH$_4$), sodium borohydride (NaBH$_4$), benzotriazol-1-yl-oxytripyrrolidinophosphonium hexafluorophosphate (PyBOP), O-benzotriazole-N,N,N',N'-tetramethyl-uronium hexafluorophosphate (HBTU), O-(benzotriazol-1-yl)-N,N,N',N'-tetra methyluronium tetra fluoroborate (TBTU), 1,3-dimethyl-3,4,5,6-tetrahydro-2(1H)-pyrimidinone (DMPU).

Example 1

Pentyl-[(2S,3R)-2-methyl-4-oxooxetan-3-yl]-carbamate

Step 1. Preparation of (2R,3S)-3-hydroxy-2-{[(pentyloxy)carbonyl]amino}butanoic acid In a round bottom flask NaHCO$_3$ (13.0 g, 155.3 mmol) was suspended in THF (35 mL) and water (70 mL), then D-threonine (7.33 g, 61.6 mmol) and tetrabutylamonium bromide (0.733 g) were added. Amyl chloroformate (10 mL, 68.4 mmol) was added dropwise and the reaction vigorously stirred 18 h at rt. The mixture was diluted with water, washed twice with Et$_2$O and pH adjusted to 2 with 2M HCl solution. The aqueous phase was extracted with AcOEt, the collected organic phases were dried over Na$_2$SO$_4$, filtered and the solvent removed under vacuum to yield the tile compound (13.0 g, 90%) as pale yellow oil, which was used in the next step without further purification. R$_f$=0.26 (Cy/AcOEt 2:8+1% CH$_3$COOH; detection: ninhydrin, bromocresol green). FTIR (cm$^{-1}$): 3344, 2959, 2932, 2873, 1724, 1529, 1468, 1415 1378, 1258, 1075.

Step 2. Preparation of pentyl-[(2S,3R)-2-methyl-4-oxooxetan-3-yl]-carbamate In a four necked round bottom flask, Et$_3$N (3.75 mL, 26.9 mmol) was added to a solution of (2R,3S)-3-hydroxy-2-{[(pentyloxy)carbonyl]amino}butanoic acid (2 g, 8.96 mmol) in dry CH$_2$Cl$_2$ (100 mL) under argon. After cooling at 0° C., PyBOP (6.1 g, 11.6 mmol) was added and the mixture stirred 3 h at 0° C., then 3.5 h at rt. The solvent was removed under vacuum and crude purified by typical silica gel column chromatography, eluting with Cy/AcOEt (from 95:5 to 60:40). The resulting white solid (0.539 g) was further triturated with cyclohexane, yielding a pure compound (0.434 g, 22.5%) as white solid. MS (ESI) m/z: 214.21 [M–H]$^-$. FTIR (cm$^{-1}$): 3323, 3074, 2958, 2931, 2871, 1854, 1692, 1545, 1471, 1391, 1334, 1270, 1150, 1126, 1087, 1025, 982, 844, 823. $^1$H NMR (CDCl$_3$): δ 0.91 (t, 3H); 1.31-1.35 (m, 4H); 1.47 (d, 3H); 1.60-1.67 (m, 2H); 4.06-4.14 (m, 2H); 4.84-4.91 (m, 1H); 5.42-5.49 (m, 2H).

Example 2

Octyl-[(2S,3R)-2-methyl-4-oxooxetan-3-yl]-carbamate

Step 1. Preparation of (2R,3S)-3-hydroxy-2-{[(octyloxy)carbonyl]amino}butanoic acid In a round bottom flask, NaHCO$_3$ (9.74 g, 116 mmol) was suspended in THF (25 mL) and water (50 mL), then D-threonine (5.47 g, 46.0 mmol) and tetrabutylamonium bromide (0.547 g) were added. n-Octyl chloroformate (10 mL, 51.1 mmol) was added dropwise and the reaction vigorously stirred 18 h at rt. The mixture was then diluted with water, washed twice with Et$_2$O and pH adjusted to 2 with 2M HCl solution. The aqueous phase was extracted with AcOEt, the collected organic phases were dried over Na$_2$SO$_4$, filtered and the solvent removed under vacuum to give the title compound (3.37 g, 27%) as pale yellow oil, which was used in the next step without further purification. R$_f$=0.26 (Cy/EtOAc 2:8+1% CH$_3$COOH; detection: ninhydrin, bromocresol green). FTIR (cm$^{-1}$): 3340 (br), 2928, 2856, 1724 (br), 1526, 1261, 1074.

Step 2. Preparation of Octyl-[(2S,3R)-2-methyl-4-oxooxetan-3-yl]-carbamate

In a four-necked round bottom flask, Et$_3$N (1.5 mL, 10.9 mmol) was added to a solution of (2R,3S)-3-hydroxy-2-{[(octyloxy)carbonyl]amino}butanoic acid (1 g, 3.63 mmol) in dry CH$_2$Cl$_2$ (40 mL) under argon. After cooling at 0° C., HBTU (2.07 g, 5.45 mmol) was added and the mixture stirred 3 h at 0° C., then 3.5 h at rt. The obtained solid was filtered-off and the solvent removed under vacuum. The crude was purified by typical silica gel column chromatography, eluting with Cy/AcOEt (from 95:5 to 60:40). The resulting white solid (ca. 0.19 g) was further triturated with cyclohexane, to afford a pure compound (0.165 g, 18%) as white solid. MS (ESI) m/z: 256.31 [M–H]$^-$. FTIR (cm$^{-1}$): 3326, 2958, 2924, 2856, 1857, 1692, 1547, 1333, 1270, 1087, 1025, 845. $^1$H NMR (CDCl$_3$): δ 0.87-0.90 (t, 3H); 1.28-1.36 (m, 10H); 1.47 (t, 3H); 1.59-1.66 (m, 2H); 4.06-4.15 (m, 2H); 4.84-4.91 (m, 1H); 5.38-5.48 (m, 2H).

Example 3

2-(4-methylphenyl)ethyl-[(2S,3R)-2-methyl-4-oxooxetan-3-yl]-carbamate

Step 1: Preparation of (2R,3S)-3-hydroxy-2-({[2-(4-methylphenyl)ethoxy]carbonyl}amino) butanoic acid In a four necked round bottom flask, CDI (9.32 g, 57.4 mmol) was added to a solution of 4-methylphenethyl alcohol (4 mL, 28.7 mmol) in anhydrous DMF (60 mL) under argon. After stirring 2 h at rt, D-threonine (3.42 g, 28.7 mmol) dissolved in water (60 mL) and Et$_3$N (6 mL, 43.1 mmol) were added. The mixture was heated at 50° C. for 16 h, then allowed to cool. Water (600 mL) was added and the mixture washed with Et$_2$O (2×300 mL). The aqueous phase was acidified with 2M HCl solution then extracted with AcOEt (3×500 mL). The collected organic phases were washed with brine and then dried over Na$_2$SO$_4$, filtered and the solvent removed under vacuum. The crude was further co-evaporated with toluene, to yield a pale yellow oil (3.72 g, 46%), which was used in the next step without further purification. $R_f$=0.4 (Cy/AcOEt 2:8+1% $CH_3COOH$). FTIR ($cm^{-1}$): 3419(br), 2977, 2932, 1716, 1661, 1517, 1388, 1255, 1226, 1099, 1077, 665.

Step 2. Preparation of 2-(4-methylphenyl)ethyl [(2S, 3R)-2-methyl-4-oxooxetan-3-yl]-carbamate In a four necked round bottom flask, $Et_3N$ (7.3 mL, 52.5 mmol) was added to a solution of (2R,3S)-3-hydroxy-2-({[2-(4-methylphenyl)ethoxy]carbonyl}amino) butanoic acid (4.85 g, 17.5 mmol) in dry $CH_2Cl_2$ (190 mL) under argon. After cooling at 0° C., HBTU (9.87 g, 26.2 mmol) was added and the mixture stirred 3 h at 0° C., then 3.5 h at rt. The obtained solid was filtered-off and the solvent removed under vacuum. The crude was purified by typical silica gel column chromatography, eluting with Cy/AcOEt (from 95:5 to 60:40). The resulting white solid (0.658 g) was further triturated with cyclohexane to afford the pure title compound (0.450 g, 10%), as white solid. MS (ESI) m/z: 262.21 [M−H]⁻. FTIR ($cm^{-1}$): 3299, 3050, 2966, 2924, 2854, 1827, 1690, 1540, 1355, 1270, 1121, 1095, 1021, 844, 817. ¹H-NMR ($CDCl_3$): δ 1.42 (d, 3H); 2.33 (s, 3H); 2.90 (t, 2H); 4.31 (t, 2H); 4.81-4.88 (m, 1H); 5.39-5.46 (m, 2H); 7.08-7.13 (m, 4H).

Example 4

3-phenylpropyl-[(2S,3R)-2-methyl-4-oxooxetan-3-yl]-carbamate

Step 1. Preparation of 3-phenylpropyl-chlorocarbonate

In a four necked round bottom flask, triphosgene (5.45 g, 55.1 mmol) was dissolved in toluene (80 mL) under argon. After cooling at 0° C., pyridine (4.8 mL, 58.8 mmol) was added dropwise during 1 h and the resulting suspension stirred for further 1 h at 0° C. 3-phenyl-1-propanol (5 mL, 36.8 mmol) was added dropwise in 30 min. After stirring at rt for 24 h, the solid was filtered off and the solvent removed under vacuum, yielding the title compound (6.2 g, 85%) as pale yellow oil, which was used in the next step without further purification. FTIR ($cm^{-1}$): 3086, 3065, 3027, 2995, 2932, 2862, 1776, 1743, 1603, 1496, 1454, 1262, 1148, 745, 699.

Step 2. Preparation of (2R,3S)-3-hydroxy-2-{[(3-phenylpropoxy)carbonyl]amino}butanoic acid In a round bottom flask, $NaHCO_3$ (5.94 g, 70.7 mmol) was suspended in THF (15 mL) and water (30 mL), then D-threonine (3.34 g, 28.0 mmol) was added. 3-phenylpropyl chlorocarbonate (6.2 g, 31.2 mmol) was slowly added, followed by a catalytic amount (0.3 g) of tetrabutylamonium bromide. After stirring 18 h at rt., the mixture was diluted with water (100 mL), washed twice with $Et_2O$ (2×100 mL) and pH adjusted to 2 with 2M HCl solution. The aqueous phase was extracted with AcOEt (3×150 mL), the collected organic phases were dried over $Na_2SO_4$, filtered and the solvent removed under vacuum to give the title compound (1.43 g, 18%), as colorless oil, which was used in the next step without further purification. $R_f$=0.38 (Cy/AcOEt 2:8+1% $CH_3COOH$). FTIR ($cm^{-1}$): 3340 (br), 3064, 3030, 2982, 2939, 1730 (br), 1528, 1374, 1241, 1094, 1072, 1048, 781, 749, 703.

Step 3. Preparation of 3-phenylpropyl-[(2S,3R)-2-methyl-4-oxooxetan-3-yl]-carbamate In a four necked round bottom flask, $Et_3N$ (1.4 ml, 10.1 mmol) was added to a solution of (2R,3S)-3-hydroxy-2-{[(3-phenylpropoxy)carbonyl]amino}butanoic acid (0.95 g, 3.38 mmol) in dry $CH_2Cl_2$ (40 mL) under argon. After cooling at 0° C., HBTU (1.92 g, 5.07 mmol, 1.5 eq) was added and the mixture stirred 3 h at 0° C., then 16 h at rt. The obtained solid was filtered off and the solvent removed under vacuum. The crude was purified by typical silica gel column chromatography, eluting with Cy/AcOEt (from 95:5 to 60:40). The resulting white solid (0.280 g) was further triturated with cyclohexane to afford the pure title compound (0.240 g, 31%), as white solid. MS (ESI) m/z: 262.27 [M−H]⁻. $R_f$=0.29 (Cy/EtOAc 8:2; detection: phosphomolybdic acid). FTIR ($cm^{-1}$): 3328, 3064, 3030, 2972, 2929, 2859, 1851, 1691, 1542, 1333, 1270, 1130, 1083, 1024, 843, 822, 697. ¹H NMR ($CDCl_3$): δ 1.46 (d, 3H); 1.93-2.00 (m, 2H); 2.67-2.71 (m, 2H); 4.09-4.18 (m, 2H); 4.84-4.90 (m, 1H); 5.38-5.48 (m, 2H); 7.11-7.31 (m, 5H).

Example 5

4-phenylbutyl-[(2S,3R)-2-methyl-4-oxooxetan-3-yl]-carbamate

Step 1. Preparation of (2R,3S)-3-hydroxy-2-{[(4-phenylbutoxy)carbonyl]amino}butanoic acid In a four necked round bottom flask, CDI (10.6 g, 65.5 mmol) was added to a solution of 4-phenylbutan-1-ol (5 mL, 32.8 mmol) in anhydrous DMF (70 mL) under argon. After stirring 2 h at rt, D-threonine (3.90 g, 32.8 mmol) dissolved in water (70 mL) and $Et_3N$ (6.8 mL, 49.1 mmol) were added. The mixture was heated at 50° C. for 16 h then allowed to cool. Water (700 mL) was added and the mixture washed with $Et_2O$ (3×300 mL). The aqueous phase was acidified with 2M HCl solution then extracted with AcOEt (3×500 mL). The collected organic phases were dried over $Na_2SO_4$, filtered and the solvent removed under vacuum. The crude was further co-evaporated with toluene to give a pale yellow oil (5.2 g, 54%), which was used in the next step without further purification. MS (ESI) m/z: 296[M+H]⁺; 294[M−H]⁻. $R_f$=0.34 (Cy/AcOEt 2:8+1% $CH_3COOH$). FTIR ($cm^{-1}$): 3332 (br), 3027, 2978, 2938, 2863, 1719 (br), 1525, 1253, 1069, 779, 748, 699.

Step 2. Preparation of 4-phenylbutyl-[(2S,3R)-2-methyl-4-oxooxetan-3-yl]-carbamate In a four necked round bottom flask, $Et_3N$ (5.5 mL, 39.4 mmol) was added to a solution of (2R,3S)-3-hydroxy-2-{[(4-phenylbutoxy)carbonyl]amino}butanoic acid (3.9 g, 13.1 mmol) in dry $CH_2Cl_2$ (170 mL) under argon. After cooling at 0° C., HBTU (7.5 g, 19.7 mmol) was added and the mixture stirred 3 h at 0° C., then 3.5 h at rt. The obtained solid was filtered-off and the solvent removed under vacuum. The crude was purified by typical silica gel automatic column chromatography, eluting with Cy/AcOEt (from 95:5 to 60:40). The resulting pale yellow oil (0.61 g) was further crystallized from cyclohexane to afford the pure title compound, (0.23 g, 6%), as white solid. MS (ESI) m/z: 276.24 [M−H]⁻. FTIR ($cm^{-1}$):

3312, 3060, 3026, 2942, 2861, 1826, 1694, 1545, 1337, 1269, 1126, 1023. $^1$H NMR (CDCl$_3$): δ 1.45 (d, 3H); 1.66-1.70 (m, 4H); 2.63-2.66 (m, 2H); 4.09-4.18 (m, 2H); 4.83-4.89 (m, 1H); 5.36 (br d, 1H); 5.45 (m, 1H); 7.16-7.31 (m, 5H).

Example 6

5-phenylpentyl-[(2S,3R)-2-methyl-4-oxooxetan-3-yl]-carbamate

Step 1. Preparation of 5-phenylpentyl-chlorocarbonate

In a four necked round bottom flask, triphosgene (22.0 g, 74.2 mmol) was dissolved in toluene (325 mL) under argon. After cooling at 0° C., pyridine (19.2 mL, 237.5 mmol) was added dropwise during 1 h and the resulting suspension stirred for 1 h at 0° C. 5-phenylpentanol (25 mL, 148.4 mmol) was added drop wise in 30 min. After stirring at rt for 16 h the solid was filtered-off and the solvent removed under vacuum yielding the title compound (31.7 g, 94%), which was used in the next step without further purification. R$_f$=0.75 (Cy/AcOEt 8:2). FTIR (cm$^{-1}$): 3087, 3063, 3027, 2936, 2859, 1778, 1744, 1604, 1496, 1455, 1382, 1260, 1146, 1031, 941, 835, 731, 696.

Step 2. Preparation of (2R,3S)-3-hydroxy-2-({[(5-phenylpentyl)oxy]carbonyl}amino)butanoic acid In a round bottom flask, NaHCO$_3$ (12.0 g, 143.2 mmol) was suspended in THF (30 mL) and water (60 mL), then D-threonine (6.8 g, 56.8 mmol) was added followed by 5-phenylpentyl chlorocarbonate (14.3 g, 63.1 mmol) and a catalytic amount (0.67 g) of tetrabutylamonium bromide. After stirring 18 h at rt, the mixture was diluted with water, washed twice with Et$_2$O and pH adjusted to 2 with 2M HCl solution. The aqueous phase was extracted with AcOEt (4×150 mL), the collected organic phases were washed with brine, dried over Na$_2$SO$_4$, filtered and the solvent removed under vacuum. The crude was purified by typical silica gel column chromatography, eluting with Cy/AcOEt (20:80+1% CH$_3$COOH), yielding the title compound (3.15 g, 18%), as pale yellow oil. R$_f$=0.38 (Cy/AcOEt 2:8+1% CH$_3$COOH). FTIR (cm$^{-1}$): 3332 (br), 3027, 2935, 2859, 1714, 1530, 1454, 1415, 1257, 1072, 1007, 963, 870, 779, 748, 700. $^1$H NMR (CDCl$_3$): δ 1.26 (d, 3H); 1.39 (m, 2H); 1.62-1.68 (m, 4H); 2.61 (t, 2H); 4.08 (t, 2H); 4.34 (d, 1H); 4.42 (d, 1H); 5.68 (d, 1H); 7.16-7.78 (m, 3H); 7.26-7.28 (m, 2H).

Step 3. Preparation of 5-phenylpentyl-[(2S,3R)-2-methyl-4-oxooxetan-3-yl]-carbamate In a two necked round bottom flask, Et$_3$N (0.34 ml, 2.42 mmol) was added to a solution of (2R,3S)-3-hydroxy-2-({[(5-phenylpentyl)oxy]carbonyl}amino)-butanoic acid (0.25 g, 0.81 mmol) in dry CH$_2$Cl$_2$ (10 mL) under argon. After cooling at 0° C., HTBU (0.46 g, 1.21 mmol) was added and the mixture stirred 3 h at 0° C., then 16 h at rt. The obtained solid was filtered-off and the solvent removed under vacuum. The crude was purified by typical silica gel column chromatography eluting with Cy/AcOEt (from 98:2 to 80:20). The title compound (0.107 g, 45%), was obtained as white solid, which was further triturated with cyclohexane. MS (ESI) m/z: 290.21 [M–H]$^-$. FTIR (cm$^{-1}$): 3330, 3064, 3027, 2936, 2858, 1849, 1695, 1540, 1387, 1333, 1262, 1129, 1076, 1023, 985, 921, 845, 822, 741, 697. $^1$H NMR (CDCl$_3$): δ 1.38 (m, 2H); 1.44 (d, 3H); 1.62-1.67 (m, 4H); 2.62 (t, 2H); 4.05-4.13 (m, 2H); 4.86 (m, 1H); 5.44 (t, 1H); 5.33 (d, 1H); 7.16-7.19 (m, 3H); 7.25-7.29 (m, 2H).

Example 7

[(1S)-1-methyloctyl]-N-[(2S,3R)-2-methyl-4-oxo-oxetan-3-yl]-carbamate

Step 1. Preparation of [(1S)-1-methyloctyl]-2-pyridyl carbonate and [(1S)-1-methyloctyl]-2-oxopyridine 1-carboxylate Under nitrogen atmosphere, to a stirred mixture of commercially available (2S)-nonan-2-ol (0.3 g, 2.07 mmol) in dry CH$_2$Cl$_2$ (3 mL), DMAP (0.025 g, 0.2 mmol) and di-2-pyridyl carbonate (0.54 g, 2.49 mmol) were added. The reaction mixture was left to react at rt for 15 h, then diluted with CH$_2$Cl$_2$ and washed first with a saturated NH$_4$Cl solution (4 mL) and subsequently with a saturated NaHCO$_3$ solution (4×4 mL). The organic fraction was dried over Na$_2$SO$_4$, filtered and concentrated to dryness to afford a yellowish oil (0.55 g, quant.), as a mixture (ratio 1.8:1) of [(1S)-1-methyloctyl]-2-pyridyl carbonate and [(1S)-1-methyloctyl]-2-oxopyridine 1-carboxylate. The mixture of isomers was not separated and used in the next step without any further purification. MS (ESI) m/z: 304 [M–K]$^+$, 288 [M–Na]$^+$, 266 [M–H]$^+$, 140. (ESI) m/z: 264 [M–H]$^-$.

Step 2. Preparation of (2R,3S)-3-hydroxy-2-[[(1S)-1-methyloctoxy]-carbonylamino]-butanoic acid To a stirred mixture of D-threonine (0.150 g, 1.25 mmol) and NaHCO$_3$ (0.158 g, 1.89 mmol) in water (3 mL), the crude mixture containing [(1S)-1-methyloctyl]-2-pyridyl carbonate and [(1S)-1-methyloctyl]-2-oxopyridine 1-carboxylate (0.501 g, 1.88 mmol) in THF (3 mL) was added. After 15 h at rt, the crude mixture was rotary evaporated to remove the organics and subsequently extracted with Et$_2$O (3×5 mL). The aqueous phase was acidified with 2M HCl solution to pH 2-3 and subsequently extracted with AcOEt (3×10 mL). The organic fraction was dried over Na$_2$SO$_4$, filtered and concentrated to dryness to afford the title compound (0.220 g, 62%) as transparent oil, which was used in the next step without further purification. MS (ESI) m/z: 290 [M–H]$^+$; (ESI) m/z: 288 [M–H]$^-$. $^1$H NMR (DMSO-d$_6$): δ 0.87 (t, J=6.8 Hz, 3H), 1.09 (d, J=6.4 Hz, 3H), 1.15 (d, J=6.2 Hz, 3H), 1.21-1.34 (m, 10H), 1.40-1.57 (m, 2H), 3.92 (dd, J=3.4, 9.0 Hz, 1H), 4.01-4.11 (m, 1H), 4.60-4.70 (m, 1H), 6.55 (d, J=9.0 Hz, 1H), 12.49 (s, 1H).

Step 3. Preparation of [(1S)-1-methyloctyl]-N-[(2S,3R)-2-methyl-4-oxo-oxetan-3-yl]-carbamate Under nitrogen atmosphere at 0° C., to a stirred mixture of (2R,3S)-3-hydroxy-2-[[(1S)-1-methyloctoxy]-carbonylamino]-butanoic acid (0.2 g, 0.69 mmol) in dry CH$_2$Cl$_2$ (20 mL), Et$_3$N (0.29 mL, 2.07 mmol) and subsequently TBTU (0.27 g, 0.83 mmol) were added. The mixture was left stirring 1 h at 0° C. and 15 h at rt. Upon full conversion of the starting material, the organics were removed under reduced pressure, and the resulting crude product absorbed over silica gel and purified by typical column chromatography, eluting with Cy/AcOEt (from 100:0 to 40:60) to give the title compound (0.1 g, 53%) as a white solid. MS (ESI) m/z: 272 [M–H]$^+$; (ESI) m/z: 270 [M–H]$^-$. $^1$H NMR (DMSO-d$_6$): δ 0.85 (t, J=6.8 Hz, 3H), 1.15 (d, J=6.3 Hz, 3H), 1.20-1.31 (m, 10H), 1.34 (d, J=6.4 Hz, 3H), 1.41-1.56 (m, 2H), 4.63-4.74 (m, 1H), 4.83 (dq, J=6.3 Hz, 1H), 5.39 (dd, J=6.3, 9.3 Hz, 1H), 8.11 (d, J=9.3 Hz, 1H).

Example 8

(1S) and (1R)-1-(4-phenylphenyl)-ethyl-N-[(2S,3R)-2-methyl-4-oxo-oxetan-3-yl]-carbamate Step 1. Preparation of 1-(4-phenylphenyl)ethyl-2-pyridyl-carbonate and 1-(4-phenylphenyl)-ethyl-2-oxopyridine 1-carboxylate Under nitrogen atmosphere, to a stirred mixture of commercially available 1-(4-phenylphenyl)-ethanol (0.4 g, 2.01 mmol) in dry $CH_2Cl_2$ (4 mL), DMAP (0.024 g, 0.2 mmol) and di-2-pyridyl carbonate (0.52 g, 2.42 mmol) were added. The reaction mixture was left to react at rt for 15 h, then diluted with $CH_2Cl_2$ and washed first with a saturated $NH_4Cl$ solution (3 mL) and subsequently with a saturated $NaHCO_3$ solution (4×3 mL). The organic fraction was dried over $Na_2SO_4$, filtered and concentrated to dryness to afford a yellowish oil (0.63 g, 98%) as a mixture (ratio 1.7:1) of 1-(4-phenylphenyl)ethyl-2-pyridyl-carbonate and 1-(4-phenylphenyl)ethyl-2-oxopyridine 1-carboxylate. The mixture of isomers was not separated and used in the next step without any further purification. MS (ESI) m/z: 342 [M−Na]$^+$, 276, 181.

Step 2. Preparation of (2R,3S)-3-hydroxy-2-[[-(1S)-(4-phenylphenyl)-ethoxy]carbonylamino]-butanoic acid and (2R,3S)-3-hydroxy-2-[[-(1R)-(4-phenylphenyl)-ethoxy]carbonylamino]-butanoic acid To a stirred mixture of D-threonine (0.150 g, 1.25 mmol) and $NaHCO_3$ (0.158 g, 1.89 mmol) in water (3.5 mL), the crude mixture containing 1-(4-phenylphenyl)ethyl-2-pyridyl-carbonate and 1-(4-phenylphenyl)-ethyl-2-oxopyridine-1-carboxylate (0.60 g, 1.88 mmol) in THF (3.5 mL) was added. After 15 h at rt the crude mixture was rotary evaporated to remove the organics and subsequently extracted with $Et_2O$ (3×5 mL). The aqueous phase was acidified with 2M HCl solution to pH 2-3 and subsequently extracted with AcOEt (3×10 mL). The organic fraction was dried over $Na_2SO_4$, filtered and concentrated to dryness to afford the title compound (0.39 g, 90%) as a mixture (ratio 1:1) of two diastereoisomers, as transparent oil, which was used in the next step without further purification. MS (ESI) m/z: 366 [M−Na]$^+$, 361 [M−NH$_4$]$^+$; (ESI) m/z: 342 [M−H]$^-$. $^1$H NMR (DMSO-d$_6$) (as a 1:1 mixture of diastereoisomers): δ 1.06 (d, J=6.4 Hz, 3H), 1.12 (d, J=6.4 Hz, 3H), 1.50 (d, J=6.5 Hz, 6H), 3.92 (dd, J=3.4, 9.1 Hz, 1H), 3.94 (dd, J=3.4, 9.2 Hz, 1H), 4.02-4.11 (m, 2H), 5.74 (dq, J=6.3 Hz, 2H), 6.88 (d, J=8.9 Hz, 1H), 6.89 (d, J=9.0 Hz, 1H), 7.32-7.50 (m, 10H), 7.62-7.69 (m, 8H), 12.49 (s, 2H).

Step 3. Preparation of (1S) and (1R)-1-(4-phenylphenyl)-ethyl-N-[(2S,3R)-2-methyl-4-oxo-oxetan-3-yl]-carbamate Under nitrogen atmosphere at 0° C., to a stirred mixture of (2R,3S)-3-hydroxy-2-[[-1-(4-henylphenyl)-ethoxy]carbonylamino]-butanoic acid (0.4 g, 1.16 mmol) in dry $CH_2Cl_2$ (20 mL), $Et_3N$ (0.49 mL, 3.49 mmol) and subsequently TBTU reagent (0.45 g, 1.39 mmol) were added. The mixture was left stirring 1 h at 0° C. and 15 h at rt. Upon full conversion of the starting material, the organics were removed under reduced pressure, and the resulting crude product absorbed over silica gel and purified by typical column chromatography, eluting with Cy/AcOEt (from 100:0 to 30:70) to give the title compound (0.18 g, 47%) as a mixture (ratio 1:1) of diastereoisomers, as a white solid. MS (ESI) m/z: 348 [M−Na]$^+$; (ESI) m/z: 324 [M−H]$^-$. $^1$H NMR (DMSO-d$_6$) (as a 1:1 mixture of diastereoisomers): δ 1.33 (d, J=6.3 Hz, 3H), 1.35 (d, J=6.3 Hz, 3H), 1.52 (d, J=6.6 Hz, 6H), 4.81-4.91 (m, 2H), 5.42 (dd, J=6.2, 9.2 Hz, 2H), 5.76 (q, J=6.5 Hz, 2H), 7.33-7.51 (m, 10H), 7.63-7.69 (m, 8H), 8.37 (d, J=9.3 Hz, 2H).

Example 9

(1-benzoyl-4-piperidyl)-N-[(2S,3R)-2-methyl-4-oxo-oxetan-3-yl]-carbamate

Step 1. Preparation of 1-(phenylcarbonyl)-piperidin-4-ol

In a four necked round bottom flask, under Argon atmosphere, 4-hydroxypiperidine (5.32 g, 52.6 mmol) was dissolved in $CH_2Cl_2$ (28 mL) and pyridine (28 mL). After cooling at 0° C., benzoyl chloride (6.4 mL, 55.2 mmol), dissolved in $CH_2Cl_2$ (7 mL) was drop wise added. The ice bath was removed and the mixture stirred 3 h at rt. The solid was filtered-off and the solvent removed under vacuum. Purification by typical column chromatography, eluting with $CH_2Cl_2$/MeOH (20:1) afforded the title compound (7.6 g, 70%) as pale yellow oil. $R_f$=0.21 ($CH_2Cl_2$/MeOH 20:1). MS (ESI) m/z: 206 [M−H]$^+$. FTIR (cm$^{-1}$): 3349, 3065, 3033, 3005, 2934, 2845, 1607, 1574, 1453, 1365, 1339, 1273, 1238, 1180, 1077, 998, 788, 730, 688.

Step 2. Preparation of (2R,3S)-3-hydroxy-2-[({[1-(phenylcarbonyl)piperidin-4-yl]oxy}carbonyl)amino]-butanoic acid In a four necked round bottom flask, under Argon, CDI (12.0 g, 74 mmol) was added to a solution of 1-(phenylcarbonyl)-piperidin-4-ol (7.6 g, 37 mmol) in anhydrous DMF (100 mL). After stirring 2 h at rt, D-threonine (4.42 g, 37 mmol), dissolved in $H_2O$ (70 mL) and $Et_3N$ (7.7 mL, 55.5 mmol) were added. The mixture was heated at 50° C. for 16 h, then allowed to cool to rt. Water was added and the mixture washed with $Et_2O$ (2×150 mL). The aqueous phase was acidified with 2M HCl solution then extracted with AcOEt (2×200 mL). The collected organic phases were dried over $Na_2SO_4$, filtered and the solvent removed under vacuum. The crude was purified by column chromatography using a Teledyne ISCO apparatus, eluting with AcOEt/MeOH (90:10+1% $CH_3COOH$). Mixed fractions were obtained and purified in the same manner to give a pure compound (1.83 g, 14%) as white solid. $R_f$=0.25 (AcOEt/MeOH 9:1+1% $CH_3COOH$). FTIR (cm$^{-1}$): 3407 (br), 3056, 2925, 1720, 1560, 1450, 1266, 1235, 1068, 736.

Step 3. Preparation of (1-benzoyl-4-piperidyl)-N-[(2S,3R)-2-methyl-4-oxo-oxetan-3-yl]-carbamate In a four necked round bottom flask, under Argon atmosphere, $Et_3N$ (1.2 mL, 8.56 mmol) was added to a solution of (2R,3S)-3-hydroxy-2-[({[1-(phenylcarbonyl)piperidin-4-yl]oxy}carbonyl)amino]-butanoic acid (1.0 g, 2.85 mmol) in dry $CH_2Cl_2$ (40 mL). After cooling at 0° C., HBTU (1.62 g, 4.28 mmol) was added and the mixture stirred 3 h at 0° C., then 16 h at rt. The solvent was removed under vacuum, and the resulting crude mixture was purified by column chromatography using a Teledyne ISCO apparatus, eluting with CH$_2$Cl$_2$/AcOEt (50:50). The resulting yellow solid was further purified trough reverse-phase automatic column chromatography, eluting with H$_2$O/CH$_3$CN (70:30) to afford the title compound (0.083 g, 9%) as white solid. R$_f$=0.47 (SiO$_2$, CH$_2$Cl$_2$/AcOEt 1:1); R$_f$=0.39 (C18, 7:3 H$_2$O/CH$_3$CN). MS (ESI) m/z: 333 [M−H]$^+$. FTIR (cm$^{-1}$): 3414, 3222, 3050, 2965, 2929, 2871, 1825, 1720, 1612, 1550, 1449, 1262, 1232, 1119, 1068, 1031, 837, 711. $^1$H-NMR (CDCl$_3$): δ 1.47 (d, 3H); 1.58-2.04 (m, 4H); 3.30-4.08 (m, 4H); 4.86-4.90 (m, 1H); 4.93-4.97 (m, 1H); 5.45 (t, 1H); 5.56 (br s, 1H); 7.39-7.44 (m, 5H).

Example 10

(1-methylcyclohexyl)-[(2S,3R)-2-methyl-4-oxo-oxetan-3-yl]-carbamate

Step 1. Preparation of (1-methylcyclohexyl)-(4-nitrophenyl)-carbonate

In a round bottomed flask equipped with a magnetic stirrer and a dropping funnel, CH$_2$Cl$_2$ (20 mL) was loaded followed by 1-methylcyclohexanol (2 mL, 16.1 mmol) and pyridine (2.5 mL, 32.3 mmol). The clear solution was chilled at 0° C. on an ice bath, and after 10 min a solution p-nitrophenylchloroformate (3.25 g, 16.1 mmol) in CH$_2$Cl$_2$ (10 mL) was added dropwise in a period of 10 min. A white precipitate appeared almost immediately, which changed to yellow upon leaving the mixture under stirring at rt overnight. Water (20 mL) was then added and the mixture was stirred for 10 min. The two phases were separated and the organic phase was washed again with water (20 mL) then dried over Na$_2$SO$_4$. Solvents were removed under vacuum to give an oil which was purified by typical chromatography eluting with petroleum ether/AcOEt (from 70:30 to 1:1). The title compound was obtained (1.9 g, 42%), as light yellow oil, which was used in the next step without further purification. $^1$H NMR (CDCl$_3$): δ 1.25-1.65 (m, 8H), 1.57 (s, 3H), 2.20 (m, 2H), 7.36 (d, J=9.1 Hz, 2H), 8.26 (d, J=9.1 Hz, 2H).

Step 2. Preparation of (1-methylcyclohexyl)-N-aminocarbamate

In a round bottomed flask equipped with a magnetic stirrer (1-methylcyclohexyl)-(4-nitrophenyl)-carbonate (0.816 g, 2.92 mmol) was dissolved in THF (7 mL) and after 5 min hydrazine hydrate (0.28 mL, 5.85 mmol) was added in one portion. A yellow color immediately appeared which deepened to red in 1 hr. After 3 hr at rt, 1.25M NaOH solution (20 mL) and MTBE (25 mL) were added and the mixture was stirred for 10 min. The two phases were separated and the organic phase was washed again with 1.25M NaOH solution (15 mL) for 10 min (until colorless solution), dried over Na$_2$SO$_4$ and concentrated to give a colorless oil (0.497 g, 98%), which is used in the next step without purification. $^1$H NMR (CDCl$_3$): δ 1.20-1.60 (m, 8H), 1.49 (s, 3H), 2.10 (m, 2H), 3.67 (bs, 2H), 5.81 (bs, 1H).

Step 3. Preparation of (2S,3R)-3-hydroxy-2-[(1-methylcyclohexoxy)carbonylamino]-butanoic acid In a round bottomed flask equipped with a magnetic stirrer, (1-methylcyclohexyl)-N-aminocarbamate (0.497 g, 2.89 mmol), H$_2$O (4 mL) and CH$_3$COOH (0.33 mL, 5.78 mmol) were added sequentially. The mixture was cooled to 0° C. and NaNO$_2$ (0.239 g, 3.47 mmol) dissolved in H$_2$O (1 mL) was added dropwise. The cloudy mixture was stirred for 40 min at rt, then dioxane (10 mL) was added followed by a D-threonine salt solution [prepared from D-threonine (0.516 g, 4.33 mmol) dissolved in H$_2$O (4 mL) and Na$_2$CO$_3$ (1.25 g, 11.56 mmol)]. The mixture was heated overnight at 45° C., then cooled to rt. AcOEt (50 mL) and H$_2$O (50 mL) were added and, while maintaining a vigorous stirring, the pH was adjusted to 2 with 2M HCl solution. The two phases were separated and the aqueous phase washed again with of AcOEt (15 mL) for 10 min. The combined organic portions were dried over Na$_2$SO$_4$ and concentrated to give a light yellow oil (0.503 g, 67%) which was used in the next step without further purification. MS (ESI) m/z: 282.3 [M−Na]$^+$; (ESI) m/z: 258.1 [M−H]$^-$. $^1$H NMR (DMSO-d$_6$): δ 1.09 (d, J=6.3 Hz, 3H), 1.10-1.65 (m, 8H), 1.40 (s, 3H), 2.04 (m, 2H), 3.89 (dd, J=9.3, 3.2 Hz, 1H), 4.06 (m, 1H), 6.31 (d, J=9.3, 1H), 12.08 (bs, 1H).

Step 4. Preparation of (1-methylcyclohexyl)-N-[(2S,3R)-2-methyl-4-oxo-oxetan-3-yl]-carbamate In a round bottomed flask equipped with a magnetic stirrer and a dropping funnel (2S,3R)-3-hydroxy-2-[(1-methylcyclohexoxy)carbonylamino]-butanoic acid (0.503 g, 1.95 mmol) was dissolved in anhydrous CH$_2$Cl$_2$ (50 mL). The clear yellow solution was cooled to 0° C., PyBOP (1.22 g, 2.34 mmol) was added, followed by a dropwise addition of Et$_3$N solution (0.815 mL, 5.85 mmol) in anhydrous CH$_2$Cl$_2$ (5 mL), over a period of 10 min. The crude mixture was stirred at 0° C. for 1 h then overnight at rt. The reaction was quenched by addition of 5% NaHCO$_3$ solution (50 mL) and the corresponding mixture was vigorously stirred for 10 min. The two phases were separated and the organic one collected, dried over Na$_2$SO$_4$ and concentrated to dryness to leave an oil, which was purified by typical chromatography eluting with petroleum ether/AcOEt mixtures (from 9:1 to 7:3). The title compound was obtained as white solid (0.070 g, 15%). m.p.: 92-93° C. MS (ESI) m/z: 242.2 [M−H]$^+$; (ESI) m/z: 240.1 [M−H]$^-$. $^1$H NMR (DMSO-d$_6$): δ 1.15-1.60 (m, 8H) 1.35 (d, J=6.3 Hz, 3H), 1.42 (s, 3H), 2.02 (m, 2H), 4.83 (m, 1H), 5.35 (dd, J=9.2, 6.3 Hz, 1H), 7.98 (d, J=9.2 Hz, 1H).

Example 11

(4-methyltetrahydropyran-4-yl)-N-[(2S,3R)-2-methyl-4-oxo-oxetan-3-yl]-carbamate

Step 1. Preparation of (4-methyltetrahydropyran-4-yl)-(4-nitrophenyl)-carbonate

In a flame-dried round bottomed flask equipped with a magnetic stirrer, 4-methyltetrahydropyran-4-ol (1.5 g, 12.9 mmol), prepared as described in patent application WO2004/041161, was dissolved in CH$_2$Cl$_2$ (30 mL). The mixture was chilled to 0° C. then pyridine (2.04 mL, 25.82 mmol, 2 eq) and p-nitrophenylchloroformate (3.38 g, 16.78 mmol) solution in CH$_2$Cl$_2$ (10 mL) were slowly added. A white precipitate almost immediately appeared and the mixture was stirred overnight at rt. The crude mixture was then diluted with CH$_2$Cl$_2$, washed with 1M HCl solution, saturated NaHCO$_3$ solution and finally with brine. The two phases were separated and the organic one was dried over Na$_2$SO$_4$. Removal of the organics under reduced pressure gave a crude yellow solid (3.8 g), as a 1:1 mixture of desired product and p-nitrophenylchloroformate, which was used in the next step without further purification. $^1$H NMR (CDCl$_3$): δ 1.67 (s, 3H), 1.87 (m, 2H), 2.23 (m, 2H), 3.78 (m, 4H), 7.39 (d, J=9.0 Hz, 2H), 8.29 (d, J=9.0 Hz, 2H)

Step 2. Preparation of (4-methyltetrahydropyran-4-yl)-N-aminocarbamate

In a round bottomed flask equipped with a magnetic stirrer, crude (4-methyltetrahydropyran-4-yl)-(4-nitrophenyl)-carbonate from previous step (ca. 3.8 g) was dissolved in THF (50 mL), then hydrazine hydrate (1.97 mL, 40.57 mmol) was added in one portion. A yellow color immediately appeared which deepened to red in 1 h. After 3 h, 1.25M NaOH solution (50 mL) and AcOEt (50 mL) were added and the mixture stirred for 20 min. The phases were separated and the aqueous one washed with more AcOEt (25 mL). The combined organic liquors were washed with 1.25M NaOH solution (30 mL) (until clear colorless), dried over $Na_2SO_4$ and concentrated to leave a colorless oil (0.540 g, 24% over two steps) which was used in the next step without further purification. $^1$H NMR ($CDCl_3$) δ 1.58 (s, 3H), 1.73 (m, 2H), 2.15 (m, 2H), 3.73 (m, 6H), 6.0 (bs, 1H).

Step 3. Synthesis of (2R,3S)-3-hydroxy-2-[(4-methyltetrahydropyran-4-yl)oxycarbonylamino]-butanoic acid In a round bottomed flask equipped with a magnetic stirrer (4-methyltetrahydropyran-4-yl)-N-aminocarbamate (0.540 g, 3.10 mmol), $H_2O$ (10 mL) and $CH_3COOH$ (0.35 mL, 6.20 mmol) were sequentially added. The resulting mixture was cooled to 0° C. and $NaNO_2$ (0.354 g, 3.72 mmol) dissolved in $H_2O$ (2 mL) was added dropwise. The cloudy mixture was stirred for 1.5 h at rt. Dioxane (20 mL) followed by the D-threonine salt solution [prepared from D-threonine (0.554 g, 4.65 mmol) solution in $H_2O$ (4 mL) and $Na_2CO_3$ (1.34 g, 12.40 mmol)] were added to the mixture. After being left overnight at 45° C., the crude mixture was then cooled to rt, then $H_2O$ (30 mL) and AcOEt (80 mL) were added and, while maintaining a vigorous stirring, the pH was adjusted to 2 with 2M HCl solution. The phases were separated and the aqueous one washed with AcOEt (2×50 mL). The combined organic liquors were dried over $Na_2SO_4$ and concentrated to leave a light yellow oil (0.647 g, 80%), which was used in the next step without purification. MS (ESI) m/z: 284.1 [M−Na]$^+$. $^1$H NMR (DMSO-$d_6$): δ 1.09 (d, J=6.3 Hz, 3H), 1.47 (s, 3H), 1.63 (m, 2H), 1.99 (m, 2H), 3.61 (m, 5H), 3.90 (dd, J=9.4, 6.3 Hz, 1H), 4.09 (m, 1H), 6.53 (d, J=9.4 Hz, 1H), 12.20 (bs, 1H).

Step 4. Preparation of (4-methyltetrahydropyran-4-yl)-N-[(2S,3R)-2-methyl-4-oxo-oxetan-3-yl]-carbamate In a round bottomed flask equipped with a magnetic stirrer and a dropping funnel (2R,3S)-3-hydroxy-2-[(4-methyltetrahydropyran-4-yl)oxycarbonylamino]-butanoic acid (0.2 g, 0.77 mmol) was dissolved in anhydrous $CH_2Cl_2$ (7 mL). The clear yellow solution was cooled to 0° C., PyBOP (0.48 g, 0.92 mmol) was added, followed by dropwise addition, over a period of 10 min, of $Et_3N$ (0.32 mL, 3.85 mmol) solution in anhydrous $CH_2Cl_2$ (5 mL). The crude mixture was stirred at 0° C. for 1 h then overnight at rt. The reaction was quenched by addition of 5% $NaHCO_3$ solution (10 mL) and the corresponding mixture was vigorously stirred for 10 min. The two phases were separated and the organic one collected, dried over $Na_2SO_4$ and concentrated to dryness to leave an oil, which was purified by typical chromatography eluting with petroleum ether/AcOEt (from 20:80 to 0:100) to give title compound (0.036 g, 19%) as a light yellow oil. MS (ESI) m/z: 244.1 [M−H]$^+$; (ESI) m/z: 242.2 [M−H]$^-$. $^1$H NMR (DMSO-$d_6$) δ 1.20 (d, J=6.3 Hz, 3H), 1.48 (s, 3H), 1.67 (m, 2H), 1.99 (m, 2H), 3.60 (m, 4H), 4.83 (m, 1H), 5.37 (dd, J=9.3, 6.3 Hz, 1H), 8.12 (d, J=9.3 Hz, 1H).

Example 12

Tricyclo[3.3.1.1$^{3,7}$]dec-1-yl [(2S,3R)-2-methyl-4-oxooxetan-3-yl]-carbamate

Step 1. Preparation of tricyclo[3.3.1.1$^{3,7}$]dec-1-yl chlorocarbonate

In a four necked round bottom flask, triphosgene (9.75 g, 32.8 mmol) was dissolved in toluene (140 mL) under argon atmosphere. After cooling to 0° C., pyridine (8.5 mL, 105 mmol) was added dropwise during 1 h and the resulting suspension stirred for further 1 h at 0° C. 1-Adamantanol (10.0 g, 65.7 mmol) was added portion-wise. After stirring at rt for 24 h, the solid was filtered-off and the solvent removed under vacuum to yield the title compound (12.3 g, 88%) as yellowish oil, which was used in the next step without further purification. FTIR (cm$^{-1}$): 2913, 2854, 1780, 1455, 1354, 1152, 1038, 957, 835, 802.

Step 2. Preparation of (2R,3S)-3-hydroxy-2-{[(tricyclo[3.3.1.1$^{3,7}$]dec-1-yloxy)carbonyl]amino}butanoic acid In a round bottom flask, $NaHCO_3$ (1.78 g, 21.2 mmol) was suspended in THF (4.5 mL) and $H_2O$ (9 mL), then D-threonine was added (1.0 g, 8.39 mmol). Tricyclo[3.3.1.1$^{3,7}$]dec-1-yl chlorocarbonate (2.0 g, 9.33 mmol) was added slowly, followed by a catalytic amount (0.1 g) of tetrabutylamonium bromide. After stirring 18 h at rt, the mixture was diluted with water, washed twice with $Et_2O$ and pH of aqueous phase adjusted to 2 with 2M HCl solution. The aqueous phase was extracted four times with AcOEt, the collected organic phases were dried over $Na_2SO_4$, filtered, and the solvent removed under vacuum to give the title compound (0.250 g, 10%) as white solid. $R_f$=0.38 (AcOEt+1% $CH_3COOH$, detection: ninhydrin). FTIR (cm$^{-1}$): 3421, 2911, 2852, 1718, 1509, 1254, 1068.

Step 3. Preparation of Tricyclo[3.3.1.1$^{3,7}$]dec-1-yl [(2S,3R)-2-methyl-4-oxooxetan-3-yl]-carbamate In a two necked round bottom flask, $Et_3N$ (0.34 ml, 2.42 mmol) was added to a solution of (2R,3S)-3-hydroxy-2-{[(tricyclo[3.3.1.1$^{3,7}$]dec-1-yloxy)carbonyl]amino}butanoic acid (0.240 g, 0.81 mmol) in dry $CH_2Cl_2$ (12 mL) under argon. After cooling at 0° C., HBTU (0.459 g, 1.21 mmol) was added and the mixture stirred 3 h at 0° C., then 16 h at rt. The obtained solid was filtered-off and the solvent removed under vacuum. The crude mixture was purified by typical silica gel column chromatography, eluting with Cy/AcOEt (90:10). The resulting white solid (0.093 g) was further triturated with cyclohexane to afford the pure title compound (0.065 g, 29%) as white solid. MS (ESI) m/z: 278.31 [M−H]$^-$. $R_f$=0.19 (Cy/AcOEt 9:1, detection: ninhydrin). FTIR (cm$^{-1}$): 3338, 2912, 2854, 1828, 1688, 1533, 1457, 1342, 1253, 1120, 1069, 1020, 970, 886, 820. $^1$H-NMR ($CDCl_3$): δ 1.46 (d, 3H); 1.66 (m, 6H); 2.09 (m, 4H); 2.18 (m, 5H); 4.84 (m, 1H); 5.14 (d, 1H); 5.40 (t, 1H).

Example 13 tert-Butyl-N-[(2S*,3R*)-2-ethyl-4-oxo-oxetan-3-yl]-carbamate and tert-Butyl-N-[(2S*,3S*)-2-ethyl-4-oxo-oxetan-3-yl]-carbamate

Step 1. Preparation of methyl 2-(propanoylamino)-acetate

In a round bottomed flask, at 0° C., to a stirred suspension of methyl glycinate hydrochloride (0.68 g, 5.4 mmol) in Et$_2$O (2.0 mL), propanoyl chloride (1.0 g, 10.8 mmol) and saturated K$_2$CO$_3$ solution (3.8 mL) were added. The reaction mixture was stirred at 0° C. for 3 h, then extracted with Et$_2$O (3×10 mL) and the resulting organic layer washed with saturated NaHCO$_3$ solution, H$_2$O, and brine. The aqueous phase was saturated with NaCl and further extracted with AcOEt (50 mL). The combined extracts were dried over Na$_2$SO$_4$, filtered, and concentrated under reduced pressure to give the crude title compound (0.55 g, 71%) as colorless oil, which was used in the next reaction. MS (ESI) m/z: 168 [M−Na]$^+$, 146 [M−H]$^+$.

Step 2. Preparation of methyl-2-[tert-butoxycarbonyl-(propanoyl)-amino]-acetate In a round bottomed flask, at rt, to a mixture of crude methyl 2-(propanoylamino)-acetate (0.78 g, 5.4 mmol) in CH$_3$CN (2.0 mL), di-tert-butyl dicarbonate (1.46 g, 6.7 mmol) and N,N-dimethylaminopyridine (0.053 g, 0.43 mmol) were added. After stirring at rt overnight, the reaction mixture was condensed in vacuo and the residue dissolved in AcOEt. The organic layer was washed with KHSO$_4$ solution and brine, dried over Na$_2$SO$_4$, filtered, and concentrated in vacuo affording a crude product, which was purified by typical silica gel column chromatography, eluting with petroleum ether/AcOEt (90:10) to give title compound (0.862 g, 65%) as colorless oil. MS (ESI) m/z: 268 [M−Na]$^+$. $^1$H NMR (CDCl$_3$): δ 1.18 (t, J=7.3 Hz, 3H), 1.52 (s, 9H), 2.97 (q, J=7.3 Hz, 2H), 3.76 (s, 3H), 4.48 (s, 2H).

Step 3. Preparation of methyl-2-(tert-butoxycarbonylamino)-3-oxo-pentanoate Under argon atmosphere, at −78° C., to a stirred solution of methyl-2-[tert-butoxycarbonyl-(propanoyl)-amino]-acetate (0.856 g, 3.5 mmol) in dry THF (4 mL) was initially added DMPU (0.89 g, 7.0 mmol) followed by LHMDS (1M solution in THF, 8.75 mL, 8.75 mmol) over a period of 10 min. After stirring at −78° C. for 1.5 h, the reaction mixture was quenched with saturated NH$_4$Cl solution and extracted with AcOEt (3×15 mL). The organic layer was washed with H$_2$O and brine, dried over Na$_2$SO$_4$, filtered, and concentrated in vacuo affording a crude product, which was purified by typical silica gel column chromatography, eluting with petroleum ether/AcOEt (90:10) to give pure product (0.694 g, 81%) as colorless crystals. MS (ESI) m/z: 268 [M−Na]$^+$. $^1$H NMR (CDCl$_3$): δ 1.13 (t, J=7.2 Hz, 3H), 1.47 (s, 9H), 2.57-2.87 (m, 2H), 3.82 (s, 3H), 5.07 (d, J=7.1 Hz, 1H), 5.73 (d, J=4.5 Hz, 1H).

Step 4. Preparation of anti:syn methyl-2-(tert-butoxycarbonylamino)-3-hydroxy-pentanoate In a round bottomed flask, under vigorous stirring, to a solution of methyl-2-(tert-butoxycarbonylamino)-3-oxo-pentanoate (0.48 g, 1.95 mmol) in a 1:1 mixture of THF/MeOH (8 mL), NaBH$_4$ (0.028 g, 0.73 mmol) was added at 0° C. and the reaction stirred for 2 h letting the temperature rise to rt. The reaction mixture was quenched with H$_2$O and the solvent evaporated. The crude product was dissolved in AcOEt and washed with brine, then dried over Na$_2$SO$_4$, filtered, and concentrated in vacuo affording a crude product, which was purified by typical silica gel column chromatography, eluting with petroleum ether/AcOEt (80:20) to give pure product (0.361 g, 75%), as a diasteromeric mixture (anti:syn=8:2), as a white solid. MS (ESI) m/z: 270 [M−Na]$^+$. $^1$H NMR (CDCl$_3$): δ 1.02 (t, J=7.4 Hz, 3H), 1.47 (s, 9H), 1.50-1.56 (m, 2H), 2.68 (d, J=4.7 Hz, 1H), 3.80 (s, 3H), 3.80-3.88 (m, 1H), 4.41 (d, J=1.5 Hz, 1H), 5.47 (s, 1H) (reported data refers to the major anti diastereoisomer).

Step 5. Preparation of anti:syn 2-(tert-butoxycarbonylamino)-3-hydroxy-pentanoic acid To a stirred solution of methyl-2-(tert-butoxycarbonylamino)-3-hydroxy-pentanoate (0.532 g, 2.15 mmol) in a 6:4 mixture acetone/DMF (28 mL), 1M NaOH solution (2.15 mL) was added and the reaction stirred rt for 1 h. After evaporation of the solvent, the crude mixture was dissolved in AcOEt and washed with H$_2$O at pH adjusted to 4.5 with 1M NaH$_2$PO$_4$ solution. The organic layer was then dried over Na$_2$SO$_4$, filtered, and concentrated in vacuo to give a crude product (0.425 g, 85%) as a diasteromeric mixture (anti:sin=8:2), as a white solid which was used in the next step without any further purification. MS (ESI) m/z: 256 [M−Na]$^+$. $^1$H NMR (DMSO-d$_6$): δ 0.87 (t, J=7.3 Hz, 3H), 1.39 (s, 9H), 1.39-1.44 (m, 2H), 3.51-3.61 (m, 1H), 3.90 (dd, J=5.8, 8.5 Hz, 1H,), 4.83 (s, 1H), 6.76 (d, J=8.7 Hz, 1H), 12.36 (s, 1H) (reported data refers to the major anti diastereoisomer).

Step 6. Preparation of tert-butyl-N-[(2S*,3R*)-2-ethyl-4-oxo-oxetan-3-yl]-carbamate and tert-butyl-N-[(2S*,3S*)-2-ethyl-4-oxo-oxetan-3-yl]-carbamate To a stirred solution of 2-(tert-butoxycarbonylamino)-3-hydroxy-pentanoic acid (0.173 mg, 0.74 mmol) in dry CH$_2$Cl$_2$ (17 mL), Et$_3$N (0.255 g, 2.3 mmol) and benzotriazol-1-yl-oxytripyrrolidinophosphonium hexafluorophosphate (PyBOP) (0.463 mg, 0.89 mmol) were added at rt and the reaction stirred overnight. Solvent was evaporated and the crude product purified by typical silica gel column chromatography, eluting with petroleum ether/AcOEt (90:10) to give a mixture of diastereoisomers (anti:sin=8:2) (0.081 g) as a white solid. The diastereomeric mixture was further purified by typical silica gel column chromatography, eluting with petroleum ether/TBME (from 100:0 to 80:20) to give pure diastereoisomers, tert-butyl-N-[(2S*,3R*)-2-ethyl-4-oxo-oxetan-3-yl]-carbamate (0.0095 g, 6%) and tert-butyl-N-[(2S*,3S*)-2-ethyl-4-oxo-oxetan-3-yl]-carbamate (0.0382 g, 24%), as white solids.

tert-butyl-N-[(2S*,3R*)-2-ethyl-4-oxo-oxetan-3-yl]-carbamate: MS (ESI) m/z: 238 [M−Na]$^+$. $^1$H NMR (DMSO-d$_6$): δ 0.88 (t, J=7.4 Hz, 3H), 1.41 (s, 9H), 1.59-1.83 (m, 2H), 4.57 (dd, J=6.2, 14.1 Hz, 1H), 5.39 (dd, J=6.0, 9.5 Hz, 1H,), 7.99 (d, J=9.4 Hz, 1H).

tert-butyl-N-[(2S*,3S*)-2-ethyl-4-oxo-oxetan-3-yl]-carbamate: $^1$H NMR (DMSO-d$_6$): δ 0.91 (t, J=7.4 Hz, 3H,), 1.40

(s, 9H), 1.68-1.90 (m, 2H), 4.49 (td, J=4.4, 6.8 Hz, 1H), 4.64 (dd, J=4.3, 8.1 Hz, 1H), 7.79 (d, J=8.1 Hz, 1H).

Preparation of
(3S,4R)-2-methyl-4-oxo-3-oxetanylammonium toluene-4-sulfonate

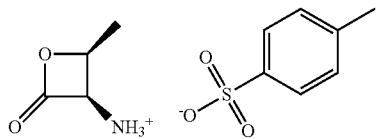

The compound was synthesized as described in Solorzano et al., *Journal of Medicinal Chemistry* 2010, 53, 5770-5781.

Example 14

(3-phenylphenyl)-methyl-N-[(2S,3R)-2-methyl-4-oxo-oxetan-3-yl]-carbamate

Step 1. Preparation of 3-phenylbenzaldehyde

In a microwave tube, to a solution of bromo-benzene (0.5 g, 3.18 mmol) dissolved in a 1:1 mixture toluene/EtOH (14 mL), 3-formylphenyl boronic acid (0.573 g, 3.82), palladium-tetrakis(triphenylphosphine) (0.184 g, 0.159 mmol) and 10% $Na_2CO_3$ solution (7 mL) were sequentially added. The reaction was run at 100° C. for 30 min under microwave irradiation. The crude product was diluted with AcOEt and brine, and extracted. The organic phase was separated, dried over $Na_2SO_4$ and filtered over a pad of celite to give an organic fraction, which was concentrated to dryness to afford the title compound (0.671 g, quant.). $^1$H NMR (CDCl$_3$): δ 8.23-7.36 (m, 9H), 10.13 (s, 1H).

Step 2. Preparation of (3-phenylphenyl)-methanol

Under nitrogen atmosphere, at 0° C., to a stirred solution of NaBH$_4$ (0.56 g, 14.7 mmol) in dry MeOH (10 mL), 3-phenylbenzaldehyde (0.67 g, 3.68 mmol) in dry MeOH (7 mL) was added via a cannula. After 1 h, the crude was quenched with water and concentrated to dryness. The resulting oil was dissolved in AcOEt and extracted with water. The organic fraction was dried over $Na_2SO_4$, filtered and subsequently purified by column chromatography using a Teledyne ISCO apparatus, eluting with Cy/TBME (from 100:0 to 50:50) to afford the title compound (0.432 g, 64%) as a pure product. $^1$H NMR (CDCl$_3$): δ 1.62-1.78 (m, 1H), 4.80 (d, J=6.0, 1H), 7.33-7.75 (m, 9H).

Step 3. Preparation of (3-phenylphenyl)methyl-2-pyridyl-carbonate and 3-phenylphenyl)methyl-2-oxopyridine 1-carboxylate Under nitrogen atmosphere, to a stirred mixture of 3-phenylphenyl methanol (0.3 g, 1.63 mmol) in dry CH$_2$Cl$_2$ (3 mL), Et$_3$N (0.340 mL, 2.44 mmol) and di-2-pyridyl carbonate (0.387 g, 1.79 mmol) were added. The reaction mixture was left at rt for 15 h, diluted with CH$_2$Cl$_2$ and washed first with a saturated NH$_4$Cl solution (3 mL) and subsequently with a saturated NaHCO$_3$ solution (3×3 mL). The organic fraction was dried over Na$_2$SO$_4$, filtered and concentrated to dryness to afford a dark oil (0.487 g, 98%), as a mixture (ratio 1:3) of 3-phenylphenyl)methyl-2-pyridyl-carbonate and 3-phenylphenyl)methyl-2-oxopyridine 1-carboxylate. The mixture of isomers was not separated and used in the next step without any further purification. MS (ESI) m/z: 328 [M–Na]$^+$, 306 [M–H]$^+$, 262, 167.

Step 4. Preparation of (3-phenylphenyl)-methyl-N-[(2S,3R)-2-methyl-4-oxo-oxetan-3-yl]-carbamate Under nitrogen atmosphere, to a stirred mixture of (3S, 4R)-2-methyl-4-oxo-3-oxetanylammonium toluene-4-sulfonate (0.120 g, 0.44 mmol) in dry CH$_2$Cl$_2$ (1 mL), DIPEA (0.072 mL, 0.44 mmol) was added dropwise. Subsequently, the crude mixture containing (3-phenylphenyl)-methyl-2-oxopyridine 1-carboxylate (0.402 g, 1.32 mmol) dissolved in dry CH$_2$Cl$_2$ (2 mL) was added. The reaction mixture was stirred 15 h at rt, concentrated to dryness and purified by column chromatography using a Teledyne ISCO apparatus, eluting with cyclohexane/TBME (from 100:0 to 70:30) to afford the title compound (0.045 g, 32%) as a white solid. MS (ESI) m/z: 334 [M–Na]$^+$. $^1$H-NMR (DMSO-d$_6$): δ 1.36 (d, J=6.4, 3H), 4.88 (dq, J$_1$=J$_2$=6.3, 1H), 5.08-5.29 (m, 2H), 5.47 (dd, J=9.3, J=6.2, 1H), 7.31-7.79 (m, 9H), 8.40 (d, J=9.3, 1H).

Example 15

5-(4-fluorophenyl)-pentyl-N-[(2S,3R)-2-methyl-4-oxo-oxetan-3-yl]-carbamate

Step 1. Preparation of
5-(4-fluorophenyl)-pentan-1-ol

Under nitrogen atmosphere, at 0° C., to a stirring mixture of LiAlH$_4$ (0.46 g, 12.23 mmol) in dry Et$_2$O (5 mL), 5-(4-fluorophenyl)-pentanoic acid (0.6 g, 3.05 mmol) in dry Et$_2$O (35 mL) was added dropwise. The mixture was left to react at rt for 4 h, then at 0° C. H$_2$O (0.46 mL), 3M KOH solution (0.46 mL) and H$_2$O (1.54 mL) were very slowly added. The mixture was stirred for 1 h at 0° C., filtered to remove the solid residue, and the organic phase dried over Na$_2$SO$_4$. The organic solution was again filtered and concentrated to dryness affording the title compound (0.53 g, 95%) as a colorless oil. $^1$H NMR (CDCl$_3$): δ 1.36-1.47 (m, 2H), 1.58-1.71 (m, 4H), 2.58-2.65 (m, 2H), 3.66 (t, J=5.8 Hz, 2H), 6.94-7.02 (m, 2H), 7.11-7.17 (m, 2H).

Step 2. Preparation of 5-(4-fluorophenyl)-pentyl-2-pyridyl-carbonate and 5-(4-fluorophenyl)-pentyl-2-oxopyridine 1-carboxylate Under nitrogen atmosphere, to a stirred mixture of 5-(4-fluorophenyl)-pentan-1-ol (0.3 g, 1.64 mmol) in dry CH$_2$Cl$_2$ (2 mL), Et$_3$N (0.34 mL, 2.5 mmol) and di-2-pyridyl carbonate (0.409 g, 1.89 mmol) were added. The reaction mixture was left to react at rt for 5 h, then diluted with CH$_2$Cl$_2$ and washed first with a saturated NH$_4$Cl solution (3 mL) and subsequently with a saturated NaHCO$_3$ solution (3×3 mL). The organic fraction was dried over Na$_2$SO$_4$, filtered and concentrated to dryness to afford an orange oil (0.44 g, 88%), as a mixture (ratio 1:5) of 5-(4-fluorophenyl)-pentyl-2-pyridyl-carbonate and 5-(4-fluorophenyl)-pentyl-2-oxopyridine 1-carboxylate. The mixture of isomers was not separated and used in the next step without any further purification. MS (ESI) m/z: 304 [M–H]$^+$, 266.

Step 3. Preparation of 5-(4-fluorophenyl)-pentyl-N-[(2S,3R)-2-methyl-4-oxo-oxetan-3-yl]-carbamate Under nitrogen atmosphere, to a stirred mixture of (3S, 4R)-2-methyl-4-oxo-3-oxetanylammonium toluene-4-sulfonate (0.100 g, 0.36 mmol) in dry CH$_2$Cl$_2$ (1 mL), DIPEA (0.060 mL, 0.36 mmol) was dropwise added. Subsequently, the crude mixture containing 5-(4-fluorophenyl)-pentyl-2-oxopyridine 1-carboxylate (0.55 g, 1.83 mmol) in dry CH$_2$Cl$_2$ (4 mL) was added. The reaction mixture was stirred 15 h at rt, concentrated to dryness and purified by column chromatography using a Teledyne ISCO apparatus, eluting with Cy/TBME (from 100:0 to 70:30). The crude product was further purified by preparative HPLC-MS to afford the title compound (0.040 g, 35%) as a white solid. MS (ESI) m/z: 310 [M–H]$^+$; (ESI) m/z: 308 [M–H]$^-$. $^1$H NMR (DMSO-d$_6$): δ 1.27-1.37 (m, 5H), 1.52-1.64 (m, 4H), 2.53-2.59 (m, 2H), 3.93-4.06 (m, 2H), 4.84 (dq, J=6.3 Hz, 1H), 5.40 (dd, J=6.1, 9.4 Hz, 1H), 7.04-7.13 (m, 2H), 7.18-7.26 (m, 2H), 8.19 (d, J=9.4 Hz, 1H).

Example 16

7-Phenylheptyl-N-[(2S,3R)-2-methyl-4-oxo-oxetan-3-yl]-carbamate

Step 1. Preparation of 7-phenylheptan-1-ol

Under nitrogen atmosphere, at 0° C., to a stirring mixture of LiAlH$_4$ (0.51 g, 13.57 mmol) in dry Et$_2$O (35 mL), 7-phenylheptanoic acid (0.7 g, 3.39 mmol) in dry Et$_2$O (5 mL) was dropwise added. The mixture was left to react at rt for 4 h, then at 0° C. H$_2$O (0.51 mL), 3M KOH solution (0.51 mL) and H$_2$O (1.70 mL) were very slowly added. The mixture was stirred for 1 h at 0° C., filtered to remove the solid residue, and the organic phase dried over Na$_2$SO$_4$. The organic solution was again filtered and concentrated to dryness affording the title compound (0.586 g, 90%) as a colorless oil. $^1$H NMR (CDCl$_3$): δ 1.17-1.27 (m, 1H), 1.34-1.43 (m, 6H), 1.53-1.71 (m, 4H), 2.59-2.67 (m, 2H), 3.66 (t, J=6.5 Hz, 2H), 7.16-7.23 (m, 3H), 7.26-7.34 (m, 2H).

Step 2. Preparation of 7-phenylheptyl-2-pyridyl-carbonate and 7-phenylheptyl-2-oxopyridine 1-carboxylate Under nitrogen atmosphere, to a stirred mixture of 7-phenylheptan-1-ol (0.44 g, 2.28 mmol) in dry CH$_2$Cl$_2$ (4 mL), DMAP (0.027 g, 0.23 mmol) and di-2-pyridyl carbonate (0.593 g, 2.74 mmol) were added. The reaction mixture was left to react at rt for 5 h, then diluted with CH$_2$Cl$_2$ and washed first with a saturated NH$_4$Cl solution (3 mL) and subsequently with a saturated NaHCO$_3$ solution (3×3 mL). The organic fraction was dried over Na$_2$SO$_4$, filtered and concentrated to dryness to afford a colorless oil (0.72 g, 98%) as a mixture (ratio 1:1.5) of 7-phenylheptyl-2-pyridyl-carbonate and 7-phenylheptyl-2-oxopyridine 1-carboxylate. The mixture of isomers was not separated and used in the next step without any further purification. MS (ESI) m/z: 352 [M–K]$^+$, 336 [M–Na]$^+$, 314 [M–H]$^+$.

Step 3. Preparation of 7-phenylheptyl-N-[(2S,3R)-2-methyl-4-oxo-oxetan-3-yl]-carbamate Under nitrogen atmosphere, to a stirred mixture of (3S, 4R)-2-methyl-4-oxo-3-oxetanylammonium toluene-4-sulfonate (0.100 g, 0.36 mmol) in dry CH$_2$Cl$_2$ (1 mL), DIPEA (0.060 mL, 0.36 mmol) was dropwise added. Subsequently, the crude mixture containing 7-phenylheptyl-2-oxopyridine 1-carboxylate (0.34 g, 1.1 mmol) in dry CH$_2$Cl$_2$ (4 mL) was added. The reaction mixture was stirred 15 h at rt, concentrated to dryness and purified by column chromatography using a Teledyne ISCO apparatus, eluting with Cy/TBME (from 100:0 to 70:30). The crude product was further purified by preparative HPLC-MS to afford the title compound (0.038 g, 33%) as a white solid. MS (ESI) m/z: 320 [M–H]$^+$; (ESI) m/z: 318 [M–H]$^-$. $^1$H NMR (DMSO-d$_6$): δ 1.24-1.38 (m, 9H), 1.49-1.62 (m, 4H), 2.53-2.61 (m, 2H), 3.93-4.07 (m, 2H), 4.85 (dq, J=6.3 Hz, 1H), 5.41 (dd, J=6.3, 9.4 Hz, 1H), 7.13-7.21 (m, 3H), 7.24-7.30 (m, 2H), 8.19 (d, J=9.4 Hz, 1H).

Example 17

(4-phenylphenyl)methyl-N-[(2S,3R)-2-methyl-4-oxo-oxetan-3-yl]-carbamate

Step 1. Preparation of (4-phenylphenyl)-methyl-2-pyridyl carbonate and (4-phenylphenyl)-methyl-2-oxopyridine 1-carboxylate Under nitrogen atmosphere, to a stirred mixture of the commercially available (4-phenylphenyl)-methanol (0.3 g, 1.63 mmol) in dry CH$_2$Cl$_2$ (4 mL), DMAP (0.01 g, 0.16 mmol) and di-2-pyridyl carbonate (0.46 g, 2.11 mmol) were added. The reaction mixture was left to react at rt for 5 h, then diluted with CH$_2$Cl$_2$ and washed first with a saturated NH$_4$Cl solution (3 mL) and subsequently with a saturated NaHCO$_3$ solution (4×3 mL). The organic fraction was dried over Na$_2$SO$_4$, filtered and concentrated to dryness to afford a dark oil (0.48 g, 96%), as a mixture (ratio 1.5:1) of (4-phenylphenyl)-methyl-2-pyridyl carbonate and (4-phenylphenyl)-methyl-2-oxopyridine 1-carboxylate. The mixture of isomers was not separated and used in the next step without any further purification. MS (ESI) m/z: 306 [M–H]$^+$, 262, 167; (ESI$^-$) m/z: 249, 205, 155.

Step 2. Preparation of (4-phenylphenyl)-methyl-N-[(2S,3R)-2-methyl-4-oxo-oxetan-3-yl]-carbamate Under nitrogen atmosphere, to a stirred mixture of (3S, 4R)-2-methyl-4-oxo-3-oxetanylammonium toluene-4-sulfonate (0.12 g, 0.44 mmol) in dry CH$_2$Cl$_2$ (1 mL), DIPEA (0.072 mL, 0.44 mmol) was dropwise added. Subsequently, the crude mixture containing (4-phenylphenyl)-methyl-2-oxopyridine 1-carboxylate (0.40 g, 1.31 mmol) in dry CH$_2$Cl$_2$ (2 mL) was added. The reaction mixture was stirred 15 h at rt, concentrated to dryness and purified by column chromatography using a Teledyne ISCO apparatus, eluting with Cy/TBME (from 100:0 to 70:30) to afford the title compound (0.04 g, 30%) as a white solid. MS (ESI) m/z: 329 [M–NH$_4$]$^+$, 350 [M–K]$^+$; (ESI) m/z: 310 [M–H]$^-$. $^1$H NMR (DMSO-d$_6$): δ 1.37 (d, J=6.4 Hz, 3H), 4.88 (dq, J=6.3 Hz, 1H), 5.12 (d, J=12.5 Hz, 1H), 5.16 (d, J=12.4 Hz, 1H), 5.47 (dd, J=6.1, 9.4 Hz, 1H), 7.35-7.41 (m, 1H), 7.45-7.51 (m, 4H), 7.66-7.71 (m, 4H), 8.40 (d, J=9.3 Hz, 1H).

Example 18

3-Benzyloxypropyl-N-[(2S,3R)-2-methyl-4-oxo-oxetan-3-yl]-carbamate

Step 1. Preparation of 3-benzyloxypropyl-2-pyridyl-carbonate and 3-benzyloxypropyl-2-oxopyridine 1-carboxylate Under nitrogen atmosphere, to a stirred mixture of the commercially available 3-benzyloxypropan-1-ol (0.3 g, 1.80 mmol) in dry CH$_2$Cl$_2$ (3 mL), DMAP (0.022 g, 0.18 mmol) and di-2-pyridyl carbonate (0.51 g, 2.34 mmol) were added.

The reaction mixture was left to react at rt for 4 h, then diluted with CH₂Cl₂ and washed first with a saturated NH₄Cl solution (3 mL) and subsequently with a saturated NaHCO₃ solution (4×3 mL). The organic fraction was dried over Na₂SO₄, filtered and concentrated to dryness to afford a pale orange oil (0.47 g, 98%), as a mixture (ratio 1.6:1) 3-benzyloxypropyl-2-pyridyl-carbonate and 3-benzyloxypropyl-2-oxopyridine 1-carboxylate. The mixture of isomers was not separated and used in the next step without any further purification. MS (ESI) m/z: 326 [M−K]⁺, 310 [M−Na]⁺, 288 [M−H]⁺, 186, 148; (ESI⁻) m/z: 286, 249, 205, 155.

Step 2. Preparation of 3-benzyloxypropyl-N-[(2S, 3R)-2-methyl-4-oxo-oxetan-3-yl]-carbamate Under nitrogen atmosphere, to a stirred mixture of (3S, 4R)-2-methyl-4-oxo-3-oxetanylammonium toluene-4-sulfonate (0.10 g, 0.36 mmol) in dry CH₂Cl₂ (1 mL), DIPEA (0.06 mL, 0.36 mmol) was dropwise added. Subsequently, the crude mixture containing 3-benzyloxypropyl-2-oxopyridine 1-carboxylate (0.294 g, 1.02 mmol) in dry CH₂Cl₂ (2 mL) was added. The reaction mixture was stirred 15 h at rt, concentrated to dryness and purified by column chromatography using a Teledyne ISCO apparatus, eluting with Cy/TBME (from 100:0 to 70:30). The crude product was further purified by preparative HPLC-MS to afford the title compound (0.045 g, 41%) as a white solid. MS (ESI) m/z: 294 [M−H]⁺; (ESI) m/z: 292 [M−H]⁻. ¹H NMR (DMSO-d₆): δ 1.34 (d, J=6.3 Hz, 3H), 1.81-1.91 (m, 2H), 3.50 (t, J=6.3 Hz, 2H), 4.04-4.16 (m, 2H), 4.47 (s, 2H), 4.85 (dq, J=6.2 Hz, 1H), 5.42 (dd, J=6.2, 9.3 Hz, 1H), 7.25-7.40 (m, 5H), 8.23 (d, J=9.4 Hz, 1H).

Example 19

4-cyclohexylbutyl-N-[(2S,3R)-2-methyl-4-oxo-oxetan-3-yl]-carbamate

Step 1. Preparation of 4-cyclohexylbutyl-2-pyridyl-carbonate and 4-cyclohexylbutyl-2-oxopyridine 1-carboxylate Under nitrogen atmosphere, to a stirred mixture of commercially available 4-cyclohexylbutan-1-ol (0.8 mL, 4.6 mmol) in dry CH₂Cl₂ (23 mL), DMAP (0.056 g, 0.46 mmol) and di-2-pyridyl carbonate (1.29 g, 5.98 mmol) were added. The reaction mixture was left to react at rt for 15 h, then diluted with CH₂Cl₂ and washed first with a saturated NH₄Cl solution (6 mL) and subsequently with a saturated NaHCO₃ solution (4×6 mL). The organic fraction was dried over Na₂SO₄, filtered and concentrated to dryness to afford a pale grey oil (1.10 g, quantitative) as a mixture (ratio 1.8:1) of 4-cyclohexylbutyl-2-pyridyl-carbonate and 4-cyclohexylbutyl-2-oxopyridine 1-carboxylate. The mixture of isomers was not separated and used in the next step without any further purification. MS (ESI) m/z: 316 [M−K]⁺, 300 [M−Na]⁺, 278 [M−H]⁺, 140. (ESI) m/z: 276 [M−H]⁻, 249, 205, 155.

Step 2. Preparation of 4-cyclohexylbutyl-N-[(2S, 3R)-2-methyl-4-oxo-oxetan-3-yl]-carbamate Under nitrogen atmosphere, to a stirred mixture of (3S, 4R)-2-methyl-4-oxo-3-oxetanylammonium toluene-4-sulfonate (0.12 g, 0.44 mmol) in dry CH₂Cl₂ (1 mL), DIPEA (0.07 mL, 0.44 mmol) was dropwise added. Subsequently, the crude mixture containing 4-cyclohexylbutyl-2-oxopyridine 1-carboxylate (0.36 g, 1.31 mmol) in dry CH₂Cl₂ (2 mL) was added. The reaction mixture was stirred 15 h at rt, concentrated to dryness and purified by column chromatography using a Teledyne ISCO apparatus, eluting with Cy/TBME (from 100:0 to 70:30). The crude product was further purified by preparative HPLC-MS to afford the title compound (0.050 g, 40%) as a white solid. MS (ESI) m/z: 284 [M−H]⁺; (ESI) m/z: 282 [M−H]⁻. ¹H NMR (DMSO-d₆): δ 0.78-0.93 (m, 2H), 1.08-1.27 (m, 7H), 1.27-1.39 (m, 1H), 1.35 (d, J=6.4 Hz, 3H), 1.49-1.73 (m, 7H), 3.94-4.06 (m, 2H), 4.85 (dq, J=6.4 Hz, 1H), 5.41 (dd, J=6.0, 9.4 Hz, 1H), 8.19 (d, J=9.4 Hz, 1H).

Example 20

(2,2-dimethyl-4-phenyl-butyl)-N-[(2S,3R)-2-methyl-4-oxo-oxetan-3-yl]-carbamate

Step 1. Preparation of 2,2-dimethyl-4-phenyl-butanoic acid

To a stirring mixture of diisopropylamine (2.2 mL, 15 mmol) and sodium hydride [60% in mineral oil] (0.66 g, 16.5 mmol) in dry THF (50 mL), isobutyric acid (1.4 mL, 15 mmol) was dropwise added. The mixture was refluxed for 15 min, cooled to 0° C., and 2.5M n-butyllithium (BuLi) in hexane (5.45 mL, 14 mmol;) was added. After 20 min at 0° C., the mixture was heated to 30-35° C. for 30 min. The solution was then cooled to 0° C. and (2-bromoethyl)-benzene (2.8 mL, 15 mmol) was slowly added over 20 min. After ca. 1 h at 30-35° C. the reaction was quenched by adding water (40 mL), while keeping the temperature below 15° C. The aqueous layer was separated, and the organic layer washed with a mixture of Et₂O/H₂O (1:1). The aqueous layers were combined, extracted with Et₂O (20 mL), acidified with 2M HCl solution, and the product was further extracted with Et₂O (2×30 mL). The combined organic layers were washed with brine, dried over Na₂SO₄, filtered and concentrated under vacuum to afford the title compound (0.619 g, 21%) as a colorless oil. ¹H NMR (CDCl₃): δ 1.31 (s, 6H), 1.86-1.95 (m, 2H), 2.59-2.68 (m, 2H), 7.17-7.33 (m, 5H).

Step 2. Preparation of 2,2-dimethyl-4-phenyl-butan-1-ol

At 0° C., under nitrogen atmosphere, to a stirring mixture of LiAlH₄ (0.49 g, 12.8 mmol) in dry Et₂O (25 mL), 2,2-dimethyl-4-phenyl-butanoic acid (0.62 g, 3.22 mmol) dissolved in Et₂O (10 mL) was added dropwise. The mixture was left at rt for 4 h, then quenched at 0° C. by slowly adding H₂O (0.5 mL) followed by 3M KOH solution (0.5 mL) and H₂O (1.64 mL). The mixture was stirred for 1 h at 0° C., then the crude was filtered and the organic phase dried over Na₂SO₄. The organic solution was concentrated to dryness affording the title compound (0.540 g, 94%) as pale yellow transparent oil. ¹H NMR (CDCl₃): δ 0.96 (s, 6H), 1.55-1.64 (m, 2H), 2.58-2.65 (m, 2H) 3.41 (s, 2H), 7.17-7.33 (m, 5H).

Step 3. Preparation of (2,2-dimethyl-4-phenyl-butyl)-2-pyridyl carbonate and (2,2-dimethyl-4-phenyl-butyl)-2-oxopyridine 1-carboxylate Under nitrogen atmosphere, to a stirred mixture of 2,2-dimethyl-4-phenyl-butan-1-ol (0.2 g, 1.53 mmol) in dry CH₂Cl₂ (3 mL), Et₃N (0.45 mL, 3.25 mmol) and di-2-pyridyl carbonate (0.51 g, 2.38 mmol) were added. The reaction mixture was left at rt for 17 h, then diluted with CH₂Cl₂ and washed first with a saturated NH₄Cl solution (3 mL) and subsequently with a saturated NaHCO₃ solution (3×3 mL). The organic fraction was dried over Na₂SO₄, filtered and concentrated to dryness to afford an orange oil (0.57 g, 88%), as a mixture (ratio 3:1) of (2,2-dimethyl-4-phenyl-butyl)-2-pyridil carbonate and (2,2-dimethyl-4-phenyl-butyl)-2-oxopyridine 1-carboxylate. The mixture of isomers was not separated and used in the next step without any further purification. MS (ESI) m/z: 322 [M−Na]$^+$, 278 [M−H]$^+$, 161.

Step 4. Preparation of 2,2-dimethyl-4-phenyl-butyl-N-[(2S,3R)-2-methyl-4-oxo-oxetan-3-yl]-carbamate Under nitrogen atmosphere, to a stirred mixture of (3S,4R)-2-methyl-4-oxo-3-oxetanylammonium toluene-4-sulfonate (0.120 g, 0.44 mmol) in dry $CH_2Cl_2$ (1 mL), DIPEA (0.072 mL, 0.44 mmol) was dropwise added. Subsequently, the crude mixture containing (2,2-dimethyl-4-phenyl-butyl)-2-oxopyridine 1-carboxylate (0.39 g, 1.32 mmol) dissolved in dry $CH_2Cl_2$ (2 mL) was added. The reaction mixture was stirred 15 h at rt, concentrated to dryness and purified by column chromatography using a Teledyne ISCO apparatus, eluting with Cy/TBME (from 100:0 to 70:30) to give the title compound (0.051 g, 37%) as colorless oil. MS (ESI) m/z: 306 [M−H]$^+$; (ESI) m/z: 304 [M−H]$^−$. $^1$H NMR (DMSO-$d_6$): δ 0.95 (s, 6H), 1.35 (d, J=6.4 Hz, 3H), 1.47-1.55 (m, 2H), 2.48-2.58 (m, 2H), 3.79-3.91 (m, 2H), 4.86 (dq, J=6.3 Hz, 1H), 5.43 (dd, J=6.1, 9.3 Hz, 1H), 7.12-7.31 (m, 5H), 8.25 (d, J=9.3 Hz, 1H).

Example 21

(1-benzyl-4-piperidyl)-N-[(2S,3R)-2-methyl-4-oxo-oxetan-3-yl]-carbamate

Step 1. Preparation of (1-benzyl-4-piperidyl)-2-pyridyl carbonate and (1-benzyl-4-piperidyl)-2-oxopyridine 1-carboxylate Under nitrogen atmosphere, to a stirred mixture of 1-benzylpiperidin-4-ol (0.3 g, 1.57 mmol) in dry $CH_2Cl_2$ (3 mL), $Et_3N$ (0.33 mL, 2.35 mmol) and di-2-pyridyl carbonate (0.508 g, 2.35 mmol) were added. The reaction mixture was left at rt for 17 h, then diluted with $CH_2Cl_2$ and washed first with a saturated $NH_4Cl$ solution (3 mL) and subsequently with a saturated $NaHCO_3$ solution (3×3 mL). The organic fraction was dried over $Na_2SO_4$, filtered and concentrated to dryness to afford a yellow oil (0.505 g, 99%), as a mixture (ratio 1:3) of (1-benzyl-4-piperidyl)-2-pyridyl carbonate and (1-benzyl-4-piperidyl)-2-oxopyridine 1-carboxylate. The mixture of isomers was not separated and used in the next step without any further purification. MS (ESI) m/z: 313 [M−H]$^+$, 218, 174.

Step 2. Preparation of (1-benzyl-4-piperidyl)-N-[(2S,3R)-2-methyl-4-oxo-oxetan-3-yl]carbamate Under nitrogen atmosphere, to a stirred mixture of (3S,4R)-2-methyl-4-oxo-3-oxetanylammonium toluene-4-sulfonate (0.120 g, 0.44 mmol) in dry $CH_2Cl_2$ (1 mL), DIPEA (0.072 mL, 0.44 mmol) was dropwise added. Subsequently, the crude mixture containing (1-benzyl-4-piperidyl)-2-oxopyridine 1-carboxylate (0.34 g, 1.09 mmol) dissolved in dry $CH_2Cl_2$ (2 mL) was added. The reaction mixture was stirred 15 h at rt, concentrated to dryness and purified by column chromatography using a Teledyne ISCO apparatus, eluting with Cy/TBME (from 100:0 to 70:30). The crude product was further purified by preparative HPLC to afford the title compound (0.050 g, 21%) as white solid. MS (ESI) m/z: 319 [M−H]$^+$; (ESI) m/z: 317 [M−H]$^−$. $^1$H NMR (DMSO-$d_6$): δ 1.34 (d, J=6.4 Hz, 3H), 1.49-1.64 (m, 2H), 1.77-1.91 (m, 2H), 2.11-2.26 (m, 2H), 2.58-2.71 (m, 2H), 3.46 (s, 2H), 4.47-4.66 (m, 1H), 4.84 (dq, J=6.3 Hz, 1H), 5.40 (dd, J=6.1, 9.4 Hz, 1H), 7.19-7.38 (m, 5H), 8.21 (d, J=9.4 Hz, 1H).

Example 22

[(1R) and (1S)-1-methyl-5-phenyl-pentyl]-N-[(2S,3R)-2-methyl-4-oxo-oxetan-3-yl]-carbamate Step 1. Preparation of 5-phenylpentan-1-ol Under nitrogen atmosphere, at 0° C., to a stirring mixture of $LiAlH_4$ (0.84 g, 22.44 mmol) in dry $Et_2O$ (55 mL), 5-phenylpentanoic acid (1.00 g, 5.61 mmol) in dry $Et_2O$ (10 mL) was added dropwise. The mixture was left to react at rt for 4 h, then at 0° C. $H_2O$ (0.85 mL), 3M KOH solution (0.85 mL) and $H_2O$ (2.85 mL) were very slowly added. The mixture was stirred for 1 h at 0° C., filtered to remove the solid residue, and the organic phase dried over $Na_2SO_4$. The organic solution was again filtered and concentrated to dryness affording the title compound (0.881 g, 95%) as a colorless oil. $^1$H NMR ($CDCl_3$): δ 1.36-1.46 (m, 2H), 1.54-1.72 (m, 5H), 2.58-2.71 (m, 2H), 3.59-3.71 (m, 2H), 7.14-7.33 (m, 5H).

Step 2. Preparation of 5-phenylpentanal

Under nitrogen atmosphere, at −78° C., to a stirred solution of oxalyl chloride (0.53 mL, 6.17 mmol) in dry $CH_2Cl_2$ (12 mL), DMSO (0.40 mL, 5.7 mmol) was added in a fast manner. After 15 min, a solution of 5-phenylpentan-1-ol (0.78 g, 4.75 mmol) in dry $CH_2Cl_2$ (6 mL) was added. The reaction mixture was stirred for 2 h at −78° C. before addition of $Et_3N$ (1.98 mL, 14.24 mmol). The solution was allowed to warm at rt, and after evaporation of $CH_2Cl_2$ the residue was taken up in $Et_2O$ and a saturated $NH_4Cl$ solution. After separation of phases the organic fraction was dried over $Na_2SO_4$, filtered and concentrated to dryness affording the title compound (0.75 g, 97%) as a pure product. $^1$H NMR ($CDCl_3$): δ 1.67-1.73 (m, 4H), 2.44-2.52 (m, 2H), 2.60-2.71 (m, 2H), 7.16-7.35 (m, 5H), 9.78 (t, J=1.8 Hz, 1H).

Step 3. Preparation of 6-phenyl-hexan-2-ol

Under nitrogen atmosphere, at −78° C., to a stirred solution of 5-phenylpentanal (0.8 g, 4.93 mmol) in dry THF (20 mL), 1.6M methyllithium (MeLi) solution in $Et_2O$ (3.39 mL, 5.42 mmol) was added dropwise. The reaction was left to stir for 2 h at −78° C. and then 1 h at rt. The reaction was then cooled at 0° C. and quenched with water. THF was rotary evaporated and the crude mixture dissolved in $CH_2Cl_2$, dried over $Na_2SO_4$, filtered and concentrated to dryness. The crude mixture was purified over silica using a Teledyne ISCO apparatus, eluting with Cy/TBME (from 100:0 to 50:50) to afford pure alcohol (0.2 g, 23%). $^1$H NMR ($CDCl_3$): δ 1.21 (d, J=6.2 Hz, 3H), 1.25-1.75 (m, 7H), 2.60-2.71 (m, 2H), 3.76-3.87 (m, 1H), 7.16-7.35 (m, 5H).

Step 4. Preparation of (1-methyl-5-phenyl-pentyl)-2-pyridyl-carbonate and (1-methyl-5-phenyl-pentyl)-2-oxopyridine 1-carboxylate Under nitrogen atmosphere, to a stirred mixture of 6-phenyl-hexan-2-ol (0.2 g, 1.12 mmol) in dry $CH_2Cl_2$ (2 mL), $Et_3N$ (0.23 mL, 1.68 mmol) and di-2-pyridyl carbonate (0.508 g, 2.35 mmol) were added. The reaction mixture was left to react at rt for 3 h, then diluted with $CH_2Cl_2$ and washed first with a saturated NH₄Cl solution (3 mL) and subsequently with a saturated NaHCO₃ solution (3×3 mL). The organic fraction was dried over Na₂SO₄, filtered and concentrated to dryness to afford a yellow oil (0.3 g, 91%), as a mixture (ratio 1:3) of (1-methyl-5-phenyl-pentyl)-2-pyridyl-carbonate and (1-methyl-5-phenyl-pentyl)-2-oxopyridine 1-carboxylate. The mixture of isomers was not separated and used in the next step without any further purification. MS (ESI) m/z: 322 [M−Na]⁺, 300 [M−H]⁺.

Step 5. Preparation of [(1R) and (1S)-1-methyl-5-phenyl-pentyl]-N-[(2S,3R)-2-methyl-4-oxo-oxetan-3-yl]-carbamate Under nitrogen atmosphere, to a stirred mixture of (3S, 4R)-2-methyl-4-oxo-3-oxetanylammonium toluene-4-sulfonate (0.100 g, 0.36 mmol) in dry CH₂Cl₂ (1 mL), DIPEA (0.060 mL, 0.36 mmol) was added dropwise. Subsequently, the crude mixture containing (1-methyl-5-phenyl-pentyl)-2-oxopyridine 1-carboxylate (0.31 g, 1.02 mmol) dissolved in dry CH₂Cl₂ (2 mL) was added. The reaction mixture was stirred 15 h at rt, concentrated to dryness and purified by column chromatography using a Teledyne ISCO apparatus, eluting with Cy/TBME (from 100:0 to 70:30). The crude product was further purified by preparative HPLC-MS to afford the title compound (0.035 g, 32%), as a pure mixture (ratio=1:1) of two diastereoisomers. MS (ESI) m/z: 306 [M−H]⁺; (ESI) m/z: 304 [M−H]⁻. ¹H NMR (DMSO-d₆): δ 1.12-1.21 (m, 6H), 1.26-1.38 (m, 10H), 1.46-1.64 (m, 8H), 2.52-2.61 (m, 4H), 4.64-4.75 (m, 2H), 4.84 (dq, J=6.2 Hz, 2H), 5.39 (dd, J=6.2, 9.3 Hz, 2H), 7.12-7.31 (m, 10H), 8.12 (d, J=9.3 Hz, 2H).

Example 23

(1-Methylcyclopentyl) N-[(2S,3R)-2-methyl-4-oxo-oxetan-3-yl]-carbamate

Step 1. Preparation of (1-methylcyclopentyl)-2-pyridyl-carbonate and (1-methylcyclopentyl)-2-oxopyridine 1-carboxylate To a stirred mixture of 1-methylcyclopentyl alcohol (0.3 g, 2.99 mmol) in dry CH₂Cl₂ (3 mL) and under nitrogen atmosphere, 4-dimethylaminopyridine (0.036 g, 0.29 mmol) and di-2-pyridyl carbonate (0.681 g, 3.14 mmol) were added. The reaction mixture was left at rt for 15 h, then diluted with CH₂Cl₂ and washed first with a saturated NH₄Cl solution and subsequently with a saturated NaHCO₃ solution. The organic fraction was dried over Na₂SO₄, filtered and concentrated to dryness to afford a yellow transparent oil (0.378 g, 57%), as a mixture (ratio 4:6) of (1-methylcyclopentyl)-2-pyridyl-carbonate and (1-methylcyclopentyl)-2-oxopyridine 1-carboxylate. The mixture of isomers was not separated and used in the next step without any further purification. MS (ESI) m/z: 260 [M−K]⁺, 244 [M−Na]⁺.

Step 2. Preparation of (1-methylcyclopentyl)-N-[(2S,3R)-2-methyl-4-oxo-oxetan-3-yl]carbamate To a stirred mixture of (3S,4R)-2-methyl-4-oxo-3-oxetanylammonium toluene-4-sulfonate (0.07 g, 0.25 mmol) in dry CH₂Cl₂ (1 mL) under nitrogen atmosphere, DIPEA (0.044 mL, 0.25 mmol) was dropwise added. Subsequently, the crude mixture containing (1-methylcyclopentyl)-2-oxopyridine 1-carboxylate (0.23 g, 1.02 mmol) in dry CH₂Cl₂ (2 mL) was added. The reaction mixture was left under stirring 15 h at rt. The crude mixture was concentrated to dryness and purified with column chromatography using a Teledyne ISCO apparatus, eluting with Cy/TBME (from 100:0 to 60:40) to afford the title compound (0.031 g, 55%) as a white solid. MS (ESI) m/z: 250 [M−Na]⁺; (ESI) m/z: 226 [M−H]⁻. ¹H-NMR (DMSO): δ 1.34 (d, J=6.3 Hz, 3H), 1.51 (s, 3H), 1.55-175 (m, 6H), 1.95-2.10 (m, 2H), 4.83 (dq, J₁=J₂=6.3 Hz, 1H), 5.36 (dd, J=9.2, 6.2 Hz, 1H), 7.99 (d, J=9.2 Hz, 1H).

Example 24

(3-butyloxetan-3-yl)-N-[(2S,3R)-2-methyl-4-oxo-oxetan-3-yl]-carbamate

Step 1. Preparation of 3-butyloxetan-3-ol

To a stirred solution of 3-oxetanone (0.5 g, 6.93 mmol) in dry THF (6 mL), at −78° C., under argon atmosphere, 2.5M solution of butyl lithium (BuLi) in hexane (3.05 mL, 7.62 mmol) was added dropwise over 10 min. The reaction was left to react 3 h at −78° C., then quenched with water and concentrated to dryness. The crude mixture was dissolved in CH₂Cl₂ and dried over Na₂SO₄. The organic solution was filtered and concentrated to dryness to afford a pale yellow oil (0.505 g). The crude product was purified by column chromatography using a Teledyne ISCO apparatus, eluting with Cy/TBME (from 100:0 to 70:30) affording the title compound (0.45 g, 50%) as transparent oil. ¹H NMR (CDCl₃): δ 0.90-1.04 (m, 3H), 1.36-1.47 (m, 4H), 1.79-1.93 (m, 2H), 4.53 (d, J=7.1, 2H), 4.59 (d, J=6.9, 2H).

Step 2. Preparation of (3-butyloxetan-3-yl) 2-pyridyl carbonate and (3-butyloxetan-3-yl) 2-oxopyridine 1-carboxylate To a stirred mixture of 3-butyloxetan-3-ol (0.2 g, 1.53 mmol) in dry CH₂Cl₂ (3 mL) and under nitrogen atmosphere, 4-dimethylaminopyridine (0.019 g, 0.15 mmol) and di-2-pyridyl carbonate (0.365 g, 1.68 mmol) were added. The reaction mixture was left at rt for 15 h, then diluted with CH₂Cl₂, washed first with a saturated NH₄Cl solution (3 mL) and subsequently with a saturated NaHCO₃ solution (3×3 mL). The organic fraction was dried over Na₂SO₄, filtered and concentrated to dryness to afford a pale brown solid (0.329 g, 86%). as a mixture (ratio 1:3) of (3-butyloxetan-3-yl) 2-pyridyl carbonate and (3-butyloxetan-3-yl) 2-oxopyridine 1-carboxylate. The mixture of isomers was not separated and used in the next step without any further purification. MS (ESI) m/z: 252 [M−H]⁺, 208, 190, 178; (ESI) m/z: 250 [M−H]⁻, 141.

Step 3. Preparation of (3-butyloxetan-3-yl)-N-[(2S,3R)-2-methyl-4-oxo-oxetan-3-yl]-carbamate Under nitrogen atmosphere, to a stirred mixture of (3S, 4R)-2-methyl-4-oxo-3-oxetanylammonium toluene-4-sulfonate (0.120 g, 0.44 mmol) in dry CH₂Cl₂ (1 mL), DIPEA (0.072 mL, 0.44 mmol) was dropwise added. Subsequently, the crude mixture containing (3-butyloxetan-3-yl)-2-oxopyridine 1-carboxylate (0.33 g, 1.31 mmol) dissolved in dry CH₂Cl₂ (2 mL) and was added. The reaction mixture was stirred 15 h at rt, then concentrated to dryness and purified by column chromatography using a Teledyne ISCO apparatus, eluting with Cy/TBME (from 100:0 to 70:30). The crude product was further purified by preparative HPLC to afford title compound (0.025 g, 22%) as white solid. MS (ESI) m/z: 258 [M−H]⁺; (ESI) m/z: 256 [M−H]⁻. ¹H NMR (DMSO-d₆):

δ 0.84-0.96 (m, 3H), 1.21-0.140 (m, 4H), 1.36 (d, J=6.3, 3H), 1.98-2.11 (m, 2H), 4.45 (d, J=7.4, 2H), 4.59 (t, J=6.6, 2H), 4.86 (dq, $J_1$=$J_2$=6.2 Hz, 1H), 5.39 (dd, $J_1$=9.3 $J_2$=6.1 Hz, 1H), 8.43 (d, J=9.2 Hz, 1H).

Example 25

(1,1-Dimethyl-5-phenyl-pentyl)-N-[(2S,3R)-2-methyl-4-oxo-oxetan-3-yl]-carbamate

Step 1. Preparation of (1,1-dimethyl-5-phenyl-pentyl)-2-pyridyl carbonate and (1,1-dimethyl-5-phenyl-pentyl)-2-oxopyridine 1-carboxylate Under nitrogen atmosphere, to a stirred mixture of 2-methyl-6-phenyl-hexan-2-ol (0.5 g, 2.66 mmol), prepared as described in Khalaf et al. *Journal Organic Chemistry* 1972, 37, 4227-4235 (compound 9), in dry $CH_2Cl_2$ (3 mL), 4-dimethylaminopyridine (0.036 g, 0.29 mmol) and di-2-pyridyl carbonate (0.618 g, 2.86 mmol) were added. The reaction mixture was left at rt for 24 h, diluted with $CH_2Cl_2$ and washed first with a saturated $NH_4Cl$ solution (3 mL) and subsequently with a saturated $NaHCO_3$ solution (3×3 mL). The organic fraction was dried over $Na_2SO_4$, filtered and concentrated to dryness to afford a yellow transparent oil (0.507 g, 62%), as a mixture (ratio 7:3) of (1,1-dimethyl-5-phenyl-pentyl)-2-pyridyl carbonate and (1,1-dimethyl-5-phenyl-pentyl)-2-oxopyridine 1-carboxylate. The mixture of isomers was not separated and used in the next step without any further purification. MS (ESI) m/z: 352 [M–K]+, 336 [M–Na]+.

Step 2. Preparation of (1,1-dimethyl-5-phenyl-pentyl)-N-[(2S,3R)-2-methyl-4-oxo-oxetan-3-yl]-carbamate Under nitrogen atmosphere, to a stirred mixture of (3S, 4R)-2-methyl-4-oxo-3-oxetanylammonium toluene-4-sulfonate (0.07 g, 0.25 mmol) in dry $CH_2Cl_2$ (1 mL), DIPEA (0.044 mL, 0.25 mmol) was dropwise added. Subsequently, the crude mixture containing (1,1-dimethyl-5-phenyl-pentyl)-2-oxopyridine 1-carboxylate (0.321 g, 1.02 mmol) dissolved in dry $CH_2Cl_2$ (2 mL) was added. The reaction mixture was stirred 15 h at rt, concentrated to dryness and purified with column chromatography using a Teledyne ISCO apparatus, eluting with Cy/TBME (from 100:0 to 70:30). The crude product was further purified by preparative HPLC to afford the title compound (0.025 g, 31%) as a white solid. MS (ESI) m/z: 342 [M–Na]+; (ESI) m/z: 318 [M–H]−. $^1$H NMR (DMSO-$d_6$): δ 1.32 (d, J=6.4 Hz, 3H), 1.30-1.39 (m, 2H), 1.36 (s, 3H), 1.37 (s, 3H), 1.62-1.50 (m, 2H), 1.83-1.69 (m, 2H), 2.62-2.54 (m, 2H), 4.82 (dq, $J_1$=$J_2$=6.2 Hz, 1H), 5.34 (dd, J=9.3, 6.1 Hz, 1H), 7.94 (d, J=9.3 Hz, 1H), 7.10-7.30 (m, 5H).

Example 26

(4-benzyloxyphenyl)-N-[(2S,3R)-2-methyl-4-oxo-oxetan-3-yl]-carbamate

Step 1. Preparation of (4-benzyloxyphenyl)-2-pyridyl carbonate and (4-benzyloxyphenyl)-2-oxopyridine 1-carboxylate Under nitrogen atmosphere, to a stirred mixture of 4-benzyloxyphenol (0.3 g, 1.5 mmol) in dry $CH_2Cl_2$ (3 mL), $Et_3N$ (0.31 mL, 2.25 mmol) and di-2-pyridyl carbonate (0.356 g, 1.64 mmol) were added. The reaction mixture was left at rt for 24 h, then diluted with $CH_2Cl_2$ and washed first with a saturated $NH_4Cl$ solution (3 mL) and subsequently with a saturated $NaHCO_3$ solution (3×3 mL). The organic fraction was dried over $Na_2SO_4$, filtered and concentrated to dryness to afford a pale brown solid (0.42 g, 87%), as a mixture (ratio 1:3) of (4-benzyloxyphenyl)-2-pyridyl carbonate and (4-benzyloxyphenyl)-2-oxopyridine 1-carboxylate. The mixture of isomers was not separated and used in the next step without any further purification. MS (ESI) m/z: 322 [M–H]+, 178.

Step 2. Preparation of (4-benzyloxyphenyl)-N-[(2S, 3R)-2-methyl-4-oxo-oxetan-3-yl]-carbamate Under nitrogen atmosphere, to a stirred mixture of (3S, 4R)-2-methyl-4-oxo-3-oxetanylammonium toluene-4-sulfonate (0.120 g, 0.44 mmol) in dry $CH_2Cl_2$ (1 mL), DIPEA (0.072 mL, 0.44 mmol) was dropwise added. Subsequently, the crude mixture containing (4-benzyloxyphenyl)-2-oxopyridine 1-carboxylate (0.423 g, 1.31 mmol) dissolved in dry $CH_2Cl_2$ (2 mL) was added. The reaction mixture was stirred 15 h at rt, concentrated to dryness and purified by column chromatography using a Teledyne ISCO apparatus, eluting with Cy/TBME (from 100:0 to 70:30). The crude product was further purified by preparative HPLC to afford the title compound (0.025 g, 17%) as white solid. MS (ESI) m/z: 328 [M–H]+; (ESI) m/z: 326 [M–H]−. $^1$H NMR (DMSO-$d_6$): δ 1.43 (d, J=6.4 Hz, 3H) 4.92 (dq, $J_1$=$J_2$=6.2 Hz, 1H), 5.10 (s, 2H), 5.51 (dd, J=9.4, 6.1 Hz, 1H), 6.94-7.53 (m, 9H), 8.78 (d, J=9.4 Hz, 1H).

Example 27

[3-(4-phenylbutypoxetan-3-yl]-N-[(2S,3R)-2-methyl-4-oxo-oxetan-3-yl]-carbamate

Step 1. Preparation of 3-(4-phenylbutyl)-oxetan-3-ol

Under argon atmosphere at −45° C., to a stirred mixture of Lithium in pellets (0.129 g, 18.7 mmol) suspended in dry $Et_2O$ (15 mL), 4-bromo-butylbenzene (1.5 g, 7.03 mmol) in dry $Et_2O$ (10 mL), was added dropwise. The reaction was left to stir at 0° C. for 3 h, then the mixture was transferred via a cannula to a solution of 3-oxetanone (0.4 g, 5.55 mmol) in dry THF (10 mL), previously cooled to −78° C. After 3 h at −78° C., the reaction mixture was quenched with a saturated $NH_4Cl$ solution, the organic solvents removed under reduced pressure. The crude mixture was then dissolved in $CH_2Cl_2$, dried over $Na_2SO_4$, concentrated to dryness and subjected to column chromatography using a Teledyne ISCO apparatus, eluting with Cy/TBME (from 100:0 to 70:30) to afford a pure compound (0.4 g, 35%) as colorless oil. $^1$H NMR (CDCl$_3$): δ 1.41-1.55 (m, 2H), 1.65-1.78 (m, 2H), 1.84-1.94 (m, 2H), 2.62-2.73 (m, 2H), 4.52 (d, J=7.2 Hz, 2H), 4.58 (d, J=7.0 Hz, 2H), 7.21 (dd, J=5.4, 7.2 Hz, 3H), 7.27-7.34 (m, 2H).

Step 2. Preparation of [3-(4-phenylbutyl)-oxetan-3-yl]-2-pyridyl-carbonate and [3-(4-phenylbutyl)-oxetan-3-yl]-2-oxopyridine 1-carboxylate Under nitrogen atmosphere, to a stirred mixture of 3-(4-phenylbutyl)-oxetan-3-ol (0.390 g, 1.89 mmol) in dry $CH_2Cl_2$ (4 mL), DMAP (0.023 g, 0.19 mmol) and di-2-pyridyl carbonate (0.531 g, 2.46 mmol) were added. The reaction mixture was left to react at rt for 17 h, then diluted with $CH_2Cl_2$ and washed first with a saturated $NH_4Cl$ solution (3 mL) and subsequently with a saturated $NaHCO_3$ solution (4×3 mL). The organic fraction was dried over $Na_2SO_4$, filtered and concentrated to dryness to afford a dark oil (0.61 g, 98%) as a mixture (ratio 1:3) of [3-(4-phenylbutyl)-oxetan-3-yl]-2-pyridyl-carbonate and [3-(4-phenylbutyl)-oxetan-3-yl]-2-oxopyridine 1-carboxylate. The mixture of isomers was not separated and used in the next step without any further purification. MS (ESI) m/z: 350 [M-Na]$^+$, 328 [M-H]$^+$, 284, 171, 129.

Step 3. Preparation of [3-(4-phenylbutyl)-oxetan-3-yl]-N-[(2S,3R)-2-methyl-4-oxo-oxetan-3-yl]-carbamate Under nitrogen atmosphere, to a stirred mixture of (3S,4R)-2-methyl-4-oxo-3-oxetanylammonium toluene-4-sulfonate (0.12 g, 0.44 mmol) in dry $CH_2Cl_2$ (1 mL), DIPEA (0.072 mL, 0.44 mmol) was added dropwise. Subsequently, the crude mixture containing [3-(4-phenylbutyl)-oxetan-3-yl]-2-oxopyridine 1-carboxylate (0.40 g, 1.31 mmol) in dry $CH_2Cl_2$ (2 mL) was added. The reaction mixture was stirred 15 h at rt, concentrated to dryness and purified by column chromatography using a Teledyne ISCO apparatus, eluting with Cy/TBME from (100:0 to 70:30). The crude product was further purified by preparative HPLC-MS to afford the title compound (0.008 g, 6%) as a white solid. MS (ESI) m/z: 334 [M-H]$^+$; (ESI) m/z: 332 [M-H]$^-$. $^1$H NMR (CDCl$_3$): δ 1.35-1.48 (m, 2H), 1.44 (d, 3H), 1.64-1.74 (m, 2H), 2.14-2.22 (m, 2H), 2.62-2.71 (m, 2H), 4.54 (d, J=7.5 Hz, 2H), 4.75 (t, J=6.9 Hz, 2H), 4.84-4.92 (m, 1H), 5.36-5.46 (m, 2H), 7.17-7.34 (m, 5H).

Example 28

[(1R) and (1S)-1-Isopropyl-5-phenyl-pentyl]-N-[(2S,3R)-2-methyl-4-oxo-oxetan-3-yl]-carbamate

Step 1. Preparation of 2-methyl-7-phenyl-heptan-3-ol

Under nitrogen atmosphere, at −78° C., to a stirred solution of 5-phenylpentanal [for the preparation see example 22] (0.4 g, 2.46 mmol) in dry Et$_2$O (40 mL), 2M isopropylmagnesiumchloride (3.2 mL, 6.4 mmol) solution in THF was added dropwise. The reaction was left to stir for 30 min at −78° C. and then 2 h at 0° C. After quenching the reaction with water, the organic solvent was rotary evaporated and the crude mixture dissolved in $CH_2Cl_2$, dried over $Na_2SO_4$, filtered and concentrated to dryness to afford pure alcohol (0.43 g, 84%) which was used in the next step without further purification. $^1$H NMR (CDCl$_3$): δ 0.90 (d, J=4.0 Hz, 3H), 0.91 (d, J=4.0 Hz, 3H), 1.32-1.75 (m, 8H), 2.60-2.67 (m, 2H), 3.33-3.39 (m, 1H), 7.15-7.31 (m, 5H).

Step 2. Preparation of (1-isopropyl-5-phenyl-pentyl)-2-pyridyl-carbonate and (1-isopropyl-5-phenyl-pentyl)-2-oxopyridine 1-carboxylate Under nitrogen atmosphere, to a stirred mixture of 2-methyl-7-phenyl-heptan-3-ol (0.43 g, 2.08 mmol) in dry $CH_2Cl_2$ (2 mL), DMAP (0.025 g, 0.2 mmol) and di-2-pyridyl-carbonate (0.540 g, 2.50 mmol) were added. The reaction mixture was left to react at rt for 15 h, then diluted with $CH_2Cl_2$ and washed first with a saturated $NH_4Cl$ solution (3 mL) and subsequently with a saturated $NaHCO_3$ solution (3×3 mL). The organic fraction was dried over $Na_2SO_4$, filtered and concentrated to dryness to afford a yellow oil (0.618 g, 90%), as a mixture (ratio 1:8) of (1-isopropyl-5-phenyl-pentyl)-2-pyridyl-carbonate and (1-isopropyl-5-phenyl-pentyl)-2-oxopyridine 1-carboxylate. The mixture of isomers was not separated and used in the next step without any further purification. MS (ESI) m/z: 328 [M-H]$^+$, 350 [M-Na]$^+$.

Step 3. Preparation of (2R,3S)-3-hydroxy-2-[(1S)-isopropyl-5-phenyl-pentoxy)-carbonylamino]-butanoic acid and (2R,3S)-3-hydroxy-2-[(1R)-isopropyl-5-phenyl-pentoxy)-carbonylamino]-butanoic acid To a stirred mixture of D-threonine (0.150 g, 1.25 mmol) and NaHCO$_3$ (0.158 g, 1.89 mmol) in H$_2$O (3.5 mL), the crude mixture containing (1-isopropyl-5-phenyl-pentyl)-2 and (1-isopropyl-5-phenyl-pentyl)-2-oxopyridine 1-carboxylate (0.62 g, 1.88 mmol) in THF (3.5 mL) was added. After 15 h at rt, the crude mixture was rotary evaporated to remove the organics and subsequently extracted with Et$_2$O (3×5 mL). The aqueous phase was acidified with 2M HCl solution to pH 2-3 and subsequently extracted with AcOEt (3×10 mL). The organic fraction was dried over $Na_2SO_4$, filtered and concentrated to dryness to afford the title compound (0.160 g, 36%) as a mixture (ratio 1:1) of two diastereoisomers, as transparent oil, which was used in the next step. MS (ESI) m/z: 352 [M-H]$^+$; (ESI) m/z: 350 [M-H]$^-$. $^1$H NMR (DMSO-d$_6$) (as a 1:1 mixture of diastereoisomers): δ 0.85 (d, J=6.7 Hz, 12H), 1.09 (d, J=6.2 Hz, 6H), 1.21-1.65 (m, 12H), 1.67-1.79 (m, 2H), 2.55 (t, J=7.7 Hz, 4H), 3.89-3.99 (m, 2H), 4.01-4.13 (m, 2H), 4.43-4.53 (m, 2H), 6.49 (d, J=8.9 Hz, 1H), 6.52 (d, J=8.9 Hz, 1H), 7.11-7.31 (m, 10H), 12.49 (s, 2H).

Step 4. Preparation of (1R)- and (1S)-(1-isopropyl-5-phenyl-pentyl)-N-[(2S,3R)-2-methyl-4-oxo-oxetan-3-yl]-carbamate Under nitrogen atmosphere at 0° C., to a stirred mixture of (2R,3S)-3-hydroxy-2-[(1-isopropyl-5-phenyl-pentoxy)-carbonylamino]-butanoic acid (0.16 g, 0.45 mmol) in dry $CH_2Cl_2$ (16 mL), Et$_3$N (0.19 mL, 1.36 mmol) and subsequently TBTU (0.17 g, 0.55 mmol) were added. The mixture was left stirring 1 h at 0° C. and 15 h at rt. Upon full conversion of the starting material, the organics were removed under reduced pressure, and the resulting crude product absorbed over silica gel and purified by typical column chromatography, eluting with Cy/AcOEt (from 100:0 to 0:100) to afford the title compound (0.055 g, 37%) as a mixture (ratio 1:1) of two diastereoisomers, as white solid. MS (ESI) m/z: 334 [M-H]$^+$; (ESI) m/z: 332 [M-H]$^-$. $^1$H NMR (DMSO-d$_6$) (as a 1:1 mixture of diastereoisomers): δ 0.84 (d, J=6.7 Hz, 6H,), 0.86 (d, J=6.7 Hz, 6H), 1.22-1.35 (m, 4H), 1.30 (d, J=6.2 Hz, 3H), 1.32 (d, J=6.2 Hz, 3H), 1.42-1.66 (m, 8H), 1.69-1.80 (m, 2H), 2.52-2.61 (m, 4H), 4.46-4.56 (m, 2H), 4.84 (dq, J=6.2 Hz, 2H), 5.33-5.43 (m, 2H), 7.13-7.21 (m, 6H), 7.23-7.30 (m, 4H), 8.13 (d, J=7.0 Hz, 1H), 8.15 (d, J=7.0 Hz, 1H).

Example 29

Cyclohexyl-N-[(2S,3R)-2-methyl-4-oxooxetan-3-yl]-carbamate

Step 1. Preparation of cyclohexyl-2-pyridyl-carbonate and cyclohexyl-2-oxopyridine 1-carboxylate Under nitrogen atmosphere, to a stirred mixture of cyclohexanol (0.3 g, 2.99 mmol) in dry $CH_2Cl_2$ (2 mL), DMAP (0.036 g, 0.3 mmol) and di-2-pyridyl-carbonate (0.777 g, 3.59 mmol) were added. The reaction mixture was left to react at rt for 15 h, then diluted with CH$_2$Cl$_2$ and washed first with a saturated NH$_4$Cl solution (3 mL) and subsequently with a saturated NaHCO$_3$ solution (3×3 mL). The organic fraction was dried over Na$_2$SO$_4$, filtered and concentrated to dryness to afford a yellow oil (0.606 g, 91%), as a mixture (ratio 1.8:1) of cyclohexyl-2-pyridyl-carbonate and cyclohexyl-2-oxopyridine 1-carboxylate. The mixture of isomers was not separated and used in the next step without any further purification. MS (ESI) m/z: 222 [M–H]$^+$, 244 [M–Na]$^+$.

Step 2. Preparation of (2R,3S)-2-(cyclohexoxycarbonylamino)-3-hydroxy-butanoic acid To a stirred mixture of D-threonine (0.150 g, 1.25 mmol) and NaHCO$_3$ (0.158 g, 1.89 mmol) in H$_2$O (3.5 mL), the crude mixture containing cyclohexyl-2-pyridyl-carbonate and cyclohexyl-2-oxopyridine 1-carboxylate (0.418 g, 1.89 mmol) in THF (3.5 mL) was added. After 15 h at rt the crude mixture was rotary evaporated to remove the organics and subsequently extracted with Et$_2$O (3×5 mL). The aqueous phase was acidified with 2M HCl solution to pH 2-3 and subsequently extracted with AcOEt (3×10 mL). The organic fraction was dried over Na$_2$SO$_4$, filtered and concentrated to dryness to afford the title compound (0.3 g, 97%) as transparent oil, which was used in the next step without further purification. MS (ESI) m/z: 246 [M–H]$^+$; (ESI) m/z: 244 [M–H]$^-$. $^1$H NMR (DMSO-d$_6$): δ 1.09 (d, J=6.2 Hz, 3H), 1.16-1.43 (m, 5H), 1.49 (s, 1H), 1.69 (s, 2H), 1.80 (s, 2H), 3.93 (dd, J=2.9, 8.8 Hz, 1H), 3.99-4.12 (m, 1H), 4.44-4.61 (m, 1H), 6.59 (d, J=8.9 Hz, 1H), 12.32 (br s, 1H).

Step 3. Preparation of Cyclohexyl-N-[(2S,3R)-2-methyl-4-oxooxetan-3-yl]-carbamate Under nitrogen atmosphere at 0° C., to a stirred mixture of (2R,3S)-2-(cyclohexoxycarbonylamino)-3-hydroxy-butanoic acid (0.3 g, 1.22 mmol) in dry CH$_2$Cl$_2$ (16 mL), Et$_3$N (0.51 mL, 3.66 mmol) and subsequently TBTU (0.47 g, 1.46 mmol) were added. The mixture was left stirring 1 h at 0° C. and 15 h at rt. Upon full conversion of the starting material, the organics were removed under reduced pressure, and the resulting crude product absorbed over silica gel and purified by typical column chromatography, eluting with Cy/AcOEt (from 100:0 to 0:100) to afford the title compound (0.098 g, 36%) as white solid. MS (ESI) m/z: 228 [M–H]$^+$; (ESI) m/z: 226 [M–H]$^-$. $^1$H NMR (DMSO-d$_6$): δ 1.14-1.42 (m, 5H), 1.34 (d, J=6.3 Hz, 3H), 1.44-1.55 (m, 1H), 1.61-1.72 (m, 2H), 1.76-1.89 (m, 2H), 4.47-4.59 (m, 1H), 4.84 (dq, J=6.3 Hz, 1H), 5.40 (dd, J=6.2, 9.3 Hz, 1H), 8.15 (d, J=9.4 Hz, 1H).

Example 30

(1s,4S) and (1r, 4R)-(4-Benzylcyclohexyl)-N-[(2S, 3R)-2-methyl-4-oxooxetan-3-yl]-carbamate Step 1. Preparation of 8-benzylidene-1,4-dioxaspiro-[4.5]-decane To a suspension of NaH (0.306 g, 12.8 mmol) in DMSO (10 mL), a solution of benzyl-triphenylphosphonium bromide (5.44 g, 12.8 mmol) in DMSO (30 mL) was slowly added at rt. The solution was stirred 30 min at rt and then further 30 min at 50° C. Upon the crude mixture turning into dark red color, a solution of 1,4-dioxaspiro[4.5]decan-8-one (2.0 g, 12.8 mmol) in DMSO (14 mL) was added. The solution was stirred at 50° C. for 16 h. The reaction mixture was quenched with water and the aqueous layer extracted with AcOEt (3×20 mL). The combined organic layers were washed with brine, dried over Na$_2$SO$_4$, filtered and concentrated to dryness to give a crude product, which was purified by column chromatography using a Teledyne ISCO apparatus, eluting with Cy/AcOEt (from 100:0 to 40:60) to afford the title compound (1.8 g, 61%) as a white solid. $^1$H NMR (CDCl$_3$): δ 1.66-1.73 (m, 2H), 1.77-1.84 (m, 2H), 2.40-2.47 (m, 2H), 2.49-2.57 (m, 2H), 3.99 (s, 4H), 6.31 (s, 1H), 7.17-7.23 (m, 3H), 7.28-7.35 (m, 2H).

Step 2. Preparation of 4-benzylidenecyclohexanone

Under vigorous stirring, at rt, 8-benzylidene-1,4-dioxaspiro-[4.5]-decane (1.8 g, 7.81 mmol) was dissolved in a acetone/HCl (10% v/v) mixture (70 mL:35 mL) and left to stir 4 h. The crude mixture was diluted in water and extracted with AcOEt (3×40 mL). The combined organic fractions were washed with brine, dried over Na$_2$SO$_4$, filtered and concentrated to dryness to afford pure title compound (1.4 g, 96%) as colorless oil. $^1$H NMR (CDCl$_3$): δ 2.44 (t, J=7.0 Hz, 2H), 2.53 (t, J=6.8 Hz, 2H), 2.65-2.72 (m, 2H), 2.74-2.80 (m, 2H), 6.49 (s, 1H), 7.21-7.27 (m, 3H), 7.32-7.39 (m, 2H).

Step 3. Preparation of (S,E)- and (R,Z)-4-benzylidenecyclohexanol

To a stirred mixture of NaBH$_4$ in dry MeOH (10 mL), at 0° C., under nitrogen atmosphere, 4-benzylidenecyclohexanone dissolved in dry MeOH (30 mL) was added. The crude mixture was left to stir at 0° C. for 1 h and subsequently quenched with water (5 mL). Methanol was rotary evaporated and the crude mixture was dissolved in AcOEt (20 mL). The organic solution was extracted with brine, dried over Na$_2$SO$_4$, filtered and concentrated to dryness to give a crude product, which was purified by column chromatography using a Teledyne ISCO apparatus, eluting with Cy/AcOEt (from 100:0 to 50:50) to afford the title compounds (1.2 g, 91%) as a mixture (ratio 1:1) of two isomers as transparent oil. $^1$H NMR (CDCl$_3$) (as a 1:1 mixture of isomers): δ 1.39-1.50 (m, 2H), 1.51-1.62 (m, 2H), 1.75-1.88 (m, 2H), 1.88-1.98 (m, 2H), 1.98-2.07 (m, 2H), 2.08-2.19 (m, 2H), 2.20-2.30 (m, 2H), 2.47 (dt, J=4.9, 13.5 Hz, 2H), 2.78 (dt, J=5.0, 13.9 Hz, 2H), 3.85-3.94 (m, 2H), 6.30 (s, 2H), 7.18-7.24 (m, 6H), 7.29-7.37 (m, 4H).

Step 4. Preparation of (1r, 4r)- and (1s, 4s)-4-benzylcyclohexanol

A solution of AcOEt (60 mL) containing (S,E)- and (R,Z)-4-benzylidenecyclohexanol (0.3 g, 1.59 mmol) was passed through an H-Cube® hydrogenator flow reactor provided with a 10% Pd/C cartridge. The system was set to full hydrogen mode at 30° C. and 1 bar (1.0 mL/min flow rate). The recovered organic solution was concentrated to dryness to afford pure title compounds (0.29 g, 95%) as a mixture (ratio 1:1) of two isomers, as transparent oil. $^1$H NMR (CDCl$_3$) (as a 1:1 mixture of isomers): δ 0.95-1.11 (m, 2H), 1.14-1.30 (m, 2H), 1.35-1.65 (m, 12H), 1.68-1.80 (m, 4H), 1.89-2.01 (m, 2H), 2.49 (d, J=7.1 Hz, 2H), 2.55 (d, J=7.2 Hz, 2H), 7.10-7.22 (m, 6H), 7.24-7.32 (m, 4H).

Step 5. Preparation of (1r, 4r)- and (1s, 4s)-4-benzylcyclohexyl-2-pyridyl carbonate and (1r,4r)- and (1s, 4s)-4-benzylcyclohexyl-2-oxopyridine 1-carboxylate Under nitrogen atmosphere, to a stirred mixture of (1r, 4r)- and (1s, 4s)-4-benzylcyclohexanol (0.67 g, 3.52 mmol) in dry CH₂Cl₂ (7 mL), DMAP (0.043 g, 0.35 mmol) and di-2-pyridyl-carbonate (0.91 g, 4.22 mmol) were added. The reaction mixture was left to react at rt for 15 h, then diluted with CH₂Cl₂ and washed first with a saturated NH₄Cl solution (3 mL) and subsequently with a saturated NaHCO₃ solution (3×3 mL). The organic fraction was dried over Na₂SO₄, filtered and concentrated to dryness to afford a yellow oil (1.0 g, 91%), as a mixture of (1r,4r)- and (1s, 4s)-4-benzylcyclohexyl-2-pyridyl carbonate and (1r, 4r)- and (1s, 4s)-4-benzylcyclohexyl-2-oxopyridine 1-carboxylate. The mixture of isomers was not separated and used in the next step without any further purification. MS (ESI) m/z: 312 [M−H]⁺, 334 [M−Na]⁺.

Step 6. Preparation of (2R,3 S)-2-(((((1r,4R)-4-benzylcyclohexyl)-oxy)-carbonyl)-amino)-3-hydroxy-butanoic acid and (2R,3 S)-2-(((((1s,4S)-4-benzylcyclohexyl)-oxy)-carbonyl)-amino)-3-hydroxy-butanoic acid To a stirred mixture of D-threonine (0.150 g, 1.25 mmol) and NaHCO3 (0.158 g, 1.89 mmol) in H2O (3.5 mL), the crude mixture containing (1r, 4R)- and (1s, 4S)-4-benzylcyclohexyl-2-pyridyl carbonate and (1r, 4r)- and (1s, 4s)-4-benzylcyclohexyl-2-oxopyridine 1-carboxylate (0.588 g, 1.89 mmol) in THF (3.5 mL) was added. After 15 h at rt, the crude mixture was rotary evaporated to remove the organics and subsequently extracted with Et₂O (3×5 mL). The aqueous phase was acidified with 2M HCl solution to pH 2-3 and subsequently extracted with AcOEt (3×10 mL). The organic fraction was dried over Na₂SO₄, filtered and concentrated to dryness to afford the title compounds (0.4 g, 95%) as a mixture (ratio 6:4) of two isomers, as transparent oil. The mixture of isomers was used in the next step without further purification. MS (ESI) m/z: 336 [M−H]⁺; (ESI) m/z: 334 [M−H]⁻. ¹H NMR (DMSO-d₆) (as a 6:4 mixture of isomers): δ 1.07 (d, J=6.4 Hz, 3H, minor isomer), 1.10 (d, J=6.4 Hz, 3H major isomer), 0.98-1.80 (m, 16H), 1.85-1.94 (m, 2H), 2.46 (d, J=7.1 Hz, 2H), 3.88-3.95 (m, 2H), 4.00-4.12 (m, 2H), 4.36-4.46 (m, 1H, minor isomer), 4.68-4.77 (m, 1H, major isomer), 6.56 (d, J=9.0 Hz, 1H, minor isomer), 6.59 (d, J=8.9 Hz, 1H, major isomer), 7.12-7.21 (m, 6H), 7.24-7.31 (m, 4H), 12.52 (br s, 2H).

Step 7. Preparation of (Is, 4S) and (1r, 4R)-(4-benzylcyclohexyl)-N-[(2S,3R)-2-methyl-4-oxo-oxetan-3-yl]-carbamate Under nitrogen atmosphere at 0° C., to a stirred mixture of (2R,3 S)-2-(((((1r,4R)-4-benzylcyclohexyl)-oxy)-carbonyl)-amino)-3-hydroxy-butanoic acid and (2R,3S)-2-(((((1s,4S)-4-benzylcyclohexyl)-oxy)-carbonyl)-amino)-3-hydroxy-butanoic acid (0.4 g, 1.20 mmol) in dry CH₂Cl₂ (40 mL), Et₃N (0.5 mL, 3.6 mmol) and subsequently TBTU (0.46 g, 1.44 mmol) were added. The mixture was left stirring 1 h at 0° C. and 15 h at rt. Upon full conversion of the starting material, the organics were removed under reduced pressure and the resulting crude product absorbed over silica gel and purified by typical column chromatography, eluting with Cy/AcOEt (from 100:0 to 0:100) to afford the title compound (0.167 g, 43%) as a mixture (ratio 7:3) of two isomers, as white solid. MS (ESI) m/z: 318 [M−H]⁺; (ESI) m/z: 316 [M−H]⁻. ¹H NMR (DMSO-d₆) (as a 7:3 mixture of isomers): δ 1.34 (d, J=6.4 Hz, 3H, minor isomer), 1.37 (d, J=6.3 Hz, 3H, major isomer), 1.00-1.99 (m, 18H), 2.48 (d, J=7.2 Hz, 2H), 4.40-4.52 (m, 1H, minor isomer), 4.73-4.80 (m, 1H, major isomer), 4.81-4.92 (m, 2H), 5.36-5.47 (m, 2H), 7.13-7.23 (m, 6H), 7.24-7.34 (m, 4H), 8.12-8.23 (m, 2H).

Example 31

(R,Z) and (S,E)-(4-Benzylidenecyclohexyl)-N-[(2S, 3R)-2-methyl-4-oxooxetan-3-yl]-carbamate Step 1. Preparation of (S,E) and (R,Z)-4-benzylidenecyclohexyl-2-pyridyl-carbonate and (S,E) and (R,Z)-4-benzylidenecyclohexyl-2-oxopyridine 1-carboxylate Under nitrogen atmosphere, to a stirred mixture of (S,E)- and (R,Z)-4-benzylidenecyclohexanol [for the preparation see example 30] (0.45 g, 2.38 mmol) in dry CH₂Cl₂ (5 mL), DMAP (0.029 g, 0.35 mmol) and di-2-pyridyl-carbonate (0.62 g, 2.86 mmol) were added. The reaction mixture was left to react at rt for 15 h, then diluted with CH₂Cl₂ and washed first with a saturated NH₄Cl solution (3 mL) and subsequently with a saturated NaHCO₃ solution (3×3 mL). The organic fraction was dried over Na₂SO₄, filtered and concentrated to dryness to afford a yellow oil (0.73 g, 98%), as a mixture (ratio 1.8:1) of (S,E) and (R,Z)-4-benzylidenecyclohexyl-2-pyridyl-carbonate and (S,E) and (R,Z)-4-benzylidenecyclohexyl-2-oxopyridine 1-carboxylate. The mixture of isomers was not separated and used in the next step without any further purification. MS (ESI) m/z: 310 [M−F]⁺, 332 [M−Na]⁺.

Step 2. Preparation of (2R,3S)-2-(((((R,Z)-4-benzylydenecyclohexyl)-oxy)-carbonyl)-amino)-3-hydroxybutanoic acid and (2R,3S)-2-(((((S,E)-4-benzylydenecyclohexyl)-oxy)-carbonyl)-amino)-3-hydroxybutanoic acid To a stirred mixture of D-threonine (0.11 g, 0.92 mmol) and NaHCO₃ (0.158 g, 1.89 mmol) in H₂O (3 mL), the crude mixture containing (S,E)- and (R,Z)-4-benzylidenecyclohexyl-2-pyridyl-carbonate and (S,E)- and (R,Z)-4-benzylidenecyclohexyl-2-oxopyridine 1-carboxylate (0.43 g, 1.38 mmol) in THF (3.5 mL) was added. After 15 h at rt, the crude mixture was rotary evaporated to remove the organics and subsequently extracted with Et₂O (3×5 mL). (0.43 g, 1.38 mmol) in THF (3.5 mL) was added. After 15 h at rt, the crude mixture was rotary evaporated to remove the organics and subsequently extracted with Et₂O (3×5 mL). The aqueous phase was acidified with 2M HCl solution to pH 2-3 and subsequently extracted with AcOEt (3×10 mL). The organic fraction was dried over Na₂SO₄, filtered and concentrated to dryness to afford the title compound (0.24 g, 76%) as a mixture (ratio 1:1) of isomers, as transparent oil. The mixture of isomers was used in the next step without further purification. MS (ESI) m/z: 334 [M−H]⁺; (ESI) m/z: 332 [M−H]⁻. ¹H NMR (DMSO-d₆) (as a 1:1 mixture of isomers): δ 1.07-1.15 (m, 6H), 1.43-1.72 (m, 4H), 1.79-2.00 (m, 4H), 2.19-2.37 (m, 4H), 2.38-2.49 (m, 4H), 2.57-2.72 (m, 2H), 3.95 (dd, J=3.4, 8.9 Hz, 2H), 4.03-4.12 (m, 2H), 4.72-4.82 (m, 2H), 6.70 (d, J=8.9 Hz, 2H,), 7.18-7.27 (m, 6H), 7.30-7.39 (m, 4H), 12.48 (s, 2H).

Step 3. Preparation of (R,Z) and (S,E)-(4-benzylidenecyclohexyl)-N-[(2S,3R)-2-methyl-4-oxo-oxetan-3-yl]-carbamate Under nitrogen atmosphere at 0° C., to a stirred mixture of (2R,3S)-2-(((((R,Z)-4-benzylydenecyclohexyl)-oxy)-carbonyl)-amino)-3-hydroxybutanoic acid and (2R,3S)-2-(((((S,E)-4-benzylydenecyclohexyl)-oxy)-carbonyl)-amino)-3-hydroxybutanoic acid (0.23 g, 0.7 mmol) in dry CH$_2$Cl$_2$ (23 mL), Et$_3$N (0.29 mL, 2.12 mmol) and subsequently TBTU (0.27 g, 0.85 mmol) were added. The mixture was left stirring 1 h at 0° C. and 15 h at rt. Upon full conversion of the starting material, the organics were removed under reduced pressure and the resulting crude product absorbed over silica gel and purified by typical column chromatography, eluting with Cy/AcOEt (from 100:0 to 0:100) to afford the title compounds (0.125 g, 56%) as a mixture (ratio 1:1) of diastereoisomers, as white solid. MS (ESI) m/z: 316 [M−H]$^+$, 338 [M−Na]$^+$; (ESI) m/z: 314 [M−H]$^−$. $^1$H NMR (DMSO-d$_6$) (as a 1:1 mixture of isomers): δ 1.35 (d, J=1.4, 6.3 Hz, 6H), 1.42-1.67 (m, 4H), 1.81-2.02 (m, 4H), 2.17-2.35 (m, 4H), 2.37-2.46 (m, 2H), 2.57-2.68 (m, 2H), 4.73-4.82 (m, 2H), 4.85 (dq, J=6.3 Hz, 2H), 5.43 (dd, J=6.3, 9.4 Hz, 2H), 6.31 (s, 2H), 7.17-7.25 (m, 6H), 7.29-7.36 (m, 4H), 8.23 (d, J=9.4 Hz, 2H).

Example 32

5-Phenylpentyl-N-[(2S,3S)-2-methyl-4-oxo-oxetan-3-yl]-carbamate

Step 1. Preparation of 5-phenyl-pentyl-2-pyridyl-carbonate and 5-phenyl-pentyl-2-oxopyridine 1-carboxylate Under nitrogen atmosphere, to a stirred mixture of 5-phenylpentan-1-ol (0.38 g, 2.34 mmol) in dry CH$_2$Cl$_2$ (2 mL), DMAP (0.028 g, 0.23 mmol) and di-2-pyridyl-carbonate (0.61 g, 2.80 mmol) were added. The reaction mixture was left to react at rt for 15 h, then diluted with CH$_2$Cl$_2$ and washed first with a saturated NH$_4$Cl solution (3 mL) and subsequently with a saturated NaHCO$_3$ solution (3×3 mL). The organic fraction was dried over Na$_2$SO$_4$, filtered and concentrated to dryness to afford a yellow oil (0.64 g, quant.), as a mixture (ratio 1.8:1) of 5-phenyl-pentyl-2-pyridyl-carbonate and 5-phenyl-pentyl-2-oxopyridine 1-carboxylate. The mixture of isomers was not separated and used in the next step without any further purification. MS (ESI) m/z: 286 [M−H]$^+$, 308 [M−Na]$^+$.

Step 2. Preparation of (2S,3S)-3-hydroxy-2-(5-phenylpentoxycarbonylamino)-butanoic acid To a stirred mixture of L-allo-threonine (0.150 g, 1.25 mmol) and NaHCO$_3$ (0.158 g, 1.89 mmol) in H$_2$O (3.5 mL), the crude mixture containing 1-(4-phenylphenyl)ethyl-2-pyridyl-carbonate and 5-phenyl-pentyl-2-oxopyridine 1-carboxylate (0.538 g, 1.89 mmol) in THF (3.5 mL) was added. After 15 h at rt, the crude mixture was rotary evaporated to remove the organics and subsequently extracted with Et$_2$O (3×5 mL). The aqueous phase was acidified with 2M HCl solution to pH 2-3 and subsequently extracted with AcOEt (3×10 mL). The organic fraction was dried over Na$_2$SO$_4$, filtered and concentrated to dryness to afford the title compound (0.35 g, 89%) as transparent oil, which was used in the next step without further purification. MS (ESI) m/z: 310 [M−H]$^+$; (ESI) m/z: 308 [M−H]$^−$. $^1$H NMR (DMSO-d$_6$): δ 1.08 (d, J=6.1 Hz, 3H), 1.28-1.39 (m, 2H), 1.50-1.64 (m, 4H), 2.57 (t, J=7.7 Hz, 2H), 3.83-3.98 (m, 4H), 7.12 (d, J=8.7 Hz, 1H), 7.14-7.21 (m, 3H), 7.23-7.30 (m, 2H) 12.32 (br s, 1H).

Step 3. Preparation of 5-phenylpentyl-N-[(2S,3S)-2-methyl-4-oxo-oxetan-3-yl]-carbamate Under nitrogen atmosphere at 0° C., to a stirred mixture of (2S,3S)-3-hydroxy-2-(5-phenylpentoxycarbonylamino)-butanoic acid (0.35 g, 1.13 mmol) in dry CH$_2$Cl$_2$ (35 mL), Et$_3$N (0.47 mL, 3.39 mmol) and subsequently TBTU (0.43 g, 1.35 mmol) were added. The mixture was left stirring 1 h at 0° C. and 15 h at rt. Upon full conversion of the starting material, the organics were removed under reduced pressure, and the resulting crude product absorbed over silica gel and purified by typical column chromatography, eluting with Cy/AcOEt (from 100:0 to 0:100) to afford the title compound (0.223 g, 76%), as white solid. MS (ESI) m/z: 292 [M−H]$^+$; (ESI) m/z: 290 [M−H]$^−$. $^1$H NMR (DMSO-d$_6$): δ 1.28-1.39 (m, 2H), 1.48 (d, J=6.1 Hz, 3H), 1.54-1.65 (m, 4H), 2.57 (t, J=8.4, 16.2 Hz, 2H), 4.00 (t, J=6.6 Hz, 2H), 4.64-4.80 (m, 2H), 7.14-7.23 (m, 3H), 7.23-7.33 (m, 2H), 8.05 (d, J=7.9 Hz, 1H).

Example 33

Phenethyl-N-[(2S,3R)-2-methyl-4-oxo-oxetan-3-yl]-carbamate

Step 1. Preparation of phenethyl-2-pyridyl-carbonate and phenethyl-2-oxopyridine 1-carboxylate Under nitrogen atmosphere, to a stirred mixture of 2-phenylethanol (0.3 g, 2.45 mmol) in dry CH$_2$Cl$_2$ (2 mL), DMAP (0.030 g, 0.24 mmol) and di-2-pyridyl-carbonate (0.64 g, 2.94 mmol) were added. The reaction mixture was left to react at rt for 15 h, then diluted with CH$_2$Cl$_2$ and washed first with a saturated NH$_4$Cl solution (3 mL) and subsequently with a saturated NaHCO$_3$ solution (3×3 mL). The organic fraction was dried over Na$_2$SO$_4$, filtered and concentrated to dryness to afford a yellow oil (0.55 g, 92%), as a mixture (ratio 1.8:1) of phenethyl-2-pyridyl-carbonate and phenethyl-2-oxopyridine 1-carboxylate. The mixture of isomers was not separated and used in the next step without any further purification. MS (ESI) m/z: 244 [M−H]$^+$, 266 [M−Na]$^+$.

Step 2. Preparation of (2R,3S)-3-Hydroxy-2-(phenethyloxycarbonylamino)-butanoic acid To a stirred mixture of D-threonine (0.150 g, 1.25 mmol) and NaHCO$_3$ (0.158 g, 1.89 mmol) in H$_2$O (3.5 mL), the crude mixture containing phenethyl-2-pyridyl-carbonate and phenethyl-2-oxopyridine 1-carboxylate (0.459 g, 1.89 mmol) in THF (3.5 mL) was added. After 15 h at rt, the crude mixture was rotary evaporated to remove the organics and subsequently extracted with Et$_2$O (3×5 mL). The aqueous phase was acidified with 2M HCl solution to pH 2-3 and subsequently extracted with AcOEt (3×10 mL). The organic fraction was dried over Na$_2$SO$_4$, filtered and concentrated to dryness to afford the title compound (0.35 g, 89%) as transparent oil, which was used in the next step without further purification. MS (ESI) m/z: 268 [M−H]$^+$; (ESI) m/z: 266 [M−H]$^−$. $^1$H NMR (DMSO-d$_6$): δ 1.09 (d, J=6.4 Hz, 3H), 2.89 (t, J=6.9 Hz, 2H), 3.94 (dd, J=3.4, 9.0 Hz, 1H), 4.04-4.11 (m, 1H), 4.13-4.24 (m, 2H), 6.75 (d, J=9.0 Hz, 1H), 7.20-7.33 (m, 5H) 11.95 (br s, 1H).

Step 3. Preparation of phenethyl-N-[(2S,3R)-2-methyl-4-oxo-oxetan-3-yl]-carbamate Under nitrogen atmosphere at 0° C., to a stirred mixture of (2R,3S)-3-hydroxy-2-(phenethyloxycarbonylamino)-butanoic acid (0.35 g, 1.30 mmol) in dry CH$_2$Cl$_2$ (35 mL), Et$_3$N (0.54 mL, 3.90 mmol) and subsequently TBTU (0.50 g, 1.56 mmol) were added. The mixture was left stirring 1 h at 0° C. and 15 h at rt. Upon full conversion of the starting material, the organics were removed under reduced pressure, and the resulting crude product absorbed over silica gel and purified by typical column chromatography, eluting with Cy/AcOEt (from 100:0 to 0:100) to afford the title compound (0.185 g, 57%) as white solid. MS (ESI) m/z: 250 [M−H]$^+$; (ESI) m/z: 249 [M−H]$^−$. $^1$H NMR (DMSO-d$_6$): δ 1.33 (d, J=6.3 Hz, 3H), 2.89 (t, J=6.8 Hz, 2H), 4.15-4.29 (m, 2H), 4.84 (dq, J=6.3 Hz, 1H), 5.40 (dd, J=6.1, 9.4 Hz, 1H), 7.19-7.36 (m, 5H), 8.23 (d, J=9.4 Hz, 1H).

Example 34

6-Phenylhexyl-N-[(2S,3R)-2-methyl-4-oxo-oxetan-3-yl]-carbamate

Step 1. Preparation of 6-phenylhexyl-2-pyridyl-carbonate and 6-phenylhexyl-2-oxopyridine 1-carboxylate Under nitrogen atmosphere, to a stirred mixture of 6-phenylhexan-1-ol (0.3 g, 1.68 mmol) in dry CH$_2$Cl$_2$ (3 mL), DMAP (0.02 g, 0.17 mmol) and di-2-pyridyl-carbonate (0.44 g, 2.02 mmol) were added. The reaction mixture was left to react at rt for 15 h, then diluted with CH$_2$Cl$_2$ and washed first with a saturated NH$_4$Cl solution (3 mL) and subsequently with a saturated NaHCO$_3$ solution (3×3 mL). The organic fraction was dried over Na$_2$SO$_4$, filtered and concentrated to dryness to afford a yellow oil (0.43 g, 86%), as a mixture (ratio 1.8:1) of 6-phenylhexyl-2-pyridyl-carbonate and 6-phenylhexyl-2-oxopyridine 1-carboxylate. The mixture of isomers was not separated and used in the next step without any further purification. MS (ESI) m/z: 300 [M−H]$^+$,322 [M−Na]$^+$.

Step 2. Preparation of (2R,3S)-3-hydroxy-2-(6-phenylhexoxycarbonylamino)-butanoic acid To a stirred mixture of D-threonine (0.12 g, 1.0 mmol) and NaHCO$_3$ (0.13 g, 1.5 mmol) in H$_2$O (3.5 mL), the crude mixture containing 6-phenylhexyl-2-pyridyl-carbonate and 6-phenylhexyl-2-oxopyridine 1-carboxylate (0.45 g, 1.5 mmol) in THF (3.5 mL) was added. After 15 h at rt, the crude mixture was rotary evaporated to remove the organics and subsequently extracted with Et$_2$O (3×5 mL). The aqueous phase was acidified with 2M HCl solution to pH 2-3 and subsequently extracted with AcOEt (3×10 mL). The organic fraction was dried over Na$_2$SO$_4$, filtered and concentrated to dryness to afford the title compound (0.25 g, 78%) as transparent oil, which was used in the next step without further purification. MS (ESI) m/z: 324 [M−H]$^+$; (ESI) m/z: 322 [M−H]$^−$. $^1$H NMR (DMSO-d$_6$): δ 1.08 (d, J=6.4 Hz, 3H), 1.24-1.40 (m, 4H), 1.46-1.63 (m, 4H), 2.56 (t, J=7.6 Hz, 2H), 3.88-3.99 (m, 3H), 4.00-4.12 (m, 1H), 6.67 (d, J=9.0 Hz, 1H), 7.13-7.21 (m, 3H), 7.22-7.31 (m, 2H), 12.40 (br s, 1H).

Step 3. Preparation of 6-phenylhexyl-N-[(2S,3R)-2-methyl-4-oxo-oxetan-3-yl]-carbamate Under nitrogen atmosphere at 0° C., to a stirred mixture of (2R,3S)-3-hydroxy-2-(6-phenylhexoxycarbonylamino)-butanoic acid (0.25 g, 0.78 mmol) in dry CH$_2$Cl$_2$ (25 mL), Et$_3$N (0.33 mL, 2.35 mmol) and subsequently TBTU (0.30 g, 1.2 mmol) were added. The mixture was left stirring 1 h at 0° C. and 15 h rt. Upon full conversion of the starting material, the organics were removed under reduced pressure, and the resulting crude product absorbed over silica gel and purified by typical column chromatography, eluting with Cy/AcOEt (from 100:0 to 0:100) to afford the title compound (0.12 g, 50%) as white solid. MS (ESI) m/z: 306 [M−H]$^+$; (ESI) m/z: 304 [M−H]$^−$. $^1$H NMR (DMSO-d$_6$): δ 1.26-1.39 (m, 4H), 1.34 (d, J=6.4 Hz, 3H), 1.48-1.65 (m, 4H), 2.54-2.61 (m, 2H), 3.91-4.06 (m. 2H), 4.84 (dq, J=6.3 Hz, 1H), 5.41 (dd, J=6.1, 9.4 Hz, 1H), 7.11-7.31 (m, 5H), 8.19 (d, J=9.4 Hz, 1H).

Example 35

5-Cyclohexylpentyl-N-[(2S,3R)-2-methyl-4-oxo-oxetan-3-yl]-carbamate

Step 1. Preparation of 5-cyclohexylpentan-1-ol

Under nitrogen atmosphere, at 0° C., to a stirring mixture of 2M LiAlH$_4$ (13.04 mL, 26.08 mmol) solution in Et$_2$O in dry Et$_2$O (67 mL), 5-cyclohexylpentanoic acid (1.2 g, 6.52 mmol) in dry Et$_2$O (2 mL) was added dropwise. The mixture was left to react at rt for 4 h, then upon full conversion of the starting material, at 0° C., H$_2$O (13.04 mL), 3M KOH (13.04 mL) solution and H$_2$O (43.65 mL) were very slowly added. The mixture was stirred for 1 h at 0° C., filtered to remove the solid residue, and the remaining organic phase dried over Na$_2$SO$_4$. The organic solution was again filtered and concentrated to dryness affording the title compound (0.98 g, 88%) as a colorless oil. $^1$H NMR (DMSO-d$_6$): δ 0.77-0.93 (m, 2H), 1.06-1.34 (m, 10H), 1.35-1.47 (m, 2H), 1.56-1.76 (m, 5H), 3.37 (t, J=6.6 Hz, 2H).

Step 2. Preparation of 5-cyclohexylpentyl 2-pyridyl carbonate and 5-cyclohexylpentyl 2-oxopyridine 1-carboxylate Under nitrogen atmosphere, to a stirred mixture of 5-cyclohexylpentan-1-ol (0.55 g, 3.23 mmol) in dry CH$_2$Cl$_2$ (3 mL), DMAP (0.04 g, 0.32 mmol) and di-2-pyridyl-carbonate (0.91 g, 4.19 mmol) were added. The reaction mixture was left to react at rt for 15 h, then diluted with CH$_2$Cl$_2$ and washed first with a saturated NH$_4$Cl solution (3 mL) and subsequently with a saturated NaHCO$_3$ solution (3×3 mL). The organic fraction was dried over Na$_2$SO$_4$, filtered and concentrated to dryness to afford a yellow oil (0.92 g, 98%), as a mixture (ratio 1.8:1) of 5-cyclohexylpentyl 2-pyridyl carbonate and 5-cyclohexylpentyl 2-oxopyridine 1-carboxylate. The mixture of isomers was not separated and used in the next step without any further purification. MS (ESI) m/z: 292 [M−H]$^+$,314 [M−Na]$^+$.

Step 3. Preparation of (2R,3S)-2-(5-cyclohexylpentoxycarbonylamino)-3-hydroxy-butanoic acid To a stirred mixture of D-threonine (0.15 g, 1.25 mmol) and NaHCO$_3$ (0.16 g, 1.89 mmol) in H$_2$O (3.5 mL), the crude mixture containing 5-cyclohexylpentyl 2-pyridyl carbonate and 5-cyclohexylpentyl 2-oxopyridine 1-carboxylate (0.55 g, 1.5 mmol) in THF (3.5 mL) was added. After 15 h at rt, the crude mixture was rotary evaporated to remove the organics and subsequently extracted with Et$_2$O (3×5 mL). The aqueous phase was acidified with 2M HCl solution to pH 2-3 and subsequently extracted with AcOEt (3×10 mL). The organic fraction was dried over Na$_2$SO$_4$, filtered and concentrated to dryness to afford the title compound (0.32 g, 81%) as transparent oil, which was used in the next step without further purification. MS (ESI) m/z: 316 [M−H]$^+$; (ESI) m/z: 314 [M−H]$^−$. $^1$H NMR (DMSO-d$_6$): δ 0.77-0.93 (m, 2H), 1.02-1.37 (m, 13H), 1.45-1.72 (m, 7H), 3.88-3.99 (m, 3H), 4.01-4.11 (m, 1H), 6.66 (d, J=9.0 Hz, 1H), 11.77 (br s, 1H).

Step 4. Preparation of 5-cyclohexylpentyl-N-[(2S, 3R)-2-methyl-4-oxo-oxetan-3-yl]-carbamate Under nitrogen atmosphere at 0° C., to a stirred mixture of (2R,3S)-2-(5-cyclohexylpentoxycarbonylamino)-3-hydroxy-butanoic acid (0.32 g, 1.02 mmol) in dry $CH_2Cl_2$ (30 mL), $Et_3N$ (0.43 mL, 3.08 mmol) and subsequently TBTU (0.39 g, 1.2 mmol) were added. The mixture was left stirring 1 h at 0° C. and 15 h rt. Upon full conversion of the starting material, the organics were removed under reduced pressure, and the resulting crude product absorbed over silica gel and purified by typical column chromatography, eluting with Cy/AcOEt (from 100:0 to 0:100) to afford the title compound (0.12 g, 39%) as white solid. MS (ESI) m/z: 298 [M–H]$^+$; (ESI) m/z: 296 [M–H]$^-$. $^1$H NMR: δ 0.78-0.93 (m, 2H), 1.05-1.33 (m, 10H), 1.36 (d, J=6.4 Hz, 3H), 1.51-1.72 (m, 7H), 3.92-4.09 (m, 2H), 4.86 (dq, J=6.3 Hz, 1H), 5.42 (dd, J=6.1, 9.4 Hz, 1H), 8.20 (d, J=9.4 Hz, 1H).

Example 36

2-Phenethyloxyethyl-N-[(2S,3R)-2-methyl-4-oxo-oxetan-3-yl]-carbamate

Step 1. Preparation of 2-phenethyloxyacetic acid

To a stirred mixture of phenethyl alcohol (1.0 g, 8.18 mmol) in DMSO (16 mL) under nitrogen flow, NaH (0.39 g, 16.37 mmol) was added in one portion and the mixture was stirred at 60° C. for 10 min. Following the addition of chloroacetic acid (0.77 g, 8.18 mmol), the reaction mixture was heated at 80° C. for 3 h. The cooled mixture was then poured into $H_2O$ and the aqueous phase acidified to pH 1.0 with a 2.0 N HCl solution. The aqueous phase was then extracted with EtOAc (3×20 mL), and the combined organic phase washed with brine and dried over $Na_2SO_4$ to afford the title compound (1.11 g, 75%), which was used in the following step without further purification. $^1$H NMR (DMSO-d$_6$): δ 2.83 (t, J=7.0 Hz, 2H), 3.67 (t, J=7.0 Hz, 2H), 4.00 (s, 2H), 7.15-7.32 (m, 5H), 12.64 (s, 1H).

Step 2. Preparation of 2-phenethyloxyethanol

Under nitrogen atmosphere, at 0° C., to a stirring mixture of LiAlH$_4$ (0.93 g, 24.63 mmol) in dry $Et_2O$ (60 mL), 2-phenethyloxyacetic acid (1.1 g, 6.15 mmol) in dry $Et_2O$ (6 mL) was added dropwise. The mixture was left to react at rt for 4 h, then at 0° C. $H_2O$ (0.93 mL), 3.0 M KOH solution (0.93 mL) and $H_2O$ (3.12 mL) were very slowly added. The mixture was stirred at 0° C. for 1 h, filtered to remove the solid residue, and the organic phase dried over $Na_2SO_4$. The organic solution was again filtered and concentrated to dryness. The crude mixture was purified by column chromatography using a Teledyne ISCO apparatus, eluting with Cy:EtOAc (from 100:0 to 60:40) affording the title compound (0.69 g, 68%) as a colorless oil. $^1$H NMR (DMSO-d$_6$): δ 2.81 (t, J=7.1 Hz, 2H), 3.40-3.44 (m, 2H), 3.45-3.51 (m, 2H), 3.60 (t, J=7.1 Hz, 2H), 4.55 (t, J=5.4 Hz, 1H), 7.15-7.30 (m, 5H).

Step 3. Preparation of 2-phenethyloxyethyl 2-pyridyl carbonate and 2-phenethyloxyethyl-2-oxopyridine-1-carboxylate Under nitrogen atmosphere, to a stirred mixture of 2-phenethyloxyethanol (0.35 g, 2.11 mmol) in dry $CH_2Cl_2$ (3.5 mL), DMAP (0.025 g, 0.21 mmol) and di-2-pyridyl carbonate (0.54 g, 2.53 mmol) were added. The reaction mixture was left at rt for 17 h, then diluted with $CH_2Cl_2$ and washed first with a saturated $NH_4Cl$ solution (3.0 mL) and subsequently with a saturated $NaHCO_3$ solution (3×3 mL). The organic fraction was dried over $Na_2SO_4$, filtered and concentrated to dryness to afford an orange oil (0.57 g, 88%), as a mixture (ratio 1.8:1) of 2-phenethyloxyethyl-2-pyridyl carbonate and 2-phenethyloxyethyl-2-oxopyridine-1-carboxylate. The mixture of isomers was not separated and used in the next step without any further purification. MS (ESI) m/z: 310 [M–Na]$^+$, 288 [M–H]$^+$.

Step 4. Preparation of (2R,3S)-3-hydroxy-2-(2-phenethyloxyethoxy-carbonylamino)-butanoic acid To a stirred mixture of D-threonine (0.15 g, 1.25 mmol) and $NaHCO_3$ (0.16 g, 1.25 mmol) in $H_2O$ (3.0 mL), the crude isomeric mixture containing 2-phenethyloxyethyl-2-pyridyl carbonate and 2-phenethyloxyethyl-2-oxopyridine-1-carboxylate (0.54 g, 1.89 mmol) in THF (3.0 mL) was added. After 15 h at rt, the crude mixture was rotary evaporated to remove the organics and subsequently extracted with $Et_2O$ (3×5 mL). The aqueous phase was acidified with 2.0 M HCl solution to pH 2-3 and subsequently extracted with EtOAc (3×10 mL). The organic fraction was dried over $Na_2SO_4$, filtered and concentrated to dryness to afford the title compound (0.38 g, 94%) as transparent oil, which was used in the next step without further purification. MS (ESI) m/z: 312 [M–H]+; (ESI) m/z: 310 [M–H]–. $^1$H NMR (DMSO-d$_6$): δ 1.09 (d, J=6.4 Hz, 3H), 2.81 (t, J=7.1 Hz, 2H), 3.55-3.66 (m, 4H), 3.93 (dd, J=3.4, 8.9 Hz, 1H), 4.00-4.15 (m, 3H), 6.83 (d, J=8.9 Hz, 1H), 7.14-7.32 (m, 5H), 12.20 (s, 1H).

Step 5. Preparation of 2-phenethyloxyethyl-N-[(2S, 3R)-2-methyl-4-oxo-oxetan-3-yl]-carbamate Under nitrogen atmosphere at 0° C., to a stirred mixture of (2R,3S)-3-hydroxy-2-(2-phenethyloxyethoxy-carbonylamino)-butanoic acid (0.46 g, 1.18 mmol) in dry $CH_2Cl_2$ (35 mL), $Et_3N$ (0.49 mL, 3.55 mmol) and subsequently TBTU (0.30 g, 1.42 mmol) were added. The mixture was left stirring 1 h at 0° C. and 15 h at rt. Upon full conversion of the starting material, the organics were removed under reduced pressure, and the resulting crude product absorbed over silica gel and purified by typical column chromatography, eluting with Cy:EtOAc (from 100:0 to 0:100) to afford the pure title compound (0.18 g, 60%) as white solid. MS (ESI) m/z: 294 [M–H]$^+$; (ESI) m/z: 292 [M–H]$^-$. $^1$H NMR (DMSO-d$_6$): δ 1.35 (d, J=6.4 Hz, 3H), 2.81 (t, J=7.1 Hz, 2H), 3.59 (t, 1H), 3.62 (t, J=6.3 Hz, 1H), 4.05-4.21 (m, 2H), 4.85 (dq, J=6.3 Hz, 1H), 5.43 (dd, J=6.1, 9.4 Hz, 1H), 7.15-7.33 (m, 5H), 8.33 (d, J=9.4 Hz, 1H).

Example 37

5-Phenylpentyl-N-[(2R,3S)-2-methyl-4-oxo-oxetan-3-yl]-carbamate

Step 1. Preparation of 5-phenyl-pentyl-2-pyridyl-carbonate and 5-phenyl-pentyl-2-oxopyridine 1-carboxylate Under nitrogen atmosphere, to a stirred mixture of 5-phenylpentan-1-ol (0.38 g, 2.34 mmol) in dry $CH_2Cl_2$ (2.0 mL), DMAP (0.028 g, 0.23 mmol) and di-2-pyridyl-carbonate (0.61 g, 2.80 mmol) were added. The reaction mixture was left to react for 15 h at rt, then diluted with $CH_2Cl_2$ and washed first with a saturated $NH_4Cl$ solution (3.0 mL) and subsequently with a saturated NaHCO₃ solution (3×3 mL). The organic fraction was dried over Na₂SO₄, filtered and concentrated to dryness to afford a yellow oil (0.64 g, quant.), as a mixture (ratio 1.8:1) of 5-phenyl-pentyl-2-pyridyl-carbonate and 5-phenyl-pentyl-2-oxopyridine 1-carboxylate. The mixture of isomers was not separated and used in the next step without any further purification. MS (ESI) m/z: 286 [M–H]⁺, 308 [M–Na]⁺.

Step 2. Preparation of (2S,3R)-2-(5-phenylpentoxy-carbonylamino)-3-hydroxy-butanoic acid To a stirred mixture of L-threonine (0.150 g, 1.25 mmol) and NaHCO₃ (0.158 g, 1.89 mmol) in H₂O (3.5 mL), the crude mixture containing 5-phenyl-pentyl-2-pyridyl-carbonate and 5-phenyl-pentyl-2-oxopyridine 1-carboxylate (0.538 g, 1.89 mmol) in THF (3.5 mL) was added. After 15 h at rt, the crude mixture was rotary evaporated to remove the organics and subsequently extracted with Et₂O (3×5 mL). The aqueous phase was acidified with 2.0 M HCl solution to pH 2-3 and subsequently extracted with EtOAc (3×10 mL). The organic fraction was dried over Na₂SO₄, filtered and concentrated to dryness to afford the title compound (0.33 g, 88%) as transparent oil, which was used in the next step without further purification. MS (ESI) m/z: 332 [M–Na]⁺, 327 [M–NH₄]⁺; (ESI) m/z: 308 [M–H]⁻. ¹H NMR (DMSO-d₆) δ 1.08 (d, J=6.3 Hz, 3H), 1.29-1.39 (m, 2H), 1.53-1.63 (m, 4H), 2.57 (t, J=7.7 Hz, 2H), 3.89-3.99 (m, 3H), 4.01-4.11 (m, 1H), 6.67 (d, J=9.0 Hz, 1H), 7.13-7.30 (m, 5H), 12.33 (s, 1H).

Step 3. Preparation of 5-phenylpentyl-N-[(2R,3S)-2-methyl-4-oxo-oxetan-3-yl]-carbamate Under nitrogen atmosphere at 0° C., to a stirred mixture of (2S,3R)-3-hydroxy-2-(5-phenylpentoxy-carbonylamino)-butanoic acid (0.3 g, 0.89 mmol) in dry CH₂Cl₂ (30 mL), Et₃N (0.37 mL, 2.67 mmol) and subsequently TBTU (0.34 g, 1.06 mmol) were added. The mixture was left stirring 1 h at 0° C. and 15 h at rt. Upon full conversion of the starting material, the organics were removed under reduced pressure, and the resulting crude product absorbed over silica gel and purified by typical column chromatography, eluting with Cy:EtOAc (from 100:0 to 0:100) to afford the title compound (0.18 g, 70%), as white solid. [α]²⁵_D +21.3 (c 0.1, CHCl₃). MS (ESI) m/z: 292 [M–H]⁺; (ESI) m/z: 290 [M–H]⁻. ¹H NMR (DMSO-d₆) δ 1.37-1.28 (m, 2H), 1.33 (d, J=6.4 Hz, 3H), 1.64-1.53 (m, 4H), 2.57 (t, J=7.7 Hz, 2H), 4.06-3.93 (m, 2H), 4.84 (dq, J=6.1, 6.4 Hz, 1H), 5.40 (dd, J=6.1, 9.4 Hz, 1H), 7.30-7.13 (m, 5H), 8.19 (d, J=9.4 Hz, 1H).

Example 38

5-Phenylpentyl-N-[(2R,3S)-2-methyl-4-oxo-oxetan-3-yl]-carbamate

Step 1. Preparation of 5-phenyl-pentyl-2-pyridyl-carbonate and 5-phenyl-pentyl-2-oxopyridine 1-carboxylate Under nitrogen atmosphere, to a stirred mixture of 5-phenylpentan-1-ol (0.38 g, 2.34 mmol) in dry CH₂Cl₂ (2.0 mL), DMAP (0.028 g, 0.23 mmol) and di-2-pyridyl-carbonate (0.61 g, 2.80 mmol) were added. The reaction mixture was left to react for 15 h at rt, then diluted with CH₂Cl₂ and washed first with a saturated NH₄Cl solution (3.0 mL) and subsequently with a saturated NaHCO₃ solution (3×3 mL). The organic fraction was dried over Na₂SO₄, filtered and concentrated to dryness to afford a yellow oil (0.64 g, quant.), as a mixture (ratio 1.8:1) of 5-phenyl-pentyl-2-pyridyl-carbonate and 5-phenyl-pentyl-2-oxopyridine 1-carboxylate. The mixture of isomers was not separated and used in the next step without any further purification. MS (ESI) m/z: 286 [M–H]⁺, 308 [M–Na]⁺.

Step 2. Preparation of (2R,3R)-2-(5-phenylpentoxy-carbonylamino)-3-hydroxy-butanoic acid To a stirred mixture of D-allo-threonine (0.10 g, 0.83 mmol) and NaHCO₃ (0.11 g, 1.25 mmol) in H₂O (3.5 mL), the crude mixture containing 5-phenyl-pentyl-2-pyridyl-carbonate and 5-phenyl-pentyl-2-oxopyridine 1-carboxylate (0.36 g, 1.25 mmol) in THF (3.0 mL) was added. After 15 h at rt, the crude mixture was rotary evaporated to remove the organics and subsequently extracted with Et₂O (3×5 mL). The aqueous phase was acidified with 2.0 M HCl solution to pH 2-3 and subsequently extracted with EtOAc (3×10 mL). The organic fraction was dried over Na₂SO₄, filtered and concentrated to dryness to afford the title compound (0.23 g, 89%) as colorless oil, which was used in the next step without further purification. MS (ESI) m/z: 332 [M–Na]⁺, 327 [M–NH₄]⁺; (ESI) m/z: 308 [M–H]⁻. ¹H NMR (DMSO-d₆) δ 1.08 (d, J=6.0 Hz, 3H), 1.28-1.39 (m, 2H), 1.59 (t, J=9.0 Hz, 4H), 2.57 (t, J=7.7 Hz, 2H), 3.80-4.00 (m, 4H), 7.10 (d, J=8.1 Hz, 1H), 7.13-7.22 (m, 3H), 7.22-7.31 (m, 2H), 12.33 (s, 1H).

Step 3. Preparation of 5-phenylpentyl-N-[(2R,3R)-2-methyl-4-oxo-oxetan-3-yl]-carbamate Under nitrogen atmosphere at 0° C., to a stirred mixture of (2R,3R)-3-hydroxy-2-(5-phenylpentoxy-carbonylamino)-butanoic acid (0.23 g, 0.74 mmol) in dry CH₂Cl₂ (23 mL), Et₃N (0.31 mL, 2.22 mmol) and subsequently TBTU (0.28 g, 0.88 mmol) were added. The mixture was left stirring 1 h at 0° C. and 15 h at rt. Upon full conversion of the starting material, the organics were removed under reduced pressure, and the resulting crude product absorbed over silica gel and purified by typical column chromatography, eluting with Cy:EtOAc (from 100:0 to 0:100) to afford the title compound (0.15 g, 69%), as white solid. [α]²⁵_D +28.23 (c 0.1, CHCl₃). MS (ESI) m/z: 292 [M–H]⁺; (ESI) m/z: 290 [M–H]⁻. ¹H NMR (DMSO-d₆) δ 1.38-1.27 (m, 2H), 1.47 (d, J=6.1 Hz, 3H), 1.64-1.53 (m, 4H), 2.59-2.54 (m, 2H), 3.98 (t, J=6.6 Hz, 2H), 4.77-4.64 (m, 2H), 7.21-7.13 (m, 3H), 7.31-7.24 (m, 2H), 8.04 (d, J=7.9 Hz, 1H).

Example 39

Hexyl-N-[(2S,3R)-2-methyl-4-oxo-oxetan-3-yl]-carbamate

Step 1. Preparation of hexyl-2-pyridyl-carbonate and hexyl-2-oxopyridine-1-carboxylate Under nitrogen atmosphere, to a stirred mixture of hexan-1-ol (0.3 g, 2.93 mmol) in dry CH₂Cl₂ (3.0 mL), DMAP (0.03 g, 0.29 mmol) and di-2-pyridyl-carbonate (0.76 g, 3.52 mmol) were added. The reaction mixture was left to react for 15 h at rt, then diluted with CH₂Cl₂ and washed first with a saturated NH₄Cl solution (3.0 mL) and subsequently with a saturated NaHCO₃ solution (3×3 mL). The organic fraction was dried over Na₂SO₄, filtered and concentrated to dryness to afford a yellow oil (0.58 g, 90%), as a mixture (ratio 1.8:1) of hexyl-2-pyridyl-carbonate and hexyl-2-oxopyridine-1-carboxylate. The mixture of isomers was not separated and used in the next step without any further purification. MS (ESI) m/z: 224 [M−H]+, 246 [M−Na]+.

Step 2. Preparation of (2R,3S)-3-hydroxy-2-(hexoxycarbonylamino)-butanoic acid To a stirred mixture of D-threonine (0.150 g, 1.25 mmol) and NaHCO$_3$ (0.158 g, 1.89 mmol) in H$_2$O (3.5 mL), the crude mixture containing hexyl-2-pyridyl-carbonate and hexyl-2-oxopyridine-1-carboxylate (0.45 g, 1.89 mmol) in THF (3.5 mL) was added. After 15 h at rt, the crude mixture was rotary evaporated to remove the organics and subsequently extracted with Et$_2$O (3×5 mL). The aqueous phase was acidified with 2.0 M HCl solution to pH 2-3 and subsequently extracted with EtOAc (3×10 mL). The organic fraction was dried over Na$_2$SO$_4$, filtered and concentrated to dryness to afford the title compound (0.27 g, 88%) as transparent oil, which was used in the next step without further purification. $^1$H NMR (DMSO-d$_6$) δ 0.83-0.90 (m, 3H), 1.08 (d, J=6.3 Hz, 3H), 1.21-1.36 (m, 6H), 1.49-1.59 (m, 2H), 3.89-3.99 (m, 3H), 4.01-4.11 (m, 1H), 6.67 (d, J=9.0 Hz, 1H), 12.30 (br s, 1H).

Step 3. Preparation of hexyl-N-[(2S,3R)-2-methyl-4-oxooxetan-3-yl]-carbamate Under nitrogen atmosphere at 0° C., to a stirred mixture of employing (2R,3S)-2-(hexoxycarbonylamino)-3-hydroxy-butanoic acid (0.27 g, 1.10 mmol) in dry CH$_2$Cl$_2$ (27 mL), Et$_3$N (0.46 mL, 3.31 mmol) and subsequently TBTU (0.42 g, 1.32 mmol) were added. The mixture was left stirring 1 h at 0° C. and 15 h at rt. Upon full conversion of the starting material, the organics were removed under reduced pressure, and the resulting crude product absorbed over silica gel and purified by typical column chromatography, eluting with Cy:EtOAc (from 100:0 to 0:100) to afford the title compound (0.18 g, 73%), as white solid. [α]$^{25}_D$ −25.1 (c 0.1, CHCl$_3$). MS (ESI) m/z: 230 [M−H]+; (ESI) m/z: 228 [M−H]−. $^1$H NMR (DMSO-d$_6$) δ 0.86 (t, J=6.9 Hz, 3H), 1.38-1.21 (m, 6H), 1.34 (d, J=6.4 Hz, 3H), 1.62-1.50 (m, 2H), 4.07-3.93 (m, 2H), 4.84 (dq, J=6.1, 6.4 Hz, 1H), 5.40 (dd, J=6.1, 9.3 Hz, 1H), 8.19 (d, J=9.3 Hz, 1H).

Example 40

Heptyl-N-[(2S,3R)-2-methyl-4-oxo-oxetan-3-yl]-carbamate

Step 1. Preparation of heptyl-2-pyridyl-carbonate and heptyl-2-oxopyridine-1-carboxylate Under nitrogen atmosphere, to a stirred mixture of heptan-1-ol (0.3 g, 2.58 mmol) in dry CH$_2$Cl$_2$ (3.0 mL), DMAP (0.03 g, 0.29 mmol) and di-2-pyridyl-carbonate (0.67 g, 3.1 mmol) were added. The reaction mixture was left to react for 15 h at rt, then diluted with CH$_2$Cl$_2$ and washed first with a saturated NH$_4$Cl solution (3.0 mL) and subsequently with a saturated NaHCO$_3$ solution (3×3 mL). The organic fraction was dried over Na$_2$SO$_4$, filtered and concentrated to dryness to afford a yellow oil (0.59 g, 96%), as a mixture (ratio 1.8:1) of heptyl-2-pyridyl-carbonate and heptyl-2-oxopyridine-1-carboxylate. The mixture of isomers was not separated and used in the next step without any further purification. MS (ESI) m/z: 238 [M−H]+, 260 [M−Na]+.

Step 2. Preparation of (2R,3S)-3-hydroxy-2-(heptoxycarbonylamino)-butanoic acid To a stirred mixture of D-threonine (0.15 g, 1.25 mmol) and NaHCO$_3$ (0.158 g, 1.89 mmol) in H$_2$O (3.5 mL), the crude mixture containing heptyl-2-pyridyl-carbonate and heptyl-2-oxopyridine-1-carboxylate (0.45 g, 1.89 mmol) in THF (3.5 mL) was added. After 15 h at rt, the crude mixture was rotary evaporated to remove the organics and subsequently extracted with Et$_2$O (3×5 mL). The aqueous phase was acidified with 2.0 M HCl solution to pH 2-3 and subsequently extracted with EtOAc (3×10 mL). The organic fraction was dried over Na$_2$SO$_4$, filtered and concentrated to dryness to afford the title compound (0.3 g, 91%) as transparent oil, which was used in the next step without further purification. $^1$H NMR (DMSO-d$_6$) δ 0.86 (t, J=6.8 Hz, 3H), 1.08 (d, J=6.4 Hz, 3H), 1.18-1.36 (m, 8H), 1.46-1.61 (m, 2H), 3.87-4.01 (m, 3H), 4.01-4.14 (m, 1H), 6.67 (d, J=9.0 Hz, 1H) 12.20 (br s, 1H).

Step 3. Preparation of heptyl-N-[(2S,3R)-2-methyl-4-oxo-oxetan-3-yl]-carbamate Under nitrogen atmosphere at 0° C., to a stirred mixture of employing (2R,3S)-2-(heptoxycarbonylamino)-3-hydroxy-butanoic acid (0.3 g, 1.14 mmol) in dry CH$_2$Cl$_2$ (30 mL), Et$_3$N (0.48 mL, 3.44 mmol) and subsequently TBTU (0.44 g, 1.37 mmol) were added. The mixture was left stirring 1 h at 0° C. and 15 h at rt. Upon full conversion of the starting material, the organics were removed under reduced pressure, and the resulting crude product absorbed over silica gel and purified by typical column chromatography, eluting with Cy:EtOAc (from 100:0 to 0:100) to afford the title compound (0.10 g, 37%), as white solid.

[α]$^{25}_D$ −23.1 (c 0.1, CHCl$_3$). MS (ESI) m/z: 244 [M−H]+; (ESI) m/z: 242 [M−H]−. $^1$H NMR (DMSO-d$_6$) δ 0.86 (t, J=6.9 Hz, 3H), 1.32-1.20 (m, 8H), 1.34 (d, J=6.4 Hz, 3H), 1.60-1.49 (m, 2H), 4.07-3.93 (m, 2H), 4.84 (dq, J=6.1, 6.4 Hz, 1H), 5.40 (dd, J=6.1, 9.4 Hz, 1H), 8.19 (d, J=9.4 Hz, 1H).

Example 41

5-Phenylpentyl-N-methyl-N-[(2S,3R)-2-methyl-4-oxo-oxetan-3-yl]-carbamate

Step 1. Preparation of (2R,3S)-3-benzyloxy-2-[tert-butoxycarbonyl-(methyl)-amino]-butanoic acid In a round bottom flask, under argon atmosphere, commercially available (2R,3S)-3-benzyloxy-2-(tert-butoxycarbonyl-amino)-butanoic acid was dissolved in dry THF (15 mL). Subsequently at 0° C., NaH (60% dispersion in mineral oil, 0.21 g, 5.33 mmol) was added in one portion. The reaction mixture was left to stir at the same temperature for 10 min and then MeI (0.95 mL, 15.22 mmol) followed by DMF (0.75 mL) were sequentially added. The reaction was left for 2.0 h at 0° C. and for 15 h at rt, then quenched with H$_2$O (15 mL), diluted with EtOAc (30 mL) and acidified to pH 2 by dropwise addition of 2.0 N HCl aqueous solution. The organic layer was separated and the aqueous phase was back-extracted with EtOAc (2×30 mL). The organic phase was dried over Na$_2$SO$_4$, filtered and concentrated to dryness. The crude mixture was purified by column chromatography using a Teledyne ISCO apparatus eluting with Cy:TBME (60:40) to give the title compound (1.1 g, 67%), as a mixture of two rotamers (2:1 ratio), as a colorless oil. $^1$H NMR (DMSO-d$_6$) δ 1.13-1.20 (m, 6H), 1.36 (s, 9H, minor rotamer), 1.41 (s, 9H, major rotamer), 2.84 (s, 3H, minor rotamer), 2.87 (s, 3H, major rotamer), 4.13-4.24 (m, 2H), 4.34-4.40 (m, 2H), 4.49 (d, J=5.5 Hz, 1H, minor rotamer), 4.57-4.62 (m, 2H), 4.71 (d, J=5.2 Hz, 1H, major rotamer), 7.23-7.35 (m, 10H).

Step 2. Preparation of (2R,3S)-2-[tert-butoxycarbonyl-(methyl)-amino]-3-hydroxy-butanoic acid (2R,3S)-3-Benzyloxy-2-[tert-butoxycarbonyl-(methyl)-amino]-butanoic acid (0.5 g, 1.55 mmol) was dissolved in abs. EtOH (100 mL). The solution was passed through the H-Cube® hydrogenator flow reactor provided with a 10% Pd/C cartridge [flow rate=1.0 mL/min, P=1.0 bar, T=60° C.]. The hydrogenated solution was concentrated to dryness to afford title compound (0.35 g, 96%), as a mixture of two rotamers (1:1.3 ratio), as a colorless oil. $^1$H NMR (DMSO-$d_6$) δ 1.06-1.12 (m, 6H), 1.36 (s, 9H, minor rotamer), 1.40 (s, 9H, major rotamer), 2.86 (s, 3H, minor rotamer), 2.89 (s, 3H, major rotamer), 4.15-4.27 (m, 2H), 4.33 (m, 1H, minor rotamer), 4.47 (d, J=5.3 Hz, 1H, major rotamer).

Step 3. Preparation of [(1R,2S)-1-carboxy-2-hydroxy-propyl]-methyl-ammonium toluene-4-sulfonate In a heart-shaped flask, (2R,3S)-2-[tert-butoxycarbonyl-(methyl)-amino]-3-hydroxy-butanoic acid (0.086 g, 0.37 mmol) was mixed with p-TsOH (0.073, 0.39 mmol) and the solid mixture was cooled to 0° C. Subsequently TFA (2.0 mL) was added over 10 min and the reaction mixture was left to react for 15 min at 0° C. The solution was rotary evaporated maintaining the bath below 30° C. and the obtained oil was left under vacuum for 1 h. The oil was then dissolved in dry Et$_2$O to form a white precipitate. The solution was decanted and the solid washed several times with the same solvent to give a pure product (0.11 g, quant.), as a white sticky solid. $^1$H NMR (DMSO-$d_6$) δ 1.25 (d, J=6.5 Hz, 3H), 2.29 (s, 3H), 2.60 (s, 3H), 3.73-3.82 (m, 1H), 4.02-4.11 (m, 1H), 7.11 (d, J=8.1 Hz, 2H), 7.48 (d, J=8.1 Hz, 2H).

Step 4. Preparation of (2R,3S)-3-hydroxy-2-[methyl-(5-phenylpentoxycarbonyl)-amino]-butanoic acid To a stirred mixture of [(1R,2S)-1-carboxy-2-hydroxy-propyl]-methyl-ammonium toluene-4-sulfonate (0.1 g, 0.33 mmol) and NaHCO$_3$ (0.05 g, 0.65 mmol) in H$_2$O (1.0 mL), the isomeric mixture containing 5-phenyl-pentyl-2-pyridyl-carbonate and 5-phenyl-pentyl-2-oxopyridine 1-carboxylate (0.14 g, 0.49 mmol) [prepared as for Example 37, step 1] in THF (1.0 mL) was added. After 15 h at rt, the crude mixture was rotary evaporated to remove the organics, diluted and subsequently extracted with Et$_2$O (3×5 mL). The aqueous phase was acidified with 2.0 M HCl solution to pH 2-3 and subsequently extracted with EtOAc (3×10 mL). The organic fraction was dried over Na$_2$SO$_4$, filtered and concentrated to dryness to afford the title compound (0.05 g, 45%), as a mixture of two rotamers (1.5:1 ratio), as a colorless sticky oil. $^1$H NMR (DMSO-$d_6$) δ 1.07 (d, J=6.3 Hz, 6H), 1.27-1.40 (m, 4H), 1.51-1.66 (m, 8H), 2.53-2.60 (m, 4H), 2.90 (s, 3H, minor rotamer), 2.91 (s, 3H, major rotamer), 3.92-4.02 (m, 4H), 4.16-4.27 (m, 2H), 4.32 (d, J=5.8 Hz, 1H, minor rotamer), 4.47 (d, J=5.4 Hz, 1H, major rotamer), 7.13-7.31 (m, 10H).

Step 5. Preparation of 5-phenylpentyl-N-methyl-N-[(2S,3R)-2-methyl-4-oxo-oxetan-3-yl]-carbamate To a stirred mixture of (2R,3S)-3-hydroxy-2-[methyl-(5-phenylpentoxycarbonyl)-amino]-butanoic acid (0.04 g, 0.14 mmol) in dry CH$_2$Cl$_2$ (5.0 mL), under nitrogen atmosphere at 0° C., Et$_3$N (0.06 mL, 0.41 mmol) and subsequently TBTU (0.05 g, 0.17 mmol) were added. The mixture was left stirring at 0° C. for 1 h and at rt for 15 h. Upon full conversion of the starting material, the organics were removed under reduced pressure, and the resulting crude product absorbed over silica gel and purified by column chromatography, eluting with Cy:EtOAc (from 100:0 to 0:100) to afford the title compound (0.01 g, 23%), as a mixture of two rotamers (1:1.5 ratio), as a colorless oil. $[α]^{25}_D$ −16.66 (c 0.1, CHCl$_3$). $^1$H NMR (DMSO-$d_6$) δ 1.29-1.41 (m, 10H), 1.53-1.69 (m, 8H), 2.58 (t, J=7.6 Hz, 4H), 2.93 (s, 6H), 3.98-4.11 (m, 4H), 4.77-4.89 (m, 2H), 5.24-5.33 (m, 1H, major rotamer), 5.35-5.43 (m, 1H, minor rotamer), 7.13-7.32 (m, 10H).

Example 42

(4-Cyclohexylphenyl)-methyl-N-[(2S,3R)-2-methyl-4-oxo-oxetan-3-yl]-carbamate

Step 1. Preparation of (4-cyclohexylphenyl)-methanol

Under nitrogen atmosphere, at 0° C., to a stirring mixture of LiAlH$_4$ (2.0 M THF solution, 5.3 mL, 10.53 mmol) in dry Et$_2$O (10 mL), commercially available 4-cyclohexylbenzoic acid (0.5 g, 2.45 mmol) in dry Et$_2$O (5.0 mL) was added dropwise. The mixture was left to react at rt for 4 h, then at 0° C. H$_2$O (0.45 mL), 3.0 M KOH solution (0.45 mL) and H$_2$O (2.0 mL) were very slowly added. The mixture was stirred for 1 h at 0° C., filtered to remove the solid residue, and the organic phase dried over Na$_2$SO$_4$. The organic solution was again filtered and concentrated to dryness affording the title compound (0.46 g, quant.), which was used in the next step without any further purification. $^1$H NMR (CDCl$_3$): δ 8.05-7.94 (m, 2H), 7.35-7.23 (m, 2H), 4.39 (q, 2H, J=7.12 Hz), 2.59 (tt, 1H J=11.41, 3.27 Hz), 1.97-1.73 (m, 5H), 1.53-1.34 (m, 6H).

Step 2. Preparation of (4-cyclohexylphenyl)-methyl-2-pyridyl carbonate and (4-cyclohexylphenyl)-methyl-2-oxopyridine-1-carboxylate Under nitrogen atmosphere, to a stirred mixture of (4-cyclohexylphenyl)-methanol (0.3 g, 1.58 mmol) in dry CH$_2$Cl$_2$ (2 mL), DMAP (0.019 g, 0.16 mmol) and di-2-pyridyl-carbonate (0.411 g, 1.90 mmol) were added. The reaction mixture was left to react at rt for 15 h, then diluted with CH$_2$Cl$_2$ and washed first with a saturated NH$_4$Cl solution (3.0 mL) and subsequently with a saturated NaHCO$_3$ solution (3×3 mL). The organic fraction was dried over Na$_2$SO$_4$, filtered and concentrated to dryness to afford a colorless oil (0.464 g, 95%), as a mixture (ratio 1.8:1) of (4-cyclohexylphenyl)-methyl-2-pyridyl carbonate and (4-cyclohexylphenyl)-methyl-2-oxopyridine-1-carboxylate. The mixture of isomers was not separated and used in the next step without any further purification. MS (ESI) m/z: 350 [M-K]$^+$.

Step 3. Preparation of (2R,3S)-2-[(4-cyclohexylphenyl)-methoxy-carbonylamino]-3-hydroxy-butanoic acid To a stirred mixture of D-threonine (0.119 g, 1.0 mmol) and NaHCO$_3$ (0.125 g, 1.49 mmol) in H$_2$O (3.0 mL), the crude mixture containing (4-cyclohexylphenyl)-methyl-2-pyridyl carbonate and (4-cyclohexylphenyl)-methyl-2-oxopyridine-1-carboxylate (0.464 g, 1.49 mmol) in THF (3.0 mL) was added. After 15 h at rt, the crude mixture was rotary evaporated to remove the organics and subsequently extracted with Et$_2$O (3×5 mL). The aqueous phase was acidified with 2.0 M HCl solution to pH 2-3 and subsequently extracted with EtOAc (3×10 mL). The organic fraction was dried over Na$_2$SO$_4$, filtered and concentrated to dryness to afford the title compound (0.32 g, 96%) as transparent oil, which was used in the next step without further purification. MS (ESI) m/z: 353 [M−NH$_4$]$^+$; (ESI) m/z: 334 [M−H]$^-$. $^1$H NMR (DMSO-d$_6$): δ 1.08 (d, J=6.4 Hz, 3H), 1.07-1.55 (m, 6H), 1.63-1.86 (m, 5H), 3.94 (dq, J=3.6, 9.0 Hz, 1H), 4.07 (dd, J=3.6, 6.4 Hz, 1H), 5.00 (s, 2H), 6.88 (d, J=9.0 Hz, 1H), 7.20 (d, J=7.9 Hz, 2H), 7.27 (d, J=7.95 Hz, 2H), 12.54 (s, 1H).

Step 4. Preparation of (4-cyclohexylphenyl)-methyl-N-[(2S,3R)-2-methyl-4-oxo-oxetan-3-yl]-carbamate Under nitrogen atmosphere at 0° C., to a stirred mixture of (2R,3S)-2-[(4-cyclohexylphenyl)-methoxycarbonylamino]-3-hydroxy-butanoic acid (0.32 g, 0.95 mmol) in dry CH$_2$Cl$_2$ (30 mL), Et$_3$N (0.397 mL, 2.85 mmol) and subsequently TBTU (0.366 g, 1.14 mmol) were added. The mixture was left stirring 1 h at 0° C. and 15 h at rt. Upon full conversion of the starting material, the organics were removed under reduced pressure, and the resulting crude product absorbed over silica gel and purified by column chromatography using a Teledyne ISCO apparatus, eluting with Cy:EtOAc (from 100:0 to 70:30) to afford the title compound (0.06 g, 20%) as white solid. MS (ESI) m/z: 316 [M−H]$^+$, 335 [M−NH$_4$]$^+$. $^1$H NMR (DMSO-d$_6$): δ 1.34 (d, J=6.3 Hz, 3H), 1.07-1.55 (m, 6H), 1.63-1.86 (m, 5H), 4.86 (dq, J=6.1, 6.3 Hz, 1H), 5.00 (d, J=12.2 Hz, 1H), 5.05 (d, J=12.2 Hz, 1H), 5.44 (dd, J=6.1, 9.4 Hz, 1H), 7.22 (d, J=8.2 Hz, 2H), 7.27 (d, J=8.2 Hz, 2H), 8.31 (d, J=9.4 Hz, 1H).

Example 43

1,3-Benzodioxol-5-yl-methyl-N-[(2S,3R)-2-methyl-4-oxo-oxetan-3-yl]-carbamate

Step 1. Preparation of 1,3-benzodioxol-5-yl-methyl-2-pyridyl carbonate and 1,3-benzodioxol-5-yl-methyl-2-oxopyridine-1-carboxylate Under nitrogen atmosphere, to a stirred mixture of 1,3-benzodioxol-5-yl-methanol (0.3 g, 1.97 mmol) in dry CH$_2$Cl$_2$ (2.0 mL), DMAP (0.024 g, 0.20 mmol) and di-2-pyridyl-carbonate (0.51 g, 2.36 mmol) were added. The reaction mixture was left to react at rt for 15 h, then diluted with CH$_2$Cl$_2$ and washed first with a saturated NH$_4$Cl solution (3.0 mL) and subsequently with a saturated NaHCO$_3$ solution (3×3 mL). The organic fraction was dried over Na$_2$SO$_4$, filtered and concentrated to dryness to afford a colorless oil (0.506 g, 94%), as a mixture (ratio 1.8:1) of 1,3-benzodioxol-5-yl-methyl-2-pyridyl carbonate and 1,3-benzodioxol-5-yl-methyl-2-oxopyridine-1-carboxylate. The mixture of isomers was not separated and used in the next step without any further purification. MS (ESI) m/z: 312 [M−K]$^+$.

Step 2. Preparation of (2R,3S)-2-(1,3-benzodioxol-5-yl-methoxycarbonylamino)-3-hydroxy-butanoic acid To a stirred mixture of D-threonine (0.146 g, 1.23 mmol) and NaHCO$_3$ (0.155 g, 1.85 mmol) in H$_2$O (3.0 mL), the crude mixture containing 1,3-benzodioxol-5-yl-methyl-2-pyridyl carbonate and 1,3-benzodioxol-5-yl-methyl-2-oxopyridine-1-carboxylate (0.506 g, 1.85 mmol) in THF (3.0 mL) was added. After 15 h at rt, the crude mixture was rotary evaporated to remove the organics and subsequently extracted with Et$_2$O (3×5 mL). The aqueous phase was acidified with 2.0 M HCl solution to pH 2-3 and subsequently extracted with EtOAc (3×10 mL). The organic fraction was dried over Na$_2$SO$_4$, filtered and concentrated to dryness to afford the title compound (0.337 g, 92%) as transparent oil, which was used in the next step without further purification. MS (ESI) m/z: 315 [M−NH$_4$]$^+$; (ESI) m/z: 296 [M−H]$^-$. $^1$H NMR (DMSO-d$_6$): δ 1.09 (d, J=6.4 Hz, 3H), 3.95 (dd, J=3.5, 9.0 Hz, 1H), 3.99-4.08 (dq, J=3.5, 6.4 Hz, 1H), 6.01 (s, 2H), 4.95 (s, 2H), 6.78-7.00 (m, 3H).

Step 3. Preparation of 1,3-benzodioxol-5-yl-methyl-N-[(2S,3R)-2-methyl-4-oxo-oxetan-3-yl]-carbamate Under nitrogen atmosphere at 0° C., to a stirred mixture of (2R,3S)-2-(1,3-benzodioxol-5-yl-methoxycarbonylamino)-3-hydroxy-butanoic acid (0.337 g, 1.13 mmol) in dry CH$_2$Cl$_2$ (30 mL), Et$_3$N (0.473 mL, 3.39 mmol) and subsequently TBTU (0.436 g, 1.36 mmol) were added. The mixture was left stirring 1 h at 0° C. and 15 h at rt. Upon full conversion of the starting material, the organics were removed under reduced pressure, and the resulting crude product absorbed over silica gel and purified by column chromatography using a Teledyne ISCO apparatus, eluting with Cy:EtOAc (from 100:0 to 70:30) to afford the title compound (0.132 g, 42%), as white solid. MS (ESI) m/z: 318 [M−K]$^+$. $^1$H NMR (DMSO-d$_6$): δ 1.33 (d, J=6.3 Hz, 3H), 4.84 (dq, J=6.1, 6.3 Hz, 1H), 4.94 (d, J=12.0 Hz, 1H), 4.99 (d, J=12.0 Hz, 1H), 5.44 (dd, J=6.1, 9.4 Hz, 1H), 6.01 (s, 2H), 6.79-6.98 (m, 3H), 8.30 (d, J=9.4 Hz, 1H).

Example 44

[4-[4-(Trifluoromethyl)-phenyl]-phenyl]-methyl-N-[(2S,3R)-2-methyl-4-oxo-oxetan-3-yl]-carbamate Step 1. Preparation of [4-[4-(trifluoromethyl)-phenyl]-phenyl]-methanol Under nitrogen atmosphere, at 0° C., to a stirring mixture of LiAlH$_4$ (2.0 M THF solution, 3.0 mL, 6.00 mmol) in dry THF (10 mL), commercially available 4-[4-(trifluoromethyl)-phenyl]-benzoic acid (0.4 g, 1.5 mmol) in dry THF (10 mL) was added dropwise. The mixture was left to react at rt for 4 h, then at 0° C. H$_2$O (0.23 mL), 3.0 M KOH solution (0.23 mL) and H$_2$O (0.77 mL) were very slowly added. The mixture was stirred for 1 h at 0° C., filtered to remove the solid residue, and the organic phase dried over Na$_2$SO$_4$. The organic solution was again filtered, concentrated to dryness and the resulting crude product purified by column chromatography using a Teledyne ISCO apparatus, eluting with Cy:EtOAc (from 100:0 to 70:30) to afford the title compound (0.3 g, 79%), as white solid. $^1$H NMR (DMSO-d$_6$): δ 4.56 (d, J=5.7 Hz, 2H), 5.25 (t, J=5.7 Hz, 1H), 7.45 (d, J=8.1 Hz, 2H), 7.70 (d, J=8.1 Hz, 2H), 7.81 (d, J=8.1 Hz, 2H), 7.89 (d, J=8.1 Hz, 2H).

Step 2. Preparation of 2-pyridyl-[4-[4-(trifluoromethyl)-phenyl]-phenyl]-methyl carbonate and [4-[4-(trifluoromethyl)-phenyl]-phenyl]-methyl-2-oxopyridine-1-carboxylate Under nitrogen atmosphere, to a stirred mixture of [4-[4-(trifluoromethyl)-phenyl]-phenyl]-methanol (0.3 g, 1.19 mmol) in dry CH$_2$Cl$_2$ (2.0 mL), DMAP (0.015 g, 0.12 mmol)

and di-2-pyridyl-carbonate (0.309 g, 1.43 mmol) were added. The reaction mixture was left to react at rt for 15 h, then diluted with $CH_2Cl_2$ and washed first with a saturated $NH_4Cl$ solution (3.0 mL) and subsequently with a saturated $NaHCO_3$ solution (3×3 mL). The organic fraction was dried over $Na_2SO_4$, filtered and concentrated to dryness to afford a colorless oil (0.3 g, 68%), as a mixture (ratio 1.8:1) of 2-pyridyl-[4-[4-(trifluoromethyl)-phenyl]-phenyl]-methyl carbonate and [4-[4-(trifluoromethyl)-phenyl]-phenyl]-methyl-2-oxopyridine-1-carboxylate. The mixture of isomers was not separated and used in the next step without any further purification. MS (ESI) m/z: 396 [M−Na]$^+$, 412 [M-K]$^+$.

Step 3. Preparation of (2R,3S)-3-hydroxy-2-[[4-[4-(trifluoromethyl)-phenyl]-phenyl]-methoxycarbonylamino]-butanoic acid To a stirred mixture of D-threonine (0.063 g, 0.53 mmol) and $NaHCO_3$ (0.067 g, 0.8 mmol) in $H_2O$ (3.0 mL), the crude mixture containing 2-pyridyl-[4-[4-(trifluoromethyl)-phenyl]-phenyl]-methyl carbonate and [4-[4-(trifluoromethyl)-phenyl]-phenyl]-methyl-2-oxopyridine-1-carboxylate (0.3 g, 0.8 mmol) in THF (3.0 mL) was added. After 15 h at rt, the crude mixture was rotary evaporated to remove the organics and subsequently extracted with $Et_2O$ (3×5 mL). The aqueous phase was acidified with 2.0 M HCl solution to pH 2-3 and subsequently extracted with EtOAc (3×10 mL). The organic fraction was dried over $Na_2SO_4$, filtered and concentrated to dryness to afford the title compound as transparent oil (0.21 g, quant.), which was used in the next step without further purification. MS (ESI) m/z: 415 [M−$NH_4$]$^+$; (ESI) m/z: 396 [M−H]$^-$. $^1$H NMR (DMSO-d$_6$): δ 1.11 (d, J=6.4 Hz, 3H), 3.97 (dd, J=3.5, 8.9 Hz, 1H), 4.05-4.12 (dq, J=3.5, 6.4 Hz, 1H), 5.13 (s, 2H), 7.00 (d, J=8.9 Hz, 1H), 7.51 (d, J=8.1 Hz, 2H), 7.75 (d, J=8.1 Hz, 2H), 7.82 (d, J=8.1 Hz, 2H), 7.91 (d, J=8.1 Hz, 2H), 12.59 (s, 1H).

Step 4. Preparation of [4-[4-(trifluoromethyl)-phenyl]-phenyl]-methyl-N-[(2S,3R)-2-methyl-4-oxo-oxetan-3-yl]-carbamate Under nitrogen atmosphere at 0° C., to a stirred mixture of (2R,3S)-3-hydroxy-2-[[4-[4-(trifluoromethyl)-phenyl]-phenyl]-methoxycarbonylamino]-butanoic acid (0.210 g, 0.53 mmol) in dry $CH_2Cl_2$ (30 mL), $Et_3N$ (0.222 mL, 1.59 mmol) and subsequently TBTU (0.205 g, 0.64 mmol) were added. The mixture was left stirring 1 h at 0° C. and 15 h at rt. Upon full conversion of the starting material, the organics were removed under reduced pressure, and the resulting crude product absorbed over silica gel and purified by column chromatography using a Teledyne ISCO apparatus, eluting with Cy:EtOAc (from 100:0 to 70:30) to afford the title compound (0.04 g, 20%), as white solid. MS (ESI) m/z: 397 [M−$NH_4$]$^+$, 418 [M-K]$^+$. $^1$H NMR (DMSO-d$_6$): δ 1.36 (d, J=6.3 Hz, 3H), 4.87 (dq, J=6.1, 6.3 Hz, 1H), 5.13 (d, J=7.5 Hz, 1H), 5.18 (d, J=7.5 Hz, 1H), 5.47 (dd, J=6.1, 9.4 Hz, 1H), 7.51 (d, J=8.1 Hz, 2H), 7.77 (d, J=8.1 Hz, 2H), 7.82 (d, J=8.1 Hz, 2H), 7.91 (d, J=8.1 Hz, 2H), 8.41 (d, J=9.4 Hz, 1H).

Example 45

[4-(3-Thienyl)-phenyl]-methyl-N-[(2S,3R)-2-methyl-4-oxo-oxetan-3-yl]-carbamate

Step 1. Preparation of [4-(3-thienyl)-phenyl]-methanol

Under nitrogen atmosphere, at 0° C., to a stirring mixture of $LiAlH_4$ (2.0 M THF solution, 3.92 mL, 7.84 mmol) in dry THF (6.0 mL), commercially available 4-(3-thienyl)-benzoic acid (0.4 g, 1.96 mmol) in dry THF (30 mL) was added dropwise. The mixture was left to react at rt for 4 h, then at 0° C. $H_2O$ (0.30 mL), 3.0 M KOH solution (0.30 mL) and $H_2O$ (1.0 mL) were very slowly added. The mixture was stirred for 1 h at 0° C., filtered to remove the solid residue, and the organic phase dried over $Na_2SO_4$. The organic solution was again filtered and concentrated to dryness, affording the title compound (0.222 g, 65%), which was used in the next step without any further purification. $^1$H NMR (DMSO-d$_6$): δ 4.51 (d, J=5.75 Hz, 2H), 5.17 (t, J=5.75 Hz, 1H), 7.35 (d, J=8.1 Hz, 2H), 7.52-7.57 (m, 1H), 7.63 (dd, J=2.9, 5.0 Hz, 1H), 7.67 (d, J=8.1 Hz, 2H), 7.81-7.86 (m, 1H).

Step 2. Preparation of 2-pyridyl-[4-(3-thienyl)-phenyl]-methyl carbonate

Under nitrogen atmosphere, to a stirred mixture of [4-(3-thienyl)-phenyl]-methanol (0.22 g, 1.16 mmol) in dry $CH_2Cl_2$ (2.0 mL), DMAP (0.015 g, 0.12 mmol) and di-2-pyridyl-carbonate (0.3 g, 1.39 mmol) were added. The reaction mixture was left to react at rt for 15 h, then diluted with $CH_2Cl_2$ and washed first with a saturated $NH_4Cl$ solution (3.0 mL) and subsequently with a saturated $NaHCO_3$ solution (3×3 mL). The organic fraction was dried over $Na_2SO_4$, filtered and concentrated to dryness to afford a white solid (0.263 g, 73%), as a mixture (ratio 1.8:1) of 2-pyridyl-[4-(3-thienyl)-phenyl]-methyl carbonate and [4-(3-thienyl)-phenyl]-methyl-2-oxopyridine-1-carboxylate. The mixture of isomers was not separated and used in the next step without any further purification. MS (ESI) m/z: 334 [M−Na]$^+$, 350 [M-K]$^+$.

Step 3. Preparation of (2R,3S)-3-hydroxy-2-[[4-(3-thienyl)-phenyl]-methoxy-carbonylamino]-butanoic acid To a stirred mixture of D-threonine (0.067 g, 0.56 mmol) and $NaHCO_3$ (0.07 g, 0.84 mmol) in $H_2O$ (3.0 mL), the crude mixture containing 2-pyridyl-[4-(3-thienyl)-phenyl]-methyl carbonate and [4-(3-thienyl)-phenyl]-methyl-2-oxopyridine-1-carboxylate (0.263 g, 0.84 mmol) in THF (3.0 mL) was added. After 15 h at rt, the crude mixture was rotary evaporated to remove the organics and subsequently extracted with $Et_2O$ (3×5 mL). The aqueous phase was acidified with 2.0 M HCl solution to pH 2-3 and subsequently extracted with EtOAc (3×10 mL). The organic fraction was dried over $Na_2SO_4$, filtered and concentrated to dryness to afford the title compound (0.188 g, quant.) as white solid, which was used in the next step without further purification. MS (ESI) m/z: 353 [M−$NH_4$]$^+$. $^1$H NMR (DMSO-d$_6$) δ: 1.10 (d, J=6.4 Hz, 3H), 3.97 (dd, J=3.5, 8.9 Hz, 1H), 4.08 (dq, J=3.5, 6.4 Hz, 1H), 5.07 (s, 2H), 6.96 (d, J=8.9 Hz, 1H), 7.41 (d, J=8.1 Hz, 2H), 7.53-7.60 (m, 1H), 7.64 (dd, J=2.9, 5.0 Hz, 1H), 7.72 (d, J=8.1 Hz, 2H), 7.86-7.91 (m, 1H), 12.58 (s, 1H).

Step 4. Preparation of [4-(3-thienyl)-phenyl]-methyl-N-[(2S,3R)-2-methyl-4-oxo-oxetan-3-yl]-carbamate Under nitrogen atmosphere at 0° C., to a stirred mixture of (2R,3S)-3-hydroxy-2-[[4-(3-thienyl)-phenyl]-methoxy-carbonylamino]-butanoic acid (0.188 g, 0.56 mmol) in dry $CH_2Cl_2$ (30 mL), $Et_3N$ (0.234 mL, 1.68 mmol) and subsequently TBTU (0.215 g, 0.67 mmol) were added. The mixture was left stirring 1 h at 0° C. and 15 h at rt. Upon full conversion of the starting material, the organics were removed under reduced pressure, and the resulting crude product absorbed over silica gel and purified by column chromatography using a Teledyne ISCO apparatus, eluting with Cy:EtOAc (from 100:0 to 70:30) to afford the title compound (0.048 g, 27%), as white solid. MS (ESI) m/z: 335 [M−NH$_4$]$^+$, 356 [M−K]$^+$. $^1$H NMR (DMSO-d$_6$) δ: 1.35 (d, J=6.3 Hz, 3H), 4.87 (dq, J=6.1, 6.3 Hz, 1H), 5.07 (d, J=12.45 Hz, 1H), 5.12 (d, J=12.45 Hz, 1H), 5.46 (dd, J=6.1, 9.5 Hz, 1H), 7.40 (d, J=8.1 Hz, 2H), 7.55-7.60 (m, 1H), 7.64 (dd, J=2.9, 5.1 Hz, 1H), 7.73 (d, J=8.1 Hz, 2H), 7.86-7.91 (m, 1H), 8.38 (d, J=9.5 Hz, 1H).

Example 46

[4-(Cyclohexoxy)-phenyl]-methyl-N-[(2S,3R)-2-methyl-4-oxo-oxetan-3-yl]-carbamate Step 1. Preparation of ethyl 4-(cyclohexoxy)-benzoate Ethyl 4-hydroxybenzoate (1.0 g, 6.02 mmol) and cyclohexene (6.0 mL) were mixed together and boron trifluoride diethyl etherate (0.38 mL, 3.01 mmol) was then added. The mixture was heated under reflux for 2 h and then cooled to rt. EtOAc (20 mL) was added and the solution washed with 5% NaOH solution (3×40 mL) and with H$_2$O (50 mL). The organic layer was dried over Na$_2$SO$_4$ and the solvent was evaporated. The crude product was absorbed over silica gel and purified by column chromatography using a Teledyne ISCO apparatus, eluting with Cy:EtOAc (from 100:0 to 90:10) to afford the title compound (1.17 g, 78%), as white solid. MS (ESI) m/z: 249 [M−H]$^+$; $^1$H NMR (DMSO-d$_6$): δ 1.29 (t, J=7.1 Hz, 3H), 1.33-1.49 (m, 5H), 1.50-1.59 (m, 1H), 1.63-1.79 (m, 2H), 1.89-1.98 (m, 2H), 4.26 (q, J=7.1 Hz, 2H), 4.41-4.49 (m, 1H), 7.02 (d, J=8.8 Hz, 2H), 7.87 (d, J=8.8 Hz, 2H).

Step 2. Preparation of [4-(cyclohexoxy)-phenyl]-methanol

Under nitrogen atmosphere, at 0° C., to a stirring mixture of LiAlH$_4$ (2.0 M THF solution, 9.42 mL, 18.84 mmol) in dry THF (6.0 mL), 4-(cyclohexoxy)-benzoate (1.17 g, 4.71 mmol) in dry THF (30 mL) was added dropwise. The mixture was left to react at rt for 4 h, then at 0° C. H$_2$O (0.70 mL), 3.0 M KOH solution (0.70 mL) and H$_2$O (1.6 mL) were very slowly added. The mixture was stirred for 1 h at 0° C., filtered to remove the solid residue, and the organic phase dried over Na$_2$SO$_4$. The organic solution was again filtered and concentrated to dryness, affording the title compound (0.57 g, 59%), which was used in the next step without any further purification. $^1$H NMR (DMSO-d$_6$): δ 1.21-1.47 (m, 5H), 1.49-1.57 (m, 1H), 1.64-1.77 (m, 2H), 1.87-1.95 (m, 2H), 4.25-4.33 (m, 1H), 4.40 (d, J=5.7 Hz, 2H), 5.00 (t, J=5.7 Hz, 1H), 6.87 (d, J=8.5 Hz, 2H), 7.19 (d, J=8.5 Hz, 2H).

Step 3. Preparation of (4-cyclohexylphenyl)-methyl-2-pyridyl carbonate and [4-(cyclohexoxy)-phenyl]-methyl-2-oxopyridine-1-carboxylate Under nitrogen atmosphere, to a stirred mixture of [4-(cyclohexoxy)-phenyl]-methanol (0.571 g, 2.77 mmol) in dry CH$_2$Cl$_2$ (4.0 mL), DMAP (0.034 g, 0.28 mmol) and di-2-pyridyl-carbonate (0.717 g, 3.32 mmol) were added. The reaction mixture was left to react at r.t. for 15 h, then diluted with CH$_2$Cl$_2$ and washed first with a saturated NH$_4$Cl solution (3.0 mL) and subsequently with a saturated NaHCO$_3$ solution (3×3 mL). The organic fraction was dried over Na$_2$SO$_4$, filtered and concentrated to dryness to afford a colorless oil (0.779 g, 86%), as a mixture (ratio 1.8:1) of (4-cyclohexylphenyl)-methyl-2-pyridyl carbonate and (4-cyclohexylphenyl)-methyl-2-oxopyridine-1-carboxylate. The mixture of isomers was not separated and used in the next step without any further purification. MS (ESI) m/z: 366 [M−K]$^+$.

Step 4. Preparation of (2R,3S)-2-[[4-(cyclohexoxy)-phenyl]-methoxy-carbonylamino]-3-hydroxy-butanoic acid To a stirred mixture of D-threonine (0.08 g, 0.67 mmol) and NaHCO$_3$ (0.084 g, 1.0 mmol) in H$_2$O (3.0 mL), the crude mixture containing (4-cyclohexylphenyl)-methyl-2-pyridyl carbonate and [4-(cyclohexoxy)-phenyl]-methyl-2-oxopyridine-1-carboxylate (0.327 g, 1.0 mmol) in THF (3.0 mL) was added. After 15 h at r.t., the crude mixture was rotary evaporated to remove the organics and subsequently extracted with Et$_2$O (3×5 mL). The aqueous phase was acidified with 2.0 M HCl solution to pH 2-3 and subsequently extracted with EtOAc (3×10 mL). The organic fraction was dried over Na$_2$SO$_4$, filtered and concentrated to dryness to afford the title compound (0.214 g, 91%) as transparent oil, which was used in the next step without further purification. MS (ESI) m/z: 369 [M−NH$_4$]$^+$; (ESI) m/z: 350 [M−H]$^−$. $^1$H NMR (DMSO-d$_6$): δ 1.08 (d, J=6.3 Hz, 3H), 1.21-1.48 (m, 5H), 1.48-1.57 (m, 1H), 1.66-1.74 (m, 2H), 1.87-1.95 (m, 2H), 3.95 (dd, J=3.4, 9.0 Hz, 1H), 4.06 (dq, J=3.4, 6.3 Hz, 1H), 4.29-4.36 (m, 1H), 6.84 (d, J=9.0 Hz, 1H), 6.91 (d, J=8.3 Hz, 2H), 7.27 (d, J=8.3 Hz, 2H).

Step 5. Preparation of [4-(cyclohexoxy)-phenyl]-methyl-N-[(2S,3R)-2-methyl-4-oxo-oxetan-3-yl]-carbamate Under nitrogen atmosphere at 0° C., to a stirred mixture of (2R,3S)-2-[[4-(cyclohexoxy)-phenyl]-methoxy-carbonylamino]-3-hydroxy-butanoic acid (0.214 g, 0.61 mmol) in dry CH$_2$Cl$_2$ (30 mL), Et$_3$N (0.255 mL, 1.83 mmol) and subsequently TBTU (0.234 g, 0.73 mmol) were added. The mixture was left stirring 1 h at 0° C. and 15 h at r.t. Upon full conversion of the starting material, the organics were removed under reduced pressure, and the resulting crude product absorbed over silica gel and purified by column chromatography using a Teledyne ISCO apparatus, eluting with Cy:EtOAc (from 100:0 to 70:30) to afford the title compound (0.085 g, 42%), as white solid. MS (ESI) m/z: 372 [M−K]$^+$, 351 [M−NH$_4$]$^+$. $^1$H NMR (DMSO-d$_6$): δ 1.33 (d, J=6.5 Hz, 3H), 1.36-1.47 (m, 5H), 1.49-1.62 (m, 1H), 1.66-1.74 (m, 2H), 1.87-1.95 (m, 2H), 4.28-4.37 (m, 1H), 4.85 (dq, J=6.3, 6.5 Hz, 1H), 4.96 (d, J=11.9 Hz, 1H), 5.01 (d, J=11.9 Hz, 1H), 5.44 (dd, J=6.3, 9.5 Hz, 1H), 6.92 (d, J=8.4 Hz, 2H), 7.27 (d, J=8.4 Hz, 2H), 8.28 (d, J=9.5 Hz, 1H).

Example 47

5-Phenylpentyl-N-[(2R*,3R*)-2-ethyl-4-oxo-oxetan-3-yl]-carbamate

Step 1. Preparation of ethyl 2-(dibenzylamino)-acetate

To a stirred solution of ethyl chloroacetate (1.0 g, 8.16 mmol) in EtOH (5.0 mL), dibenzylamine (2.09 g, 10.6 mmol) was added and the mixture heated at 140° C. in a microwave reactor for 20 min. After evaporation of the solvent, the crude was dissolved in CH$_2$Cl$_2$ and washed with a 1.0 M KOH solution and brine, then dried over Na$_2$SO$_4$, filtered, and concentrated in vacuo to give a crude product, as an oil. Purification by column chromatography using a Teledyne ISCO apparatus, eluting with Cy:EtOAc (98:2), gave the title compound (1.85 g, 80%), as a white solid. MS (ESI) m/z: 284 [M−H]+[$^1$H NMR as previously reported in literature: *Synthesis*, 1985, 9, 850-855].

Step 2. Preparation of ethyl (2S*)-2-(dibenzylamino)-3-oxo-pentanoate

In a round bottomed flask, at −78° C., under argon atmosphere, a solution of DIPA (0.3 mL, 2.12 mmol) in dry THF (10 ml) was treated with n-BuLi (2.5 M in n-hexane, 0.776 mL, 1.94 mmol). After 30 min a solution of ethyl 2-(dibenzylamino)-acetate (0.5 g, 1.77 mmol) in dry THF (10 ml) was added dropwise via a cannula. After 15 min, propanoyl chloride (0.46 mL, 5.29 mmol) was added dropwise at −78° C. and the mixture stirred for 10 min at rt. The reaction was then quenched with $H_2O$, and $Et_2O$ was subsequently added. The organic layer was washed with brine, dried over $Na_2SO_4$, filtered, and concentrated in vacuo to give a crude product, as an oil. Purification by column chromatography using a Teledyne ISCO apparatus, eluting with Cy:AcOEt (98:2) gave a pure compound (0.6 g), as a mixture of two tautomers (ketone:enol=ca. 85:15), as a colorless oil. MS (ESI) m/z: 340 [M−H]+; (ESI) m/z: 338 [M−H]−. $^1$H NMR (DMSO-$d_6$) δ 0.90 (t, J=7.24 Hz, 3H), 1.23 (t, J=7.07 Hz, 3H), 2.53-2.61 (m, 1H), 2.69 (dq, J=7.23, 18.13 Hz, 1H), 3.72-3.88 (m, 4H), 4.12-4.22 (m, 3H), 7.11-7.47 (m, 10H) (reported data refer to the major ketone tautomer).

Step 3. Preparation of ethyl (2S*)-2-(tert-butoxy-carbonylamino)-3-oxo-pentanoate In a pear flask, at rt, to a solution of ethyl (2S*)-2-(dibenzylamino)-3-oxo-pentanoate (1.3 g, 3.83 mmol) in EtOH (90 ml), di-tert-butyl dicarbonate (1.67 g, 7.66 mmol) was added. The mixture was passed through the HCube® hydrogenator flow reactor, using 10% Pd(OH)$_2$/C as catalyst [flow:1.0 mL/min, P=1.0 bar, T=70° C.]. After evaporation of the solvent, the crude product was purified by column chromatography using a Teledyne ISCO apparatus, eluting with Cy:AcOEt (from 90:10 to 50:50) to afford the title product (0.546 g, 55% over 2 steps), as a colorless oil. MS (ESI) m/z: 282 [M−Na]+; (ESI) m/z: 258 [M−H]−. $^1$H NMR (DMSO-$d_6$) δ 0.93 (t, J=7.20 Hz, 3H), 1.20 (t, J=7.09 Hz, 3H), 1.39 (s, 9H), 2.60 (qd, J=2.16, 7.10 Hz, 2H), 4.07-4.22 (m, 2H), 4.91 (d, J=8.00 Hz, 1H), 7.51 (d, J=7.94 Hz, 1H).

Step 4. Preparation of ethyl (2R*,3R*) and (2R*,3S*)-2-(tert-butoxy-carbonylamino)-3-hydroxy-pentanoate In a round bottomed flask, at 0° C., under nitrogen atmosphere, to a stirred solution of ethyl (2S*)-2-(tert-butoxy-carbonylamino)-3-oxo-pentanoate (0.39 g, 1.5 mmol) in a 1:1 mixture of THF/EtOH (5.0 mL), NaBH$_4$ (0.022 g, 0.58 mmol) was added. The reaction was allowed to warm to rt over a period of 1 h, then quenched with $H_2O$ and the solvent evaporated. The crude mixture was dissolved in AcOEt, washed with brine, dried over $Na_2SO_4$, filtered, and concentrated in vacuo. Chromatographic purification using a Teledyne ISCO apparatus, eluting with Cy:AcOEt (from 100:0 to 80:20), afforded the title compound (0.2 g, 53%), as a mixture of diastereoisomers (anti:syn=8:2), as a colorless oil. MS (ESI) m/z: 284 [M−Na]+; (ESI) m/z: 320 [M−CH$_3$COO]−. $^1$H NMR (DMSO-$d_6$) δ 0.87 (t, J=7.37 Hz, 3H), 1.19 (t, J=7.07 Hz, 3H), 1.39 (s, 9H), 1.41-1.59 (m, 2H), 3.50-3.60 (m, 1H), 3.93 (dd, J=6.13, 8.52 Hz, 1H), 3.99-4.17 (m, 2H), 4.87 (d, J=5.57 Hz, 1H), 6.96 (d, J=8.51 Hz, 1H) (reported data refer to the major anti diastereoisomer).

Step 5. Preparation of (2R*,3R*) and (2R*,3S*)-2-amino-3-hydroxy-pentanoic acid In a 35 ml microwave vial, the diastereomeric mixture containing ethyl (2R*,3R*) and (2R*,3S*)-2-(tert-butoxy-carbonylamino)-3-hydroxy-pentanoate (0.2 g, 0.81 mmol) was dissolved in a 6.0 M HCl solution (15 mL) and stirred at 130° C. for 30 min. The reaction mixture was concentrated under reduced pressure giving a yellowish solid crude product, as a diastereoisomeric mixture (anti:syn=8:2), which was used without further purification in the following step. MS (ESI) m/z: 134 [M−H]+; (ESI) m/z: 132 [M−H]−. $^1$H NMR (DMSO-$d_6$) δ 0.92 (t, J=7.36 Hz, 3H), 1.42-1.64 (m, 2H), 3.80 (ddd, J=3.25, 5.80, 11.72 Hz, 1H), 3.86 (d, J=3.02 Hz, 1H), 4.36 (s, 1H), 8.26 (s, 3H) (reported data refer to the major anti diastereoisomer).

Step 6. Preparation of (2R*,3R*) and (2R*,3S*)-3-hydroxy-2-(5-phenylpentoxy-carbonylamino)-pentanoic acid To a stirred diastereomeric mixture containing (2R*,3R*) and (2R*,3S*)-2-amino-3-hydroxy-pentanoic acid (0.107 g, 0.81 mmol) and NaHCO$_3$ (0.102 g, 1.21 mmol) in $H_2O$ (2.0 mL), at rt, the isomeric mixture containing 5-phenyl-pentyl-2-pyridyl-carbonate and 5-phenyl-pentyl-2-oxopyridine-1-carboxylate (0.346 g, 1.21 mmol) [prepared as for example 32, step 1] in THF (2.0 mL) was added. After 15 h at rt, the crude mixture was rotary evaporated to remove the organics and subsequently extracted with $Et_2O$ (3×10 mL). The aqueous phase was acidified with 2.0 M HCl solution to pH 2-3 and subsequently extracted with AcOEt (3×20 mL). The organic fraction was dried over $Na_2SO_4$, filtered and concentrated to dryness to afford the title compound (0.155 g, 60% over 2 steps), as a diastereoisomeric mixture (anti:syn=8:2), as an off-white solid, which was used in the next step without further purification. MS (ESI) m/z: 324[M−H]+; (ESI) m/z: 322 [M−H]−. $^1$H NMR (DMSO-$d_6$) δ 0.86 (t, J=7.41 Hz, 3H), 1.27-1.50 (m, 4H), 1.51-1.67 (m, 4H), 2.57 (t, J=7.69 Hz, 2H), 3.52-3.66 (m, 1H), 3.93 (t, J=6.63 Hz, 3H), 4.83 (s, 1H), 7.10 (d, J=8.73 Hz, 1H), 7.13-7.22 (m, 3H), 7.22-7.30 (m, 2H), 12.35 (s, 1H) (reported data refer to the major anti diastereoisomer).

Step 7. Preparation of 5-phenylpentyl-N-[(2R*,3R*)-2-ethyl-4-oxo-oxetan-3-yl]-carbamate Under nitrogen atmosphere, to a stirred mixture of (2R*, 3R*)-3-hydroxy-2-(5-phenylpentoxy-carbonylamino)-pentanoic acid and (2R*,3S*)-3-hydroxy-2-(5-phenylpentoxy-carbonylamino)-pentanoic acid (0.155 g, 0.48 mmol) in dry $CH_2Cl_2$, (20.0 mL), at 0° C., Et$_3$N (0.2 mL, 1.44 mmol) and subsequently TBTU (0.185 g, 0.58 mmol) were added. The mixture was left stirring at 0° C. for 1 h and at rt for 15 h. The organics were then removed under reduced pressure, and the resulting crude product purified by column chromatography, using a Teledyne ISCO apparatus, eluting with Cy:AcOEt (from 100:0 to 80:20) to afford the title compound (0.075 g, 57%), as pure anti diastereoisomer, as white solid. MS (ESI) m/z: 323 [M−NH$_4$]+; (ESI) m/z: 304 [M−H]−. $^1$H NMR (DMSO-$d_6$) δ 0.90 (t, J=7.41 Hz, 3H), 1.26-1.38 (m, 2H), 1.58 (p, J=7.71, 8.27 Hz, 4H), 1.67-1.90 (m, 2H), 2.57 (t, J=7.65 Hz, 2H), 3.98 (t, J=6.60 Hz, 2H), 4.51 (td, J=4.28, 6.84 Hz, 1H), 4.69 (dd, J=4.32, 8.12 Hz, 1H), 7.09-7.32 (m, 5H), 8.06 (d, J=8.09 Hz, 1H).

Example 48

(4-Phenylphenyl)-methyl-N-[(2R*,3R*)-2-ethyl-4-oxo-oxetan-3-yl]-carbamate

Steps 1 to 5, as for Example 47.

Step 6. Preparation of (2R*,3R*) and (2R*,3S*)-3-hydroxy-2-[(4-phenylphenyl)-methoxy-carbonylamino]-pentanoic acid To a stirred diastereomeric mixture containing (2R*,3R*) and (2R*,3S*)-2-amino-3-hydroxy-pentanoic acid (0.108 g, 0.81 mmol) and NaHCO₃ (0.204 g, 2.43 mmol) in H₂O (2.0 mL), at rt, the isomeric mixture containing (4-phenylphenyl)-methyl-2-pyridyl carbonate and (4-phenylphenyl)-methyl-2-oxopyridine-1-carboxylate (0.37 g, 1.22 mmol) [prepared as for example 17, step 1] in THF (2.0 mL) was added. After 15 h at rt, the crude mixture was rotary evaporated to remove the organics and subsequently extracted with Et₂O (3×10 mL). The aqueous phase was acidified with 2.0 M HCl solution to pH 2-3 and subsequently extracted with AcOEt (3×20 mL). The organic fraction was dried over Na₂SO₄, filtered and concentrated to dryness to afford the title compound (0.206 g, 74% over 2 steps), as a diastereoisomeric mixture (anti:syn=8:2), as an off-white solid, which was used in the next step without further purification. MS (ESI) m/z: 361 [M–NH₄]⁺; (ESI) m/z: 342 [M–H]⁻. ¹H NMR (DMSO-d₆) δ 0.87 (t, J=7.38 Hz, 3H), 1.36-1.55 (m, 2H), 3.55-3.69 (m, 1H), 3.94-4.05 (m, 1H), 4.73-4.99 (m, 1H), 5.08 (s, 2H), 7.29-7.54 (m, 6H), 7.57-7.77 (m, 4H), 11.38-13.49 (m, 1H) (reported data refer to the major anti diastereoisomer).

Step 7. Preparation of (4-phenylphenyl)-methyl-N-[(2R*,3R*)-2-ethyl-4-oxo-oxetan-3-yl]-carbamate Under nitrogen atmosphere, to a stirred mixture of (2R*,3R*)-3-hydroxy-2-[(4-phenylphenyl)-methoxycarbonylamino]-pentanoic acid and (2R*,3S*)-3-hydroxy-2-[(4-phenylphenyl)-methoxycarbonylamino]-pentanoic acid (0.193 g, 0.56 mmol) in dry CH₂Cl₂ (25.0 mL), at 0° C., Et₃N (0.235 mL, 1.69 mmol) and subsequently TBTU (0.217 g, 0.67 mmol) were added. The mixture was left stirring at 0° C. for 1 h and at rt for 15 h. The organics were then removed under reduced pressure, and the resulting crude product purified by column chromatography, using a Teledyne ISCO apparatus, eluting with Cy/AcOEt (from 90:10 to 80:20) to afford the pure title compound (0.089 g, 57%), as pure anti diastereoisomer, as white solid. MS (ESI) m/z: 343 [M–NH₄]⁺; (ESI) m/z: 324 [M–H]⁻. ¹H NMR (DMSO-d₆) δ 0.92 (t, J=7.38 Hz, 3H), 1.68-1.94 (m, 2H), 4.49-4.60 (m, 1H), 4.76 (dd, J=4.32, 8.08 Hz, 1H), 5.12 (s, 2H), 7.33-7.42 (m, 1H), 7.42-7.53 (m, 4H), 7.62-7.76 (m, 4H), 8.25 (d, J=8.09 Hz, 1H).

Example 49

5-Phenylpentyl-N-[(2S*,3R*)-2-ethyl-4-oxo-oxetan-3-yl]-carbamate

Step 1. Preparation of ethyl (2S*,3R*)-2-(dibenzylamino)-3-hydroxy-pentanoate To a stirred solution of ethyl (2S*)-2-(dibenzylamino)-3-oxo-pentanoate [prepared as for example 47, step 1] (0.6 g, 1.76 mmol) in EtOH (30 mL), at rt, a solution of NH₄Cl (1.89 g, 35.29 mmol) in H₂O (8.0 mL) was added. NaBH₄ (0.667 g, 17.6 mmol) was then added in small portions. After 1 h from the last addition, the reaction was quenched with H₂O and the solvent evaporated. The crude mixture was taken up with H₂O and CH₂Cl₂ and pH corrected to 9 with 20% NH₄OH aqueous solution. After extraction, the organic phase was dried over Na₂SO₄, filtered, and concentrated in vacuo to give a crude product, as an oil. Purification by column chromatography using a Teledyne ISCO apparatus, eluting with Cy:AcOEt (90:10), gave the title compound (0.33 g, 55% over 2 steps), as a pure syn diastereoisomer, as a colorless oil. MS (ESI) m/z: 342 [M–H]⁺. ¹H NMR (DMSO-d₆) δ 0.75 (t, J=7.38 Hz, 3H), 1.26 (t, J=7.11 Hz, 3H), 1.30-1.52 (m, 2H), 3.14 (d, J=6.88 Hz, 1H), 3.67 (d, J=14.07 Hz, 2H), 3.85 (tt, J=4.61, 7.61 Hz, 1H), 4.08 (d, J=14.02 Hz, 2H), 4.11-4.25 (m, 2H), 4.66 (d, J=4.59 Hz, 1H), 7.20-7.27 (m, 2H), 7.28-7.41 (m, 8H).

Step 2. Preparation of ethyl (2S*,3R*)-2-amino-3-hydroxy-pentanoate

In a pear flask, at rt, ethyl (2S*,3R*)-2-(dibenzylamino)-3-hydroxy-pentanoate (0.165 g, 0.48 mmol) was dissolved in EtOH (12 mL) and passed through the H-Cube® hydrogenator flow reactor, using 10% Pd/C as catalyst [flow:1.0 mL/min; P=1.0 bar, T=70° C.]. After evaporation of the solvent, the title compound was obtained as yellowish oil and used without further purification in the following step. MS (ESI) m/z: 162 [M–H]⁺.

Step 3. Preparation of (2S*,3R*)-2-amino-3-hydroxy-pentanoic acid

In a 35 ml microwave vial, ethyl (2S*,3R*)-2-amino-3-hydroxy-pentanoate (0.078 g, 0.48 mmol) was dissolved in a 6.0 M HCl aqueous solution (7.0 mL) and stirred at 130° C. for 30 min. The reaction mixture was concentrated under reduced pressure and the resulting yellowish solid was used without further purification in the following step. MS (ESI) m/z: 134 [M–H]⁺; (ESI) m/z: 132 [M–H]⁻.

Step 4. Preparation of (2S*,3R*)-3-hydroxy-2-(5-phenylpentoxy-carbonylamino)-pentanoic acid To a stirred mixture of (2S*,3R*)-2-amino-3-hydroxy-pentanoic acid (0.068 g, 0.51 mmol) and NaHCO₃ (0.128 g, 1.53 mmol) in H₂O (2.0 mL), at rt, the isomeric mixture containing 5-phenyl-pentyl-2-pyridyl-carbonate and 5-phenyl-pentyl-2-oxopyridine-1-carboxylate (0.218 g, 0.77 mmol) [prepared as for example 32, step 1] in THF (2.0 mL) was added. After 15 h at rt, the crude mixture was rotary evaporated to remove the organics and subsequently extracted with Et₂O (3×10 mL). The aqueous phase was acidified with 2.0 M HCl solution to pH 2-3 and subsequently extracted with AcOEt (3×20 mL). The organic fraction was dried over Na₂SO₄, filtered and concentrated to dryness to afford the title compound (0.076 g, 46% over 3 steps), as an off-white solid, which was used in the next step without further purification. MS (ESI) m/z: 324 [M–NH₄]⁺; (ESI) m/z: 322 [M–H]⁻. ¹H NMR (DMSO-d₆) δ 0.85 (t, J=7.38 Hz, 3H), 1.28-1.49 (m, 4H), 1.50-1.68 (m, 4H), 2.58 (t, J=7.67 Hz, 2H), 3.79 (td, J=2.93, 6.83 Hz, 1H), 3.97 (t, J=6.60 Hz, 2H), 3.99-4.11 (m, 1H), 6.63 (d, J=9.23 Hz, 1H), 7.12-7.32 (m, 5H).

Step 5. Preparation of 5-phenylpentyl-N-[(2S*,3R*)-2-ethyl-4-oxo-oxetan-3-yl]-carbamate Under nitrogen atmosphere, to a stirred mixture of (2S*,3R*)-3-hydroxy-2-(5-phenylpentoxy-carbonylamino)-pentanoic acid (0.07 g, 0.22 mmol) in dry $CH_2Cl_2$ (10 mL), at 0° C., $Et_3N$ (0.091 mL, 0.65 mmol) and subsequently TBTU (0.083 g, 0.26 mmol) were added. The mixture was left stirring at 0° C. for 1 h and at rt for 15 h. The organics were then removed under reduced pressure, and the resulting crude product purified by column chromatography, using a Teledyne ISCO apparatus, eluting with Cy:AcOEt (from 90:10 to 70:30) to afford the pure title compound (0.043 g, 65%), as a white solid. MS (ESI) m/z: 323 $[M-NH_4]^+$; (ESI) m/z: 304 $[M-H]^-$. $^1H$ NMR (DMSO-$d_6$) δ 0.89 (t, J=7.43 Hz, 3H), 1.27-1.41 (m, 2H), 1.45-1.64 (m, 4H), 1.64-1.95 (m, 2H), 2.58 (t, J=7.66 Hz, 2H), 4.01 (t, J=6.49 Hz, 2H), 4.60 (dt, J=6.08, 8.01 Hz, 1H), 5.45 (dd, J=6.02, 9.42 Hz, 1H), 7.05-7.38 (m, 5H), 8.23 (d, J=9.41 Hz, 1H).

Example 50

(4-Phenylphenyl)-methyl-N-[(2S*,3R*)-2-ethyl-4-oxo-oxetan-3-yl]-carbamate

Steps 1 to 3, as for Example 49.

Step 4. Preparation of (2S*,3R*)-3-hydroxy-2-[(4-phenylphenyl)-methoxy-carbonylamino]-pentanoic acid To a stirred mixture of (2S*,3R*)-2-amino-3-hydroxy-pentanoic acid (0.068 g, 0.51 mmol) and $NaHCO_3$ (0.128 g, 1.53 mmol) in $H_2O$ (2.0 mL), at rt, the isomeric mixture containing (4-phenylphenyl)-methyl-2-pyridyl carbonate and (4-phenylphenyl)-methyl-2-oxopyridine-1-carboxylate (0.233 g, 0.77 mmol) [prepared as for example 17, step 1] in THF (2.0 mL) was added. After 15 h at rt, the crude mixture was rotary evaporated to remove the organics and subsequently extracted with $Et_2O$ (3×10 mL). The aqueous phase was acidified with 2.0 M HCl solution to pH 2-3 and subsequently extracted with AcOEt (3×20 mL). The organic fraction was dried over $Na_2SO_4$, filtered and concentrated to dryness to afford the title compound (0.164 g, 93% over 3 steps), as an off-white solid, which was used in the next step without further purification. MS (ESI) m/z: 361 $[M-NH_4]^+$; (ESI) m/z: 342 $[M-H]^-$. $^1H$ NMR (DMSO-$d_6$) δ 0.85 (t, J=7.38 Hz, 3H), 1.42 (p, J=7.31 Hz, 2H), 3.81 (td, J=3.02, 6.87 Hz, 1H), 4.07 (dd, J=3.04, 9.23 Hz, 1H), 4.66 (s, 1H), 5.10 (s, 2H), 6.92 (d, J=9.21 Hz, 1H), 7.28-7.56 (m, 5H), 7.59-7.78 (m, 4H), 12.59 (s, 1H).

Step 5. Preparation of (4-phenylphenyl)-methyl-N-[(2S*,3R*)-2-ethyl-4-oxo-oxetan-3-yl]-carbamate Under nitrogen atmosphere, to a stirred mixture of (2S*,3R*)-3-hydroxy-2-[(4-phenylphenyl)-methoxy-carbonylamino]-pentanoic acid (0.15 g, 0.44 mmol) in dry $CH_2Cl_2$ (20.0 mL), at 0° C., $Et_3N$ (0.183 mL, 1.31 mmol) and subsequently TBTU (0.168 g, 0.52 mmol) were added. The mixture was left stirring at 0° C. for 1 h and at rt for 15 h. The organics were then removed under reduced pressure, and the resulting crude product purified by column chromatography, using a Teledyne ISCO apparatus, eluting with Cy:AcOEt (from 100:0 to 70:30) to afford the pure title compound (0.054 g, 38%), as white solid. MS (ESI) m/z: 343 $[M-NH_4]^+$; (ESI) m/z: 324 $[M-H]^-$. $^1H$ NMR (DMSO-$d_6$) δ 0.88 (t, J=7.41 Hz, 3H), 1.56-1.88 (m, 2H), 4.61 (dt, J=6.07, 8.06 Hz, 1H), 5.11 (d, J=12.92 Hz, 1H), 5.15 (d, J=12.92 Hz, 1H), 5.49 (dd, J=5.97, 9.45 Hz, 1H), 7.29-7.57 (m, 5H), 7.60-7.78 (m, 4H), 8.41 (d, J=9.41 Hz, 1H).

Example 51

5-Phenylpentyl-N-[(2R*,3R*)-2-isopropyl-4-oxo-oxetan-3-yl]-carbamate

Step 1. Preparation of ethyl (2R*)-2-(dibenzylamino)-4-methyl-3-oxo-pentanoate In a round bottomed flask, at −78° C., under argon atmosphere, a solution of DIPA (1.6 ml, 9.3 mmol) in dry THF (40 ml) was treated with n-BuLi (2.5 M in n-hexane, 3.4 ml, 8.5 mmol). After 30 min a solution of ethyl 2-(dibenzylamino)-acetate [prepared as described in Example 47, step 1] (2.2 g, 7.8 mmol) in dry THF (40 ml) was added dropwise via cannula. After 15 min, 2-methyl-propanoyl chloride (2.4 mL, 23.3 mmol) was added dropwise at −78° C. and the mixture stirred for 10 min at rt. The reaction was then quenched with $H_2O$, and $Et_2O$ was subsequently added. The organic layer was washed with brine, dried over $Na_2SO_4$, filtered, and concentrated in vacuo to give a crude product, as an oil. Purification by column chromatography using a Teledyne ISCO apparatus, eluting with Cy:AcOEt (98:2) gave a crude compound (3.2 g) as a mixture of two tautomers (ketone:enol=ca. 65:35), as a colorless oil, which was used without further purification in the following step. Ketone isomer: MS (ESI) m/z: 354 $[M-H]^+$; (ESI) m/z: 352 $[M-H]^-$. $^1H$ NMR (DMSO-$d_6$) δ 0.86 (d, J=6.73 Hz, 3H), 0.91 (d, J=7.01 Hz, 3H), 1.22 (t, J=7.11 Hz, 3H), 2.99 (hept, J=6.90 Hz, 1H), 3.78 (d, J=14.11 Hz, 2H), 3.84 (d, J=14.13 Hz, 2H), 4.10-4.24 (m, 2H), 4.29 (s, 1H), 7.17-7.48 (m, 10H). Enol isomer: MS (ESI) m/z: 354 $[M-H]^+$; (ESI) m/z: 352 $[M-H]^-$. $^1H$ NMR (DMSO-$d_6$) δ 0.48 (s, 3H), 0.50 (s, 3H), 1.43 (t, J=7.09 Hz, 3H), 3.16-3.28 (m, 1H), 3.90 (d, J=12.66 Hz, 2H), 3.96 (d, J=12.66 Hz, 2H), 4.38 (q, J=7.08 Hz, 2H), 7.10-7.46 (m, 10H), 12.32 (s, 1H).

Step 2. Preparation of ethyl (2R*)-2-(tert-butoxy-carbonylamino)-4-methyl-3-oxo-pentanoate In a pear flask, at rt, to a solution of ethyl (2R*)-2-(dibenzylamino)-4-methyl-3-oxo-pentanoate (1.0 g, 2.83 mmol) in EtOH (60 ml), di-tert-butyl dicarbonate (1.24 g, 5.67 mmol) was added. The mixture was passed through the HCube® hydrogenator flow reactor, using 10% $Pd(OH)_2/C$ as catalyst [flow:1.0 mL/min, P=1.0 bar, T=70° C.]. After evaporation of the solvent, the crude product was purified by column chromatography using a Teledyne ISCO apparatus, eluting with Cy:AcOEt (from 90:10 to 50:50) to afford the title product (0.58 g, 75% over 2 steps), as a colorless oil. MS (ESI) m/z: 274 $[M-H]^+$; (ESI) m/z: 272 $[M-H]^-$. $^1H$ NMR (DMSO-$d_6$): δ 1.02 (d, J=6.87 Hz, 6H), 1.19 (t, J=7.11 Hz, 3H), 1.39 (s, 9H), 2.95 (p, J=6.87 Hz, 1H), 3.99-4.29 (m, 2H), 5.05 (d, J=8.16 Hz, 1H), 7.56 (d, J=8.14 Hz, 1H).

Step 3. Preparation of ethyl (2R*,3R*)- and (2R*,3S*)-2-(tert-butoxy-carbonylamino)-3-hydroxy-4-methyl-pentanoate In a round bottomed flask, at 0° C., under nitrogen atmosphere, to a stirred solution of ethyl (2R*)-2-(tert-butoxy-carbonylamino)-4-methyl-3-oxo-pentanoate (0.58 g, 2.13 mmol) in a 1:1 mixture of THF/EtOH (6.0 mL), $NaBH_4$ (0.021 g, 0.53 mmol) was added. The reaction was allowed to warm to rt over a period of 2.0 h, then quenched with H$_2$O and the solvent evaporated. The crude mixture was dissolved in AcOEt, washed with brine, dried over Na$_2$SO$_4$, filtered, and concentrated in vacuo. Chromatographic purification using a Teledyne ISCO apparatus, eluting with Cy:AcOEt (from 100:0 to 70:30), afforded the title compound (0.28 g, 48%), as a diastereoisomeric mixture (anti:syn=8:2), as a colorless oil. MS (ESI) m/z: 298 [M−Na]$^+$; (ESI) m/z: 334 [M−CH$_3$COO]$^−$. $^1$H NMR (DMSO-d$_6$) δ 0.80 (d, J=6.73 Hz, 3H), 0.88 (d, J=6.78 Hz, 3H), 1.18 (t, J=7.08 Hz, 3H), 1.37 (s, 9H), 1.67-1.87 (m, 1H), 3.40 (q, J=5.82 Hz, 1H), 3.95-4.05 (m, 1H), 4.03-4.12 (m, 2H), 4.84 (d, J=5.99 Hz, 1H), 6.98 (d, J=8.76 Hz, 1H) (reported data refer to the major anti diastereoisomer).

Step 4. Preparation of (2R*,3R*)- and (2R*,3S*)-2-amino-3-hydroxy-4-methyl-pentanoic acid In a 35 ml microwave vial, the diastereomeric mixture containing ethyl (2R*,3R*)- and (2R*,3S*)-2-(tert-butoxycarbonylamino)-3-hydroxy-4-methyl-pentanoate (0.1 g, 0.36 mmol) was dissolved in a 6.0 M HCl solution (15 mL) and stirred at 130° C. for 1 h. The reaction mixture was extracted with Et$_2$O (3×10 ml), and the aqueous phase concentrated under reduced pressure giving a white crude solid (0.15 g). The resulting diastereoisomeric mixture (anti:syn=8:2) was used without further purification in the following step. MS (ESI) m/z: 148 [M−H]$^+$; (ESI) m/z: 146 [M−H]$^−$. $^1$H NMR (DMSO-d$_6$) δ 0.91 (dd, J=6.56, 10.18 Hz, 6H), 1.92 (p, J=7.10 Hz, 1H), 3.42 (d, J=8.47 Hz, 1H), 3.79-3.99 (m, 1H), 5.71 (s, 1H), 7.69-8.64 (m, 3H), 13.54 (s, 1H) (reported data refer to the major anti diastereoisomer) [see also *Tetrahedron* 2001, 57, 8267-8276].

Step 5. Preparation of (2R*,3R*)- and (2R*,3S*)-3-hydroxy-4-methyl-2-(5-phenylpentoxy-carbonylamino)-pentanoic acid To a stirred diastereomeric mixture containing (2R*,3R*)- and (2R*,3S*)-2-amino-3-hydroxy-4-methyl-pentanoic acid (0.058 g, 0.4 mmol) and NaHCO$_3$ (0.035 g, 0.4 mmol) in H$_2$O (2.0 mL), at rt, the isomeric mixture containing 5-phenyl-pentyl-2-pyridyl-carbonate and 5-phenyl-pentyl-2-oxopyridine-1-carboxylate (0.38 g, 1.4 mmol) [prepared as for example 32, step 1] in THF (2.0 mL) was added. After 15 h at rt, the crude mixture was rotary evaporated to remove the organics and subsequently extracted with Et$_2$O (3×10 mL). The aqueous phase was acidified with 2.0 M HCl solution to pH 2-3 and subsequently extracted with AcOEt (3×20 mL). The organic fraction was dried over Na$_2$SO$_4$, filtered and concentrated to dryness to afford the title compound (0.079 g, 59% over 2 steps), as a diastereoisomeric mixture (anti:syn=8:2), as an off-white solid, which was used in the next step without further purification. MS (ESI) m/z: 338 [M−H]$^+$; (ESI) m/z: 336 [M−H]$^−$. $^1$H NMR (DMSO-d$_6$) δ 0.81 (d, J=6.69 Hz, 3H), 0.88 (d, J=6.77 Hz, 3H), 1.32 (tt, J=5.81, 9.52 Hz, 2H), 1.57 (td, J=4.08, 8.39 Hz, 4H), 1.70-1.84 (m, 1H), 2.56 (t, J=7.71 Hz, 2H), 3.40 (t, J=6.09 Hz, 1H), 3.93 (t, J=6.61 Hz, 2H), 3.96-4.04 (m, 1H), 4.84 (s, 1H), 7.12-7.21 (m, 4H), 7.27 (t, J=7.49 Hz, 2H), 12.00-12.96 (s, 1H) (reported data refer to the major anti diastereoisomer).

Step 6. Preparation of 5-phenylpentyl-N-[(2R*,3R*)-2-isopropyl-4-oxo-oxetan-3-yl]-carbamate Under nitrogen atmosphere, to a stirred mixture of (2R*,3R*)-3-hydroxy-4-methyl-2-(5-phenylpentoxy-carbonylamino)-pentanoic acid and (2R*,3S*)-3-hydroxy-4-methyl-2-(5-phenylpentoxy-carbonylamino)-pentanoic acid (0.076 g, 0.24 mmol) in dry CH$_2$Cl$_2$ (10.0 mL), at 0° C., Et$_3$N (0.2 mL, 1.44 mmol) and subsequently TBTU (0.091 g, 0.28 mmol) were added. The mixture was left stirring at 0° C. for 1 h and at rt for 15 h. The organics were then removed under reduced pressure, and the resulting crude product purified by column chromatography, using a Teledyne ISCO apparatus, eluting with Cy:AcOEt (from 100:0 to 80:20) to afford the pure title compound (0.041 g, 56%), as pure anti diastereoisomer, as white solid. MS (ESI) m/z: 337 [M−NH$_4$]$^+$; (ESI) m/z: 318 [M−H]$^−$. $^1$H NMR (DMSO-d$_6$) δ 0.87 (d, J=6.75 Hz, 3H), 0.95 (d, J=6.55 Hz, 3H), 1.27-1.43 (m, 2H), 1.49-1.69 (m, 4H), 1.87-2.08 (m, 1H), 2.57 (t, J=7.67 Hz, 2H), 3.99 (t, J=6.59 Hz, 2H), 4.22 (dd, J=4.39, 9.13 Hz, 1H), 4.73 (dd, J=4.40, 8.18 Hz, 1H), 7.10-7.35 (m, 5H), 8.06 (d, J=8.16 Hz, 1H).

Example 52

(4-Phenylphenyl)-methyl-N-[(2R*,3R*)-2-isopropyl-4-oxo-oxetan-3-yl]-carbamate

Steps 1 to 4, as for Example 51.

Step 5. Preparation of (2R*,3R*)- and (2R*,3S*)-3-hydroxy-4-methyl-2-[(4-phenylphenyl)-methoxy-carbonylamino]-pentanoic acid To a stirred diastereomeric mixture containing (2R*,3R*)- and (2R*,3S*)-2-amino-3-hydroxy-4-methyl-pentanoic acid (0.05 g, 0.34 mmol) and NaHCO$_3$ (0.03 g, 0.34 mmol) in H$_2$O (2.0 mL), at rt, the isomeric mixture containing (4-phenylphenyl)-methyl-2-pyridyl carbonate and (4-phenylphenyl)-methyl-2-oxopyridine-1-carboxylate (0.45 g, 1.48 mmol) [prepared as for example 17, step 1] in THF (2.0 mL) was added. After 15 h at rt, the crude mixture was rotary evaporated to remove the organics and subsequently extracted with Et$_2$O (3×10 mL). The aqueous phase was acidified with 2.0 M HCl solution to pH 2-3 and subsequently extracted with AcOEt (3×20 mL). The organic fraction was dried over Na$_2$SO$_4$, filtered and concentrated to dryness to afford the title compound (0.06 g, 50% over 2 steps), as a diastereoisomeric mixture (anti:syn=8:2), as an off-white solid, which was used in the next step without further purification. MS (ESI) m/z: 358 [M−H]$^+$; (ESI) m/z: 356 [M−H]$^−$. $^1$H NMR (DMSO-d$_6$) δ 0.82 (d, J=6.55 Hz, 3H), 0.88 (d, J=6.92 Hz, 3H), 1.62-1.79 (m, 1H), 3.17 (dd, J=2.87, 9.15 Hz, 1H), 3.51 (d, J=9.16 Hz, 1H), 5.05 (s, 2H), 7.32-7.41 (m, 1H), 7.41-7.52 (m, 4H), 7.66 (td, J=1.74, 6.70, 7.42 Hz, 4H) (reported data refer to the major anti diastereoisomer).

Step 6. Preparation of (4-phenylphenyl)-methyl-N-[(2R*,3R*)-2-isopropyl-4-oxo-oxetan-3-yl]-carbamate Under nitrogen atmosphere, to a stirred mixture of (2R*,3R*)-3-hydroxy-4-methyl-2-[(4-phenylphenyl)-methoxy-carbonylamino]-pentanoic acid and (2R*,3S*)-3-hydroxy-4-methyl-2-[(4-phenylphenyl)-methoxy-carbonylamino]-pentanoic acid (0.059 g, 0.17 mmol) in dry CH$_2$Cl$_2$ (7.0 mL), at 0° C., Et$_3$N (0.07 mL, 0.5 mmol) and subsequently TBTU (0.065 g, 0.2 mmol) were added. The mixture was left stirring at 0° C. for 1 h and at rt for 15 h. The organics were then removed under reduced pressure, and the resulting crude product purified by column chromatography, using a Teledyne ISCO apparatus, eluting with Cy:AcOEt (from 90:10 to 80:20) to afford the pure title compound (0.01 g, 17%), as pure anti diastereoisomer, as white solid. MS (ESI) m/z: 357 [M−NH$_4$]$^+$; (ESI) m/z: 338 [M−H]$^−$. $^1$H NMR (DMSO-d$_6$) δ 0.89 (d, J=6.79 Hz, 3H), 0.97 (d, J=6.57 Hz, 3H), 1.81-2.12 (m, 1H), 4.26 (dd, J=4.38, 9.11 Hz, 1H), 4.80 (dd, J=4.39, 8.16 Hz, 1H), 5.12 (s, 2H), 7.29-7.54 (m, 5H), 7.63-7.77 (m, 4H), 8.26 (d, J=8.21 Hz, 1H).

Example 53

5-Phenylpentyl-N-[(2S*,3R*)-2-isopropyl-4-oxo-oxetan-3-yl]-carbamate

Step 1. Preparation of ethyl (2S*,3R*)-2-(dibenzy-lamino)-3-hydroxy-4-methyl-pentanoate To a stirred solution of ethyl (2S*)-2-(dibenzylamino)-3-oxo-pentanoate [prepared as for example 47, step 1] (2.76 g, 7.8 mmol) in EtOH (90 mL), at rt, a solution of NH$_4$Cl (8.34 g, 156 mmol) in H$_2$O (23 mL) was added. NaBH$_4$ (2.95 g, 78 mmol) was then added in small portions. After 1 h from the last addition, the reaction was quenched with H$_2$O and the solvent evaporated. The crude mixture was taken up with H$_2$O and CH$_2$Cl$_2$ and pH corrected to 9 with 20% NH$_4$OH aqueous solution. After extraction, the organic phase was dried over Na$_2$SO$_4$, filtered, and concentrated in vacuo to give a crude product, as an oil. Purification by column chromatography using a Teledyne ISCO apparatus, eluting with Cy:AcOEt (90:10), gave the title compound (1.33 g, 48% over 2 steps), as a pure syn diastereoisomer, as a colorless oil. MS (ESI) m/z: 356 [M−H]$^+$. $^1$H NMR (DMSO-d$_6$) δ 0.66 (d, J=6.69 Hz, 3H), 0.71 (d, J=6.68 Hz, 3H), 1.26 (t, J=7.09 Hz, 3H), 1.66 (h, J=6.63 Hz, 1H), 3.24 (d, J=7.12 Hz, 1H), 3.63 (d, J=13.94 Hz, 2H), 3.63 (m, 1H) 4.06 (d, J=14.06 Hz, 2H), 4.10-4.27 (m, 2H), 4.61 (d, J=4.60 Hz, 1H), 7.15-7.45 (m, 10H).

Step 2. Preparation of ethyl (2S*,3R*)-2-amino-3-hydroxy-4-methyl-pentanoate

In a pear flask, at rt, ethyl (2S*,3R*)-2-(dibenzylamino)-3-hydroxy-4-methyl-pentanoate (1.24 g, 3.5 mmol) was dissolved in EtOH (75 mL) and passed through the H-Cube® hydrogenator flow reactor, using 10% Pd/C as catalyst [flow: 1.0 mL/min; P=1.0 bar, T=70° C.]. After evaporation of the solvent, the title compound (0.57 g, quant.) was obtained as yellowish oil and used without further purification in the following step. MS (ESI) m/z: 176 [M−H]$^+$. $^1$H NMR (DMSO-d$_6$) δ 0.83 (d, J=6.72 Hz, 3H), 0.90 (d, J=6.69 Hz, 3H), 1.19 (t, J=7.10 Hz, 3H), 1.64-1.80 (m, 1H), 3.29 (dd, J=3.36, 8.06 Hz, 1H), 3.35 (d, J=3.37 Hz, 1H), 4.08 (qd, J=0.99, 7.13 Hz, 2H).

Step 3. Preparation of (2S*,3R*)-2-amino-3-hydroxy-4-methyl-pentanoic acid

In a 35 ml microwave vial, ethyl (2S*,3R*)-2-amino-3-hydroxy-4-methyl-pentanoate (0.232 g, 1.33 mmol) was dissolved in a 6.0 M HCl aqueous solution (25 mL) and stirred at 130° C. for 1 h. The reaction mixture was extracted with Et$_2$O (3×15 mL), the aqueous phase was concentrated under reduced pressure resulting in a white solid (0.23 g, 81%), which was used without further purification in the following step. MS (ESI) m/z: 148 [M−H]$^+$; (ESI) m/z: 146 [M−H]$^−$. $^1$H NMR (DMSO-d$_6$) δ 0.87 (d, J=6.64 Hz, 3H), 0.93 (d, J=6.50 Hz, 3H), 1.74 (tq, J=5.79, 6.46, 11.64 Hz, 1H), 3.51-3.60 (m, 1H), 3.92 (s, 1H), 5.76 (s, 1H), 8.12 (s, 3H), 13.72 (s, 1H) [see also Tetrahedron 2001, 57, 8267-8276].

Step 4. Preparation of (2S*,3R*)-3-hydroxy-4-methyl-2-(5-phenylpentoxy-carbonylamino)-pentanoic acid To a stirred mixture of (2S*,3R*)-2-amino-3-hydroxy-4-methyl-pentanoic acid (0.152 g, 1.04 mmol) and NaHCO$_3$ (0.088 g, 1.05 mmol) in H$_2$O (6.0 mL), at rt, the isomeric mixture containing 5-phenyl-pentyl-2-pyridyl-carbonate and 5-phenyl-pentyl-2-oxopyridine-1-carboxylate (0.96 g, 1.21 mmol) [prepared as for example 32, step 1] in THF (6.0 mL) was added. After 15 h at rt, the crude mixture was rotary evaporated to remove the organics and subsequently extracted with Et$_2$O (3×10 mL). The aqueous phase was acidified with 2.0 M HCl solution to pH 2-3 and subsequently extracted with AcOEt (3×20 mL). The organic fraction was dried over Na$_2$SO$_4$, filtered and concentrated to dryness to afford the title compound (0.145 g, 41%), as a yellowish solid, which was used in the next step without further purification. MS (ESI) m/z: 338 [M−H]$^+$; (ESI) m/z: 336 [M−H]$^−$. $^1$H NMR (DMSO-d$_6$) δ 0.80 (d, J=6.63 Hz, 3H), 0.93 (d, J=6.49 Hz, 3H), 1.28-1.41 (m, 2H), 1.50-1.69 (m, 4H), 1.81-1.91 (m, 1H), 2.57 (d, J=7.67 Hz, 2H), 3.47 (d, J=8.36 Hz, 1H), 3.89-3.99 (m, 2H), 4.15 (dd, J=2.83, 9.47 Hz, 1H), 4.58 (s, 1H), 6.64 (d, J=9.43 Hz, 1H), 7.10-7.32 (m, 5H), 12.43 (s, 1H).

Step 5. Preparation of 5-phenylpentyl-N-[(2S*,3R*)-2-isopropyl-4-oxo-oxetan-3-yl]-carbamate Under nitrogen atmosphere, to a stirred mixture of (2S*,3R*)-3-hydroxy-4-methyl-2-(5-phenylpentoxy-carbonylamino)-pentanoic acid (0.14 g, 0.43 mmol) in dry CH$_2$Cl$_2$ (20 mL), at 0° C., Et$_3$N (0.18 mL, 1.3 mmol) and subsequently TBTU (0.17 g, 0.55 mmol) were added. The mixture was left stirring at 0° C. for 1 h and at rt for 15 h. The organics were then removed under reduced pressure, and the resulting crude product purified by column chromatography, using a Teledyne ISCO apparatus, eluting with Cy:AcOEt (from 100:0 to 80:20) to afford the pure title compound (0.052 g, 40%), as pure syn diastereoisomer, as a white solid. MS (ESI) m/z: 337 [M−NH$_4$]$^+$; (ESI) m/z: 318 [M−H]$^−$. $^1$H NMR (DMSO-d$_6$) δ 0.75 (d, J=6.57 Hz, 3H), 0.96 (d, J=6.51 Hz, 3H), 1.25-1.39 (m, 2H), 1.52-1.65 (m, 4H), 2.03 (dt, J=6.53, 10.83 Hz, 1H), 2.57 (t, J=7.67 Hz, 2H), 4.01 (t, J=6.58 Hz, 2H), 4.24 (dd, J=5.92, 10.84 Hz, 1H), 5.44 (dd, J=5.92, 9.53 Hz, 1H), 7.13-7.34 (m, 5H), 8.27 (d, J=9.52 Hz, 1H).

Example 54

(4-Phenylphenyl)-methyl-N-[(2S*,3R*)-2-isopropyl-4-oxo-oxetan-3-yl]-carbamate

Steps 1 to 3, as for Example 53.

Step 4. Preparation of (2S*,3R*)-3-hydroxy-4-methyl-2-[(4-phenylphenyl)-methoxy-carbonylamino]-pentanoic acid To a stirred diastereomeric mixture containing (2S*,3R*)-2-amino-3-hydroxy-4-methyl-pentanoic acid (0.156 g, 1.06 mmol) and NaHCO$_3$ (0.09 g, 1.06 mmol) in H$_2$O (5.0 mL), at rt, the isomeric mixture containing (4-phenylphenyl)-methyl-2-pyridyl carbonate and (4-phenylphenyl)-methyl-2-oxopyridine-1-carboxylate (1.4 g, 4.6 mmol) [prepared as for example 17, step 1] in THF (5.0 mL) was added. After 15 h at rt, the crude mixture was rotary evaporated to remove the organics and subsequently extracted with Et$_2$O (3×10 mL). The aqueous phase was acidified with 2.0 M HCl solution to pH 2-3 and subsequently extracted with AcOEt (3×20 mL). The organic fraction was dried over Na$_2$SO$_4$, filtered and concentrated to dryness to afford the title compound (0.196 g, 52% over two steps), as a yellowish solid, which was used in the next step without further purification. MS (ESI) m/z: 375 [M−NH$_4$]$^+$; (ESI) m/z: 356 [M−H]$^-$. $^1$H NMR (DMSO-d$_6$) δ 0.82 (d, J=6.66 Hz, 3H), 0.92 (d, J=6.39 Hz, 3H), 1.54-1.70 (m, 1H), 3.51 (t, J=8.38 Hz, 1H), 4.20 (dd, J=2.88, 9.42 Hz, 1H), 4.63 (d, J=8.86 Hz, 1H), 5.11 (s, 2H), 6.94 (d, J=9.44 Hz, 1H), 7.37 (t, J=6.55 Hz, 1H), 7.44-7.52 (m, 4H), 7.63-7.75 (m, 4H), 12.57 (s, 1H).

Step 5. Preparation of (4-phenylphenyl)-methyl-N-[(2S*,3R*)-2-isopropyl-4-oxo-oxetan-3-yl]-carbamate Under nitrogen atmosphere, to a stirred mixture of (2S*,3R*)-3-hydroxy-4-methyl-2-[(4-phenylphenyl)-methoxycarbonylamino]-pentanoic acid (0.193 g, 0.54 mmol) in dry CH$_2$Cl$_2$ (25 mL), at 0° C., Et$_3$N (0.23 mL, 1.65 mmol) and subsequently TBTU (0.21 g, 0.65 mmol) were added. The mixture was left stirring at 0° C. for 1 h and at rt for 15 h. The organics were then removed under reduced pressure, and the resulting crude product purified by column chromatography, using a Teledyne ISCO apparatus, eluting with Cy:AcOEt (from 90:10 to 80:20) to afford the pure title compound (0.041 g, 22%), as pure syn diastereoisomer, as white solid. MS (ESI) m/z: 357 [M−NH$_4$]$^+$; (ESI) m/z: 338 [M−H]$^-$. $^1$H NMR (DMSO-d$_6$) δ 0.76 (d, J=6.58 Hz, 3H), 0.95 (d, J=6.50 Hz, 3H), 1.93-2.13 (m, 1H), 4.25 (dd, J=5.93, 10.87 Hz, 1H), 5.14 (s, 2H), 5.48 (dd, J=5.90, 9.49 Hz, 1H), 7.34-7.52 (m, 5H), 7.61-7.70 (m, 4H), 8.46 (d, J=9.48 Hz, 1H).

Example 55

(1,1-Dimethyl-5-phenyl-pentyl)-N-[(2R*,3R*)-2-isopropyl-4-oxo-oxetan-3-yl]-carbamate Steps 1 to 4, as for Example 51.

Step 5. Preparation of (2R*,3R*)- and (2R*,3S*)-2-[(1,1-dimethyl-5-phenyl-pentoxy)-carbonylamino]-3-hydroxy-4-methyl-pentanoic acid To a stirred diastereomeric mixture containing (2R*,3R*)- and (2R*,3S*)-2-amino-3-hydroxy-4-methyl-pentanoic acid (0.16 g, 1.08 mmol) and NaHCO$_3$ (0.23 g, 2.7 mmol) in H$_2$O (4.0 mL), at rt, the isomeric mixture containing (1,1-dimethyl-5-phenyl-pentyl)-2-pyridyl carbonate and (1,1-dimethyl-5-phenyl-pentyl)-2-oxopyridine-1-carboxylate (0.93 g, 2.98 mmol) [prepared as for example 25, step 1] in THF (4.0 mL) was added. After 15 h at rt, the crude mixture was rotary evaporated to remove the organics and subsequently extracted with Et$_2$O (3×10 mL). The aqueous phase was acidified with 2.0 M HCl solution to pH 2-3 and subsequently extracted with AcOEt (3×20 mL). The organic fraction was dried over Na$_2$SO$_4$, filtered and concentrated to dryness to afford a crude product (0.117 g), mainly consisting of the title compound, as a diastereoisomeric mixture (anti:syn=8:2), together with unreacted starting material. The crude mixture was used in the next step without further purification. MS (ESI) m/z: 388 [M−NH$_4$]$^+$; (ESI) m/z: 364 [M−H]$^-$.

Step 6. Preparation of (1,1-dimethyl-5-phenyl-pentyl)-N-[(2R*,3R*)-2-isopropyl-4-oxo-oxetan-3-yl]-carbamate Under nitrogen atmosphere, to a stirred mixture of (2R*,3R*)-2-[(1,1-dimethyl-5-phenyl-pentoxy)-carbonylamino]-3-hydroxy-4-methyl-pentanoic acid and (2R*,3S*)-2-[(1,1-dimethyl-5-phenyl-pentoxy)-carbonylamino]-3-hydroxy-4-methyl-pentanoic acid (0.11 g, 0.30 mmol) in dry CH$_2$Cl$_2$ (15 mL), at 0° C., Et$_3$N (0.126 mL, 0.9 mmol) and subsequently TBTU (0.116 g, 0.36 mmol) were added. The mixture was left stirring at 0° C. for 1 h and at rt for 15 h. The organics were then removed under reduced pressure, and the resulting crude product purified by column chromatography, using a Teledyne ISCO apparatus, eluting with Cy:AcOEt (from 100:0 to 80:20) to afford the pure title compound (0.019 g, 18%), as pure anti diastereoisomer, as white solid. MS (ESI) m/z: 365 [M−NH$_4$]$^+$; (ESI) m/z: 346 [M−H]$^-$. $^1$H NMR (DMSO-d$_6$) δ 0.86 (d, J=6.66 Hz, 3H), 0.95 (d, J=6.54 Hz, 3H), 1.27-1.35 (m, 2H), 1.36 (s, 6H), 1.55 (p, J=7.56 Hz, 2H), 1.66-1.85 (m, 2H), 1.96 (dt, J=6.52, 8.91 Hz, 1H), 2.57 (t, J=7.71 Hz, 2H), 4.17 (dd, J=4.40, 9.09 Hz, 1H), 4.69 (dd, J=4.40, 8.33 Hz, 1H), 7.11-7.33 (m, 5H), 7.81 (d, J=8.32 Hz, 1H).

Example 56

5-Phenylpentyl-N-[(2R*,3R*)-2-tert-butyl-4-oxo-oxetan-3-yl]-carbamate

Step 1. Preparation of ethyl (2S*)-2-(dibenzylamino)-4,4-dimethyl-3-oxo-pentanoate In a round bottomed flask, at −78° C., under argon atmosphere, a solution of DIPA (0.29 mL, 2.12 mmol) in dry THF (10 ml) was treated with n-BuLi (2.5 M in n-hexane, 0.776 mL, 1.94 mmol). After 30 min a solution of ethyl 2-(dibenzylamino)-acetate [prepared as described in Example 47, step 1] (0.5 g, 1.77 mmol) in dry THF (10 mL) was added dropwise via cannula. After 15 min, trimethylacetyl chloride (0.53 mL, 3.53 mmol) was added dropwise at −78° C. and the mixture stirred for 10 min at rt. The reaction was then quenched with H$_2$O, and Et$_2$O was subsequently added. The organic layer was washed with brine, dried over Na$_2$SO$_4$, filtered, and concentrated in vacuo to give a crude product as an oil. Purification by column chromatography using a Teledyne ISCO apparatus, eluting with Cy:AcOEt (98:2) gave the title compound (0.492 g, 76%) as a colorless oil. MS (ESI) m/z: 368 [M−H]$^+$; (ESI) m/z: 366 [M−H]$^-$. $^1$H NMR (DMSO-d$_6$) δ 0.93 (s, 9H), 1.16-1.25 (m, 3H), 3.79 (d, J=13.97 Hz, 2H), 3.98 (d, J=13.96 Hz, 2H), 4.07-4.25 (m, 2H), 4.60 (s, 1H), 7.20-7.41 (m, 10H).

Step 2. Preparation of ethyl (2S*)-2-(tert-butoxycarbonylamino)-4,4-dimethyl-3-oxo-pentanoate In a pear flask, at rt, to a solution of (2S*)-2-(dibenzylamino)-4,4-dimethyl-3-oxo-pentanoate (2.5 g, 6.8 mmol) in EtOH (150 ml), di-tert-butyl dicarbonate (2.96 g, 13.6 mmol) was added. The resulting solution was divided into two aliquots and each passed through the H-Cube® hydrogenator flow reactor, using 10% Pd(OH)$_2$/C as catalyst [flow:1.0 mL/min, P=1.0 bar, T=70° C.]. The aliquots were combined and, after evaporation of the solvent, the crude product was purified by column chromatography using a Teledyne ISCO apparatus, eluting with Cy:AcOEt (from 90:10 to 50:50) to afford the title product (1.24 g, 64%), as a colorless oil. MS (ESI) m/z: 286 [M−H]$^-$. $^1$H NMR (DMSO-d$_6$) δ 1.15 (s, 9H), 1.18 (t, J=7.10 Hz, 3H), 1.39 (s, 9H), 4.12 (q, J=7.09 Hz, 2H), 5.32 (d, J=8.75 Hz, 1H), 7.64 (d, J=8.72 Hz, 1H).

Step 3. Preparation of ethyl (2R*,3R*)- and (2R*, 3S*)-2-(tert-butoxy-carbonylamino)-3-hydroxy-4,4-dimethyl-pentanoate In a round bottomed flask, at 0° C., under nitrogen atmosphere, to a stirred solution of (2S*)-2-(tert-butoxy-carbonylamino)-4,4-dimethyl-3-oxo-pentanoate (1.19 g, 4.12 mmol) in a 1:1 mixture of THF/EtOH (26 mL), NaBH$_4$ (0.058.5 g, 1.55 mmol) was added. The reaction was allowed to warm to rt over a period of 1 h, then quenched with H$_2$O and the solvent evaporated. The crude mixture was dissolved in AcOEt, washed with brine, dried over Na$_2$SO$_4$, filtered, and concentrated in vacuo. Chromatographic purification using a Teledyne ISCO apparatus, eluting with Cy:AcOEt (70:30) afforded the title compound (0.995 g, 83%), as a diastereoisomeric mixture (anti:syn=9:1), as a colorless oil. MS (ESI) m/z: 312 [M−Na]$^+$; (ESI) m/z: 348 [M−CH$_3$COO]$^−$. $^1$H NMR (DMSO-d$_6$) δ 0.86 (s, 9H), 1.17 (t, J=7.03 Hz, 3H), 1.36 (s, 9H), 3.37 (t, J=6.39 Hz, 1H), 4.03 (q, J=7.05 Hz, 2H), 4.08-4.17 (m, 1H), 5.01 (d, J=5.94 Hz, 1H), 7.15 (d, J=8.75 Hz, 1H).

Step 4. Preparation of (2R*,3R*)- and (2R*,3S*)-2-amino-3-hydroxy-4,4-dimethyl-pentanoic acid In a round-bottomed flask, the diastereomeric mixture containing (2R*,3R*)- and (2R*,3S*)-2-(tert-butoxy-carbonylamino)-3-hydroxy-4,4-dimethyl-pentanoate (0.4 g, 1.38 mmol) was dissolved in a 6.0 M HCl solution (30 mL). The resulting solution was divided into two equal aliquots and stirred at 130° C. for 1 h. All portions were joined and the reaction mixture extracted with Et$_2$O (3×20 mL). The aqueous phase was concentrated under reduced pressure giving a yellowish solid crude product, as a diastereoisomeric mixture (anti:syn=9:1), which was used without further purification in the following step. MS (ESI) m/z: 162 [M−H]$^+$; (ESI) m/z: 160 [M−H]$^−$.

Step 5. Preparation of (2R*,3R*)- and (2R*,3S*)-3-hydroxy-4,4-dimethyl-2-(5-phenylpentoxy-carbonylamino)-pentanoic acid To a stirred diastereomeric mixture containing (2R*,3R*)- and (2R*,3S*)-2-amino-3-hydroxy-4,4-dimethyl-pentanoic acid (0.23 g, 1.38 mmol) and NaHCO$_3$ (0.118 g, 1.4 mmol) in H$_2$O (5.0 mL), at rt, the isomeric mixture containing 5-phenyl-pentyl-2-pyridyl-carbonate and 5-phenyl-pentyl-2-oxopyridine-1-carboxylate (0.57 g, 2.0 mmol) [prepared as for example 32, step 1] in THF (5.0 mL) was added. After 15 h at rt, the crude mixture was rotary evaporated to remove the organics and subsequently extracted with Et$_2$O (3×10 mL). The aqueous phase was acidified with 2.0 M HCl solution to pH 2-3 and subsequently extracted with AcOEt (3×20 mL). The organic fraction was dried over Na$_2$SO$_4$, filtered and concentrated to dryness to afford the title compound (0.34 g, 70% over 2 steps), as a diastereoisomeric mixture (anti:syn=9:1), as an off-white solid, which was used in the next step without further purification. MS (ESI) m/z: 352 [M−H]$^+$; (ESI) m/z: 350 [M−H]$^−$. $^1$H NMR (DMSO-d$_6$) δ 0.87 (s, 9H), 1.27-1.41 (m, 2H), 1.57 (q, J=7.46 Hz, 4H), 2.57 (t, J=7.70 Hz, 2H), 3.36 (t, J=7.52 Hz, 2H, under water signal), 3.85-4.15 (m, 3H), 7.13-7.32 (m, 5H), 7.32 (d, J=8.56 Hz, 1H), 11.91 (s, 1H) (reported data refer to the major anti diastereoisomer).

Step 6. Preparation of 5-phenylpentyl-N-[(2R*,3R*)-2-tert-butyl-4-oxo-oxetan-3-yl]-carbamate Under nitrogen atmosphere, to a stirred mixture of (2R*, 3R*)-3-hydroxy-4,4-dimethyl-2-(5-phenylpentoxy-carbonylamino)-pentanoic acid and (2R*,3S*)-3-hydroxy-4,4-dimethyl-2-(5-phenylpentoxy-carbonylamino)-pentanoic acid (0.325 g, 0.92 mmol) in dry CH$_2$Cl$_2$ (40 mL). at 0° C., Et$_3$N (0.38 mL, 2.77 mmol) (0.2 mL, 1.44 mmol) and subsequently TBTU (0.356 g, 1.11 mmol) were added. The mixture was left stirring at 0° C. for 1 h and at rt for 15 h. The organics were then removed under reduced pressure, and the resulting crude product purified by column chromatography, using a Teledyne ISCO apparatus, eluting with Cy:AcOEt (from 90:10 to 70:30) to afford the title compound (0.165 g, 54%), as pure anti diastereoisomer, as white solid. MS (ESI) m/z: 351 [M−NH$_4$]$^+$; (ESI) m/z: 332 [M−H]$^−$. $^1$H NMR (DMSO-d$_6$) δ 0.94 (s, 9H), 1.29-1.39 (m, 2H), 1.52-1.65 (m, 4H), 2.58 (t, J=7.65 Hz, 2H), 4.01 (t, J=6.59 Hz, 2H), 4.33 (d, J=4.66 Hz, 1H), 4.76 (dd, J=4.65, 8.16 Hz, 1H), 7.11-7.36 (m, 5H), 8.05 (d, J=8.15 Hz, 1H).

Example 57

(4-Phenyl-phenyl)-methyl-N-[(2R*,3R*)-2-tert-butyl-4-oxo-oxetan-3-yl]-carbamate

Steps 1 to 3, as for Example 56.

Step 4. Preparation of (2R*,3R*)- and (2R*,3S*)-3-hydroxy-4,4-dimethyl-2-[(4-phenyl-phenyl)-methoxy-carbonylamino]-pentanoic acid To a stirred diastereomeric mixture containing (2R*,3R*)- and (2R*,3S*)-2-amino-3-hydroxy-4,4-dimethyl-pentanoic acid (0.288 g, 1.78 mmol) and NaHCO$_3$ (0.15 g, 1.8 mmol) in H$_2$O (7.0 mL), at rt, the isomeric mixture containing (4-phenylphenyl)-methyl-2-pyridyl carbonate and (4-phenylphenyl)-methyl-2-oxopyridine-1-carboxylate (0.82 g, 2.68 mmol) [prepared as for example 17, step 1] in THF (7.0 mL) was added. After 15 h at rt, the crude mixture was rotary evaporated to remove the organics and subsequently extracted with Et$_2$O (3×10 mL). The aqueous phase was acidified with 2.0 M HCl solution to pH 2-3 and subsequently extracted with AcOEt (3×20 mL). The organic fraction was dried over Na$_2$SO$_4$, filtered and concentrated to dryness to afford the title compound (0.21 g, 32% over 2 steps), as a diastereoisomeric mixture (anti:syn=9:1), as an off-white solid, which was used in the next step without further purification. MS (ESI) m/z: 410 [M−K]$^+$; (ESI) m/z: 370 [M−H]$^−$. $^1$H NMR (DMSO-d$_6$) δ 0.88 (s, 9H), 3.40 (d, J=7.37 Hz, 1H), 4.09-4.18 (m, 1H), 5.08 (s, 2H), 5.08 (s, broad, 1H), 7.33-7.53 (m, 5H), 7.60 (d, J=8.97 Hz, 1H), 7.63-7.72 (m, 4H), 12.21 (s, 1H) (reported data refer to the major anti diastereoisomer).

Step 5. Preparation of (4-phenyl-phenyl)-methyl-N-[(2R*,3R*)-2-tert-butyl-4-oxo-oxetan-3-yl]-carbamate Under nitrogen atmosphere, to a stirred mixture of (2R*, 3R*)-3-hydroxy-4,4-dimethyl-2-[(4-phenyl-phenyl)-methoxy-carbonylamino]-pentanoic acid and (2R*,3S*)-3-hydroxy-4,4-dimethyl-2-[(4-phenyl-phenyl)-methoxy-carbonylamino]-pentanoic acid (0.203 g, 0.55 mmol) in dry CH$_2$Cl$_2$ (25 mL), at 0° C., Et$_3$N (0.23 mL, 1.65 mmol) and subsequently TBTU (0.21 g, 0.66 mmol) were added. The mixture was left stirring at 0° C. for 1 h and at rt for 15 h. The organics were then removed under reduced pressure, and the resulting crude product purified by column chromatography, using a Teledyne ISCO apparatus, eluting with Cy:AcOEt (from 90:10 to 80:20) to afford the pure title compound (0.063 g, 58%), as pure anti diastereoisomer, as white solid. MS (ESI) m/z: 371 [M−NH$_4$]$^+$; (ESI) m/z: 352 [M−H]$^−$. $^1$H NMR (DMSO-d$_6$) δ 0.95 (s, 9H), 4.37 (d, J=4.64 Hz, 1H), 4.83 (dd, J=4.65, 8.16 Hz, 1H), 5.14 (s, 2H), 7.32-7.56 (m, 5H), 7.60-7.75 (m, 4H), 8.25 (d, J=8.12 Hz, 1H).

Example 58

5-Phenylpentyl-N-[(2S*,3R*)-2-tert-butyl-4-oxo-oxetan-3-yl]-carbamate

Step 1. Preparation of ethyl (2S*,3R*)-2-(dibenzylamino)-3-hydroxy-4,4-dimethyl-pentanoate To a stirred solution of ethyl ethyl (2S*)-2-(dibenzylamino)-4,4-dimethyl-3-oxo-pentanoate [prepared as for example 47, step 1] (0.637 g, 1.73 mmol) in EtOH (22 mL), at rt, a solution of NH$_4$Cl (1.86 g, 34.7 mmol) in H$_2$O (7.0 mL) was added. NaBH$_4$ (0.656 g, 17.3 mmol) was then added in small portions. After 1 h from the last addition, the reaction was quenched with H$_2$O and the solvent evaporated. The crude mixture was taken up with H$_2$O and CH$_2$Cl$_2$ and pH corrected to 9 with 20% NH$_4$OH aqueous solution. After extraction, the organic phase was dried over Na$_2$SO$_4$, filtered, and concentrated in vacuo to give a crude product, as an oil. Purification by column chromatography using a Teledyne ISCO apparatus, eluting with Cy:AcOEt (90:10), gave the title compound (0.55 g, 86%), as a pure syn diastereoisomer, as a colorless oil. MS (ESI) m/z: 370 [M−H]$^+$. $^1$H NMR (DMSO-d$_6$) δ 0.63 (s, 9H), 1.31 (t, J=7.10 Hz, 3H), 3.18 (d, J=9.26 Hz, 1H), 3.39 (d, J=13.54 Hz, 2H), 3.63 (d, J=8.98 Hz, 1H), 3.92 (d, J=13.53 Hz, 2H), 4.10-4.31 (m, 2H), 4.35 (s, 1H), 7.20-7.47 (m, 10H).

Step 2. Preparation of ethyl (2S*,3R*)-2-amino-3-hydroxy-4,4-dimethyl-pentanoate In a pear flask, at rt, ethyl (2S*,3R*)-2-(dibenzylamino)-3-hydroxy-4,4-dimethyl-pentanoate (2.0 g, 5.6 mmol) was dissolved in EtOH (110 mL) and passed through the H-Cube® hydrogenator flow reactor, using 10% Pd/C as catalyst [flow:1.0 mL/min; P=1.0 bar, T=70° C.]. After evaporation of the solvent, the title compound (0.74 g, 70%) was obtained as yellowish oil and used without further purification in the following step. MS (ESI) m/z: 190 [M−H]$^+$. $^1$H NMR (DMSO-d$_6$) δ 0.90 (s, 9H), 1.20 (t, J=7.11 Hz, 3H), 3.35 (d, J=2.95 Hz, 1H), 3.44 (d, J=2.92 Hz, 1H), 4.05-4.13 (m, 2H).

Step 3. Preparation of (2S*,3R*)-2-amino-3-hydroxy-4,4-dimethyl-pentanoic acid

In a round-bottomed flask, ethyl (2S*,3R*)-2-amino-3-hydroxy-4,4-dimethyl-pentanoate (0.596 g, 3.7 mmol) was dissolved in a 6.0 M HCl solution (70 mL). The resulting solution was divided into two equal aliquots and stirred at 130° C. for 1 h. All portions were joined and the reaction mixture extracted with Et$_2$O (3×50 ml). The aqueous phase was concentrated under reduced pressure and the resulting yellowish solid crude product (0.675 g, 93%) was used without further purification in the following reaction. MS (ESI) m/z: 162 [M−H]$^+$; (ESI) m/z: 160 [M−H]$^−$. $^1$H NMR (DMSO-d$_6$) δ 0.91 (s, 9H), 3.66 (d, J=3.24 Hz, 1H), 3.89 (s, 1H), 5.95 (d, J=6.39 Hz, 1H), 7.92 (s, 3H), 13.88 (s, 1H).

Step 4. Preparation (2R*,3S*)-3-hydroxy-4,4-dimethyl-2-(5-phenyl-pentoxy-carbonylamino)-pentanoic acid To a stirred mixture of (2S*,3R*)-2-amino-3-hydroxy-4,4-dimethyl-pentanoic acid (0.36 g, 2.24 mmol) and NaHCO$_3$ (0.188 g, 2.24 mmol) in H$_2$O (15 mL), at rt, the isomeric mixture containing 5-phenyl-pentyl-2-pyridyl-carbonate and 5-phenyl-pentyl-2-oxopyridine-1-carboxylate (1.95 g, 6.84 mmol) [prepared as for example 32, step 1] in THF (15 mL) was added. After 15 h at rt, the crude mixture was rotary evaporated to remove the organics and subsequently extracted with Et$_2$O (3×40 mL). The aqueous phase was acidified with 2.0 M HCl solution to pH 2-3 and subsequently extracted with AcOEt (3×40 mL). The organic fraction was dried over Na$_2$SO$_4$, filtered and concentrated to dryness to afford the title compound (0.346 g, 44%), as an off-white solid, which was used in the next step without further purification. MS (ESI) m/z: 352 [M−H]$^+$; (ESI) m/z: 350 [M−H]$^−$. $^1$H NMR (DMSO-d$_6$) δ 0.86 (s, 9H), 1.33 (tt, J=5.95, 9.00 Hz, 2H), 1.57 (ddt, J=3.93, 6.59, 10.94 Hz, 4H), 2.57 (t, J=7.70 Hz, 2H), 3.59 (s, 1H), 3.87-4.03 (m, 2H), 4.12-4.21 (m, 1H), 6.25 (d, J=9.37 Hz, 1H), 7.10-7.32 (m, 5H), 11.55 (s, 1H).

Step 5. Preparation 5-phenylpentyl-N-[(2S*,3R*)-2-tert-butyl-4-oxo-oxetan-3-yl]-carbamate Under nitrogen atmosphere, to a stirred mixture of (2R*,3S*)-3-hydroxy-4,4-dimethyl-2-(5-phenyl-pentoxy-carbonylamino)-pentanoic acid (0.346 g, 0.98 mmol) in dry CH$_2$Cl$_2$ (45 mL), at 0° C., Et$_3$N (0.41 mL, 2.95 mmol) and subsequently TBTU (0.38 g, 1.20 mmol) were added. The mixture was left stirring at 0° C. for 1 h and at rt for 15 h. The organics were then removed under reduced pressure, and the resulting crude product purified by column chromatography, using a Teledyne ISCO apparatus, eluting with Cy:AcOEt (from 90:10 to 70:30) to afford the pure title compound (0.125 g, 38%), as white solid. MS (ESI) m/z: 351 [M−NH$_4$]$^+$; (ESI) m/z: 332 [M−H]$^−$. $^1$H NMR (DMSO-d$_6$) δ 0.93 (s, 9H), 1.34 (h, J=6.37, 7.16 Hz, 2H), 1.53-1.65 (m, 4H), 2.57 (t, J=7.69 Hz, 2H), 4.02 (q, J=6.25 Hz, 2H), 4.36 (d, J=6.24 Hz, 1H), 5.56 (dd, J=6.32, 8.47 Hz, 1H), 7.07-7.34 (m, 5H), 8.38 (d, J=8.48 Hz, 1H).

Example 59

(4-Phenyl-phenyl)-methyl-N-[(2S*,3R*)-2-tert-butyl-4-oxo-oxetan-3-yl]-carbamate

Steps 1 to 3, see example 58.

Step 4. Preparation of (2S*,3R*)-3-hydroxy-4,4-dimethyl-2-[(4-phenyl-phenyl)-methoxy-carbonylamino]-pentanoic acid To a stirred mixture of (2S*,3R*)-2-amino-3-hydroxy-4,4-dimethyl-pentanoic acid (0.353 g, 2.19 mmol) and NaHCO$_3$ (0.184 g, 0.84 mmol) in H$_2$O (15 mL), at rt, the isomeric mixture containing (4-phenylphenyl)-methyl-2-pyridyl carbonate and (4-phenylphenyl)-methyl-2-oxopyridine-1-carboxylate (0.815 g, 2.2 mmol) [prepared as for example 17, step 1] in THF (15 mL) was added. After 15 h at rt, the crude mixture was rotary evaporated to remove the organics and subsequently extracted with Et$_2$O (3×20 mL).

The aqueous phase was acidified with 2.0 M HCl solution to pH 2-3 and subsequently extracted with AcOEt (3×20 mL). The organic fraction was dried over $Na_2SO_4$, filtered and concentrated to dryness to afford the title compound (0.181 g, 21%), which was used in the next step without further purification. MS (ESI) m/z: 410 [M−K]$^+$; (ESI) m/z: 370 [M−H]$^−$.

Step 5. Preparation of (4-phenyl-phenyl)-methyl-N-[(2S*,3R*)-2-tert-butyl-4-oxo-oxetan-3-yl]-carbamate Under nitrogen atmosphere, to a stirred mixture of (2S*, 3R*)-3-hydroxy-4,4-dimethyl-2-[(4-phenyl-phenyl)-methoxy-carbonylamino]-pentanoic acid (0.18 g, 0.48 mmol) in dry $CH_2Cl_2$ (20 mL), at 0° C., $Et_3N$ (0.203 mL, 1.45 mmol) and subsequently TBTU (0.186 g, 0.6 mmol) were added. The mixture was left stirring at 0° C. for 1 h and at rt for 15 h. The organics were then removed under reduced pressure, and the resulting crude product purified by column chromatography, using a Teledyne ISCO apparatus, eluting with Cy:AcOEt (from 90:10 to 80:20) to afford the pure title compound (0.011 g, 6%), as a white solid. MS (ESI) m/z: 371 [M−NH$_4$]$^+$; (ESI) m/z: 352 [M−H]$^−$. $^1$H NMR (DMSO-d$_6$) δ 0.93 (s, 9H), 4.38 (d, J=6.24 Hz, 1H), 5.15 (d, J=2.85 Hz, 2H), 5.61 (dd, J=6.18, 8.50 Hz, 1H), 7.23-7.81 (m, 9H), 8.58 (d, J=8.48 Hz, 1H).

Example 60

Effect of Compound 6 on Carrageenan-Induced Inflammatory Responses in Mice

The results herein demonstrate the anti-inflammatory activity of compound 6 and its pharmacological mechanism. NAAA is predominantly expressed in innate immune cells, suggesting a role for this enzyme in inflammation. Previous studies have shown that NAAA inhibitors cause profound anti-inflammatory effects in mice by increasing PEA signalling through the nuclear receptor PPAR-alpha (see Solorzano C, et al (2009) Proc Natl Acad Sci USA. 106:20966-71).

The Methods include the following: Carragenan (1%) was injected into the left hind paw of Swiss albino mice. Paw edema was measured using a plethysmometer. Cutaneous hyperalgesia (thermal) was assesed by the plantar test (see Hargreaves K, et a 1 (1988), Pain 32: 77-88). Compound 6 was administered topically. Data were analysed by ANOVA followed by Bonferroni's test for multiple comparisons.

This Example, and FIGS. 3-6, demonstrate that compound 6 produces marked anti-inflammatory and anti-hyperalgesic effects in the carrageenan model of acute inflammation. As previously shown for other NAAA inhibitors, these effects are mediated by PPAR-alpha.

Example 61

Effect on Skin Integrity: Comparison with Steroids

The results herein demonstrate the effect of repeated topical administration of compound 6 on skin integrity.

This experiment evaluated the effect of repeated (14 days) topical dosing with compound 6 or dexamethasone on skin integrity The results demonstated that repeated administration of topical steroids such as dexamethasone causes skin atrophy, which is a serious limitation to the therapeutic use of these agents (See Schoepe et al (2006), Exp Dermatol 15: 406-420). The results also show that PPAR-alpha activators counteract adverse events of glucocorticoids on epidermis (see Demerjian et al, (2009), Exp Dermatol 18: 643-649)

The methods included the following. Drug or vehicle were given topical to both ears of CD1 mice for 14 days. Ear thickness was determined by using a micrometer. Histopathological analyses were conducted on formalin-fixed, paraffin-embedded ear sections 5 mm thick and stained with Hematoxylin-Eosin. Epidermal thickness was measured with standard morphometric methods from 12 different samplings spanning the treated area of each ear. Data were analysed by ANOVA followed by Bonferroni's test for multiple comparisons. Repeated administration (14 days) of compound 6 (1 and 30%) did not affect skin integrity measured as reduction of ear thickness. The histopathological and morphometric analysis of ears showed no alterations of cellular structure. The results show that the repeated administration of dexamethasone caused skin atrophy as suggested by a significant reduction in skin thickness. Histopathological and morphometric analyses revealed that dexamethasone-induced skin atrophy was associated with: Reduction of epidermis thickness; Loss of epidermal cytoarchitecture, from multilayered columnar epithelium to a single layer; and Morphological changes of keratinocytes (smaller and flattened).

These results show that compound 6 does not demonstrate the limitation to long term use that certain steroids do with regard to the disruption of skin integrity (skin atrophy). This is an unexpected results and a significant advancement in the treatment of skin related disorders.

Example 62

DNFB-Induced Dermatitis in Mice

The results herein demonstrate the effects of compound 6 in DNFB dermatitis.

The results herein demonstrate the effect on increase of ear edema (flares).

This experiment determined the efficacy of compound 6 in the DNFB model of contact dermatitis. This experiment also compared compound 6 with certain reference compounds.

This experiment tested several criteria including the following. NAAA inhibitors are shown to exert a marked anti-inflammatory effects by preventing PEA degradation and reinstating PEA activation of PPARα (see Solorzano C, et al (2009) Proc Natl Acad Sci USA. 106:20966-71). PEA has been shown to have a protective effect in human and animal dermatitis (see Petrosino et al, (2010), Allergy, 65:698-711). PPARα-deficient mice are shown to be more sensitive to contact allergens than are wild-type mice (Dubrac et al, (2011), EurJ Immunol, 41:1-12)

The methods included the following. Dermatitis was produced in mice using 2-4 dinitrofluorobenzene (DNFB) as described by Buckley and Nijkamp (1994), *Am J Respir Grit Care Med* 149:400-7. Mice were sensitized on two consecutive days with a 0.5% DNFB solution applied to the shaved abdomen. At day 8, the ears were challenged with a 0.2% DNFB solution. Ear thickness was determined by using a micrometer. Scratching was evaluated as number of episodes per 60 minutes period. Data were analysed by ANOVA followed by the Bonferroni's test. See also Hargreaves K, et al (1988), *Pain* 32: 77-88 for related information.

The results herein show that compound 6 reverses established DNFB-induced ear edema (therapeutic effect). In the repeated dosing protocol compound 6 is effective in the dose-range of 0.01-1%. Full efficacy is observed after 3 days of administration. Compound 6 efficacy is also noted in a single dosing protocol. Full efficacy is seen at doses of 10-30%.

Compound 6 prevents DNFB-induced increased ear edema (prophylactic effect). A repeated dosing protocol was used (8 days before DNFB challenge). Efficacy is complete at doses of 0.1-1%.

The results herein also show the effects on the immune response of Compound 6 in DNFB-induced dermatitis This experiment expands the efficacy profile of compound 6 on the immunological alterations commonly associated with dermatitis This works shows that atopic dermatitis is characterized by dysregulation of the immune response mainly due to a T cell dominant inflammation (see Leung et al; (2004), *J. Clinical Investigation,* 113:651-657). This work shows that DNFB is a chemical hapten that activates T cells (Heylings et al, (1996) Toxicology. 109: 57-65). Also, this work shows that compound 6 is effective on DNFB-induced edema The methods include the following. Dermatitis in mice was induced with 2-4 Dinitrofluorobenzene (DNFB) as previously described. IL-4, IL-5, IFN-g, and IgE blood levels were determined by immunoassays. The effect of compound 6 was tested using a single treatment protocol. Data were analysed by ANOVA followed by Bonferroni's test for multiple comparisons The results herein show that topical administration of compound 6 normalizes compromised immunological responses in DNFB dermatitis. The results herein also show that a single administration of compound 6 provides full efficacy at a dose range of 1 to 30%. The results herein show that the effect of compound 6 is superior to that of steroids. Also, the effects of compound 6 are mediated by normalization of PEA and OEA signaling at PPAR-α.

Effects of Compound 6 in DNFB Dermatitis—Breaking the Itch-Scratch Cycle

This experiment expands the efficacy profile of compound 6 to dermatitis-associated scratching.

The itch-scratch cycle is a common medical issue associated with atopic dermatitis and other dermatoses. Exacerbation of scratching can lead to skin lesions thus creating a suitable environment for pathogens to cause infection and flaring of symptoms. Very little is available to break the itch-scratch cycle.

This experiment shows that compound 6 is effective on other dermatitis-associated effects.

The methods include the following. Itching in mice was induced with DNFB as previously described. Additional studies were done with 48/80 model (an inducer of mast cell degranulation). 48/80 was given subcutaneously (30 mg per kg). Data were analysed by ANOVA followed by Bonferroni's test for multiple comparisons. The topical administration of a single dose of compound 6 prevented itching (assessed as scratching) in mice. In the DNFB model compound 6 is effective at doses as low as 0.001%. Full effect is seen at 1-3%.

In the 48/80 model of mast cell degranulation compound 6 is effective at doses as low as 0.01% and the effect is maximal at 1%. In the DNFB model, compound 6 is very effective either on established symptoms (therapeutic effect) or on prevention of symptom development (prophylactic effect). This experiment also shows that pharmacological potency was maximized by a repeated administration protocol, but efficacy was seen also after single dosing indicating that the compound is suitable for a loading dose approach. Further, DFNB in mice causes dysregulation of the immunological response as it has been observed in atopic dermatitis patients. The results herein show that compound 6 is able to stabilize the immunological profile following DNFB administration. This effect is a further index of therapeutic efficacy.

The results herein show that compound 6 is able to reduce scratching due to either DNFB irritation or 48/80-induced mast cell degranulation. This suggests efficacy in a largely intractable symptom. In the experimental protocols herein, the efficacy of compound 6 was comparable or superior, to that of reference drugs. Accordingly, compound 6 is a promising compound to treat atopic dermatitis and other dermatoses associated with itch.

The content of all references recited herein is incorporated by reference herein for all purposes and in the entirety.

Example 62

Inhibition of h-NAAA

Human NAAA (h-NAAA) Protein Preparation

The assay was run in Optiplate 96-wells black plates, in a total reaction volume of 200 mL. NAAA protein preparations (4 ng) were pre-incubated for 10 minutes with various concentrations of test compounds or vehicle control (5% DMSO) in 100 mM citrate/phosphate buffer (pH 4.5) containing 3.0 mM DTT, 0.1% Triton X-100, 0.05% BSA, 150 mM NaCl. N-(4-methyl-2-oxo-chromen-7-yl)-hexadecanamide was used as a substrate (5.0 µM) and the reaction carried over for 30 minutes at 37° C. Fluorescence in the samples was quantified in a Perkin Elmer Envision plate reader using an excitation wavelength of 360 nm and emission 460 nm. $IC_{50}$ values were calculated by non-linear regression analysis of log [concentration]/inhibition curves using GraphPad Prism 5 (GraphPad Software Inc., CA—USA) applying a standard slope curve fitting.

UPLC/MS h-NAAA Assay

NAAA protein preparation (10 µg) was pre-incubated with various concentrations of test compound or vehicle control in 100 mM $NaH_2PO_4$, 100 mM Tri Sodium Citrate Dehydrate, 0.1% Triton-X 100, 3 mM DTT, pH 4.5 for 30 min at 37° C. Duplicate samples were then incubated with 50 µM C17:1 10-cis-heptadecenoylethanolamide (Avanti Polar Lipids, Alabaster, Ala.—USA) at 37° C. for 30 minutes. The reaction was terminated by the addition of 0.2 mL of cold methanol containing 1 nmol of heptadecanoic acid (NuChek Prep, Elysian, Minn.—USA) as internal standard. Samples were then analyzed by UPLC/MS. Heptadecenoic and heptadecanoic acids were eluted on an Acquity UPLC BEH C18 column (50 mm length, 2.1 mm i.d., 1.7 µm pore size, Waters) isocratically at 0.5 mL/min for 1.5 min with a solvent mixture of 95% methanol and 5% water, both containing 0.25% Acetic Acid and 5 mM Ammonium Acetate. The column temperature was 40° C. Electrospray ionization was in the negative mode, capillary voltage was 2.7 kV, cone voltage was 45 V, extractor voltage was 3 V. The source temperature was 150° C. with a desolvation temperature of 400° C. $N_2$ was used as drying gas at a cone flow of 100 L/hour and a desolvation flow of 800° C. The [M−H]-ion was monitored in the selected-ion monitoring mode (m/z values: heptadecenoic acid 267.37, heptadecanoic acid 269.37). Calibration curves were generated using commercial heptadecenoic acid (NuCheck Prep) Inhibition of NAAA activity was calculated as reduction of heptadecenoic acid in the samples compared to vehicle controls. $IC_{50}$ values were calculated by non-linear regression analysis of log [concentration]/inhibition curves using GraphPad Prism 5 (GraphPad Software Inc., CA—USA) applying a standard slope curve fitting.

Fluorogenic h-NAAA Assay

The assay was run in Optiplate 96-wells black plates, in a total reaction volume of 200 µL. NAAA protein preparation (4.0 µg) was pre-incubated for 10 min with various concentrations of test compounds or vehicle control (5% DMSO) in 100 mM citrate/phosphate buffer (pH 4.5) containing 3.0 mM DTT, 0.1% Triton X-100, 0.05% BSA, 150 mM NaCl. N-(4-methyl-2-oxo-chromen-7-yl)-hexadecanamide was used as a substrate (5.0 µM) and the reaction carried over for 30 min at 37° C. The samples were then read in a Perkin Elmer Envision plate reader using an excitation wavelength of 360 nm and emission 460 nm. IC50 values were calculated by non-linear regression analysis of log [concentration]/inhibition curves using GraphPad Prism 5 (GraphPad Software Inc., CA—USA) applying a standard slope curve fitting.

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

What is claimed is:

1. A compound of the formula:

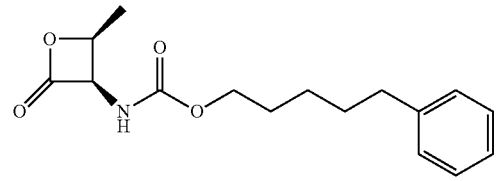 [SMILES: C[C@@H]1OC(=O)[C@@H]1NC(=O)OCCCCCc1ccccc1]

or a pharmaceutically acceptable salt thereof or ester of such compound.

2. A pharmaceutical composition comprising a compound of claim 1, or a pharmaceutically acceptable salt thereof, and a pharmaceutically acceptable carrier.

* * * * *